(12) United States Patent
Goodfellow et al.

(10) Patent No.: US 9,370,515 B2
(45) Date of Patent: Jun. 21, 2016

(54) MIXED LINEAGE KINASE INHIBITORS AND METHOD OF TREATMENTS

(71) Applicants: CALIFIA BIO, INC., San Diego, CA (US); UNIVERSITY OF ROCHESTER, Rochester, NY (US)

(72) Inventors: Val S. Goodfellow, Encinitas, CA (US); Thong X. Nguyen, San Diego, CA (US); Satheesh B. Ravula, San Diego, CA (US); Harris A. Gelbard, Pittsford, NY (US)

(73) Assignees: CALIFIA BIO, INC., San Diego, CA (US); UNIVERSITY OF ROCHESTER, Rochester, NY (US)

( * ) Notice: Subject to any disclaimer, the term of this patent is extended or adjusted under 35 U.S.C. 154(b) by 0 days.

(21) Appl. No.: 14/201,673

(22) Filed: Mar. 7, 2014

(65) Prior Publication Data

US 2014/0256733 A1    Sep. 11, 2014

Related U.S. Application Data

(60) Provisional application No. 61/774,211, filed on Mar. 7, 2013.

(51) Int. Cl.
| | | |
|---|---|---|
| *A61K 31/5025* | (2006.01) | |
| *A61K 45/06* | (2006.01) | |
| *C07D 487/04* | (2006.01) | |
| *C07D 513/04* | (2006.01) | |
| *A61K 31/427* | (2006.01) | |
| *A61K 31/4402* | (2006.01) | |
| *A61K 31/513* | (2006.01) | |
| *A61K 31/536* | (2006.01) | |

(52) U.S. Cl.
CPC ........... *A61K 31/5025* (2013.01); *A61K 31/427* (2013.01); *A61K 31/4402* (2013.01); *A61K 31/513* (2013.01); *A61K 31/536* (2013.01); *A61K 45/06* (2013.01); *C07D 487/04* (2013.01); *C07D 513/04* (2013.01)

(58) Field of Classification Search
CPC . A61K 31/5025; A61K 45/06; C07D 513/04; C07D 487/04
USPC .......................................... 514/248; 544/236
See application file for complete search history.

(56) References Cited

U.S. PATENT DOCUMENTS

| | | | |
|---|---|---|---|
| 7,713,975 | B1 | 5/2010 | Hellberg et al. |
| 2007/0093490 | A1* | 4/2007 | Prien et al. ............... 514/248 |
| 2008/0153813 | A1 | 6/2008 | Chen et al. |
| 2009/0093475 | A1* | 4/2009 | Prien et al. ............... 514/233.2 |
| 2012/0053175 | A1 | 3/2012 | Gelbard et al. |
| 2012/0058997 | A1 | 3/2012 | Xu et al. |

FOREIGN PATENT DOCUMENTS

| | | |
|---|---|---|
| EP | 2463289 | 6/2012 |
| JP | 2009227599 A | 10/2009 |
| JP | 2009298710 A | 12/2009 |
| WO | 2006/087530 A1 | 8/2006 |
| WO | 2007/013673 A1 | 2/2007 |
| WO | 2007/025090 A2 | 3/2007 |
| WO | 2007/025540 A2 | 3/2007 |
| WO | 2007/147647 A1 | 12/2007 |
| WO | 2008/025822 A1 | 3/2008 |
| WO | 2008/030579 A2 | 3/2008 |
| WO | 2008/052734 A1 | 5/2008 |
| WO | 2008/058126 A2 | 5/2008 |
| WO | 2008/072682 A1 | 6/2008 |
| WO | 2008/135785 A1 | 11/2008 |
| WO | 2009/041456 A1 | 4/2009 |
| WO | 2009/060197 A1 | 5/2009 |
| WO | 2009/106577 A1 | 9/2009 |
| WO | 2009/133070 A1 | 11/2009 |
| WO | 2009/140128 A2 | 11/2009 |
| WO | 2010/002846 A1 | 1/2010 |
| WO | 2011/015652 A1 | 2/2011 |
| WO | 2011/101640 A1 | 8/2011 |
| WO | 2012/034091 A1 | 3/2012 |
| WO | 2012/052745 A1 | 4/2012 |
| WO | 2012/069202 A1 | 5/2012 |
| WO | 2012/087519 A1 | 6/2012 |

OTHER PUBLICATIONS

Camus et al., Oncogene (2012) 31, 4333-4342.*
Banker et al., (1995).*
Wolff et al (1995).*
Vippagunta et al (2001).*
Itoh, T., et al., "Synthetic studies of potential antimetabolites. XXII. Synthesis of 5- and 6-aminoimidazo[4,5-b]pyridine ribonucleosides (a new type of adenosine analog) by coupling reactions", Hetrocycles, 8:443-41 (1977).
PCT International Application No. PCT/US2014/022111, International Seach Report and Written Opinion mailed Jun. 23, 2014.

* cited by examiner

*Primary Examiner* — Paul V Ward
(74) *Attorney, Agent, or Firm* — Pillsbury Winthrop Shaw Pittman LLP

(57) ABSTRACT

Provided herein are imidazopyridine compounds having an inhibitory effect on mixed lineage kinases (MLKs), methods of their synthesis, and methods of their therapeutic. Also provided are pharmaceutical compositions comprising the compounds and methods of using the compounds and pharmaceutical compositions.

19 Claims, 5 Drawing Sheets

MIXED LINEAGE KINASE INHIBITORS AND METHOD OF TREATMENTS

CROSS-REFERENCE TO RELATED APPLICATIONS

This application claims the benefit of priority Application Ser. No. 61/774,211, filed on Mar. 7, 2013, which is expressly incorporated herein by reference in its entirety.

GOVERNMENT SUPPORT

This work was supported in part by Small Business Innovation Research Grants 1R43MH093270-01 and 2R44MH093270-02 from the National Institutes of Mental Health of the National Institutes of Health. The government has certain rights in the invention.

FIELD OF THE INVENTION

The present disclosure relates to imidazopyridine compounds having an inhibitory effect on mixed lineage kinases (MLKs), including family members in groups (e.g., MLK-1, MLK-2, MLK-3), and their synthesis. The disclosure also relates to pharmaceutical compositions comprising the compounds disclosed herein, and methods for therapeutic and/or prophylactic use of these compounds. In a particular aspect, the disclosure relates to compounds that inhibit the MLK-3 family.

INTRODUCTION

Mixed lineage kinases (MLKs) are MAPK kinase kinases that target activated c-Jun N-terminal kinases (JNK) and p38 MAPK for activation in response to diverse stimuli associated with cell stress. As a result, MLKs regulate a broad range of cellular processes. MLK-3 is the most widely expressed MLK family and is present in neurons.

JNKs are major control nodes in mammalian apoptotic cell death pathways. For example, GTP-bound forms of the G proteins Rac1 and Cdc42 promote autophosphorylation and activation of MLKs which, in turn, phosphorylate and activate mitogen-activated protein kinase kinases 4 and 7 ($MKK_4$ or $MKK_7$), which ultimately phosphorylate and activate JNKs. MLK-3 is widely distributed and up-regulated in inflammatory states in various organs including the brain and heart. The first generation, pan-MLK inhibitor CEP-1347 has been shown to protect primary rat hippocampal neurons as well as dorsal root ganglion neurons from the otherwise lethal effects of exposure to HIV-1 gp120. (Bodner, A., Toth, P. T. & Miller, R. J. Activation of c-Jun N-terminal kinase mediates gp120IIIB- and nucleoside analogue-induced sensory neuron toxicity. *Exp Neurol* 188, 246-253 (2004); Bodner, A. et al. Mixed lineage kinase 3 mediates gp120IIIB-induced neurotoxicity. *J Neurochem* 82, 1424-1434 (2002)). Neurotoxic HIV gene products Tat and gp120 induce autophosphorylation and activation of MLK-3 in primary rat neurons and this process can be abolished by the addition of CEP-1347. CEP-1347 enhances survival of both rat and human neurons and inhibited the activation of human monocytes after exposure to Tat and gp120. Furthermore, overexpression of wild-type MLK-3 leads to the induction of neuronal death, whereas expression of a dominant negative MLK-3 mutant protected neurons from the toxic effects of Tat. CEP-1347 is neuroprotective in an in vivo model of HIV-1 infection, reversing microglial activation and restoring normal synaptic architecture, as well as restoring macrophage secretory profiles to a trophic vs. toxic phenotype in response to HIV-1 infection. (Eggert, D. et al. Neuroprotective activities of CEP-1347 in models of neuroAIDS. *J Immunol* 184, 746-756 (2010)). Collectively, these studies suggest that MLK-3 activity is increased by HIV-1 neurotoxins, resulting in downstream signaling events that trigger neuronal death and damage, along with monocyte activation (accompanied by release of inflammatory cytokines). Unfortunately CEP-1347, a close analog of staurosporine, is non-specific for MLK-3, and is a large molecule where no evidence has been published showing that it penetrates the CNS. Pharmacokinetic studies in mice have demonstrated poor CNS penetration for CEP-1347. (Goodfellow et al, Discovery, synthesis, and characterization of an orally bioavailable, brain penetrant inhibitor of mixed lineage kinase 3, *J Med Chem* 56 8032-48 (2013). Further, development of CEP-1347 was halted for unknown reasons.

The central nervous system (CNS) can be infected and injured by HIV-1, leading to the development of HIV-Associated Neurocognitive Disorders (HAND). Recent estimates of the prevalence of HAND suggest that over 50% of the population living with AIDS is affected. Because combination antiretroviral therapy (cART), even in CNS penetrating forms, has not altered the prevalence of HAND (Heaton, R. et al. HIV-associated Neurocognitive Impairment Remains Prevalent in the Era of Combination ART: The CHARTER Study. 16*th Conference on Retroviruses and Opportunistic Infections;* 2009), new therapeutic strategies for counteracting the effects of HIV infection in the CNS are needed. Preliminary studies have shown that inhibition of key signaling kinases is likely one of the best strategies for affecting HAND-related inflammatory and cellular injury cascades. Sui, Z. et al. Inhibition of mixed lineage kinase 3 prevents HIV-1 Tat-mediated neurotoxicity and monocyte activation. *J Immunol* 177, 702-711 (2006); Dewhurst, S., Maggirwar, S. B., Schifitto, G., Gendelman, H. E. & Gelbard, H. A. Glycogen synthase kinase 3 beta (GSK-3 beta) as a therapeutic target in neuroAIDS. *J Neuroimmune Pharmacol* 2, 93-96 (2007).

MLK-3 also modulates neuroinflammation through effects on cytokine production by microglia and brain macrophages. In particular, CEP-1347-mediated inhibition of MLK-3 results in a significant decrease in Tat-stimulated release of tumor necrosis factor alpha (TNF-α) and interleukin (IL)-6 by macrophage and microglia. (Sui, Z., Kovacs, A. D. & Maggirwar, S. B. Recruitment of active glycogen synthase kinase-3 into neuronal lipid rafts. *Biochem Biophys Res Commun* 345, 1643-1648 (2006)). Similar results have been demonstrated in macrophages with CNS penetrant MLK-3 inhibitor URMC-099. (Goodfellow et al, 2013.) TNF-α mediates a significant part of Tat-mediated toxicity in models of HAND, and inhibition of this pathway by CEP-1347 may account for the reduction in neuroinflammation observed in an in vivo model for HAND. Recently a the potent and brain penetrant MLK3 inhibitor, URMC-099 has demonstrated in vivo efficacy for preservation of normal synaptic architecture and reversal of neuroinflammation following CNS exposure to HIV-1 Tat. (Marker et al, The new small-molecule mixed-lineage kinase 3 inhibitor URMC-099 is neuroprotective and anti-inflammatory in models of human immunodeficiency virus-associated neurocognitive disorders, *J Neurosci* 24 9998-10010 (2013).) URMC-099 however is not a selective inhibitor of MLK3. In order to limit off target activity there is a need to identify and develop compounds with greater specificity for MLK3.

Previously it has been shown that blockade of the MLK-3 pathway may interfere with the neurotoxic effect of beta amyloid oligomers. (Xu Y, Hou X Y, Liu Y, Zong Y Y, Different protection of K252a and N-acetyl-L-cysteine against amyloid-beta peptide-induced cortical neuron apoptosis involving inhibition of MLK3-MKK7-JNK3 signal cascades. J Neurosci Res. 2009 March; 87(4):918-27).) Inhibition of the C-jun/JNK pathway blocks hyperphosphorylation of tau in cultured hippocampal neurons. (J. Neurosci. 2009 Jul. 15; 29(28):9078-89). Consequently, MLK-3 inhibitors may be of value in the treatment of Alzheimer disease and other neurodegenerative diseases involving the C-jun/JNK pathway.

Recent evidence also suggests that acute and temporary blockade of the c-jun/JNK pathway at early stages of stroke may improve outcomes. (J. Neurosci. 2012 Jun. 13; 32(24): 8112-5).

Attenuation of microglial activation via MLK-3 inhibition protects hippocampal synapses in experimental autoimmune encephalomyelitis models of multiple sclerosis. MLK-3 inhibitors may be useful for the treatment of multiple sclerosis and other inflammatory neurological diseases. (Bellizzi M and Gelbard, H. Neurology Apr. 25, 2012; 78 (Meeting Abstracts 1): PO5.112.)

Small molecule inhibition of MLK-3 attenuates cardiac fibroblast activation and pathologic cardiac remodeling. (Martin, M. L., Dewhurst, S., Gelbard, H. A., Goodfellow, V., Blaxall, B. C.; Circulation Research 111 (4) A88 (2012)). Consequently, MLK-3 inhibitors may be useful for the treatment of heart failure.

MLK-3 blockade inhibits stellate cell proliferation in the liver and pancreas and may be useful for treatment of cirrhotic diseases of these organs. (Cancer Research 59 2195-2202 (1999)). MLK3 blockade may serve as a useful treatment for steatohepatitis. (Ibrahim S H, Gores G J, Hirsova P, Kirby M, Miles L, Jaeschke A, Kohli R. Mixed lineage kinase 3 deficient mice are protected against the high fat high carbohydrate diet-induced steatohepatitis. (*Liver Int.* 2013 Oct. 6. PMID:24256559)

Inhibition of MLK-3 may also be useful for the treatment of various cancers such as cancers of the pancreas and breast. (*Cancer Growth and Metastasis* 2010:3 1-9). MLK-3 regulates the proliferation of some tumor cell types, including human schwannoma and meningioma cells and breast cancer cells also over-express MLK-3 (Chen J, Miller E M, Gallo K A. Oncogene. 2010; 29(31):4399-411). RNA-mediated knockdown of MLK-3 inhibits growth and lymph node metastasis of human breast cancer cells in a mouse xenograft model. (Oncogene. 2011 PMC: 3297722)). MLK-3 inhibitors may be efficacious in treating metastasized breast tumors and compounds which are highly CNS penetrant may be especially useful in treating metastasized tumors in the brain associated with breast cancer.

Both HAND and Parkinson's Dementia have similar underlying pathology involving dopaminergic pathways and synaptodendritic damage. Destruction of striatal dopaminergic neurons results in a significant loss of dendritic spines on medium spiny projection neurons (MSNs) in Parkinson's disease. MSNs are the main output neurons of the striatum. MSNs are the primary synaptic target of both nigrostriatal dopaminergic and cortico-striatal glutamatergic afferent neurons. Dendritic spines are critical sites for synaptic integration. For a treatment for Parkinson's Disease to be effective, dopaminergic neurotransmission must be normalized and MSN spine loss and dendritic atrophy need to be reversed. The MLK3 inhibitor, CEP-1347, was developed as a clinical candidate for Parkinson's Disease. CEP-1347 exhibited striking positive activity in numerous in vitro and in vivo models for PD including neuroprotection using methamphetamine-exposed human mesencephalic-derived neurons. CEP-1347 prevented the induction of neuronal cell death, motor deficits and neuronal degeneration in the MPTP model of Parkinsonism in mice and monkeys. However, the compound failed to exhibit efficacy in human trials for preventing the development of disease progression in early stage Parkinson's Disease. (PRECEPT GROUP, Mixed lineage kinase inhibitor CEP-1347 fails to delay disability in early Parkinson disease, Neurology 15 1480-90 (2007).) The only available pharmacokinetic data for CEP-1347 shows wide patient variability of plasma levels for the drug in patients, suggesting metabolic or induction issues. (Ma et al, J Neurovirol 19 254-60 (2013.) Pharmacokinetic studies in mice have shown very poor blood brain barrier penetration for CEP-1347 (Goodfellow et al, 2013). A compound with substantially increased ability to maintain high brain concentration levels may offer better potential for treating Parkinson's Disease.

Accordingly, there still is a great need to develop potent inhibitors of MLKs, including groups MLK-3, that are useful in treating various conditions associated with MLK activation.

SUMMARY OF THE INVENTION

Disclosed herein are compounds having an inhibitory effect on MLKs, including the families MLK-1, MLK-2, and MLK-3. Also provided are pharmaceutical compositions thereof, methods of preparation thereof, and methods of use thereof, such as in treatment of a malcondition mediated by MLKs receptor activation, or when modulation or potentiation of MLK-3 receptor is medically indicated.

DETAILED DESCRIPTION OF THE INVENTION

Figure 1:
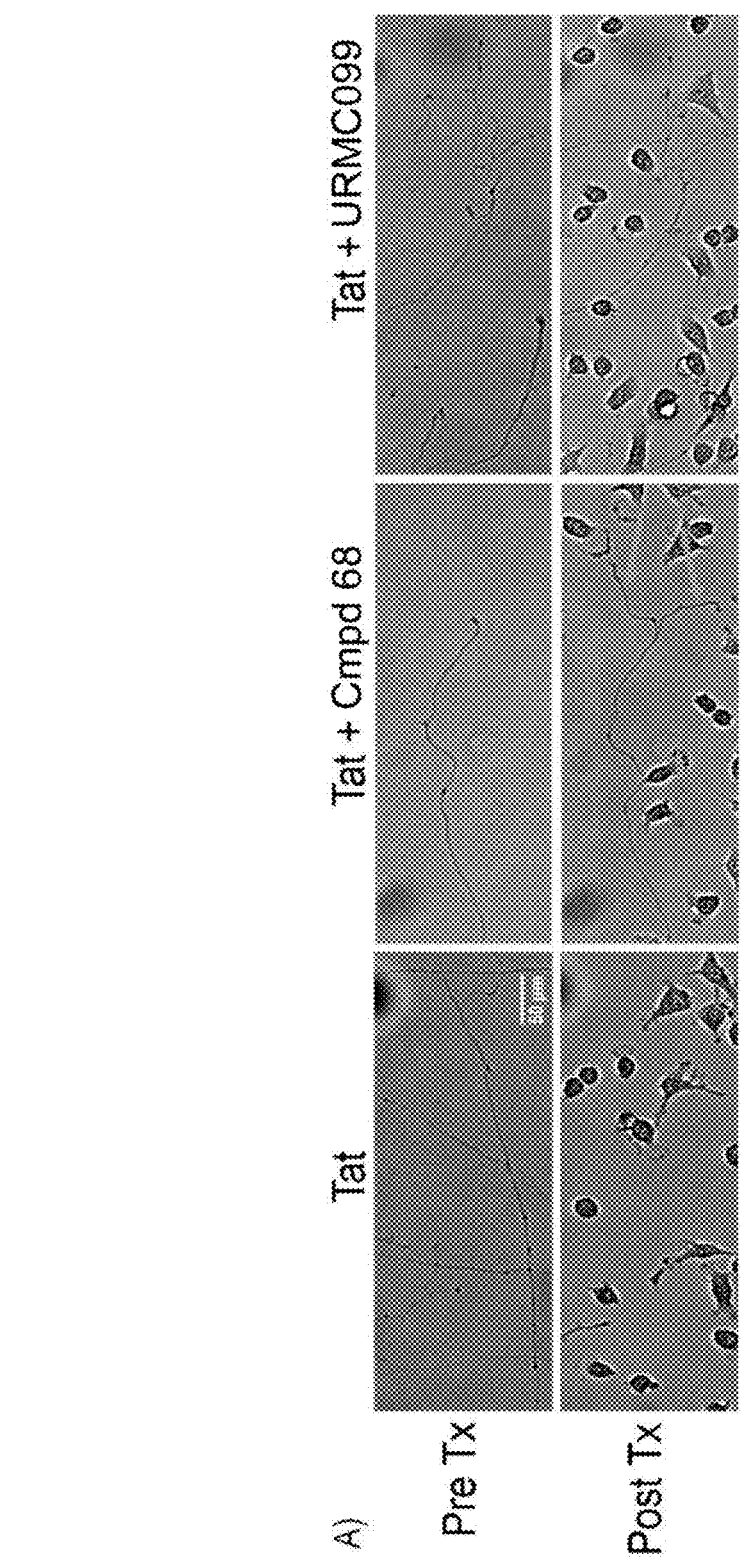
FIG. 1 shows images of E18 primary hippocampal neurons which were plated in microfluidic chambers before and after introduction of BV-2 microglial cells treated with HIV-1 Tat (1 ug/mL) and test inhibitor compounds (100 nM). Arrows show examples of continued axonogenesis in the presence of Tat-activated microglia, facilitated by a compound of the present disclosure (Compound 68).

Certain embodiments of the present disclosure provides a compound having the structure of Formula I

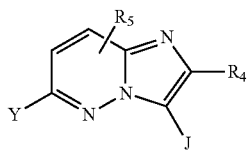

I or a pharmaceutically acceptable isomer, isotope, enantiomer, salt, ester, prodrug, hydrate or solvate thereof, wherein
J has a structure of

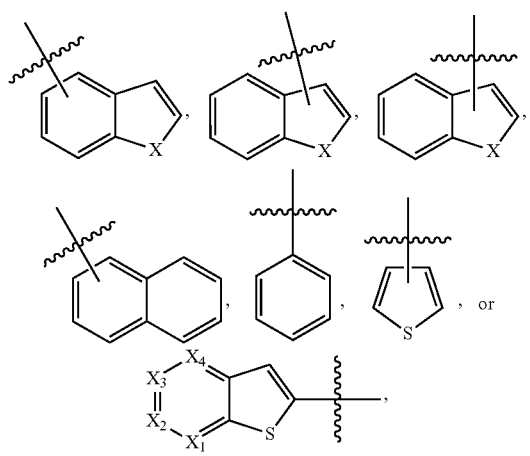

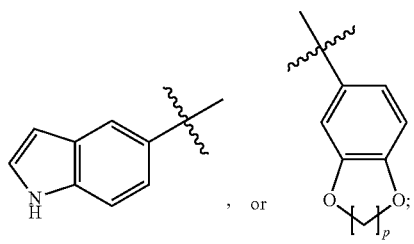

where J (i.e., any carbon atom on J) can be optionally substituted with up to four $R_{10}$, each $R_{10}$ can be independently selected from the group consisting of halo, alkyl, haloalkyl, alkoxy, haloalkoxy —OH, and —$OCOR_6$;

X can be $NR_{12}$ or S;

$X_1$, $X_2$, $X_3$, and $X_4$ can be H or N and wherein no more than one of $X_1$, $X_2$, $X_3$, and $X_4$ is N;

Y can be —W—$(CH_2)_n$—$R_1$,

W can be null, phenylene, or —$NR_6$-phenylene, where the $NR_6$ is attached to the imidazopyridazine core structure of Formula I;

$R_1$ can be —$NR_2R_3$, or piperazinyl, where the nitrogen atom of the piperazinyl can be optionally substituted with alkyl or alkoxy;

$R_2$ can be H or alkyl; $R_3$ can be selected from the group consisting of $C_2$-$C_{10}$ alkyl, aryl, heteroaryl, cycloalkyl, and heterocycloalkyl, where any atom of $R_3$ can be optionally substituted with one or more $R_7$; or $R_2$ and $R_3$ taken together with the N atom to which they are attached form a 3- to 7-membered heterocyclic ring optionally substituted with $R_8$;

$R_4$ can be H or alkyl;

$R_5$ can be H, alkyl, or $NHR_9$;

$R_6$ can be H or alkyl;

each $R_7$ can be independently alkyl, cycloalkyl, alkoxy, cycloalkoxy, cycloalkylalkoxy, perhaloalkoxy, halo, oxo, —OH, hydroxyalkyl, —$COOR_{11}$, or —O—$(CH_2)_m$—OH;

$R_8$ can be alkoxy, hydroxyalkyl, or $COOR_{11}$;

$R_9$ can be H, alkyl, or cycloalkyl;

$R_{11}$ can be H, or alkyl;

$R_{12}$ can be H, or alkyl;

n can be 0 or 1;

m can be 1, 2, or 3; and p can be 1, 2, or 3;

with the proviso that if J is an unsubstituted benzothiophene, then $R_3$ is either aryl or heteroaryl, where any atom of $R_3$ can be optionally substituted with one or more $R_7$.

In certain of such embodiments, the disclosure provides compounds where J can be selected from the group consisting of

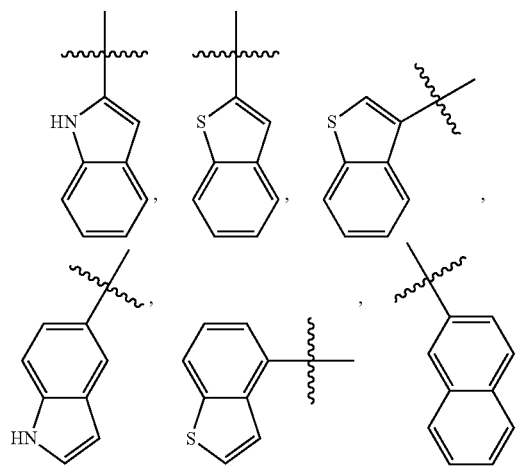

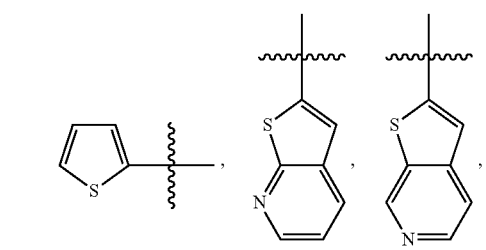

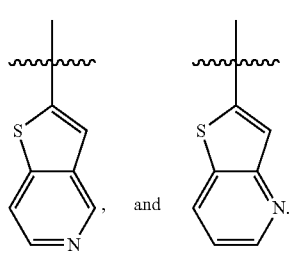

In certain embodiments, J can be

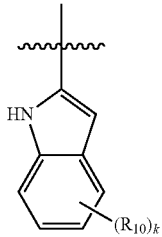

wherein each $R_{10}$ can be independently selected from the group consisting of F, Cl, —OH, methyl, methoxy, ethoxy, propoxy, isopropoxy, and —OCOCH$_3$; and k can be 0, 1, 2, or 3.

In certain embodiments, J can be

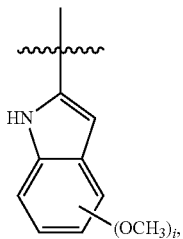

wherein i can be 0 or 1, 2.

In certain embodiments, wherein J can be

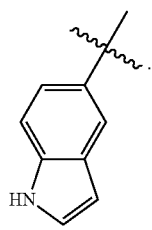

In certain embodiments, J can be

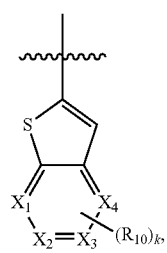

wherein each $R_{10}$ can be independently selected from the group consisting of F, Cl, —OH, methyl, methoxy, ethoxy, propoxy, isopropoxy, and —OCOCH$_3$; and k can be 0, 1, 2, or 3. In certain embodiments, $R_{10}$ can be —OH or —OCOCH$_3$. In one embodiment, each of $X_1$, $X_2$, $X_3$, and $X_4$ can be CH. In one embodiment, $X_1$ can be N, and each of $X_2$, $X_3$, and $X_4$ can be CH. In one embodiment, $X_2$ can be N, and each of $X_1$, $X_3$, and $X_4$ can be CH. In one embodiment, $X_3$ can be N, and each of $X_1$, $X_2$, and $X_4$ can be CH. In one embodiment, $X_4$ can be N, and each of $X_1$, $X_2$, and $X_3$ can be CH.

In certain embodiments, J can be

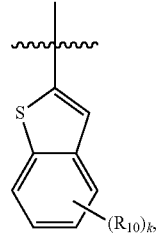

wherein each $R_{10}$ can be independently selected from the group consisting of F, Cl, —OH, methyl, methoxy, ethoxy, propoxy, isopropoxy, and —OCOCH$_3$; and k can be 0, 1, 2, or 3.

In certain embodiments, J is

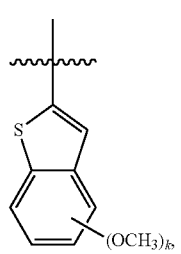

wherein k can be 0, 1, or 2.

In certain embodiments, J is

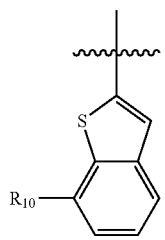

wherein $R_{10}$ can be selected from the group consisting of F, Cl, —OH, methyl, methoxy, ethoxy, propoxy, isopropoxy, and —OCOCH$_3$.

In certain embodiments, the disclosure provides compounds where Y can be —W—(CH$_2$)$_n$—R$_1$. In certain embodiments, Y can be R$_1$. In certain embodiments, R$_1$ can be —NR$_2$R$_3$.

In certain embodiments, R$_2$ can be H.

In certain embodiments, R$_3$ can be C$_2$-C$_{10}$ alkyl, aryl, and cycloalkyl, where any atom of R$_3$ can be optionally substituted with one or more R$_7$, where any atom of R$_3$ can be optionally substituted with one or more R$_7$. In certain embodiments, R$_3$ can be phenyl optionally substituted with one or more R$_7$, wherein each R$_7$ can be independently selected from the group consisting of hydroxyl, methoxy, —COOH, —O—(CH$_2$)$_m$—OH, cyclopropylmethoxy, cyclopentylmethoxy, and isopropyl. In certain embodiments, each R$_7$ can be independently selected from the group consisting of methoxy, —COOH, and —O—(CH$_2$)$_3$—OH.

In certain embodiments, R$_3$ can be C$_2$-C$_{10}$ alkyl or cycloalkyl, where any atom of R$_3$ can be optionally substituted with one or more R$_7$.

In certain embodiments, $R_3$ can be aryl. In further embodiments, $R_3$ can be phenyl. In certain embodiments, $R_3$ can be phenyl substituted with one or more $R_7$, where each $R_7$ can be independently selected from the group consisting of hydroxyl, methoxy, —COOH, —O—$(CH_2)_m$—OH, cyclopropylmethoxy, cyclopentylmethoxy, and isopropyl. In further embodiments, each $R_7$ can be independently selected from the group consisting of methoxy, —COOH, and —O—$(CH_2)_3$—OH. In certain embodiments, $R_3$ can be phenyl substituted with at least one $R_7$ and wherein the at least one $R_7$ can be methoxy. In certain embodiments, the at least one methoxy substituent can be substituted at the ortho position of the phenyl. In certain embodiments, the at least one methoxy substituent can be substituted at the meta position of the phenyl.

In certain embodiments, $R_3$ can be 3,4-dimethoxyphenyl. In certain embodiments, $R_3$ can be further substituted with —COOH or —O—$(CH_2)_m$—OH. In certain embodiments, $R_3$ can be further substituted with —O—$(CH_2)_3$—OH. In certain embodiments, $R_3$ can be phenyl substituted with at least one $R_7$. In certain of such embodiments, $R_7$ can be —COOH. In further of such embodiment, one of the at least one —COOH substituent of the phenyl can be at the meta position of the phenyl.

In certain embodiments, $R_3$ can be cycloalkyl. In certain of such embodiments, the cyclohexyl can be substituted with one or more $R_7$, where each $R_7$ can be independently selected from the group consisting of alkyl, —OH, hydroxyalkyl, and alkoxy. In certain embodiments, the one or more $R_7$ can be each independently selected from the group consisting of methyl, —OH, hydroxymethyl, and methoxy. In certain embodiments, the cyclohexyl can be substituted with one $R_7$ at the 3-position of the cyclohexyl. In certain embodiments, the cyclohexyl can be substituted with one $R_7$ at the 4-position of the cyclohexyl. In certain embodiments, the cyclohexyl can be disubstituted with two $R_7$ at the 4-position of the cyclohexyl.

In certain embodiments, the substituted cyclohexyl can be in the form of a pure diastereomer and/or enantiomer, as a racemate or as a non-equimolar or equimolar blend of the diastereomers and/or enantiomers.

In certain embodiments, $R_3$ can be heteroaryl.

In certain embodiments, $R_3$ can be pyridinyl. In certain of such embodiments, $R_3$ can be pyridinyl substituted with oxo or methoxy.

In certain embodiments, $R_2$ and $R_3$ taken together with the N atom to which they are attached form a 3- to 7-membered heterocyclic ring optionally substituted with $R_8$. In certain of such embodiments, the heterocyclic ring can be a 5- or 6-membered heterocyclic ring. In certain embodiments, $R_8$ is —$COOCH_3$, or hydroxymethyl.

In certain embodiments, W can be 1,3-phenylene or 1,4-phenylene. In certain of such embodiments, n can be 0 or 1. In certain embodiments, $R_1$ can be piperazinyl. In certain of such embodiments, the nitrogen atom of the piperazinyl can be substituted with methyl.

In certain embodiments, W can be —$NR_6$-phenylene. In certain of such embodiments, the phenylene group can be 1,3-phenylene or 1,4-phenylene. In certain of such embodiments, n can be 0 or 1. In certain embodiments, $R_1$ can be piperazinyl. In certain of such embodiments, the nitrogen atom of the piperazinyl can be substituted with methyl.

In certain embodiments, Y can be

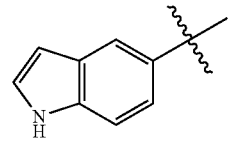

In certain embodiments, $R_4$ can be H. In other embodiments, $R_4$ can be alkyl, such as, lower alkyl including methyl, ethyl, n-propyl, i-propyl, n-butyl, i-butyl, t-butyl, etc.

In certain embodiments, $R_5$ can be H.

Certain embodiments of the present disclosure provides a compound having the structure of Formula II

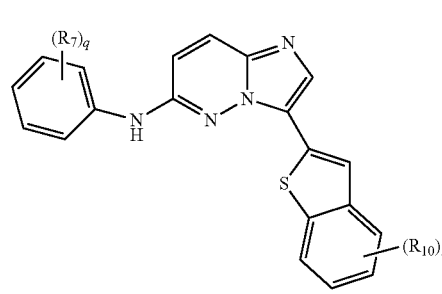

or a pharmaceutically acceptable isomer, isotope, enantiomer, salt, ester, prodrug, hydrate or solvate thereof, wherein
each $R_{10}$ can be independently selected from the group consisting of halo, alkyl, alkoxy, —OH, and —$OCOR_6$;
each $R_7$ can be independently alkyl, cycloalkyl, alkoxy, cycloalkoxy, cycloalkylalkoxy, perhaloalkoxy, halo, oxo, —OH, hydroxyalkyl, —$COOR_{11}$, or —O—$(CH_2)_m$—OH;
k can be 0, 1, 2, or 3; and
q can be 0, 1, 2, or 3.

In certain embodiments, each $R_7$ can be independently selected from the group consisting of methoxy, —COOH, and —O—$(CH_2)_3$—OH.

In certain embodiments, wherein q can be 1, 2, or 3 and at least one of $R_7$ can be methoxy.

Certain embodiments of the present disclosure provides a compound having the structure of Formula III

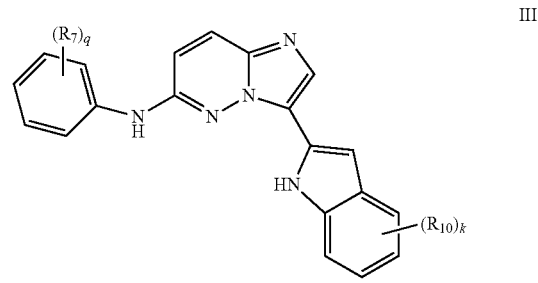

or a pharmaceutically acceptable isomer, isotope, enantiomer, salt, ester, prodrug, hydrate or solvate thereof, wherein
each $R_{10}$ can be independently selected from the group consisting of halo, alkyl, alkoxy, —OH, and —$OCOR_6$;
each $R_7$ can be independently alkyl, cycloalkyl, alkoxy, cycloalkoxy, cycloalkylalkoxy, perhaloalkoxy, halo, oxo, —OH, hydroxyalkyl, —$COOR_{11}$, or —O—$(CH_2)_m$—OH;
k can be 0, 1, 2, or 3; and
q can be 0, 1, 2, or 3.

In certain embodiments, each R$_7$ can be independently selected from the group consisting of methoxy, —COOH, and —O—(CH$_2$)$_3$—OH.

In certain embodiments, q can be 1, 2, or 3 and at least one of R$_7$ can be methoxy.

Certain embodiments of the present disclosure provides a compound having the structure of Formula IV

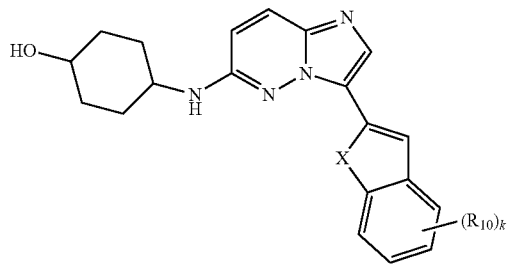

IV or a pharmaceutically acceptable isomer, isotope, enantiomer, salt, ester, prodrug, hydrate or solvate thereof, wherein
X can be NH or S;
each R$_{10}$ can be independently selected from the group consisting of halo, alkyl, alkoxy, —OH, and —OCOR$_6$; and
k can be 0, 1, 2, or 3.

In further embodiments, the present disclosure provides a compound having the structure of Formula IV-A

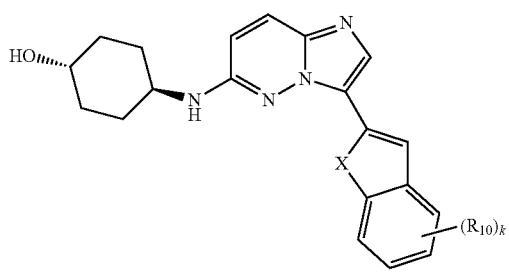

IV-A or a pharmaceutically acceptable isomer, isotope, enantiomer, salt, ester, prodrug, hydrate or solvate thereof.

In certain embodiments, X can be NH. In certain embodiments, X can be S. In certain embodiments, k can be 1. In certain embodiments, R$_{10}$ can be alkoxy. In further embodiments, R$_{10}$ can be methoxy.

Certain embodiments of the present disclosure provides a compound having the structure of Formula V

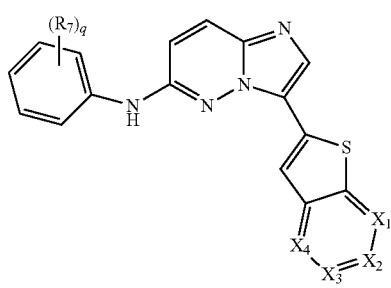

V or a pharmaceutically acceptable isomer, isotope, enantiomer, salt, ester, prodrug, hydrate or solvate thereof, wherein
each R$_7$ can be independently alkyl, cycloalkyl, alkoxy, cycloalkoxy, cycloalkylalkoxy, perhaloalkoxy, halo, oxo, —OH, hydroxyalkyl, —COOR$_{11}$, or —O—(CH$_2$)$_m$—OH;
q can be 1, 2, or 3; and
each X$_1$, X$_2$, X$_3$, and X$_4$ can be independently H or N and wherein no more than one of X$_1$, X$_2$, X$_3$, and X$_4$ is N.

Certain embodiments of the present disclosure provides a compound having the structure of Formula VI

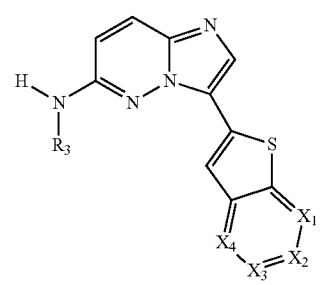

VI or a pharmaceutically acceptable isomer, isotope, enantiomer, salt, ester, prodrug, hydrate or solvate thereof, wherein
R$_3$ can be selected from the group consisting of C$_2$-C$_{10}$ alkyl, aryl, and cycloalkyl; and
each X$_1$, X$_2$, X$_3$, and X$_4$ can be independently H or N and wherein no more than one of X$_1$, X$_2$, X$_3$, and X$_4$ is N.

Certain embodiments of the present disclosure provides a compound having the structure of Formula VII

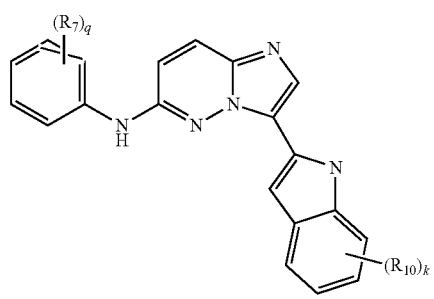

VII or a pharmaceutically acceptable isomer, isotope, enantiomer, salt, ester, prodrug, hydrate or solvate thereof, wherein
each R$_7$ can be independently alkyl, cycloalkyl, alkoxy, cycloalkoxy, cycloalkylalkoxy, perhaloalkoxy, halo, oxo, —OH, hydroxyalkyl, —COOR$_{11}$, or —O—(CH$_2$)$_m$—OH;
q can be 1, 2, or 3;
each R$_{10}$ can be independently selected from the group consisting of F, Cl, —OH, methoxy, ethoxy, propoxy, isopropoxy, and —OCOCH$_3$; and
k can be 0, 1, 2, or 3.

Certain embodiments of the present disclosure provides a compound having the structure of Formula VIII

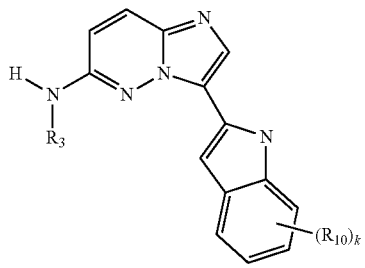

VIII or a pharmaceutically acceptable isomer, isotope, enantiomer, salt, ester, prodrug, hydrate or solvate thereof, wherein $R_3$ can be selected from the group consisting of $C_2$-$C_{10}$ alkyl, aryl, and cycloalkyl;

each $R_{10}$ can be independently selected from the group consisting of F, Cl, —OH, methoxy, ethoxy, propoxy, isopropoxy, and —OCOCH$_3$; and k can be 0, 1, 2, or 3.

Certain embodiments of the present invention provide pharmaceutical compositions including a compound of the invention, and a pharmaceutical carrier, excipient or diluent. In this aspect of the invention, the pharmaceutical composition can comprise one or more of the compounds described herein.

In certain embodiments, the disclosure provides one or more of the following compounds 3-9, 11-50, 52-102, 104, 107, 110-112, 114, 115, 118, 119-127, 129-132, 134-143, 148-150, 158-163, 166-221, or any pharmaceutically acceptable salt, ester, prodrug, homolog, tautomer, stereoisomer, isotope, hydrate, or solvate thereof. In certain of such embodiments, the disclosure provides a compound selected from compounds 3-5, 67, 68, 87, 169, 170, 175, 177, 206, 213, 215-216, and 218 or any pharmaceutically acceptable salt, ester, prodrug, homolog, tautomer, steroisomer, isotope, or hydrate, or solvate thereof.

In certain embodiments, a pharmaceutical composition comprising a compound having the structure of Formula I can be provided:

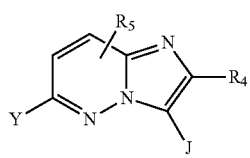

I or a pharmaceutically acceptable isomer, isotope, enantiomer, salt, ester, prodrug, hydrate or solvate thereof, wherein J has a structure of

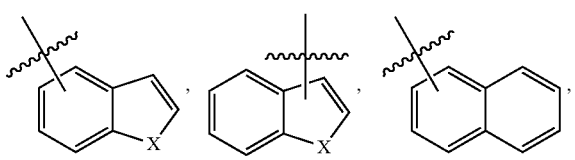

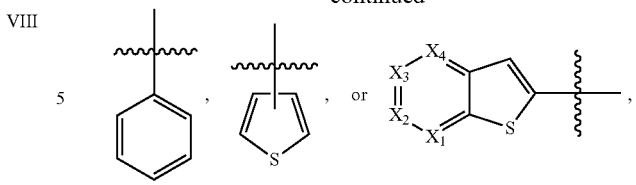

where J can be optionally substituted with up to four $R_{10}$, each $R_{10}$ can be independently selected from the group consisting of halo, alkyl, haloalkyl, alkoxy, haloalkoxy, —OH, and —OCOR$_6$;

X can be NR$_{12}$ or S;

each $X_1$, $X_2$, $X_3$, and $X_4$ can be independently CH or N and wherein no more than one of $X_1$, $X_2$, $X_3$, and $X_4$ is N;

Y can be —W—(CH$_2$)n-R$_1$,

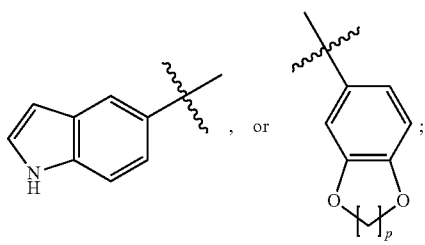

W can be null, phenylene, or —NR$_6$-phenylene, where the NR$_6$ is attached to the imidazopyridazine core structure of Formula I;

$R_1$ can be —NR$_2$R$_3$, or piperazinyl, where the nitrogen atom of the piperazinyl can be optionally substituted with alkyl or alkoxy;

$R_2$ can be H or alkyl; $R_3$ can be selected from the group consisting of $C_2$-$C_{10}$ alkyl, aryl, heteroaryl, cycloalkyl, and heterocycloalkyl, where any atom of $R_3$ can be optionally substituted with one or more $R_7$; or $R_2$ and $R_3$ taken together with the N atom to which they are attached form a 3- to 7-membered heterocyclic ring optionally substituted with $R_8$;

$R_4$ can be H or alkyl;

$R_5$ can be H, alkyl, or NHR$_9$;

$R_6$ can be H or alkyl;

each $R_7$ can be independently alkyl, cycloalkyl, alkoxy, cycloalkoxy, cycloalkylalkoxy, perhaloalkoxy, halo, oxo, —OH, hydroxyalkyl, —COOR$_{11}$, or —O—(CH$_2$)$_m$—OH;

$R_8$ can be alkoxy, hydroxyalkyl, or COOR$_{11}$;

$R_9$ can be H, alkyl, or cycloalkyl;

$R_{11}$ can be H, or alkyl;

$R_{12}$ can be H, or alkyl;

n can be 0 or 1;

m can be 1, 2, or 3;

p can be 1, 2, or 3; and together with at least one pharmaceutically acceptable carrier, diluent or excipient.

In certain embodiments, a pharmaceutical composition comprising a compound of Formula II, III, IV IV-A, V, VI, VII or VIII, or any pharmaceutically acceptable salt, ester, prodrug, homolog, tautomer, stereoisomer, isotope, or hydrate, or solvate thereof, together with at least one pharmaceutically acceptable carrier, diluent or excipient is provided.

In other embodiments, a pharmaceutical composition comprising a compound of Formula II, III, IV IV-A, V, VI, VII or VIII or any pharmaceutically acceptable salt, ester, prodrug, homolog, tautomer, stereoisomer, isotope, or hydrate, or solvate thereof, and a second medicament is provided.

In certain embodiments, a pharmaceutical composition comprising a compound of the invention disclosed herein, together with at least one pharmaceutically acceptable carrier, diluent or excipient is provided. The particular carrier employed in these pharmaceutical compositions may vary depending upon the type of administration desired (e.g., intravenous, oral, topical, suppository, or parenteral).

Suitable pharmaceutically-acceptable acid addition salts may be prepared from an inorganic acid or from an organic acid. EXAMPLEs of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. EXAMPLEs of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. EXAMPLEs of pharmaceutically unacceptable base addition salts include lithium salts and cyanate salts. Although pharmaceutically unacceptable salts are not generally useful as medicaments, such salts may be useful, for example, as intermediates in the synthesis of Formula I, II, III, IV IV-A, V, VI, VII or VIII compounds, for example in their purification by recrystallization. All of these salts may be prepared by conventional means from the corresponding compound according to Formula I, II, III, IV IV-A, V, VI, VII or VIII by reacting, for example, the appropriate acid or base with the compound according to Formula I, II, III, IV IV-A, V, VI, VII or VIII. The term "pharmaceutically acceptable salts" refers to nontoxic inorganic or organic acid and/or base addition salts, see, for example, Lit et al., Salt Selection for Basic Drugs (1986), *Int J. Pharm.*, 33, 201-217, incorporated by reference herein.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as utility in processes of synthesis, purification or formulation of compounds of the invention.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patients' body, such as enzymes, to the active pharmaceutical ingredient. EXAMPLEs of prodrugs include esters of carboxylic acid groups, which can be hydrolyzed by endogenous esterases as are found in the bloodstream of humans and other mammals.

In preparing the compositions in oral liquid dosage forms (e.g., suspensions, elixirs and solutions), typical pharmaceutical media, such as water, glycols, oils, alcohols, flavoring agents, preservatives, coloring agents and the like can be employed. Similarly, when preparing oral solid dosage forms (e.g., powders, tablets and capsules), carriers such as starches, sugars, diluents, granulating agents, lubricants, binders, disintegrating agents and the like can be employed.

As set forth herein, compounds of the invention include stereoisomers, tautomers, solvates, hydrates, isotopes, esters, salts including pharmaceutically acceptable salts, and mixtures thereof. Compositions containing a compound of the invention can be prepared by conventional techniques, e.g., as described in Remington: *The Science and Practice of Pharmacy*, 19th Ed., 1995, incorporated by reference herein. The compositions can appear in conventional forms, for example capsules, tablets, aerosols, solutions, suspensions or topical applications.

Typical compositions include a compound of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example, contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances, preserving agents, sweetening agents or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment.

For parenteral administration, the carrier will typically comprise sterile water, although other ingredients that aid solubility or serve as preservatives can also be included. Furthermore, injectable suspensions can also be prepared, in which case appropriate liquid carriers, suspending agents and the like can be employed.

If a solid carrier is used for oral administration, the preparation can be tabletted, placed in a hard gelatin capsule, in powder or pellet form or it can be in the form of a troche or lozenge, for example. If a liquid carrier is used, the preparation can be in the form of a syrup, emulsion, soft gelatin capsule or sterile injectable liquid such as an aqueous or non-aqueous liquid suspension or solution or the like.

Injectable dosage forms generally include aqueous suspensions or oil suspensions which can be prepared using a suitable dispersant or wetting agent and a suspending agent. Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di- or tri-glycerides.

For injection, the formulation can also be a powder suitable for reconstitution with an appropriate solution as described above. EXAMPLEs of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials, such as silicones and biodegradable polymers, e.g., polylactide-polyglycolide. EXAMPLEs of other biodegradable polymers include poly(orthoesters) and poly(anhydrides).

For nasal administration, the preparation can contain a compound of the invention in powder form or dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives, such as parabens.

For parenteral application, particularly suitable are injectable solutions or suspensions, preferably aqueous solutions with the active compound dissolved in polyhydroxylated castor oil.

Dosage forms can be administered daily, or more than once a day, such as twice or thrice daily. Alternatively dosage forms can be administered less frequently than daily, such as every other day, or weekly, if found to be advisable by a prescribing physician.

An embodiment of the invention also encompasses prodrugs of a compound of the invention which on administration undergo chemical conversion by metabolic or other physiological processes before becoming active pharmacological substances. Conversion by metabolic or other physiological processes includes without limitation enzymatic (e.g, specific enzymatically catalyzed) and non-enzymatic (e.g., general or specific acid or base induced) chemical transformation of the prodrug into the active pharmacological substance. In general, such prodrugs will be functional derivatives of a compound of the invention which are readily convertible in vivo into a compound of the invention. Conventional procedures for the selection and preparation of suitable prodrug derivatives are described, for example, in Design of Prodrugs, Bundgaard, H., Ed., Elsevier, 1985.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In certain embodiments, the methods further include the step of lyophilizing the composition to form a lyophilized preparation.

The expression "effective amount," when used to describe use of a compound of the invention in providing therapy to a patient suffering from a disorder or malcondition mediated by MLK (including MLK-1, MLK-2, and MLK-3), refers to the amount of a compound of the invention that is effective to inhibit the activity of MLK. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result by acting as an inhibitor of MLK activity. A therapeutically effective amount is also one in which any toxic or detrimental effects of compounds of the invention are outweighed by the therapeutically beneficial effects. For example, in the context of treating a malcondition mediated by MLK, a therapeutically effective amount of an MLK inhibitor of the invention is an amount sufficient to control the malcondition, to mitigate the progress of the malcondition, or to relieve the symptoms of the malcondition. EXAMPLEs of malconditions that can be so treated include, but are not limited to, diabetes mellitus, hyperglycemia, retinopathy, nephropathy, neuropathy, ulcers, micro- and macroangiopathies, gout and diabetic foot disease, insulin resistance, metabolic syndrome, hyperinsulinemia, hypertension, hyperuricemia, obesity, edema, dyslipidemia, chronic heart failure, atherosclerosis, peripheral inflammation, cancer, hepatitis, HIV associated neurocognitive disorders, HIV associated neuropathy, Alzheimer disease, Parkinson's disease, Multiple Sclerosis, and other neurodegenerative diseases, cirrhotic diseases in liver or pancreas, and the like.

As used herein, the term "medicament" refers to any substance or combination of substances that has a beneficial and/or therapeutic effect.

As used herein, the term "subject" (as in the subject of the treatment) means both mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. EXAMPLEs of non-mammals include, but are not limited to, birds, and the like. The term "subject" does not denote a particular age or sex.

"Treating" or "treatment" refers to an alleviation of symptoms associated with a disorder or disease, or inhibition of further progression or worsening of those symptoms, or prevention or prophylaxis of the disease or disorder.

A "MLK-mediated disease" refers to a disease state which may be relieved by inhibiting MLK activity, where MLK signaling is involved in disease pathology. EXAMPLEs of MLK-mediated disorders include, stroke, diabetes mellitus, hyperglycemia, retinopathy, nephropathy, neuropathy, ulcers, micro- and macroangiopathies, gout and diabetic foot disease, insulin resistance, metabolic syndrome, hyperinsulinemia, hypertension, hyperuricemia, obesity, edema, dyslipidemia, chronic heart failure, atherosclerosis, peripheral inflammation, cancer, hepatitis, HIV associated neurocognitive disorders, HIV associated neuropathy, Alzheimer disease, Parkinson's disease, Multiple Sclerosis, and other neurodegenerative diseases, cirrhotic diseases in liver or pancreas, and the like.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. EXAMPLEs of such groups include methylcarbonyl and ethylcarbonyl. EXAMPLEs of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [R—CH=CH—), (—C::C—)]. EXAMPLEs of suitable alkenyl radicals include ethenyl, propenyl, 2-propenyl, 2-methylpropenyl, butenyl, isobutenyl, 1,4-butadienyl, isoprenyl, vinyl, and the like. Unless otherwise specified, the term "alkenyl" may include "alkenylene" groups.

The term "alkoxy," as used herein, alone or in combination, refers to an alkyl ether radical, wherein the term alkyl is as defined below. EXAMPLEs of suitable alkyl ether radicals include methoxy, ethoxy, n-propoxy, isopropoxy, n-butoxy, iso-butoxy, sec-butoxy, tert-butoxy, and the like.

Cycloalkoxy groups are alkoxy groups forming a ring structure, which can be substituted or unsubstituted, wherein the ring is either completely saturated, partially unsaturated, or fully unsaturated, wherein if there is unsaturation, the conjugation of the pi-electrons in the ring do not give rise to aromaticity. The term "cycloalkoxy" embraces saturated oxy-containing carbocyclic radicals and, unless otherwise specified, a cycloalkoxy radical typically has from 3 to 8 carbon atoms. When a cycloalkoxy radical carries two or more substituents, the substituents may be the same or different. EXAMPLEs of such cycloalkyoxy groups include cyclopropoxy, cyclobutoxy, cyclopentoxy, cyclohexoxy, cycloheptoxy, and the like.

The term "alkyl," as used herein, alone or in combination, refers to a straight-chain or branched-chain alkyl radical containing from 1 to 20 carbon atoms, and typically from 1 to 12 carbons ($C_1$-$C_{12}$ alkyl), or, in some embodiments, from 1 to 8 carbon atoms ($C_1$-$C_8$ alkyl), or, in some embodiments, from 1 to 4 carbon atoms ($C_1$-$C_4$ alkyl). Alkyl groups may be optionally substituted as defined herein. EXAMPLEs of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

Cycloalkyl groups are alkyl groups forming a ring structure, which can be substituted or unsubstituted, wherein the ring is either completely saturated, partially unsaturated, or fully unsaturated, wherein if there is unsaturation, the conjugation of the pi-electrons in the ring do not give rise to aromaticity. EXAMPLEs of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted one or more times with any of the groups listed above, for example, but not limited to, amino, hydroxy, cyano, carboxy, nitro, thio, alkoxy, and halogen groups.

Cycloalkylalkyloxy groups refer to alkyloxy groups as defined above in which a hydrogen or carbon bond of the alkyloxy group is replaced with a bond to a cycloalkyl group as defined above. EXAMPLEs of such cycloalkylalkyloxy groups include, but are not limited to, cyclopropylmethoxy, cyclopropylethoxy, cyclopropylpropoxy, cyclopropylbutoxy, cyclobutylmethoxy, cyclobutylethoxy, cyclobutylpropoxy, cyclobutylbutoxy, cyclopentylmethoxy, cyclopentylethoxy, cyclopentylpropoxy, cyclopentylbutoxy, cyclohexylmethoxy, cyclohexylethoxy, cyclohexylpropoxy, cyclohexylbutoxy, and the like.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylthio," as used herein, alone or in combination, refers to an alkyl thioether (R—S—) radical wherein the term alkyl is as defined above and wherein the sulfur may be singly or doubly oxidized. EXAMPLEs of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —CC—). EXAMPLEs of alkynyl radicals include ethynyl, propynyl, hydroxypropynyl, butyn-1-yl, Butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')—group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, refers to a cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The phrase "aryl groups" includes groups containing fused rings, such as fused aromatic-aliphatic ring systems (e.g., indanyl, tetrahydronaphthyl, and the like), and also includes substituted aryl groups that have other groups, including but not limited to alkyl, halo, amino, hydroxy, cyano, carboxy, nitro, thio, or alkoxy groups, bonded to one of the ring atoms. Representative substituted aryl groups can be mono-substituted or substituted more than once, such as, but not limited to, 2-, 3-, 4-, 5-, or 6-substituted phenyl or naphthyl groups, which can be substituted with groups including but not limited to those listed above.

The compounds of the present invention may have a particular spatial arrangement of substituents on the aromatic rings, which is related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

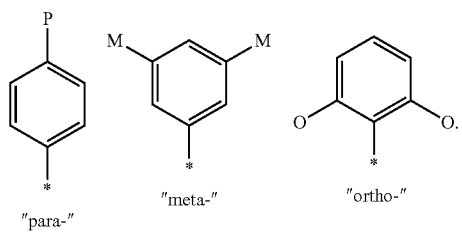

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, naphthoyl, phenylacetyl, 3-phenylpropionyl(hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical C$_6$H$_4$=derived from benzene. EXAMPLEs include benzothiophene and benzimidazole.

The term "carbamate," as used herein, alone or in combination, refers to an ester of carbamic acid (—NRC(O)O—) which may be attached to the parent molecular moiety from either the nitrogen or acid end, and which may be optionally substituted as defined herein. The term "O-carbamyl" as used herein, alone or in combination, refers to a —OC(O)NRR' group; and the term "N-carbamyl" as used herein, alone or in combination, refers to a ROC(O)NR'— group. R and R' are as defined herein, or as defined by the specifically enumerated "R" groups designated.

The term "carbonyl," as used herein, when alone includes formyl[—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom. Haloalkoxy includes perhaloalkoxy. The term "perhaloalkoxy" refers to an alkoxy group where all of the hydrogen atoms are replaced by halogen atoms. An example of perhaloalkoxy is perfluoromethoxy.

The term "haloalkyl," as used herein, alone or in combination, refers to an alkyl radical having the meaning as defined above wherein one or more hydrogens are replaced with a halogen. Specifically embraced are monohaloalkyl, dihaloalkyl, polyhaloalkyl, and perhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. EXAMPLEs of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. EXAMPLEs of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. EXAMPLEs include fluoromethylene (—CFH—), difluoromethylene (—CF$_2$—), chloromethylene (—CHCl—) and the like. The term "perhaloalkyl" as used herein, alone or in combination, refers to an alkyl group where all of the hydrogen atoms are replaced by halogen atoms. EXAMPLEs include perfluoromethyl.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms chosen from O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from O, S, and N. Additionally, a heteroaryl may contain one or two C(O), S(O), or S(O)2 groups as ring members. In certain embodiments, said heteroaryl will comprise from 5 to 10 atoms. In certain embodiments, said heteroaryl will comprise from 5 to 7 atoms. In certain embodiments, said heteroaryl will comprise from 1 to 4 heteroatoms as ring members. In further embodiments, said heteroaryl will comprise from 1 to 2 heteroatoms as ring members. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. EXAMPLEs of heteroaryl groups include pyrrolyl, pyrrolinyl, imidazolyl, pyrazolyl, pyridyl, pyrimidinyl, pyrazinyl, pyridazinyl, imidazolyl, triazinyl, triazolyl, tetrazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently chosen from N, O, and S. Additionally, a heterocycloalkyl may contain one or two C(O), S(O), or S(O)2 groups as ring members. In certain embodiments, said heterocycloalkyl will comprise from 1 to 4 heteroatoms as ring members. In further embodiments, said heterocycloalkyl will comprise from 1 to 2 heteroatoms as ring members. In certain embodiments, said heterocycloalkyl will comprise from 3 to 8 ring members in each ring. In further embodiments, said heterocycloalkyl will comprise from 3 to 7 ring members in each ring. In yet further embodiments, said heterocycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. EXAMPLEs of heterocycloalkyls include furan-2-yl, furan-3-yl, pyrrolidinyl, imidazolidinyl, pyrazolidinyl, piperidinyl, piperazinyl, and morpholinyl. The heterocycle groups may be optionally substituted unless specifically prohibited.

The term "hydroxy," as used herein, alone or in combination, refers to —OH.

The term "lower," as used herein, alone or in a combination, where not otherwise specifically defined, means containing from 1 to and including 6 carbon atoms.

The term "lower alkyl," as used herein, alone or in a combination, means $C_1$-$C_6$ straight or branched chain alkyl. The term "lower alkenyl" means $C_2$-$C_6$ straight or branched chain alkenyl. The term "lower alkynyl" means $C_2$-$C_6$ straight or branched chain alkynyl.

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms chosen from O, S, and N, or 2) bicyclic heteroaryl, wherein each of the fused rings comprises five or six ring members, comprising between them one to four heteroatoms chosen from O, S, and N.

The term "lower cycloalkyl," as used herein, alone or in combination, means a monocyclic cycloalkyl having between three and six ring members. Lower cycloalkyls may be unsaturated. EXAMPLEs of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from O, S, and N. Lower heterocycloalkyls may be unsaturated.

The term "lower amino," as used herein, alone or in combination, refers to —NRR', wherein R and R' are independently chosen from hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "nitro," as used herein, alone or in combination, refers to —NO$_2$.

The term "oxy," as used herein, alone or in combination, refer to —O—.

The term "oxo," as used herein, alone or in combination, refers to =O.

The term "perhaloalkyl" as used herein, alone or in combination, refers to an alkyl group where all of the hydrogen atoms are replaced by halogen atoms. Perhaloalkyl groups include, but are not limited to, —CF$_3$.

The term "perhaloalkoxy" refers to an alkoxy group where all of the hydrogen atoms are replaced by halogen atoms. Perhaloalkoxy groups include, but are not limited to, —OCF$_3$.

The term "haloalkyl" as used herein, alone or in combination, refers to an alkyl group where at least one of the hydrogen atoms are replaced by halogen atoms. Haloalkyl groups include, but are not limited to, fluoromethyl, difluoromethyl, trifluoromethyl, trifluoroethyl, trifluoromethylethyl, and the like.

The term "haloalkoxy" refers to an alkoxy group where at least one of the hydrogen atoms are replaced by halogen atoms. Haloalkoxy groups include, but are not limited to, fluoromethoxy, difluoromethoxy, trifluoromethoxy, trifluoroethoxy, trifluoromethylethoxy, and the like.

The term "arylene" refers to a divalent radical formed by the removal of two hydrogen atoms from one or more rings of an aryl group. One specific example, the term "phenylene" refers to a divalent radical formed by the removal of two hydrogen atoms from one or more rings of a phenyl group. EXAMPLE of phenylene groups include

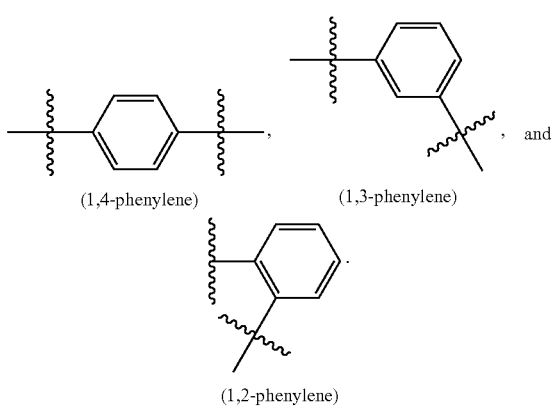

(1,4-phenylene)    (1,3-phenylene)    and (1,2-phenylene)

The terms "sulfonate," "sulfonic acid," and "sulfonic," as used herein, alone or in combination, refer the —SO$_3$H group and its anion as the sulfonic acid is used in salt formation.

The term "thio," as used herein, alone or in combination, refer to a —S— group or an ether wherein the oxygen is replaced with sulfur. The oxidized derivatives of the thio group, namely sulfinyl and sulfonyl, are included in the definition of thia and thio. The term "sulfanyl," as used herein, alone or in combination, refers to —S—. The term "sulfinyl," as used herein, alone or in combination, refers to —S(O)—. The term "sulfonyl," as used herein, alone or in combination, refers to —S(O)2-.

The term "thiol," as used herein, alone or in combination, refers to an —SH group.

The term "thiocarbonyl," as used herein, when alone includes thioformyl —C(S)H and in combination is a —C(S)— group.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and Rn where n=(1, 2, 3, . . . n), every substituent, and every term should be understood to be independent of every other in terms of selection from a group. Should any variable, substituent, or term (e.g., aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N (R)—may be attached to the parent moiety at either the carbon or the nitrogen.

When two "R" groups are said to be joined together or taken together to form a ring, it means that together with the carbon atom or a non-carbon atom (e.g., nitrogen atom), to which they are bonded, they may form a ring system. In general, they are bonded to one another to form a 3- to 7-membered ring, or a 5- to 7-membered ring. Non-limiting specific examples are the cyclopentyl, cyclohexyl, cycloheptyl, piperidinyl, piperazinyl, pyrrolidinyl, pyrrolyl, pyridinyl.

Certain compounds disclosed herein contain one or more asymmetric centers. For compounds having asymmetric centers, it should be understood that all of the optical isomers and mixtures thereof are encompassed. Where a compound exists in various tautomeric forms, the invention is not limited to any one of the specific tautomers, but rather includes all tautomeric forms. Certain compounds are described herein using a general formula that includes variables. Unless otherwise specified, each variable within such a formula is defined independently of other variables.

Compositions and Combination Treatments

Another embodiment of the invention provides compositions of the compounds of the disclosure, alone or in combination with another MLK inhibitor or another type of therapeutic agent, or both.

In certain embodiments, the disclosure provides a pharmaceutical combination comprising a compound of the disclosure and a second medicament. In various embodiments, the second medicament (or second therapeutic agent) is medically indicated for the treatment of diseases and conditions which can be affected by SGLT inhibition, such as antidiabetic agents, lipid-lowering/lipid-modulating agents, agents for treating diabetic complications, anti-obesity agents, antihypertensive agents, antihyperuricemic agents, and agents for treating chronic heart failure, atherosclerosis or related disorders. EXAMPLEs of second medicaments which can be used in combination with compounds disclosed herein include lithium, valproate and other agents used in neuroprotection, PAF receptor antagonists, antioxidants including mitochondrially-targeted antioxidants, activators of $SIRT_1$ and other sirtuins, inhibitors of indoleamine 2,3 dehydrogenase (IDO), agents which enhance trans-blood brain bather (BBB) uptake of drugs, including compounds that inhibit drug pumps at the BBB, such as ritonavir; HAART drugs and other agents for use in HIV treatment; agents for the treatment of cardiovascular, heart, and metabolic disorders, such as HMG-CoA reductase inhibitors including statins, insulin and insulin mimetics, and glycogen synthase kinase-3 beta (GSK3β) inhibitors; agents which "normalize" mitochondrial function; antiinflammatory agents including PAF receptor antagonists or PAF acetylhydrolase, cyclooxygenase inhibitors (including COX-2 selective and nonselective) such as aspirin, ibuprofen, naproxen, and celecoxib; and agents for blocking liver cell proliferation, such as JNK inhibitors.

In certain embodiments, the second medicament is used for the treatment of HIV infection or AIDS. In certain of such embodiments, the second medicament comprises atazanavir, ritonavir, zidovudine, lamivudine, or efavirenz.

In certain embodiments, MLK-3 antagonists may have a synergistic effect on HIV treatment.

In certain embodiments, the methods of treatment disclosed herein additionally comprise the administration of a second therapeutic agent, as part of a therapeutic regimen. The pharmaceutical combination (i.e., the compounds of the present disclosure and a second medicament) can be administered orally in the same dosage form, in a separate oral dosage form (e.g., sequentially or non-sequentially) or by injection together or separately (e.g., sequentially or non-sequentially).

The specific amount of the second therapeutic agent will depend on the specific agent used, and the severity and stage of diseases, and the amount(s) of a MLK inhibitor and any optional additional active agents concurrently administered to the patient.

Method of Treatments

The disclosure is based, in part, on the belief that a MLK inhibitor can work alone or in combination with another active agent to effectively treat a MLK-mediated disease.

In certain embodiments, a method is provided for treatment of a MLK-mediated disease where such method comprises administering an effective amount to a subject a compound, pharmaceutical composition or pharmaceutical combination of the disclosure. In certain embodiments, such mammal is a human.

In certain embodiments, a method is provided for inhibiting the activity, expression, or function of MLKs. In certain embodiments, the present disclosure provides selective inhibition. In certain embodiments, the disclosure provides a selective inhibitor provides selective inhibition of MLKs, especially MLK-3, over one or more other kinases.

In certain embodiments, compounds according to the disclosure exhibit a surprising and unexpected selectivity in inhibiting a MLKs. In a specific embodiment, compounds according to the disclosure exhibit a surprising and unexpected selectivity in inhibiting a MLK-3. For examples, when compared to the compounds described in Table 51, the compounds according to the invention are surprisingly more selective for a MLK-3 over other kinases.

In certain embodiments, the present disclosure also provides a method for treatment of a MLK-mediated disease comprising administering to a subject a therapeutically effective amount of a pharmaceutical composition comprising a compound having the structure of Formula I

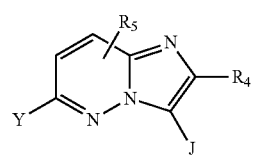

I or a pharmaceutically acceptable isomer, isotope, enantiomer, salt, ester, prodrug, hydrate or solvate thereof, wherein J has a structure of

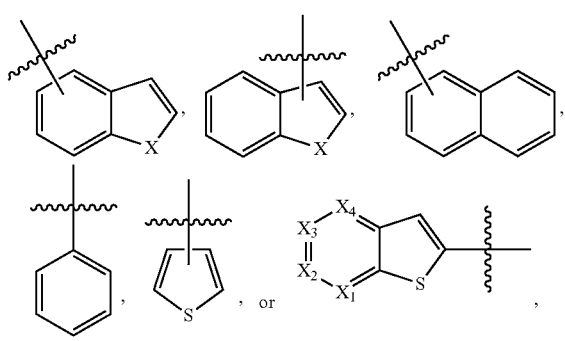

where J can be optionally substituted with up to four $R_{10}$, each $R_{10}$ can be independently selected from the group consisting of halo, alkyl, haloalkyl, alkoxy, haloalkoxy, —OH, and —OCOR$_6$; X can be N R$_{12}$ or S; each $X_1$, $X_2$, $X_3$, and $X_4$ can be independently CH or N and wherein no more than one of $X_1$, $X_2$, $X_3$, and $X_4$ can be N; Y can be —W—(CH$_2$)$_n$—R$_1$,

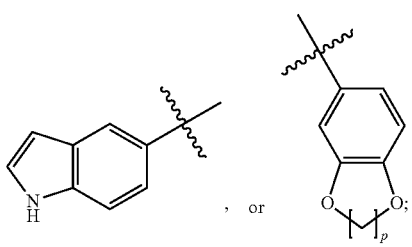

W can be null, phenylene, or —NR$_6$-phenylene, where the NR$_6$ can be attached to the imidazopyridazine core structure of Formula I; R$_1$ can be —NR$_2$R$_3$, or piperazinyl, where the nitrogen atom of the piperazinyl is optionally substituted with alkyl or alkoxy; R$_2$ can be H or alkyl; R$_3$ can be selected from the group consisting of C$_2$-C$_{10}$ alkyl, aryl, heteroaryl, cycloalkyl, and heterocycloalkyl, where any atom of R$_3$ can be optionally substituted with one or more R$_7$; or R$_2$ and R$_3$ taken together with the N atom to which they are attached form a 3- to 7-membered heterocyclic ring optionally substituted with R$_8$; R$_4$ can be H or alkyl; R$_5$ can be H, alkyl, or NHR$_9$; R$_6$ can be H or alkyl; each R$_7$ can be independently alkyl, cycloalkyl, alkoxy, cycloalkoxy, cycloalkylalkoxy, perhaloalkoxy, halo, oxo, —OH, hydroxyalkyl, —COOR$_{11}$, or —O—(CH$_2$)$_m$—OH; R$_8$ can be alkoxy, hydroxyalkyl, or COOR$_{11}$; R$_9$ can be H, alkyl, or cycloalkyl; R$_{11}$ can be H, or alkyl; R$_{12}$ can be H, or alkyl; n can be 0 or 1; m can be 1, 2, or 3; and p can be 1, 2, or 3.

In certain embodiments, a method is provided for the preparation of a medicament useful for treating a MLK-mediated disease, where the medicament comprising a pharmaceutical composition disclosed herein.

Method of Making

Another embodiment of the invention provides methods for synthesis of certain compounds including compounds of the invention. In certain other embodiments, the invention provides certain intermediate compounds associated with such methods of synthesis.

A number of embodiments of the invention have been described. Nevertheless, it will be understood that various modifications may be made without departing from the spirit and scope of the invention. Accordingly, the following examples are intended to illustrate but not limit the scope of invention described in the claims.

General Synthetic Methods for Preparing Compounds

Molecular embodiments of the present invention can be synthesized using standard synthetic techniques known to those of skill in the art. Compounds of the present invention can be synthesized using the general synthetic procedures set forth in Schemes 1-64.

EXAMPLE 1

Synthesis of Compounds 3-5, 195

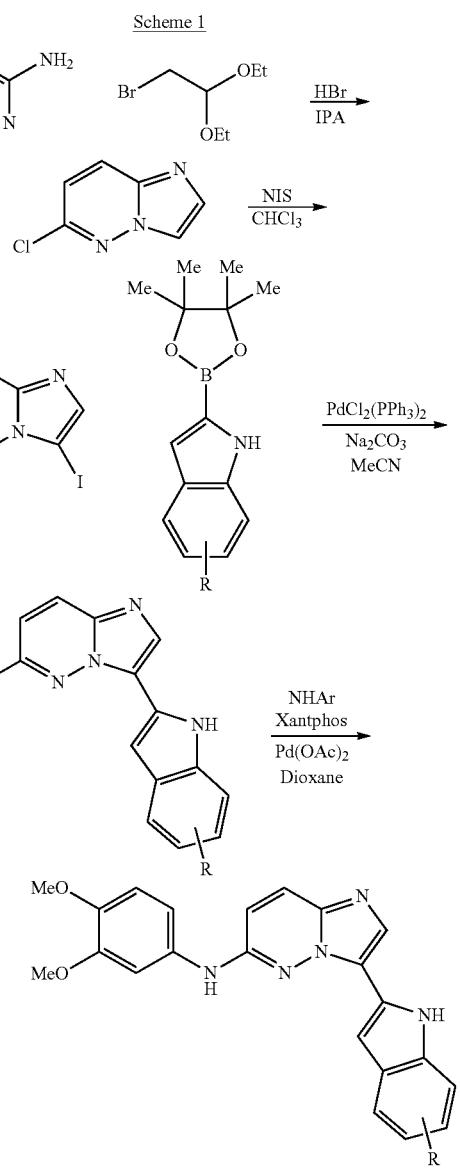

Preparation of 6-chloroimidazo[1,2-b]pyridazine

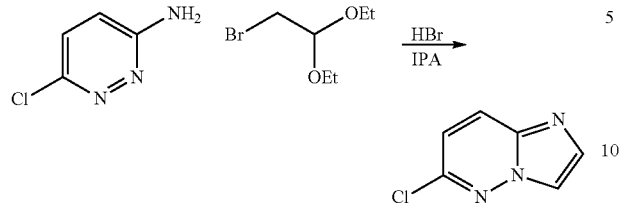

Bromoacetaldehyde diethylacetal (13.7 g, 69.5 mmol, 1.8 equiv) was added to hydrobromic acid (4.0 mL) and heated to reflux for 1.5 h. The reaction mixture was cooled to rt then poured into a reaction flask containing excess sodium bicarbonate in isopropanol. The solution was stirred for 3 min and then filtered. To the mother liquor was added 3-amino-6-chloropyridazine (5.0 g, 38.6 mmol, 1.0 equiv) and heated to reflux for 2 h. The reaction mixture was quenched with water and extracted with ethyl acetate. Purification using column chromatography gave 5.1 g of the brown solid, 86%: $^1$H NMR (400 MHz, CDCl$_3$) δ 7.89 (s, 1H), 7.88 (d, J=9.3 Hz, 1H), 7.74 (s, 1H), 7.01 (d, J=9.3 Hz, 1H).

Preparation of 6-chloro-3-iodoimidazo[1,2-b]pyridazine

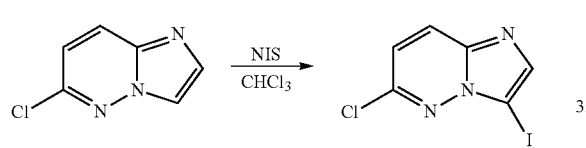

6-chloroimidazo[1,2-b]pyridazine (2.0 g, 13.0 mmol, 1.0 equiv) in chloroform (20 mL) at room temperature was added N-iodosuccinimide (2.9 g, 13.0 mmol, 1.0 equiv) then stirred vigorously overnight. The reaction mixture was diluted in water and extracted with ethyl acetate. Purification using column chromatography gave 3.3 g of the yellow solid, 90%: 1H NMR δ 8.21 (d, J=7.6 Hz, 1H), 7.96 (s, 1H), 7.41 (d, J=7.6 Hz, 1H).

Preparation of 6-chloro-3-(alkyl-1H-indol-2-yl)imidazo[1,2-b]pyridazine

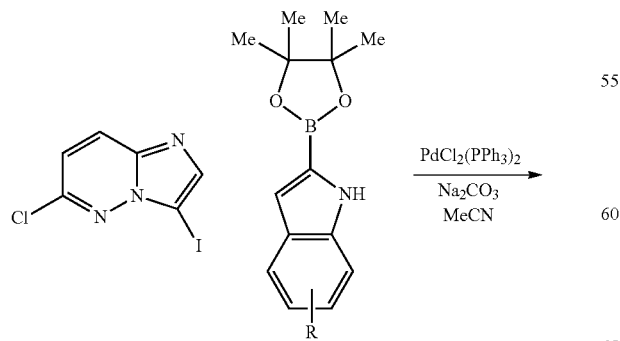

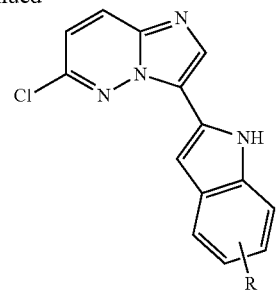

6-chloro-3-iodoimidazo[1,2-b]pyridazine (324 mg, 1.159 mmol, 1.0 equiv), in acetonitrile (10 mL), was added methoxy-2-(4,4,5,5-tetramethyl-1,3,2-dioxaborolan-2-yl)-1H-indole (1.51 mmol, 1.3 equiv), bis(triphenylphosphine)palladium(II) chloride (42 mg, 0.0579 mmol, 0.05 equiv), then sodium carbonate (11.6 mL, 1.0 M aqueous solution, 10 equiv). The reaction mixture was stirred overnight at room temperature. Purification by column chromatography gave of the product.

Preparation of 3-(alkyl-1H-indol-2-yl)-N-(3,4-dimethoxyphenyl)imidazo[1,2-b]pyridazin-6-amine

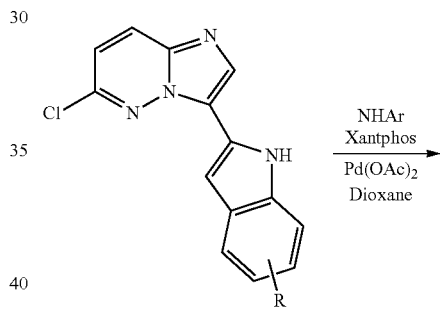

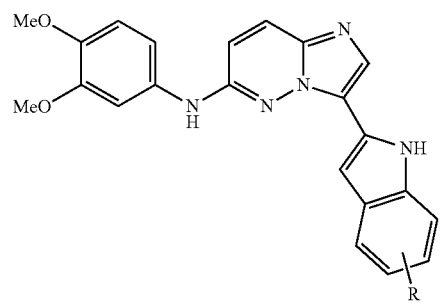

To a solution of 6-chloro-3-(7-methoxy-1H-indol-2-yl)imidazo[1,2-b]pyridazine (59 mg, 0.198 mmol, 1.0 equiv), xantphos (23 mg, 0.0395 mmol, 0.2 equiv), palladium acetate (4 mg, 0.0198 mmol, 0.1 equiv), and potassium carbonate (546 mg, 3.95 mmol, 20 equiv) in dioxane (5.0 mL) was added amine (0.395 mmol, 2.0 equiv) and heated to 100° C. for 2 h. Purification by column chromatography using 2% methanol in dichloromethane elution gave the product.

TABLE 1-a

| Cd. | Boronic Acid | Amine | Purified Compound Isolated |
|---|---|---|---|
| 3 | 5-methoxy-2-(4,4,5,5-tetramethyl-1,3,2-dioxaborolan-2-yl)-1H-indole | 3,4-dimethoxyaniline | 3-(5-methoxy-1H-indol-2-yl)-N-(3,4-dimethoxyphenyl)imidazo[1,2-b]pyridazin-6-amine |
| 4 | 6-methoxy-2-(4,4,5,5-tetramethyl-1,3,2-dioxaborolan-2-yl)-1H-indole | 3,4-dimethoxyaniline | 3-(6-methoxy-1H-indol-2-yl)-N-(3,4-dimethoxyphenyl)imidazo[1,2-b]pyridazin-6-amine |
| 5 | 7-methoxy-2-(4,4,5,5-tetramethyl-1,3,2-dioxaborolan-2-yl)-1H-indole | 3,4-dimethoxyaniline | 3-(7-methoxy-1H-indol-2-yl)-N-(3,4-dimethoxyphenyl)imidazo[1,2-b]pyridazin-6-amine |
| 195 | 7-methyl-1H-indol-2-yl-2-boronic acid | 3,4-dimethoxyaniline | N-(3,4-dimethoxyphenyl)-3-(7-methyl-1H-indol-2-yl)imidazo[1,2-b]pyridazin-6-amine |

Compounds 3-5, 195 were physically characterized by electrospray ionization mass spectrometry. Structures and molecular masses are given below in Table 1-b.

TABLE 1-b

| Cd. | Structure | IUPAC Name | [M + H]⁺ |
|---|---|---|---|
| 3 | (structure) | 3-(5-methoxy-1H-indol-2-yl)-N-(3,4-dimethoxyphenyl)imidazo[1,2-b]pyridazin-6-amine | 416.2 |
| 4 | (structure) | 3-(6-methoxy-1H-indol-2-yl)-N-(3,4-dimethoxyphenyl)imidazo[1,2-b]pyridazin-6-amine | 416.0 |
| 5 | (structure) | 3-(7-methoxy-1H-indol-2-yl)-N-(3,4-dimethoxyphenyl)imidazo[1,2-b]pyridazin-6-amine | 416.0 |

TABLE 1-b-continued

| Cd. | Structure | IUPAC Name | [M + H]+ |
|---|---|---|---|
| 195 | 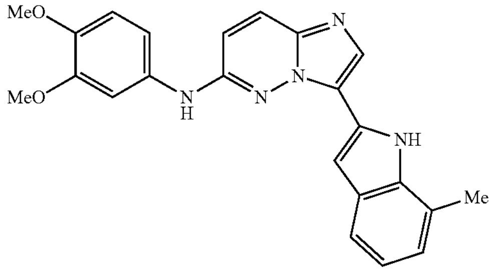 [SMILES: COc1ccc(Nc2ccc3ncc(-c4cc5cccc(C)c5[nH]4)n3n2)cc1OC] | N-(3,4-dimethoxyphenyl)-3-(7-methyl-1H-indol-2-yl)imidazo[1,2-b]pyridazin-6-amine | 400.2 |

EXAMPLE 2

Synthesis of Compounds 85-88, 159, 196

Preparation of 3-(alkyl-1H-indol-2-yl)-N-alkylimidazo[1,2-b]pyridazin-6-amine

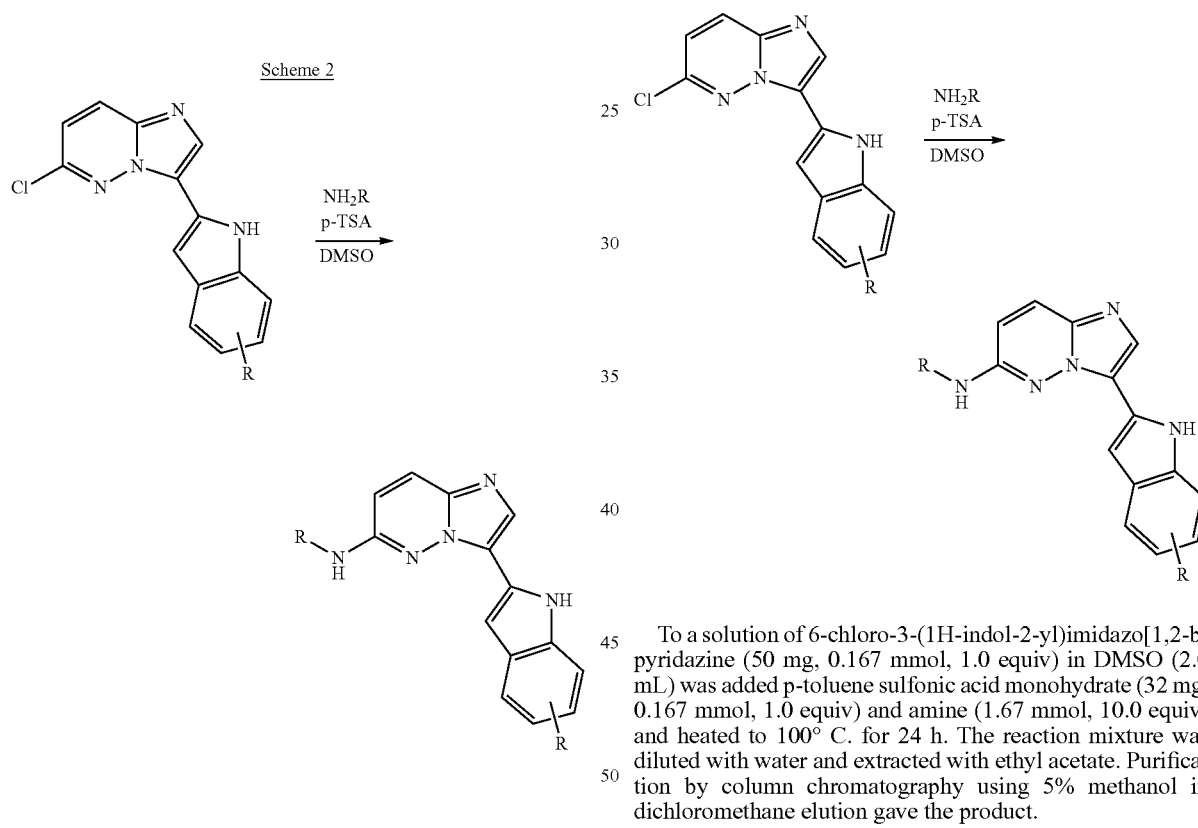

To a solution of 6-chloro-3-(1H-indol-2-yl)imidazo[1,2-b]pyridazine (50 mg, 0.167 mmol, 1.0 equiv) in DMSO (2.0 mL) was added p-toluene sulfonic acid monohydrate (32 mg, 0.167 mmol, 1.0 equiv) and amine (1.67 mmol, 10.0 equiv) and heated to 100° C. for 24 h. The reaction mixture was diluted with water and extracted with ethyl acetate. Purification by column chromatography using 5% methanol in dichloromethane elution gave the product.

TABLE 2-a

| Cd. | Boronic ester | Amine | Pure Isolated Compound |
|---|---|---|---|
| 85 | 5-methoxy-2-(4,4,5,5-tetramethyl-1,3,2-dioxaborolan-2-yl)-1H-indole | trans-4-aminocyclohexanol | trans-4-(3-(5-methoxy-1H-indol-2-yl)imidazo[1,2-b]pyridazin-6-ylamino)cyclohexanol |
| 86 | 6-methoxy-2-(4,4,5,5-tetramethyl-1,3,2-dioxaborolan-2-yl)-1H-indole | trans-4-aminocyclohexanol | trans-4-(3-(6-methoxy-1H-indol-2-yl)imidazo[1,2-b]pyridazin-6-ylamino)cyclohexanol |

TABLE 2-a-continued

| Cd. | Boronic ester | Amine | Pure Isolated Compound |
|---|---|---|---|
| 87 | 7-methoxy-2-(4,4,5,5-tetramethyl-1,3,2-dioxaborolan-2-yl)-1H-indole | trans-4-aminocyclohexanol | trans-4-(3-(7-methoxy-1H-indol-2-yl)imidazo[1,2-b]pyridazin-6-ylamino)cyclohexanol |
| 88 | 1H-indol-2-yl-2-boronic acid | trans-4-aminocyclohexanol | trans-4-(3-(1H-indol-2-yl)imidazo[1,2-b]pyridazin-6-ylamino)cyclohexanol |
| 159 | 1H-indol-2-yl-2-boronic acid | 1-propylamine | 3-(1H-indol-2-yl)-N-propylimidazo[1,2-b]pyridazin-6-amine |
| 196 | 7-methyl-1H-indol-2-yl-2-boronic acid | trans-4-aminocyclohexanol | trans-4-(3-(7-methyl-1H-indol-2-yl)imidazo[1,2-b]pyridazin-6-ylamino)cyclohexanol |
| 198 | 5-methoxy-1H-indol-2-yl-2-boronic acid | trans-4-methoxycyclohexanamine | trans-3-(5-methoxy-1H-indol-2-yl)-N-(4-methoxycyclohexyl)imidazo[1,2-b]pyridazin-6-amine |
| 199 | 7-methoxy-1H-indol-2-yl-2-boronic acid | trans-4-methoxycyclohexanamine | trans-3-(7-methoxy-1H-indol-2-yl)-N-(4-methoxycyclohexyl)imidazo[1,2-b]pyridazin-6-amine |

Compounds 85-88, 159, 196, 198-199 were physically characterized by electrospray ionization mass spectrometry. Structures and molecular masses are given below in Table 2-b.

TABLE 2-b

| Cd. | Structure | IUPAC Name | [M + H]$^+$ |
|---|---|---|---|
| 85 | 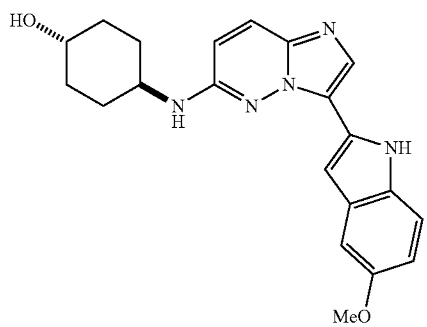 | trans-4-(3-(5-methoxy-1H-indol-2-yl)imidazo[1,2-b]pyridazin-6-ylamino)cyclohexanol | 378.2 |
| 86 | 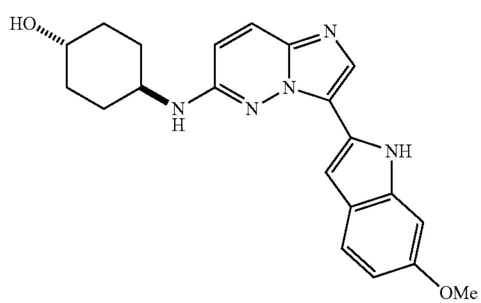 | trans-4-(3-(6-methoxy-1H-indol-2-yl)imidazo[1,2-b]pyridazin-6-ylamino)cyclohexanol | 378.4 |
| 87 | 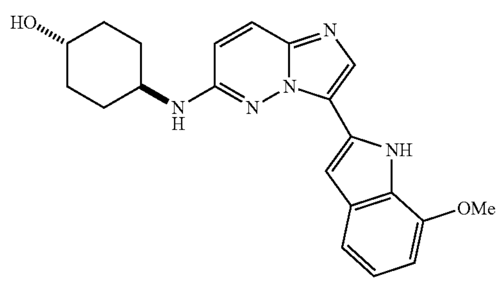 | trans-4-(3-(7-methoxy-1H-indol-2-yl)imidazo[1,2-b]pyridazin-6-ylamino)cyclohexanol | 378.2 |

TABLE 2-b-continued

| Cd. | Structure | IUPAC Name | [M + H]+ |
|---|---|---|---|
| 88 | 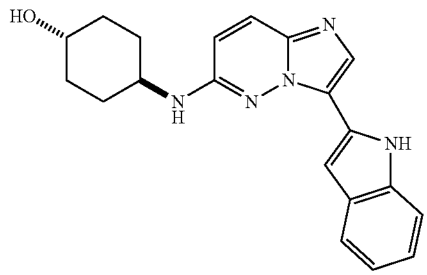 | trans-4-(3-(1H-indol-2-yl)imidazo[1,2-b]pyridazin-6-ylamino)cyclohexanol | 348.5 |
| 159 | 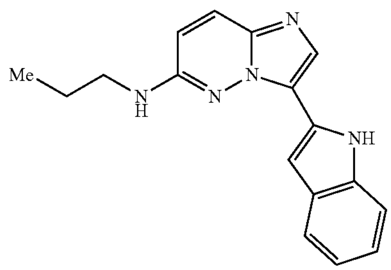 [SMILES: CCCNc1ccc2ncc(-c3cc4ccccc4[nH]3)n2n1] | 3-(1H-indol-2-yl)-N-propylimidazo[1,2-b]pyridazin-6-amine | 292.7 |
| 196 | 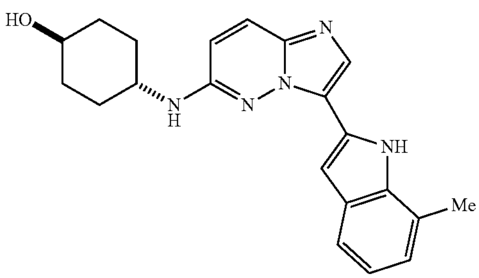 | trans-4-(3-(7-methyl-1H-indol-2-yl)imidazol[1,2-b]pyridazin-6-ylamino)cyclohexanol | 362.2 |
| 198 | 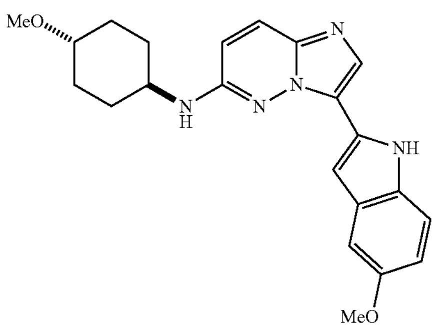 | trans-3-(5-methoxy-1H-indol-2-yl)-N-(4-methoxycyclohexyl)imidazo[1,2-b]pyridazin-6-amine | 392.5 |
| 199 | 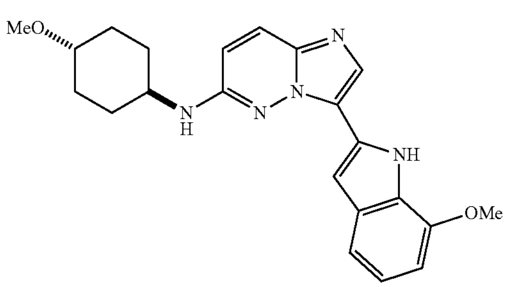 | trans-3-(7-methoxy-1H-indol-2-yl)-N-(4-methoxycyclohexyl)imidazo[1,2-b]pyridazin-6-amine | 392.3 |

EXAMPLE 2C

Synthesis of Compounds 193

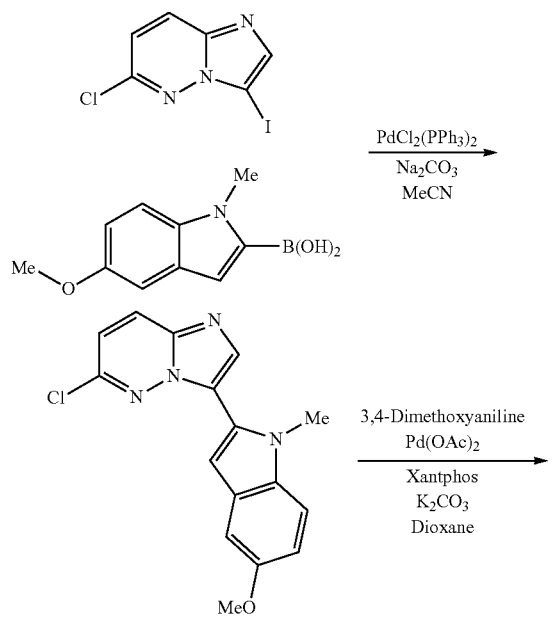

Preparation of 6-chloro-3-(5-methoxy-1-methyl-1H-indol-2-yl)imidazo[1,2-b]pyridazine

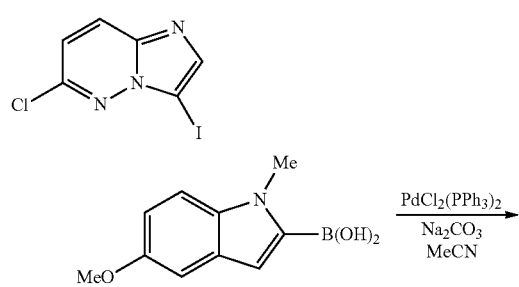

To a solution of 5-methoxy-1-methyl-1H-indol-2-yl-2-boronic acid (243 mg, 1.19 mmol, 1.2 equiv) in acetonitrile (9.88 mL) was added 6-chloro-3-iodoimidazo[1,2-b]pyridazine (276 mg, 0.988 mmol, 1.0 equiv), palladium catalyst (72 mg, 0.100 mmol, 0.1 equiv) and sodium carbonate (9.88 mL, 1.0 M, 10.0 equiv). The solution was stirred at 150° C. in the microwave for 10 minutes. Purification using column chromatography gave 200 mg of the yellow solid, 65%.

Preparation of 3-(5-methoxy-1-methyl-1H-indol-2-yl)-N-(3,4-dimethoxyphenyl)imidazo[1,2-b]pyridazin-6-amine

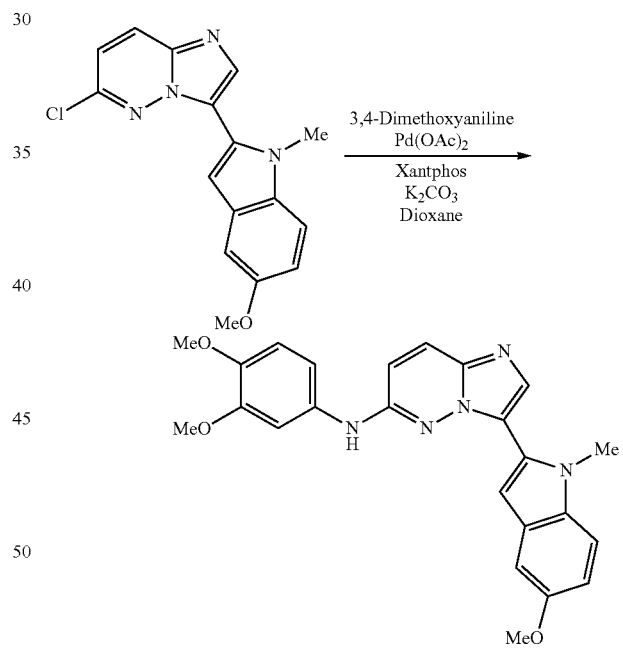

To a solution of 6-chloro-3-(5-methoxy-1-methyl-1H-indol-2-yl)imidazo[1,2-b]pyridazine (49 mg, 0.157 mmol, 1.0 equiv), xantphos (18 mg, 0.0313 mmol, 0.2 equiv), palladium acetate (4 mg, 0.0156 mmol, 0.1 equiv), and potassium carbonate (433 mg, 3.13 mmol, 20 equiv) in dioxane (5.0 mL) was added 3,4-dimethoxyaniline (26 mg, 0.172 mmol, 1.1 equiv) and heated to 110° C. for 2 h. Purification by column chromatography using 2% methanol in dichloromethane elution gave 40 mg, 0.152 mmol of the yellow solid, 59%.

Compound 193 was physically characterized by electrospray ionization mass spectrometry. Structures and molecular masses are given below in Table X.

TABLE 2C

| Cd. | Structure | IUPAC Name | [M + H]+ |
|---|---|---|---|
| 193 | 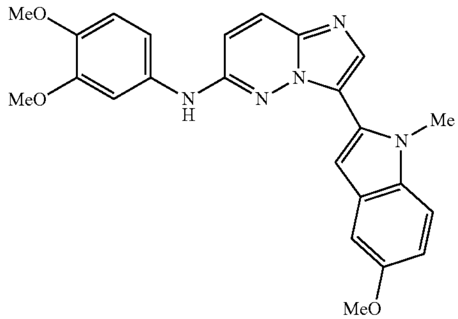 [SMILES: COc1ccc2c(c1)cc(-c1cnc3ccc(Nc4ccc(OC)c(OC)c4)nn13)n2C] | 3-(5-methoxy-1-methyl-1H-indol-2-yl)-N-(3,4-dimethoxyphenyl)imidazo[1,2-b]pyridazin-6-amine | 430.5 |

EXAMPLE 2D

Synthesis of Compound 194

Preparation of trans-4-(3-(5-methoxy-1-methyl-1H-indol-2-yl)imidazo[1,2-b]pyridazin-6-ylamino)cyclohexanol

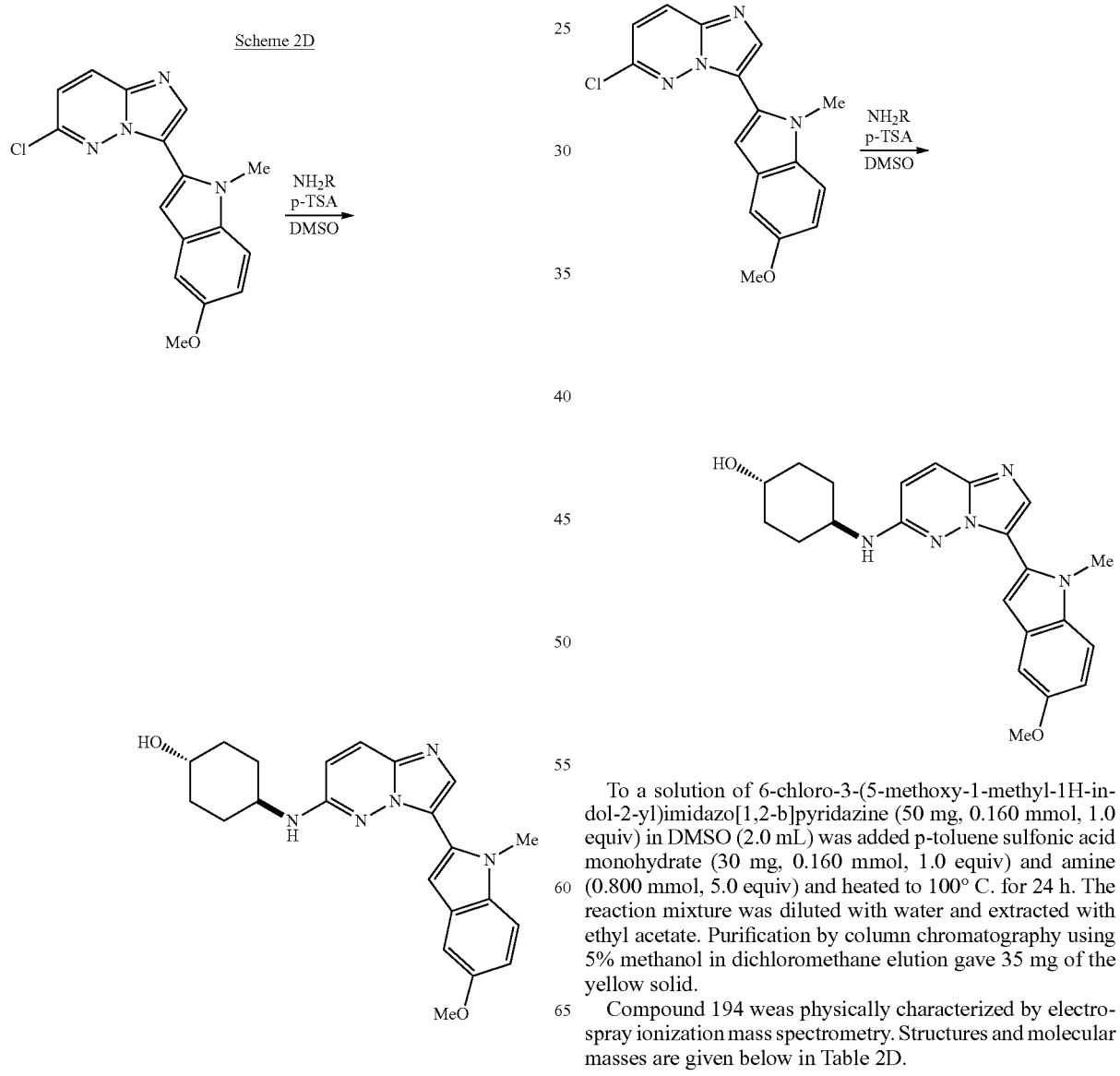

Scheme 2D

To a solution of 6-chloro-3-(5-methoxy-1-methyl-1H-indol-2-yl)imidazo[1,2-b]pyridazine (50 mg, 0.160 mmol, 1.0 equiv) in DMSO (2.0 mL) was added p-toluene sulfonic acid monohydrate (30 mg, 0.160 mmol, 1.0 equiv) and amine (0.800 mmol, 5.0 equiv) and heated to 100° C. for 24 h. The reaction mixture was diluted with water and extracted with ethyl acetate. Purification by column chromatography using 5% methanol in dichloromethane elution gave 35 mg of the yellow solid.

Compound 194 weas physically characterized by electrospray ionization mass spectrometry. Structures and molecular masses are given below in Table 2D.

TABLE 2D

| Cd. | Structure | IUPAC Name | [M + H]+ |
|---|---|---|---|
| 194 | (structure) | trans-4-(3-(5-methoxy-1-methyl-1H-indol-2-yl)imidazo[1,2-b]pyridazin-6-ylamino)cyclohexanol | 392.3 |

EXAMPLE 2E

Synthesis of Compounds 197

Preparation of 6-chloro-3-(5,6-dimethoxy-1-tosyl-1H-indol-2-yl)imidazo[1,2-b]pyridazine

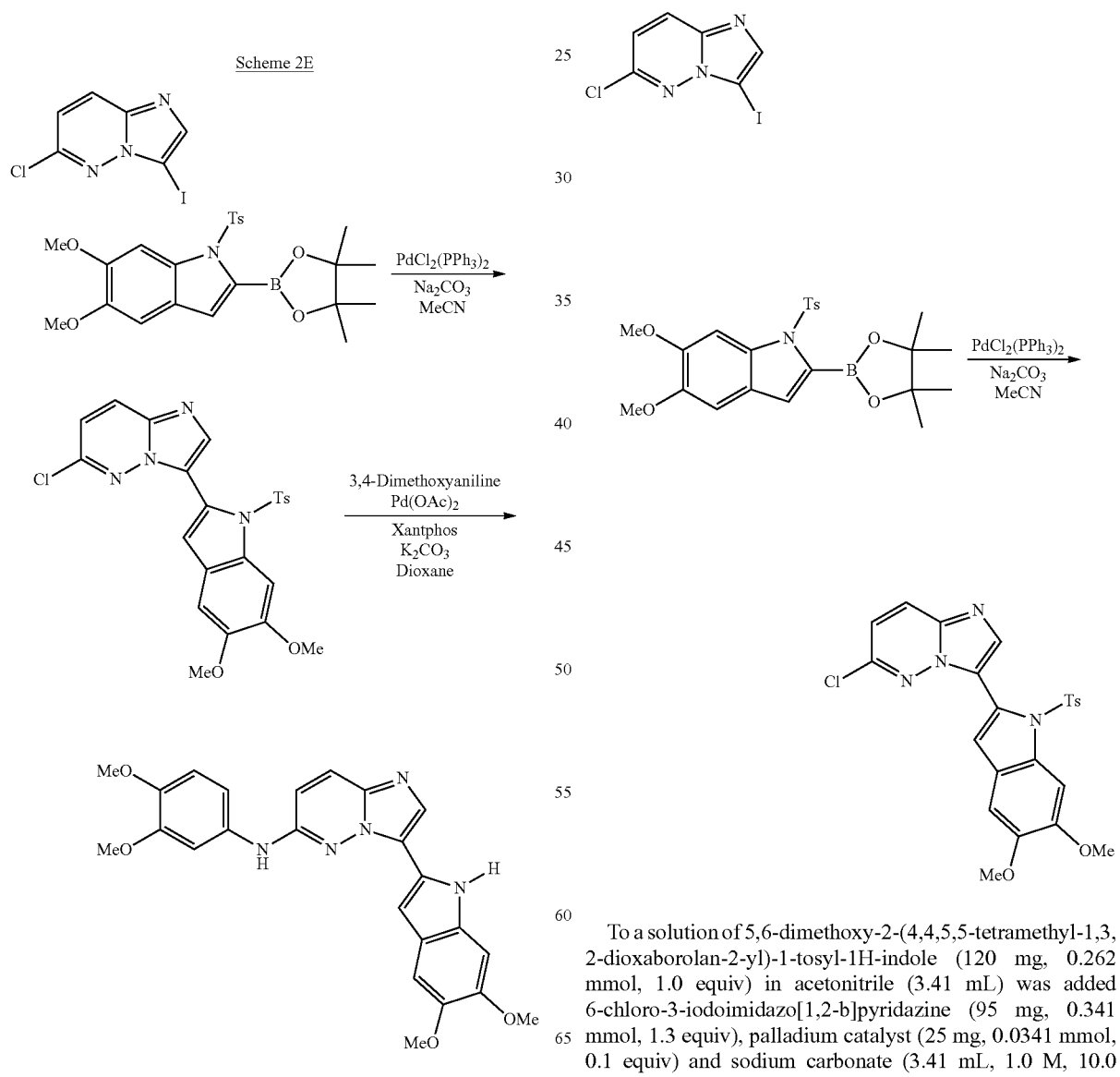

To a solution of 5,6-dimethoxy-2-(4,4,5,5-tetramethyl-1,3,2-dioxaborolan-2-yl)-1-tosyl-1H-indole (120 mg, 0.262 mmol, 1.0 equiv) in acetonitrile (3.41 mL) was added 6-chloro-3-iodoimidazo[1,2-b]pyridazine (95 mg, 0.341 mmol, 1.3 equiv), palladium catalyst (25 mg, 0.0341 mmol, 0.1 equiv) and sodium carbonate (3.41 mL, 1.0 M, 10.0 equiv). The solution was stirred at 150° C. in the microwave for 10 minutes. Purification using column chromatography gave 80 mg of the yellow solid, 63%.

Preparation of 3-(5,6-dimethoxy-1H-indol-2-yl)-N-(3,4-dimethoxyphenyl)imidazo[1,2-b]pyridazin-6-amine

EXAMPLE 3

Synthesis of Compounds 6-7

Scheme 3

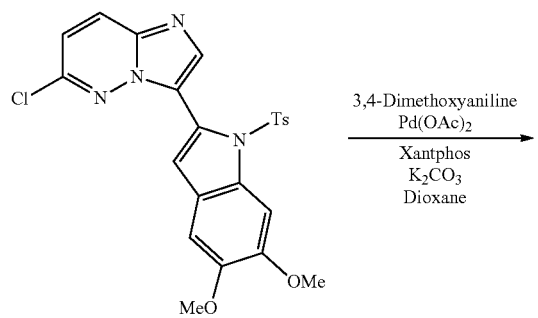

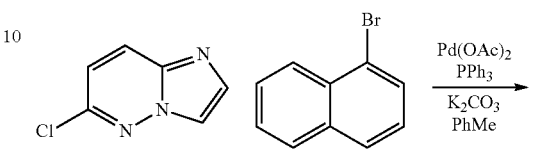

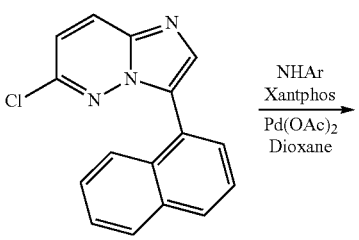

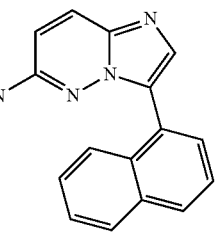

To a solution of 6-chloro-3-(5,6-dimethoxy-1-tosyl-1H-indol-2-yl)imidazo[1,2-b]pyridazine (68 mg, 0.141 mmol, 1.0 equiv), xantphos (16 mg, 0.0282 mmol, 0.2 equiv), palladium acetate (3 mg, 0.0141 mmol, 0.1 equiv), and potassium carbonate (389 mg, 2.82 mmol, 20 equiv) in dioxane (5.0 mL) was added 3,4-dimethoxyaniline (24 mg, 0.155 mmol, 1.1 equiv) and heated to 110° C. for 2 h. Purification by column chromatography using 2% methanol in dichloromethane elution gave 20 mg of the yellow solid.

TABLE 2E

| Cd. | Structure | IUPAC Name | [M + H]+ |
|---|---|---|---|
| 197 | (structure shown) | 3-(5,6-dimethoxy-1H-indol-2-yl)-N-(3,4-dimethoxyphenyl)imidazo[1,2-b]pyridazin-6-amine | 446.5 |

Preparation of 6-chloro-3-(naphthalen-1-yl)imidazo[1,2-b]pyridazine

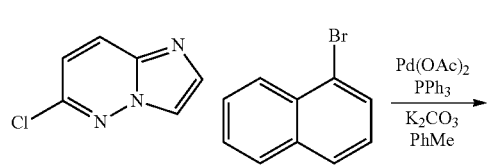

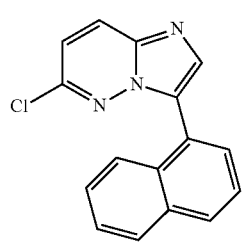

To a stirred solution of 6-chloroimidazo[1,2-b]pyridazine (1.55 g, 10.1 mmol) in 10.0 mL of toluene was added aryl bromide (2.11 mL, 15.1 mmol, 1.5 equiv), potassium carbonate (2.79 g, 18.2 mmol, 2.0 equiv), triphenylphosphine (529 mg, 2.02 mmol, 0.2 equiv) and palladium acetate (227 mg, 1.01 mmol, 0.1 equiv). The solution was stirred to reflux for 24 h. Purification by column chromatography using 50% ethyl acetate in hexanes elution gave 43% of the yellow solid.

Preparation of 3-(naphthalen-1-yl)-N-arylimidazo[1,2-b]pyridazin-6-amine

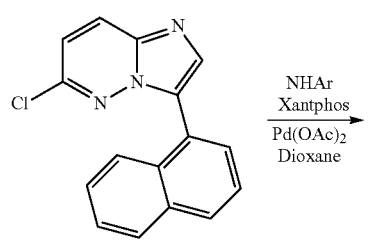

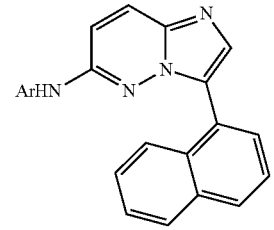

To a solution of 6-chloro-3-(naphthalen-1-yl)imidazo[1,2-b]pyridazine (50 mg, 0.179 mmol, 1.0 equiv), xantphos (21 mg, 0.0358 mmol, 0.2 equiv), palladium acetate (4 mg, 0.0179 mmol, 0.1 equiv), and potassium carbonate (495 mg, 3.58 mmol, 20 equiv) in dioxane (5.0 mL) was added amine (0.179 mmol, 1.0 equiv) and heated to 100° C. for 2 h. Purification by column chromatography using 2% methanol in dichloromethane elution gave the product.

TABLE 3-a

| Cd. | Amine | Purified Compound Isolated |
| --- | --- | --- |
| 6 | 3,4-dimethoxyaniline | N-(3,4-dimethoxyphenyl)-3-(naphthalen-1-yl)imidazo[1,2-b]pyridazin-6-amine |
| 7 | 3-aminobenzoic acid | 3-(3-(naphthalen-1-yl)imidazo[1,2-b]pyridazin-6-ylamino)benzoic acid |

Compounds 6-7 were physically characterized by electrospray ionization mass spectrometry. Structures and molecular masses are given below in Table 3-b.

TABLE 3-b

| Cd. | Structure | IUPAC Name | [M + H]+ |
| --- | --- | --- | --- |
| 6 | 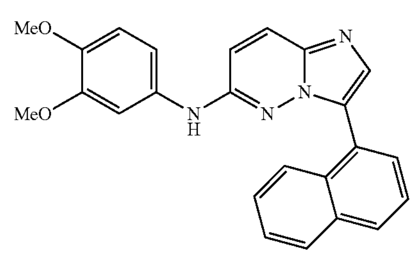 [SMILES: COc1ccc(Nc2ccc3ncc(-c4cccc5ccccc45)n3n2)cc1OC] | N-(3,4-dimethoxyphenyl)-3-(naphthalen-1-yl)imidazo[1,2-b]pyridazin-6-amine | 397.7 |

TABLE 3-b-continued

| Cd. | Structure | IUPAC Name | [M + H]+ |
|---|---|---|---|
| 7 | 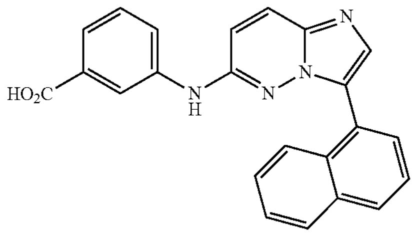 [SMILES: O=C(O)c1cccc(Nc2ccc3ncc(-c4cccc5ccccc45)n3n2)c1] | 3-(3-(naphthalen-1-yl)imidazo[1,2-b]pyridazin-6-ylamino)benzoic acid | 381.8 |

EXAMPLE 4

Synthesis of Compound 89

Scheme 4

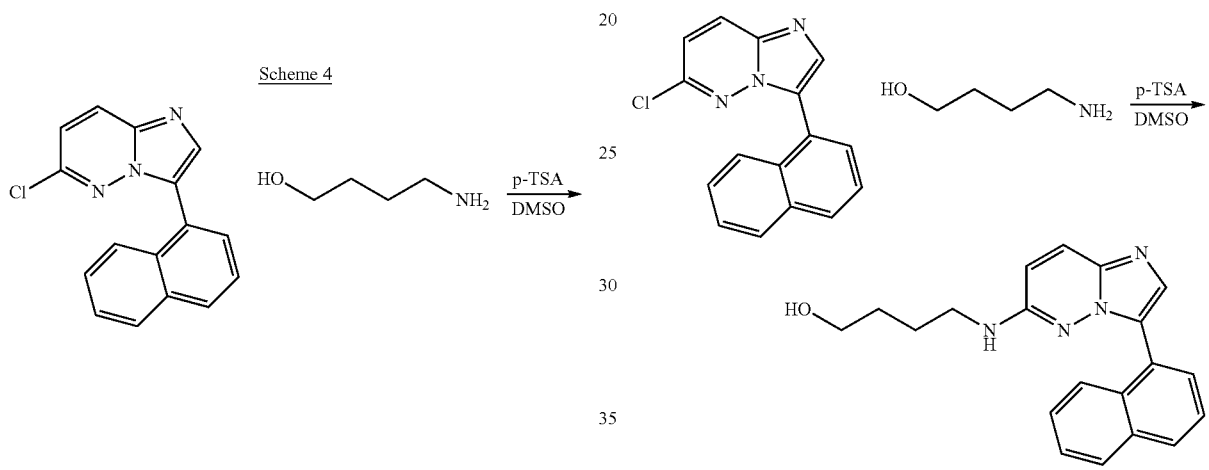

Preparation of 4-(3-(naphthalen-1-yl)imidazo[1,2-b]pyridazin-6-ylamino)butan-1-ol To a solution of 6-chloro-3-(naphthalen-1-yl)imidazo[1,2-b]pyridazine (50 mg, 0.179 mmol, 1.0 equiv) in DMSO (2.0 mL) was added p-toluene sulfonic acid monohydrate (35 mg, 0.184 mmol, 1.0 equiv) and 4-aminobutan-1-ol (200 mg, 2.24 mmol, 12.5 equiv) and heated to 100° C. for 24 h. The reaction mixture was diluted with water and extracted with ethyl acetate. Purification by column chromatography using 5% methanol in dichloromethane elution gave 30 mg of a white solid, 50%.

Compound 89 was physically characterized by electrospray ionization mass spectrometry. Structures and molecular masses are given below in Table 4-b.

TABLE 4-b

| Cd. | Structure | IUPAC Name | [M + H]+ |
|---|---|---|---|
| 89 | 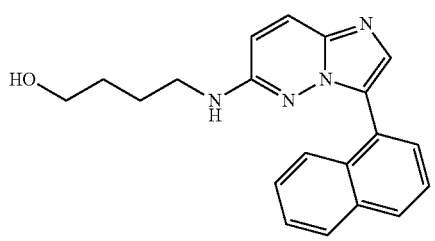 [SMILES: OCCCCNc1ccc2ncc(-c3cccc4ccccc34)n2n1] | 4-(3-(naphthalen-1-yl)imidazo[1,2-b]pyridazin-6-ylamino)butan-1-ol | 333.7 |

EXAMPLE 5

Synthesis of Compounds 8, 17-21

Scheme 5

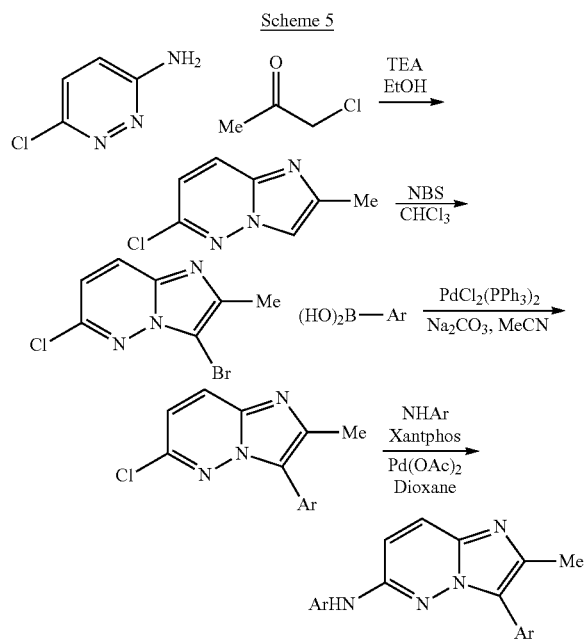

Preparation of 6-chloro-2-methylimidazo[1,2-b]pyridazine

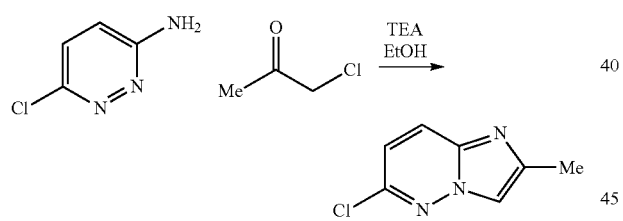

To a solution of 6-chloropyridazin-3-amine (2.35 g, 18.1 mmol, 1.0 equiv) in ethanol (15 mL) was added 1-chloropropan-2-one (2.92 mL, 36.3 mmol, 2.0 equiv) and triethylamine (2.53 mL, 18.1 mmol, 1.0 equiv). The solution was heated at 150° C. for 30 min then quenched with water. Purification by column chromatography using 30% ethyl acetate in hexanes elution gave 2.43 g of the brown solid, 80%.

Preparation of 3-bromo-6-chloro-2-methylimidazo[1,2-b]pyridazine

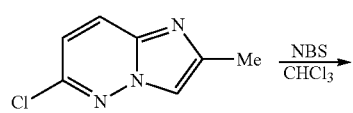

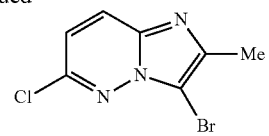

To a solution of 6-chloro-2-methylimidazo[1,2-b]pyridazine (2.00 g, 11.9 mmol, 1.0 equiv) in chloroform (50 mL) was added N-bromosuccinimide (2.55 g, 14.3 mmol, 1.2 equiv). The reaction was stirred at room temperature for 15 h. Purification by column chromatography using 50% ethyl acetate in hexanes elution gave 2.64 g of the yellow solid, 90%.

Preparation of 6-chloro-2-methyl-3-arylimidazo[1,2-b]pyridazine

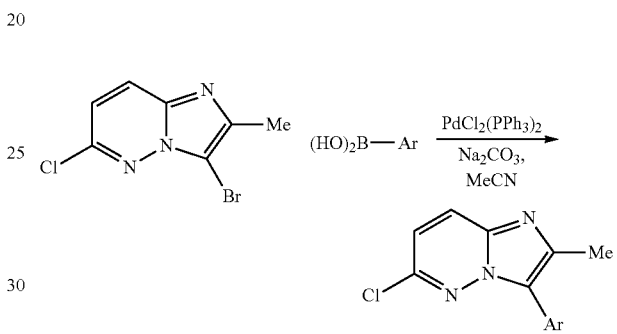

To a solution of 3-bromo-6-chloro-2-methylimidazo[1,2-b]pyridazine (865 mg, 5.16 mmol, 1.0 equiv) in acetonitrile (15 mL) was added boronic acid (5.16 mmol, 1.0 equiv), bis(triphenylphosphine)palladium(II)dichloride (0.516 mmol, 0.1 equiv), then sodium carbonate (1.0 M aqueous solution, 10 equiv). The reaction mixture was irradiated in the microwave at 150° C. for 10 min. Purification by column chromatography gave of the product.

Preparation of 2-methyl-N,3-bisarylimidazo[1,2-b]pyridazin-6-amine

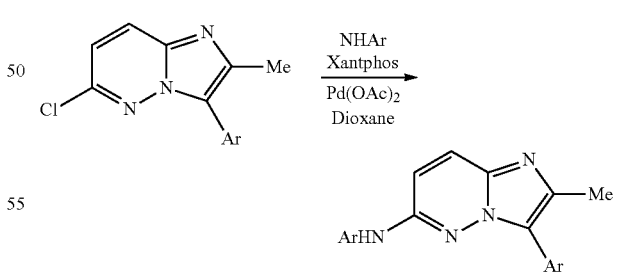

To a solution of 6-chloro-2-methyl-3-arylimidazo[1,2-b]pyridazine (100 mg, 0.33 mmol, 1.0 equiv), xantphos (39 mg, 0.07 mmol, 0.2 equiv), palladium acetate (7 mg, 0.03 mmol, 0.1 equiv), and potassium carbonate (922 mg, 6.67 mmol, 20 equiv) in dioxane (5.0 mL) was added amine (0.367 mmol, 1.1 equiv) and heated to 100° C. for 2 h. Purification by column chromatography using 2% methanol in dichloromethane elution gave the product.

TABLE 5-a

| Cd. | Boronic Acid | Amine | Purified Compound Isolated |
|---|---|---|---|
| 8 | 3-methoxyphenylboronic acid | 3,4-dimethoxyaniline | N-(3,4-dimethoxyphenyl)-3-(3-methoxyphenyl)-2-methylimidazo[1,2-b]pyridazin-6-amine |
| 17 | benzo[b]thiophen-2-yl-2-boronic acid | 3,4-dimethoxyaniline | 3-(benzo[b]thiophen-2-yl)-N-(3,4-dimethoxyphenyl)-2-methylimidazo[1,2-b]pyridazin-6-amine |
| 18 | benzo[b]thiophen-2-yl-2-boronic acid | 3-(4-methylpiperazin-1-yl)benzenamine | 3-(benzo[b]thiophen-2-yl)-2-methyl-N-(3-(4-methylpiperazin-1-yl)phenyl)imidazo[1,2-b]pyridazin-6-amine |
| 19 | benzo[b]thiophen-2-yl-2-boronic acid | 4-(4-methylpiperazin-1-yl)benzenamine | 3-(benzo[b]thiophen-2-yl)-2-methyl-N-(4-(4-methylpiperazin-1-yl)phenyl)imidazo[1,2-b]pyridazin-6-amine |
| 20 | benzo[b]thiophen-2-yl-2-boronic acid | 3-((4-methylpiperazin-1-yl)methyl)benzenamine | 3-(benzo[b]thiophen-2-yl)-2-methyl-N-(3-((4-methylpiperazin-1-yl)methyl)phenyl)imidazo[1,2-b]pyridazin-6-amine |
| 21 | benzo[b]thiophen-2-yl-2-boronic acid | 4-((4-methylpiperazin-1-yl)methyl)benzenamine | 3-(benzo[b]thiophen-2-yl)-2-methyl-N-(4-((4-methylpiperazin-1-yl)methyl)phenyl)imidazo[1,2-b]pyridazin-6-amine |

Compounds 8, 17-21 were physically characterized by electrospray ionization mass spectrometry. Structures and molecular masses are given below in Table 5-b.

TABLE 5-b

| Cd. | Structure | IUPAC Name | [M + H]⁺ |
|---|---|---|---|
| 8 | (structure shown) | N-(3,4-dimethoxyphenyl)-3-(3-methoxyphenyl)-2-methylimidazo[1,2-b]pyridazin-6-amine | 391.7 |
| 17 | (structure shown) | 3-(benzo[b]thiophen-2-yl)-N-(3,4-dimethoxyphenyl)-2-methylimidazo[1,2-b]pyridazin-6-amine | 417.7 |

TABLE 5-b-continued

| Cd. | Structure | IUPAC Name | [M + H]+ |
|---|---|---|---|
| 18 | 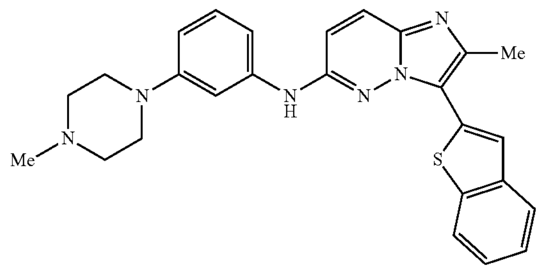 [SMILES: Cc1nc2ccc(Nc3cccc(N4CCN(C)CC4)c3)nn2c1-c1cc2ccccc2s1] | 3-(benzo[b]thiophen-2-yl)-2-methyl-N-(3-(4-methylpiperazin-1-yl)phenyl)imidazo[1,2-b]pyridazin-6-amine | 455.7 |
| 19 | 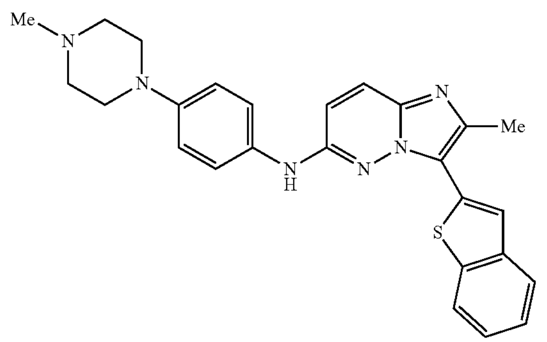 [SMILES: Cc1nc2ccc(Nc3ccc(N4CCN(C)CC4)cc3)nn2c1-c1cc2ccccc2s1] | 3-(benzo[b]thiophen-2-yl)-2-methyl-N-(4-(4-methylpiperazin-1-yl)phenyl)imidazo[1,2-b]pyridazin-6-amine | 455.7 |
| 20 | 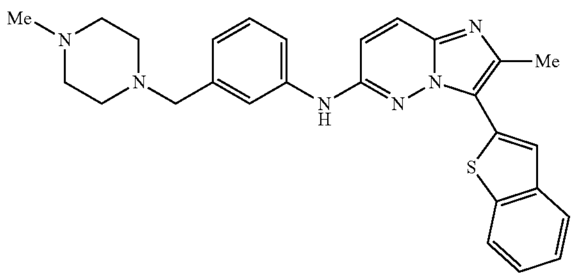 [SMILES: Cc1nc2ccc(Nc3cccc(CN4CCN(C)CC4)c3)nn2c1-c1cc2ccccc2s1] | 3-(benzo[b]thiophen-2-yl)-2-methyl-N-(3-((4-methylpiperazin-1-yl)methyl)phenyl)imidazo[1,2-b]pyridazin-6-amine | 469.8 |
| 21 | 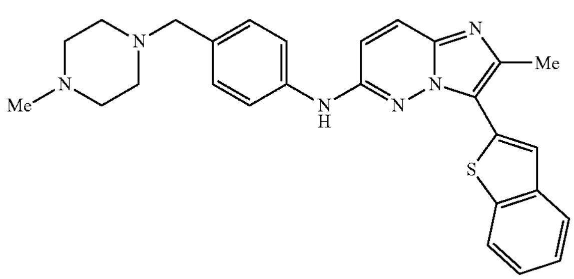 [SMILES: Cc1nc2ccc(Nc3ccc(CN4CCN(C)CC4)cc3)nn2c1-c1cc2ccccc2s1] | 3-(benzo[b]thiophen-2-yl)-2-methyl-N-(4-((4-methylpiperazin-1-yl)methyl)phenyl)imidao[1,2-b]pyridazin-6-amine | 469.7 |

EXAMPLE 6

Synthesis of Compounds 111-112, 114-115

Scheme 6

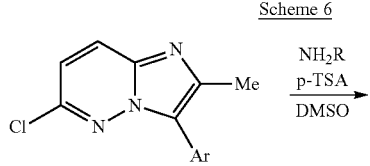

$\xrightarrow{\text{NH}_2\text{R} \; \text{p-TSA}}{\text{DMSO}}$

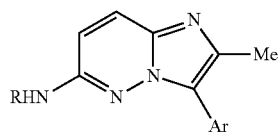

Preparation of N-alkyl-2-methyl-3-arylimidazo[1,2-b]pyridazin-6-amine

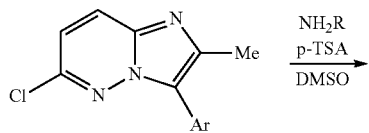

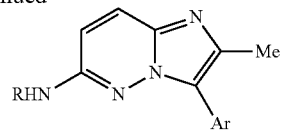

To a solution of 6-chloro-2-methyl-3-arylimidazo[1,2-b]pyridazine (150 mg, 0.500 mmol, 1.0 equiv) in DMSO (2.0 mL) was added p-toluene sulfonic acid monohydrate (95 mg, 0.500 mmol, 1.0 equiv) and amine (1.95 mmol, 4.0 equiv) and heated to 100° C. for 24 h. The reaction mixture was diluted with water and extracted with ethyl acetate. Purification by column chromatography using 5% methanol in dichloromethane elution gave the product.

TABLE 6-a

| Cd. | Boronic Acid | Amine | Purified Compound Isolated |
|---|---|---|---|
| 111 | benzo[b]thiophen-2-yl-2-boronic acid | trans-4-aminocyclohexanol | 4-(3-(benzo[b]thiophen-2-yl)-2-methylimidazo[1,2-b]pyridazin-6-ylamino)cyclohexanol |
| 112 | benzo[b]thiophen-2-yl-2-boronic acid | 2-methylpropan-1-amine | 3-(benzo[b]thiophen-2-yl)-N-isobutyl-2-methylimidazo[1,2-b]pyridazin-6-amine |
| 114 | benzo[b]thiophen-2-yl-2-boronic acid | N-methylpropyl-1-amine | 3-(benzo[b]thiophen-2-yl)-N,2-dimethyl-N-propylimidazo[1,2-b]pyridazin-6-amine |
| 115 | benzo[b]thiophen-2-yl-2-boronic acid | pentan-1-amine | 3-(benzo[b]thiophen-2-yl)-2-methyl-N-pentylimidazo[1,2-b]pyridazin-6-amine |

Compounds 111-112, 114-115 were physically characterized by electrospray ionization mass spectrometry. Structures and molecular masses are given below in Table 6-b.

TABLE 6-b

| Cd. | Structure | IUPAC Name | [M + H]⁺ |
|---|---|---|---|
| 111 | 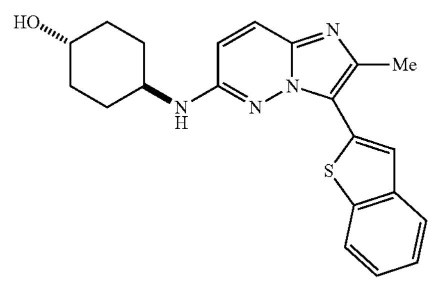 | 4-(3-(benzo[b]thiophen-2-yl)-2-methylimidazo[1,2-b]pyridazin-6-ylamino)cyclohexanol | 379.7 |
| 112 | 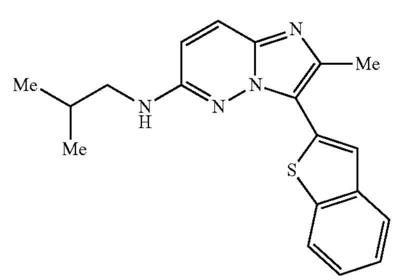 [SMILES: Cc1nc2ccc(NCC(C)C)nn2c1-c1cc2ccccc2s1] | 3-(benzo[b]thiophen-2-yl)-N-isobutyl-2-methylimidazo[1,2-b]pyridazin-6-amine | 387.6 |

TABLE 6-b-continued

| Cd. | Structure | IUPAC Name | [M + H]+ |
|---|---|---|---|
| 114 | 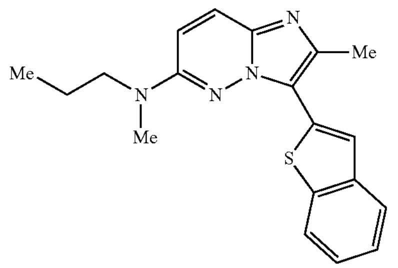 [SMILES: CCCN(C)c1ccc2nc(C)c(-c3cc4ccccc4s3)n2n1] | 3-(benzo[b]thiophen-2-yl)-N,2-dimethyl-N-propylimidazo[1,2-b]pyridazin-6-amine | 337.7 |
| 115 | 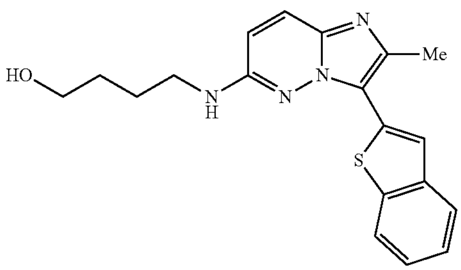 [SMILES: Cc1nc2ccc(NCCCCO)nn2c1-c1cc2ccccc2s1] | 3-(benzo[b]thiophen-2-yl)-2-methyl-N-pentylimidazo[1,2-b]pyridazin-6-amine | 353.8 |

EXAMPLE 7

Synthesis of Compounds 9, 11

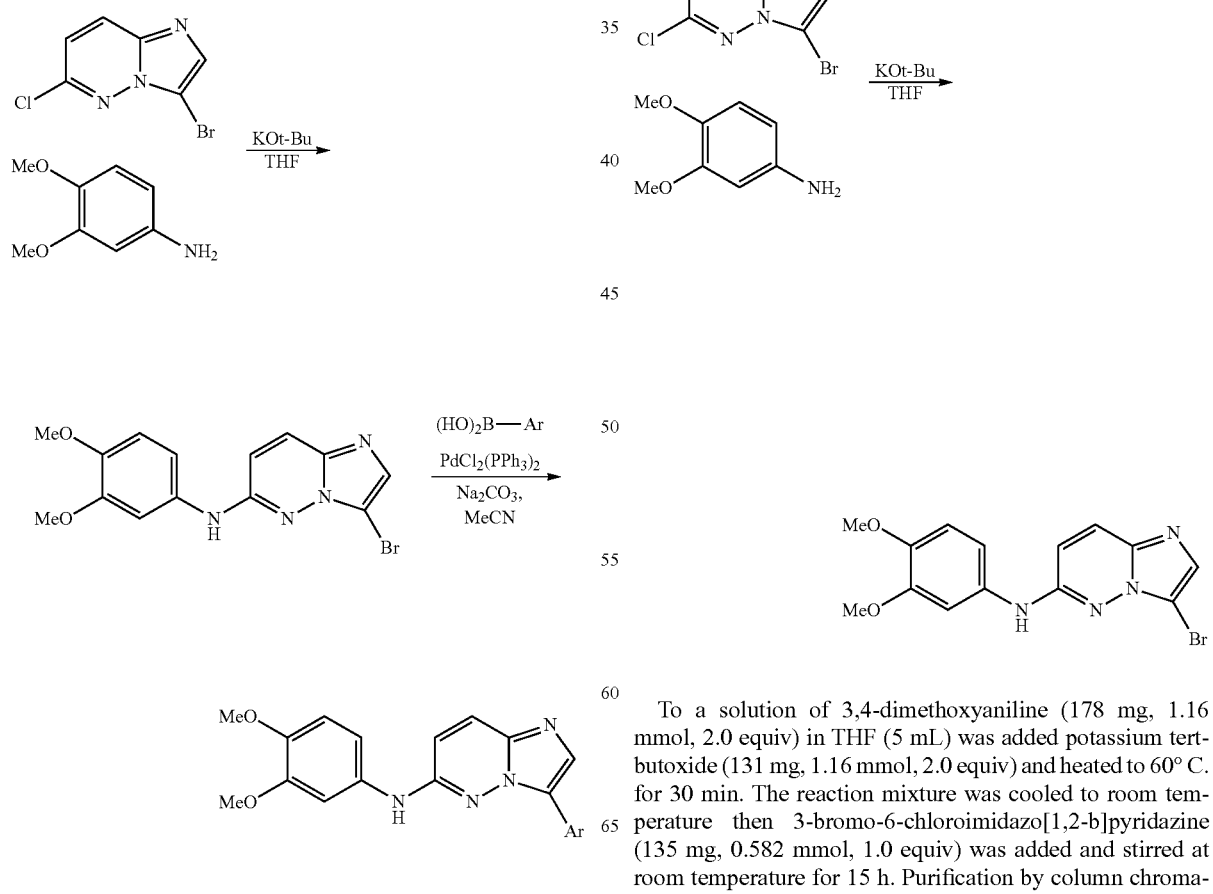

Preparation of 3-bromo-N-(3,4-dimethoxyphenyl)imidazo[1,2-b]pyridazin-6-amine

To a solution of 3,4-dimethoxyaniline (178 mg, 1.16 mmol, 2.0 equiv) in THF (5 mL) was added potassium tert-butoxide (131 mg, 1.16 mmol, 2.0 equiv) and heated to 60° C. for 30 min. The reaction mixture was cooled to room temperature then 3-bromo-6-chloroimidazo[1,2-b]pyridazine (135 mg, 0.582 mmol, 1.0 equiv) was added and stirred at room temperature for 15 h. Purification by column chromatography using 2% methanol in dichloromethane elution gave 102 mg of the dark brown solid, 50%.

Preparation of N-(3,4-dimethoxyphenyl)-3-arylimidazo[1,2-b]pyridazin-6-amine

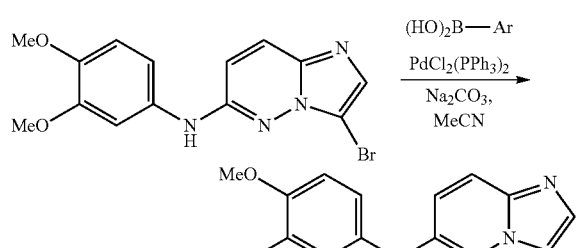

To a solution of 3-bromo-N-(3,4-dimethoxyphenyl)imidazo[1,2-b]pyridazin-6-amine (45 mg, 0.129 mmol, 1.0 equiv) in acetonitrile (1.30 mL) was added boronic acid (0.193 mmol, 1.5 equiv), bis(triphenylphosphine)palladium (II)dichloride (0.013 mmol, 0.1 equiv), then sodium carbonate (1.0 M aqueous solution, 10 equiv). The reaction mixture was irradiated in the microwave at 150° C. for 10 min. Purification by column chromatography gave of the product.

TABLE 7-a

| Cd. | Boronic Acid | Purified Compound Isolated |
|---|---|---|
| 9 | 3-hydroxyphenyl-boronic acid | 3-(6-(3,4-dimethoxyphenylamino)imidazo[1,2-b]pyridazin-3-yl)phenol |
| 11 | 3,4,5-trimethoxy-phenylboronic acid | 3-(3,4,5-trimethoxyphenyl)-N-(3,4-dimethoxyphenyl)imidazo[1,2-b]pyridazin-6-amine |

Compounds 9, 11 were physically characterized by electrospray ionization mass spectrometry. Structures and molecular masses are given below in Table 7-b.

EXAMPLE 8

Synthesis of Compounds 12-16, 22-38, 41-45, 47-48

Scheme 8

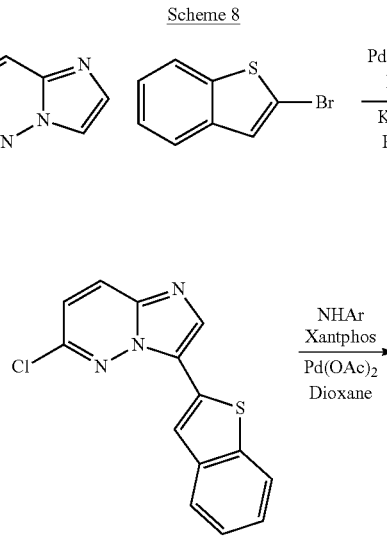

TABLE 7-b

| Cd. | Structure | IUPAC Name | [M + H]+ |
|---|---|---|---|
| 9 | 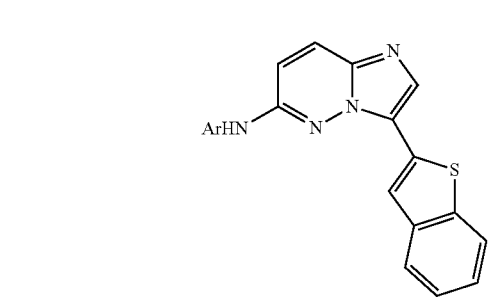 | 3-(6-(3,4-dimethoxyphenylamino)imidazo[1,2-b]pyridazin-3-yl)phenol | 363.9 |
| 11 | 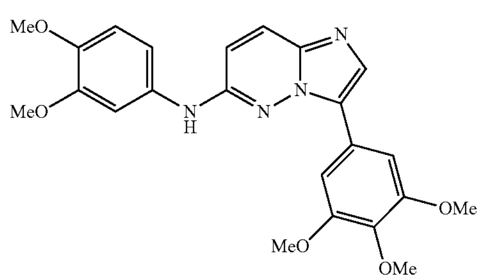 [SMILES: COc1ccc(Nc2ccc3ncc(-c4cc(OC)c(OC)c(OC)c4)n3n2)cc1OC] | 3-(3,4,5-trimethoxyphenyl)-N-(3,4-dimethoxyphenyl)imidazo[1,2-b]pyridazin-6-amine | 437.4 |

Preparation of 3-(benzo[b]thiophen-2-yl)-6-chloroimidazo[1,2-b]pyridazine

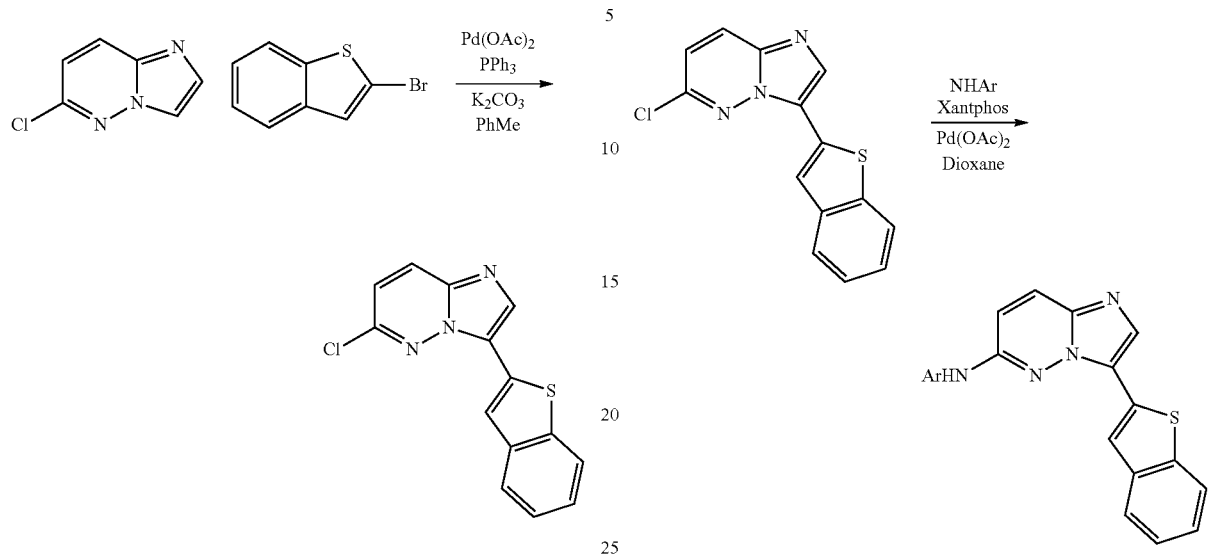

To a stirred solution of 6-chloroimidazo[1,2-b]pyridazine (1.59 g, 10.3 mmol, 1.1 equiv) in 28.0 mL of toluene was added 2-bromobenzo[b]thiophene (2.00 g, 9.38 mmol, 1.0 equiv), potassium carbonate (2.59 g, 18.8 mmol, 2.0 equiv), triphenylphosphine (592 mg, 1.88 mmol, 0.2 equiv) and palladium acetate (211 mg, 0.938 mmol, 0.1 equiv). The solution was stirred to reflux for 24 h. Purification by column chromatography using 50% ethyl acetate in hexanes elution gave 1.50 g of the yellow solid, 56%.

Preparation of 3-(benzo[b]thiophen-2-yl)-N-arylimidazo[1,2-b]pyridazin-6-amine To a solution of 6-chloro-2-methyl-3-arylimidazo[1,2-b]pyridazine (100 mg, 0.33 mmol, 1.0 equiv), xantphos (39 mg, 0.07 mmol, 0.2 equiv), palladium acetate (7 mg, 0.03 mmol, 0.1 equiv), and potassium carbonate (922 mg, 6.67 mmol, 20 equiv) in dioxane (5.0 mL) was added amine (0.367 mmol, 1.1 equiv) and heated to 100° C. for 2 h. Purification by column chromatography using 2% methanol in dichloromethane elution gave the product.

TABLE 8-a

| Cd. | Amine | Purified Compound Isolated |
| --- | --- | --- |
| 12 | 3,4-dimethoxyaniline | 3-(benzo[b]thiophen-2-yl)-N-(3,4-dimethoxyphenyl)imidazo[1,2-b]pyridazin-6-amine |
| 13 | 3-(4-methylpiperazin-1-yl)benzenamine | 3-(benzo[b]thiophen-2-yl)-N-(3-(4-methylpiperazin-1-yl)phenyl)imidazo[1,2-b]pyridazin-6-amine |
| 14 | 3,4,5-trimethoxybenzenamine | 3-(benzo[b]thiophen-2-yl)-N-(3,4,5-trimethoxyphenyl)imidazo[1,2-b]pyridazin-6-amine |
| 15 | 3-methoxybenzenamine | 3-(benzo[b]thiophen-2-yl)-N-(3-methoxyphenyl)imidazo[1,2-b]pyridazin-6-amine |
| 16 | 4-methoxybenzenamine | 3-(benzo[b]thiophen-2-yl)-N-(4-methoxyphenyl)imidazo[1,2-b]pyridazin-6-amine |
| 22 | methyl 4-aminobenzoate | methyl 4-(3-(benzo[b]thiophen-2-yl)imidazo[1,2-b]pyridazin-6-ylamino)benzoate |
| 23 | methyl 3-aminobenzoate | methyl 3-(3-(benzo[b]thiophen-2-yl)imidazo[1,2-b]pyridazin-6-ylamino)benzoate |
| 24 | 4-amino-2-methoxyphenol | 4-(3-(benzo[b]thiophen-2-yl)imidazo[1,2-b]pyridazin-6-ylamino)-2-methoxyphenol |
| 25 | methyl 4-aminobenzoate | 4-(3-(benzo[b]thiophen-2-yl)imidazo[1,2-b]pyridazin-6-ylamino)benzoic acid |
| 26 | methyl 3-aminobenzoate | 3-(3-(benzo[b]thiophen-2-yl)imidazo[1,2-b]pyridazin-6-ylamino)benzoic acid |
| 27 | 3-(4-amino-2-methoxyphenoxy)propan-1-ol | 3-(4-(3-(benzo[b]thiophen-2-yl)imidazo[1,2-b]pyridazin-6-ylamino)-2-methoxyphenoxy)propan-1-ol |
| 28 | 4-(cyclopropylmethoxy)-3-methoxybenzenamine | 3-(benzo[b]thiophen-2-yl)-N-(4-(cyclopropylmethoxy)-3-methoxyphenyl)imidazo[1,2-b]pyridazin-6-amine |
| 29 | 4-(cyclopentylmethoxy)-3-methoxybenzenamine | 3-(benzo[b]thiophen-2-yl)-N-(4-(cyclopentylmethoxy)-3-methoxyphenyl)imidazo[1,2-b]pyridazin-6-amine |
| 30 | 4-isopropoxy-3-methoxybenzenamine | 3-(benzo[b]thiophen-2-yl)-N-(4-isopropoxy-3-methoxyphenyl)imidazo[1,2-b]pyridazin-6-amine |
| 31 | 5-amino-2-methoxyphenol | 5-(3-(benzo[b]thiophen-2-yl)imidazo[1,2-b]pyridazin-6-ylamino)-2-methoxyphenol |
| 32 | 2,4-dimethoxybenzenamine | 3-(benzo[b]thiophen-2-yl)-N-(2,4-dimethoxyphenyl)imidazo[1,2-b]pyridazin-6-amine |

TABLE 8-a-continued

| Cd. | Amine | Purified Compound Isolated |
|---|---|---|
| 33 | benzo[d][1,3]dioxol-5-amine | 3-(benzo[b]thiophen-2-yl)-N-(benzo[d][1,3]dioxol-6-yl)imidazo[1,2-b]pyridazin-6-amine |
| 34 | 2-methoxypyridin-4-amine | 3-(benzo[b]thiophen-2-yl)-N-(2-methoxypyridin-4-yl)imidazo[1,2-b]pyridazin-6-amine |
| 35 | 6-methoxypyridin-2-amine | 3-(benzo[b]thiophen-2-yl)-N-(6-methoxypyridin-2-yl)imidazo[1,2-b]pyridazin-6-amine |
| 36 | 2-methoxybenzenamine | 3-(benzo[b]thiophen-2-yl)-N-(2-methoxyphenyl)imidazo[1,2-b]pyridazin-6-amine |
| 37 | 2,3-dimethoxybenzenamine | 3-(benzo[b]thiophen-2-yl)-N-(2,3-dimethoxyphenyl)imidazo[1,2-b]pyridazin-6-amine |
| 38 | 3,4-dihydro-2H-benzo[b][1,4]dioxepin-7-amine | 3-(benzo[b]thiophen-2-yl)-N-(3,4-dihydro-2H-benzo[b][1,4]dioxepin-8-yl)imidazo[1,2-b]pyridazin-6-amine |
| 41 | 2-methoxypyridin-4-amine | 4-(3-(benzo[b]thiophen-2-yl)imidazo[1,2-b]pyridazin-6-ylamino)pyridin-2-ol |
| 42 | 3-(5-amino-2-methoxyphenoxy)propan-1-ol | 3-(5-(3-(benzo[b]thiophen-2-yl)imidazo[1,2-b]pyridazin-6-ylamino)-2-methoxyphenoxy)propan-1-ol |
| 43 | methyl 5-amino-2-methoxybenzoate | 5-(3-(benzo[b]thiophen-2-yl)imidazo[1,2-b]pyridazin-6-ylamino)-2-methoxybenzoic acid |
| 44 | methyl 2-(3-hydroxypropoxy)-5-aminobenzoate | 5-(3-(benzo[b]thiophen-2-yl)imidazo[1,2-b]pyridazin-6-ylamino)-2-(3-hydroxypropoxy)benzoic acid |
| 45 | 6-methoxypyridin-2-amine | 6-(3-(benzo[b]thiophen-2-yl)imidazo[1,2-b]pyridazin-6-ylamino)pyridin-2-ol |
| 47 | 3,4-dichlorobenzenamine | 3-(benzo[b]thiophen-2-yl)-N-(3,4-dichlorophenyl)imidazo[1,2-b]pyridazin-6-amine |
| 48 | 3-(trifluoromethoxy)benzenamine | 3-(benzo[b]thiophen-2-yl)-N-(3-(trifluoromethoxy)phenyl)imidazo[1,2-b]pyridazin-6-amine |

Compounds 12-16, 22-38, 41-45, 47-48 were physically characterized by electrospray ionization mass spectrometry. Structures and molecular masses are given below in Table 8-b.

TABLE 8-b

| Cd. | Structure | IUPAC Name | [M + H]$^+$ |
|---|---|---|---|
| 12 | 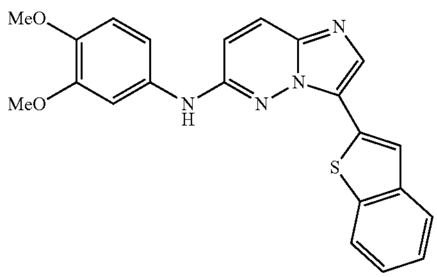 [SMILES: COc1ccc(Nc2ccc3ncc(-c4cc5ccccc5s4)n3n2)cc1OC] | 3-(benzo[b]thiophen-2-yl)-N-(3,4-dimethoxyphenyl)imidazo[1,2-b]pyridazin-6-amine | 403.6 |
| 13 | 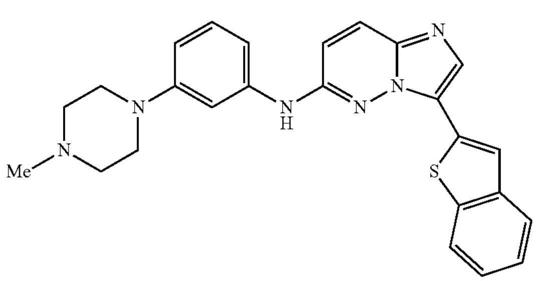 [SMILES: CN1CCN(c2cccc(Nc3ccc4ncc(-c5cc6ccccc6s5)n4n3)c2)CC1] | 3-(benzo[b]thiophen-2-yl)-N-(3-(4-methylpiperazin-1-yl)phenyl)imidazo[1,2-b]pyridazin-6-amine | 441.6 |

TABLE 8-b-continued

| Cd. | Structure | IUPAC Name | [M + H]⁺ |
|---|---|---|---|
| 14 | 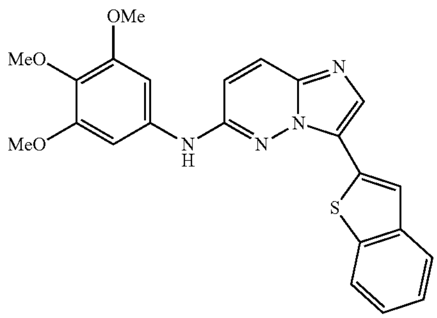 [SMILES: COc1cc(Nc2ccc3ncc(-c4cc5ccccc5s4)n3n2)cc(OC)c1OC] | 3-(benzo[b]thiophen-2-yl)-N-(3,4,5-trimethoxyphenyl)imidazo[1,2-b]pyridazin-6-amine | 433.7 |
| 15 | 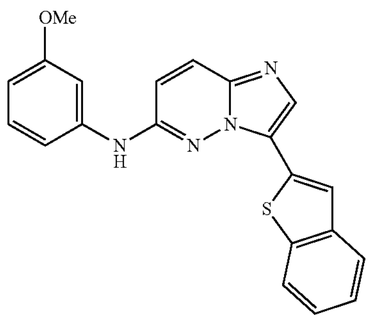 [SMILES: COc1cccc(Nc2ccc3ncc(-c4cc5ccccc5s4)n3n2)c1] | 3-(benzo[b]thiophen-2-yl)-N-(3-methoxyphenyl)imidazo[1,2-b]pyridazin-6-amine | 373.6 |
| 16 | 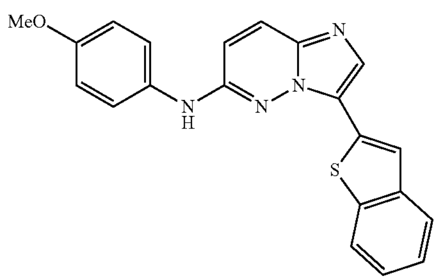 [SMILES: COc1ccc(Nc2ccc3ncc(-c4cc5ccccc5s4)n3n2)cc1] | 3-(benzo[b]thiophen-2-yl)-N-(4-methoxyphenyl)imidazo[1,2-b]pyridazin-6-amine | 373.6 |
| 22 | 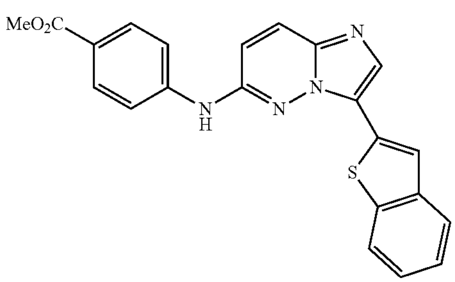 [SMILES: COC(=O)c1ccc(Nc2ccc3ncc(-c4cc5ccccc5s4)n3n2)cc1] | methyl 4-(3-(benzo[b]thiophen-2-yl)imidazo[1,2-b]pyridazin-6-ylamino)benzoate | 401.6 |
| 23 | 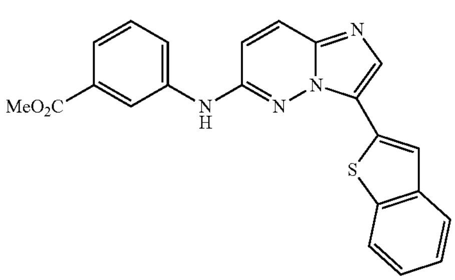 [SMILES: COC(=O)c1cccc(Nc2ccc3ncc(-c4cc5ccccc5s4)n3n2)c1] | methyl 3-(3-(benzo[b]thiophen-2-yl)imidazo[1,2-b]pyridazin-6-ylamino)benzoate | 401.7 |

TABLE 8-b-continued

| Cd. | Structure | IUPAC Name | [M + H]+ |
|---|---|---|---|
| 24 | 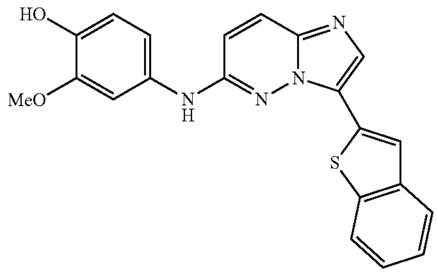 [SMILES: COc1cc(Nc2ccc3ncc(-c4cc5ccccc5s4)n3n2)ccc1O] | 4-(3-(benzo[b]thiophen-2-yl)imidazo[1,2-b]pyridazin-6-ylamino)-2-methoxyphenol | 389.6 |
| 25 | 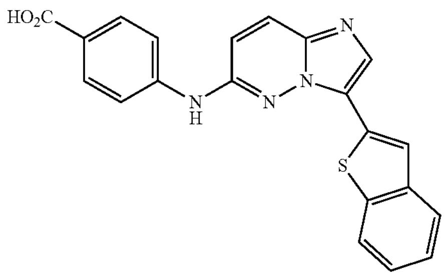 [SMILES: O=C(O)c1ccc(Nc2ccc3ncc(-c4cc5ccccc5s4)n3n2)cc1] | 4-(3-(benzo[b]thiophen-2-yl)imidazo[1,2-b]pyridazin-6-ylamino)benzoic acid | 387.6 |
| 26 | 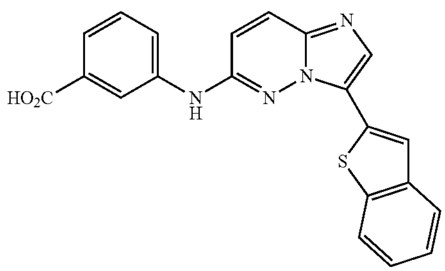 [SMILES: O=C(O)c1cccc(Nc2ccc3ncc(-c4cc5ccccc5s4)n3n2)c1] | 3-(3-(benzo[b]thiophen-2-yl)imidazo[1,2-b]pyridazin-6-ylamino)benzoic acid | 387.7 |
| 27 | 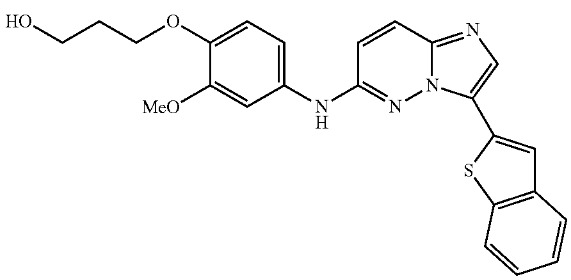 [SMILES: COc1cc(Nc2ccc3ncc(-c4cc5ccccc5s4)n3n2)ccc1OCCCO] | 3-(4-(3-(benzo[b]thiophen-2-yl)imidazo[1,2-b]pyridazin-6-ylamino)-2-methoxyphenoxy)propan-1-ol | 447.6 |
| 28 | 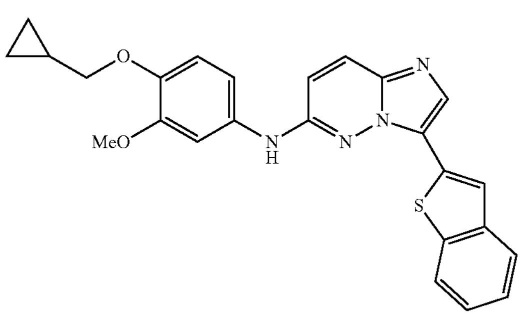 [SMILES: COc1cc(Nc2ccc3ncc(-c4cc5ccccc5s4)n3n2)ccc1OCC1CC1] | 3-(benzo[b]thiophen-2-yl)-N-(4-(cyclopropylmethoxy)-3-methoxyphenyl)imidazo[1,2-b]pyridazin-6-amine | 443.7 |

TABLE 8-b-continued

| Cd. | Structure | IUPAC Name | [M + H]+ |
|---|---|---|---|
| 29 | 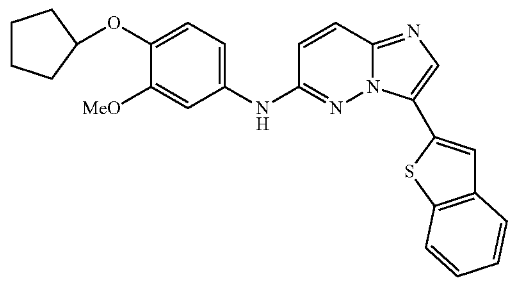 [SMILES: COc1cc(Nc2ccc3ncc(-c4cc5ccccc5s4)n3n2)ccc1OC1CCCC1] | 3-(benzo[b]thiophen-2-yl)-N-(4-(cyclopentylmethoxy)-3-methoxyphenyl)imidazo[1,2-b]pyridazin-6-amine | 457.7 |
| 30 | 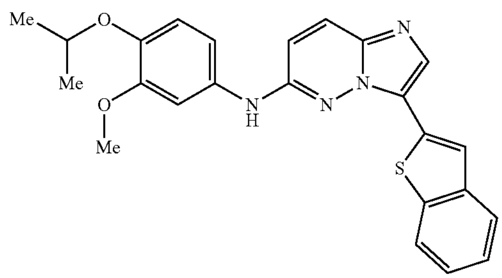 [SMILES: COc1cc(Nc2ccc3ncc(-c4cc5ccccc5s4)n3n2)ccc1OC(C)C] | 3-(benzo[b]thiophen-2-yl)-N-(4-isopropoxy-3-methoxyphenyl)imidazo[1,2-b]pyridazin-6-amine | 431.8 |
| 31 | 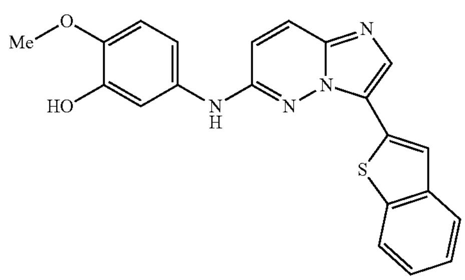 [SMILES: COc1ccc(Nc2ccc3ncc(-c4cc5ccccc5s4)n3n2)cc1O] | 5-(3-(benzo[b]thiophen-2-yl)imidazo[1,2-b]pyridazin-6-ylamino)-2-methoxyphenol | 389.8 |
| 32 | 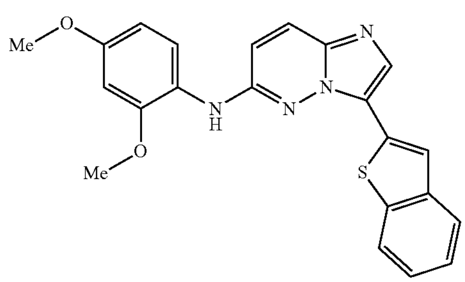 [SMILES: COc1ccc(Nc2ccc3ncc(-c4cc5ccccc5s4)n3n2)c(OC)c1] | 3-(benzo[b]thiophen-2-yl)-N-(2,4-dimethoxyphenyl)imidazo[1,2-b]pyridazin-6-amine | 403.6 |
| 33 | 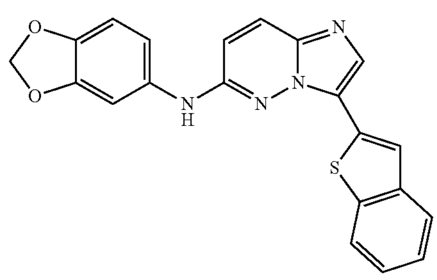 [SMILES: c1ccc2sc(-c3cnc4ccc(Nc5ccc6c(c5)OCO6)nn34)cc2c1] | 3-(benzo[b]thiophen-2-yl)-N-(benzo[d][1,3]dioxol-6-yl)imidazo[1,2-b]pyridazin-6-amine | 387.6 |

TABLE 8-b-continued

| Cd. | Structure | IUPAC Name | [M + H]+ |
|---|---|---|---|
| 34 | 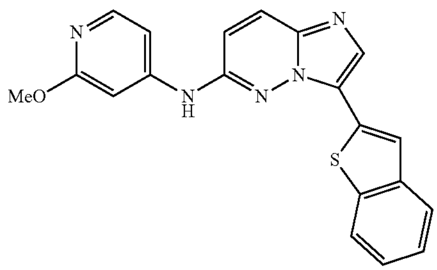 [SMILES: COc1cc(Nc2ccc3ncc(-c4cc5ccccc5s4)n3n2)ccn1] | 3-(benzo[b]thiophen-2-yl)-N-(2-methoxypyridin-4-yl)imidazo[1,2-b]pyridazin-6-amine | 374.8 |
| 35 | 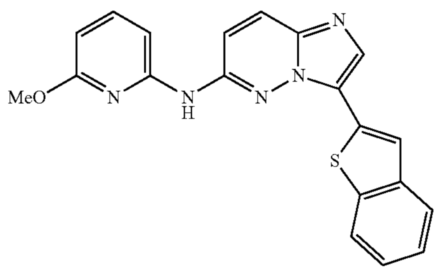 [SMILES: COc1cccc(Nc2ccc3ncc(-c4cc5ccccc5s4)n3n2)n1] | 3-(benzo[b]thiophen-2-yl)-N-(6-methoxypyridin-2-yl)imidazo[1,2-b]pyridazin-6-amine | 376.8 |
| 36 | 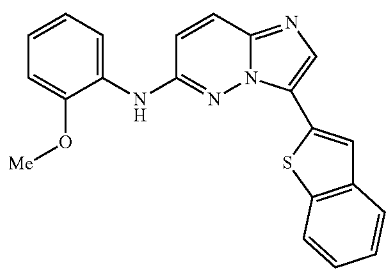 [SMILES: COc1ccccc1Nc1ccc2ncc(-c3cc4ccccc4s3)n2n1] | 3-(benzo[b]thiophen-2-yl)-N-(2-methoxyphenyl)imidazo[1,2-b]pyridazin-6-amine | 373.6 |
| 37 | 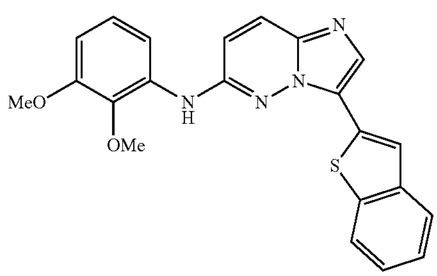 [SMILES: COc1cccc(Nc2ccc3ncc(-c4cc5ccccc5s4)n3n2)c1OC] | 3-(benzo[b]thiophen-2-yl)-N-(2,3-dimethoxyphenyl)imidazo[1,2-b]pyridazin-6-amine | 403.7 |
| 38 | 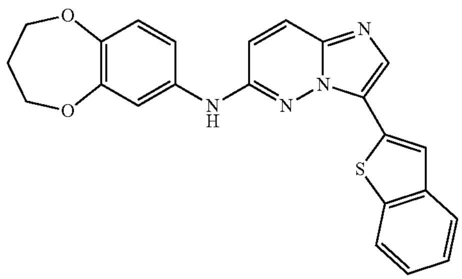 [SMILES: c1ccc2sc(-c3cnc4ccc(Nc5ccc6c(c5)OCCCO6)nn34)cc2c1] | 3-(benzo[b]thiophen-2-yl)-N-(3,4-dihydro-2H-benzo[b][1,4]dioxepin-8-yl)imidazo[1,2-b]pyridazin-6-amine | 415.8 |

TABLE 8-b-continued

| Cd. | Structure | IUPAC Name | [M + H]+ |
|---|---|---|---|
| 41 | 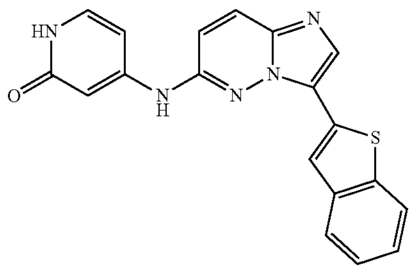 [SMILES: O=c1cc(Nc2ccc3ncc(-c4cc5ccccc5s4)n3n2)cc[nH]1] | 4-(3-(benzo[b]thiophen-2-yl)imidazo[1,2-b]pyridazin-6-ylamino)pyridin-2-ol | 360.5 |
| 42 | 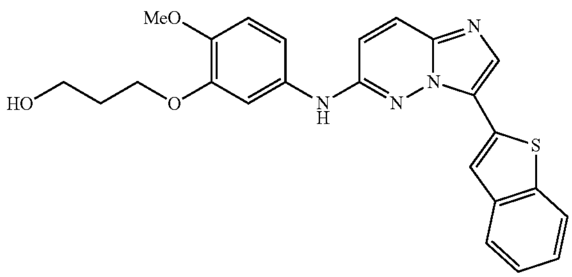 [SMILES: COc1ccc(Nc2ccc3ncc(-c4cc5ccccc5s4)n3n2)cc1OCCCO] | 3-(5-(3-(benzo[b]thiophen-2-yl)imidazo[1,2-b]pyridazin-6-ylamino)-2-methoxyphenoxy)propan-1-ol | 447.8 |
| 43 | 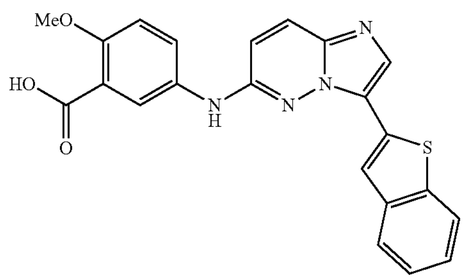 [SMILES: COc1ccc(Nc2ccc3ncc(-c4cc5ccccc5s4)n3n2)cc1C(=O)O] | 5-(3-(benzo[b]thiophen-2-yl)imidazo[1,2-b]pyridazin-6-ylamino)-2-methoxybenzoic acid | 417.9 |
| 44 | 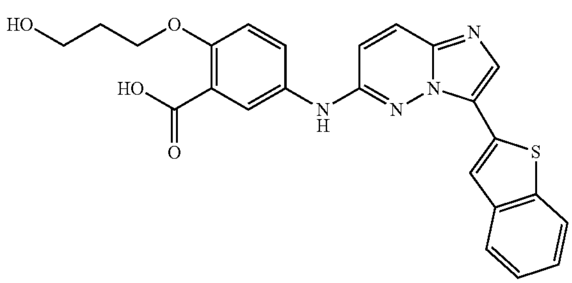 [SMILES: O=C(O)c1cc(Nc2ccc3ncc(-c4cc5ccccc5s4)n3n2)ccc1OCCCO] | 5-(3-(benzo[b]thiophen-2-yl)imidazo[1,2-b]pyridazin-6-ylamino)-2-(3-hydroxypropoxy)benzoic acid | 461.8 |
| 45 | 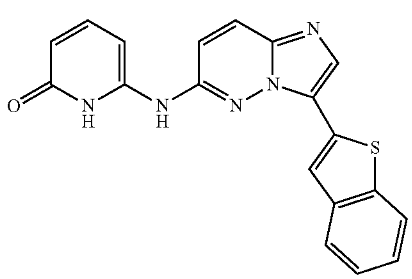 [SMILES: O=c1cccc(Nc2ccc3ncc(-c4cc5ccccc5s4)n3n2)[nH]1] | 6-(3-(benzo[b]thiophen-2-yl)imidazo[1,2-b]pyridazin-6-ylamino)pyridin-2-ol | 360.6 |

TABLE 8-b-continued

| Cd. | Structure | IUPAC Name | [M + H]+ |
|---|---|---|---|
| 47 | 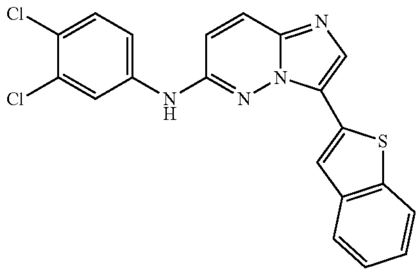 [SMILES: Clc1ccc(Nc2ccc3ncc(-c4cc5ccccc5s4)n3n2)cc1Cl] | 3-(benzo[b]thiophen-2-yl)-N-(3,4-dichlorophenyl)imidazo[1,2-b]pyridazin-6-amine | 411.4, 415.4 |
| 48 | 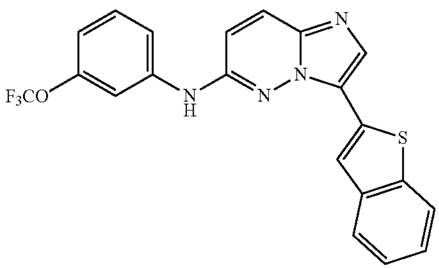 [SMILES: FC(F)(F)Oc1cccc(Nc2ccc3ncc(-c4cc5ccccc5s4)n3n2)c1] | 3-(benzo[b]thiophen-2-yl)-N-(3-(trifluoromethoxy)phenyl)imidazo[1,2-b]pyridazin-6-amine | 427.6 |

EXAMPLE 9

Synthesis of Compounds 105, 107-110, 119, 122-127, 129-132, 134-139

Preparation of 3-(benzo[b]thiophen-2-yl)-N-arylimidazo[1,2-b]pyridazin-6-amine

Scheme 9

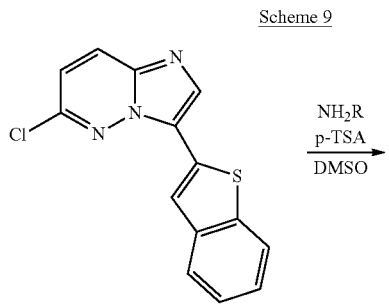

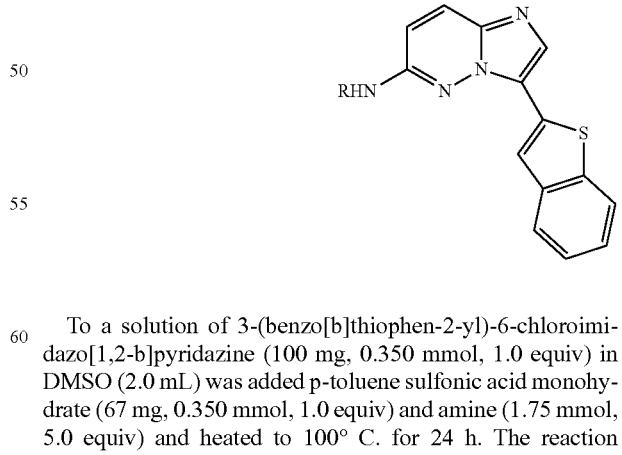

To a solution of 3-(benzo[b]thiophen-2-yl)-6-chloroimidazo[1,2-b]pyridazine (100 mg, 0.350 mmol, 1.0 equiv) in DMSO (2.0 mL) was added p-toluene sulfonic acid monohydrate (67 mg, 0.350 mmol, 1.0 equiv) and amine (1.75 mmol, 5.0 equiv) and heated to 100° C. for 24 h. The reaction mixture was diluted with water and extracted with ethyl acetate. Purification by column chromatography using 5% methanol in dichloromethane elution gave the product.

TABLE 9-a

| Cd. | Amine | Purified Compound Isolated |
|---|---|---|
| 105 | trans-4-aminocyclohexanol | trans-4-(3-(benzo[b]thiophen-2-yl)imidazo[1,2-b]pyridazin-6-ylamino)cyclohexanol |
| 107 | N-methylpropan-1-amine | 3-(benzo[b]thiophen-2-yl)-N-methyl-N-propylimidazo[1,2-b]pyridazin-6-amine |
| 108 | 2-aminoethanol | 2-(3-(benzo[b]thiophen-2-yl)imidazo[1,2-b]pyridazin-6-ylamino)ethanol |
| 109 | 3-aminopropan-1-ol | 3-(3-(benzo[b]thiophen-2-yl)imidazo[1,2-b]pyridazin-6-ylamino)propan-1-ol |
| 110 | 4-aminobutan-1-ol | 4-(3-(benzo[b]thiophen-2-yl)imidazo[1,2-b]pyridazin-6-ylamino)butan-1-ol |
| 119 | 2-(piperazin-1-yl)ethanol | 2-(4-(3-(benzo[b]thiophen-2-yl)imidazo[1,2-b]pyridazin-6-yl)piperazin-1-yl)ethanol |
| 122 | cis-3-aminocyclohexanol | cis-3-(3-(benzo[b]thiophen-2-yl)imidazo[1,2-b]pyridazin-6-ylamino)cyclohexanol |
| 123 | trans-3-aminocyclohexanol | trans-3-(3-(benzo[b]thiophen-2-yl)imidazo[1,2-b]pyridazin-6-ylamino)cyclohexanol |
| 124 | (S)-2-methylpentan-3-amine | 3-(benzo[b]thiophen-2-yl)-N-((S)-2-methylpentan-3-yl)imidazo[1,2-b]pyridazin-6-amine |
| 125 | (R)-2-methylpentan-3-amine | 3-(benzo[b]thiophen-2-yl)-N-((R)-2-methylpentan-3-yl)imidazo[1,2-b]pyridazin-6-amine |
| 126 | ((R)-pyrrolidin-2-yl)methanol | ((R)-1-(3-(benzo[b]thiophen-2-yl)imidazo[1,2-b]pyridazin-6-yl)pyrrolidin-2-yl)methanol |
| 127 | ((S)-pyrrolidin-2-yl)methanol | ((S)-1-(3-(benzo[b]thiophen-2-yl)imidazo[1,2-b]pyridazin-6-yl)pyrrolidin-2-yl)methanol |
| 129 | (R)-2-amino-4-methylpentan-1-ol | (R)-2-(3-(benzo[b]thiophen-2-yl)imidazo[1,2-b]pyridazin-6-ylamino)-4-methylpentan-1-ol |
| 130 | (S)-2-amino-4-methylpentan-1-ol | (S)-2-(3-(benzo[b]thiophen-2-yl)imidazo[1,2-b]pyridazin-6-ylamino)-4-methylpentan-1-ol |
| 131 | methyl piperidine-3-carboxylate | methyl 1-(3-(benzo[b]thiophen-2-yl)imidazo[1,2-b]pyridazin-6-yl)piperidine-3-carboxylate |
| 132 | (piperidin-3-yl)methanol | (1-(3-(benzo[b]thiophen-2-yl)imidazo[1,2-b]pyridazin-6-yl)piperidin-3-yl)methanol |
| 134 | 4-tert-butylcyclohexanamine | N-(4-tert-butylcyclohexyl)-3-(benzo[b]thiophen-2-yl)imidazo[1,2-b]pyridazin-6-amine |
| 135 | 5-aminopentan-1-ol | 5-(3-(benzo[b]thiophen-2-yl)imidazo[1,2-b]pyridazin-6-ylamino)pentan-1-ol |
| 136 | 3-(4-methylpiperazin-1-yl)propan-1-amine | 3-(benzo[b]thiophen-2-yl)-N-(3-(4-methylpiperazin-1-yl)propyl)imidazo[1,2-b]pyridazin-6-amine |
| 137 | 1-cyclohexylpiperidin-3-amine | 3-(benzo[b]thiophen-2-yl)-N-(1-cyclohexylpiperidin-3-yl)imidazo[1,2-b]pyridazin-6-amine |
| 138 | 4-amino-2-methylbutan-1-ol | 4-(3-(benzo[b]thiophen-2-yl)imidazo[1,2-b]pyridazin-6-ylamino)-2-methylbutan-1-ol |
| 139 | trans-4-aminocyclohexyl)methanol | trans-4-(3-(benzo[b]thiophen-2-yl)imidazo[1,2-b]pyridazin-6-ylamino)cyclohexyl)methanol |

Compounds 105, 107-110, 119, 122-127, 129-132, 134-139-were physically characterized by electrospray ionization mass spectrometry. Structures and molecular masses are given below in Table 9-b.

TABLE 9-b

| Cd. | Structure | IUPAC Name | [M + H]+ |
|---|---|---|---|
| 105 | 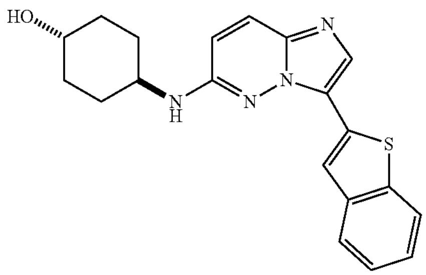 | trans-4-(3-(benzo[b]thiophen-2-yl)imidazo[1,2-b]pyridazin-6-ylamino)cyclohexanol | 365.6 |
| 107 | 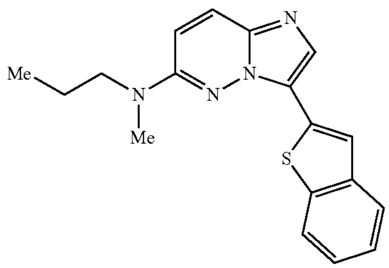 [SMILES: CCCN(C)c1ccc2ncc(-c3cc4ccccc4s3)n2n1] | 3-(benzo[b]thiophen-2-yl)-N-methyl-N-propylimidazo[1,2-b]pyridazin-6-amine | 323.6 |
| 108 | 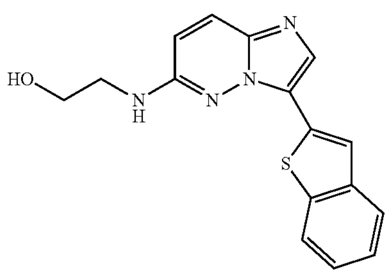 [SMILES: OCCNc1ccc2ncc(-c3cc4ccccc4s3)n2n1] | 2-(3-(benzo[b]thiophen-2-yl)imidazo[1,2-b]pyridazin-6-ylamino)ethanol | 311.7 |
| 109 | 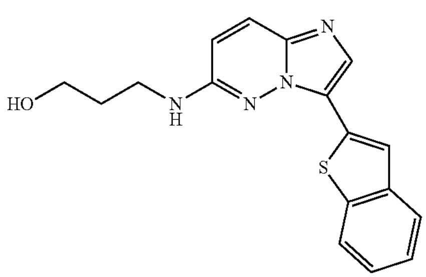 [SMILES: OCCCNc1ccc2ncc(-c3cc4ccccc4s3)n2n1] | 3-(3-(benzo[b]thiophen-2-yl)imidazo[1,2-b]pyridazin-6-ylamino)propan-1-ol | 325.6 |
| 110 | 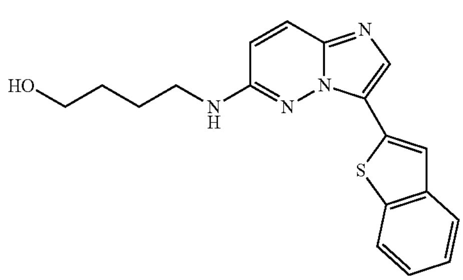 [SMILES: OCCCCNc1ccc2ncc(-c3cc4ccccc4s3)n2n1] | 4-(3-(benzo[b]thiophen-2-yl)imidazo[1,2-b]pyridazin-6-ylamino)butan-1-ol | 339.7 |

TABLE 9-b-continued

| Cd. | Structure | IUPAC Name | [M + H]+ |
|---|---|---|---|
| 119 | 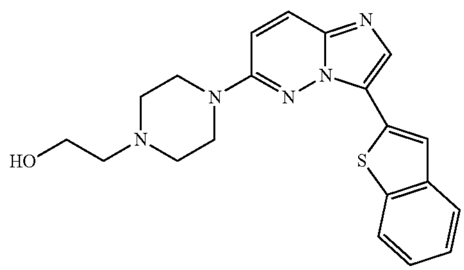 [SMILES: OCCN1CCN(c2ccc3ncc(-c4cc5ccccc5s4)n3n2)CC1] | 2-(4-(3-(benzo[b]thiophen-2-yl)imidazo[1,2-b]pyridazin-6-yl)piperazin-1-yl)ethanol | 380.8 |
| 122 | 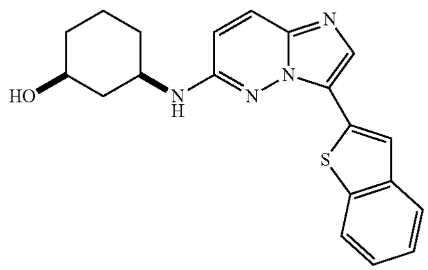 | cis-3-(3-(benzo[b]thiophen-2-yl)imidazo[1,2-b]pyridazin-6-ylamino)cyclohexanol | 365.8 |
| 123 | 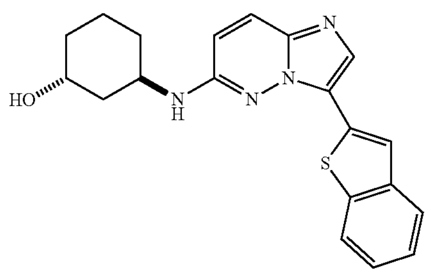 | trans-3-(3-(benzo[b]thiophen-2-yl)imidazo[1,2-b]pyridazin-6-ylamino)cyclohexanol | 365.8 |
| 124 | 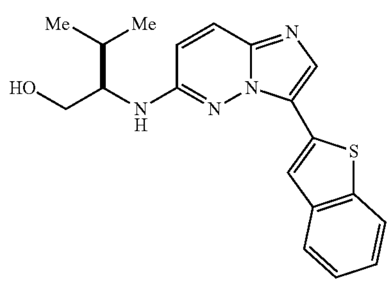 [SMILES: CC(C)[C@H](CO)Nc1ccc2ncc(-c3cc4ccccc4s3)n2n1] | 3-(benzo[b]thiophen-2-yl)-N-((S)-2-methylpentan-3-yl)imidazo[1,2-b]pyridazin-6-amine | 353.8 |
| 125 | 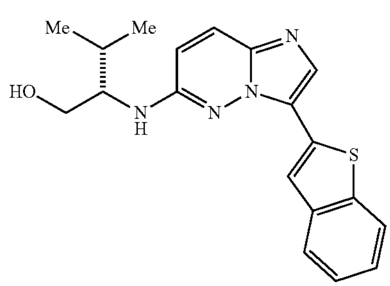 [SMILES: CC(C)[C@@H](CO)Nc1ccc2ncc(-c3cc4ccccc4s3)n2n1] | 3-(benzo[b]thiophen-2-yl)-N-((R)-2-methylpentan-3-yl)imidazo[1,2-b]pyridazin-6 amine | 353.8 |

TABLE 9-b-continued

| Cd. | Structure | IUPAC Name | [M + H]+ |
|---|---|---|---|
| 126 | 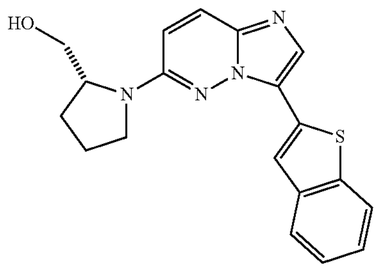 [SMILES: OC[C@H]1CCCN1c1ccc2ncc(-c3cc4ccccc4s3)n2n1] | ((R)-1-(3-(benzo[b]thiophen-2-yl)imidazo[1,2-b]pyridazin-6-yl)pyrrolidin-2-yl)methanol | 351.9 |
| 127 | 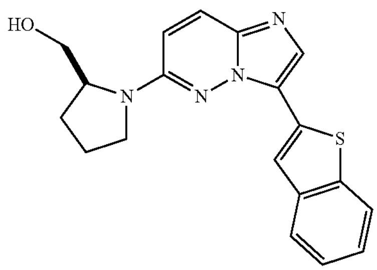 [SMILES: OC[C@@H]1CCCN1c1ccc2ncc(-c3cc4ccccc4s3)n2n1] | ((S)-1-(3-(benzo[b]thiophen-2-yl)imidazo[1,2-b]pyridazin-6-yl)pyrrolidin-2-yl)methanol | 351.7 |
| 129 | 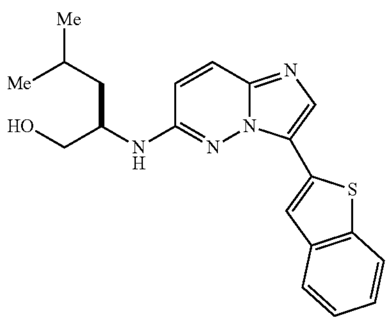 [SMILES: CC(C)C[C@H](CO)Nc1ccc2ncc(-c3cc4ccccc4s3)n2n1] | (R)-2-(3-(benzo[b]thiophen-2-yl)imidazo[1,2-b]pyridazin-6-ylamino)-4-methylpentan-1-ol | 367.7 |
| 130 | 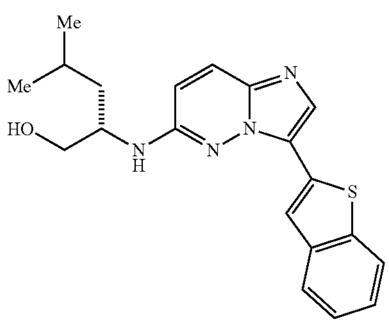 [SMILES: CC(C)C[C@@H](CO)Nc1ccc2ncc(-c3cc4ccccc4s3)n2n1] | (S)-2-(3-(benzo[b]thiophen-2-yl)imidazo[1,2-b]pyridazin-6-ylamino)-4-methylpentan-1-ol | 367.6 |
| 131 | 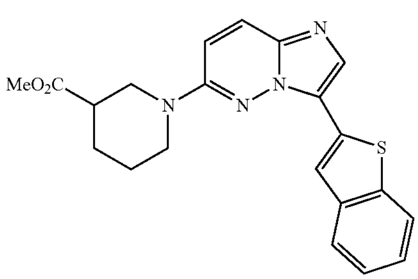 [SMILES: COC(=O)C1CCCN(c2ccc3ncc(-c4cc5ccccc5s4)n3n2)C1] | methyl 1-(3-(benzo[b]thiophen-2-yl)imidazo[1,2-b]pyridazin-6-yl)piperidine-3-carboxylate | 393.5 |

TABLE 9-b-continued

| Cd. | Structure | IUPAC Name | [M + H]+ |
|---|---|---|---|
| 132 | 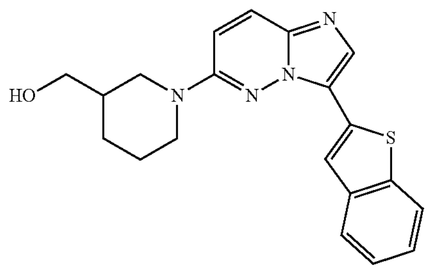 [SMILES: OCC1CCCN(c2ccc3ncc(-c4cc5ccccc5s4)n3n2)C1] | (1-(3-(benzo[b]thiophen-2-yl)imidazo[1,2-b]pyridazin-6-yl)piperidin-3-yl)methanol | 365.8 |
| 134 | 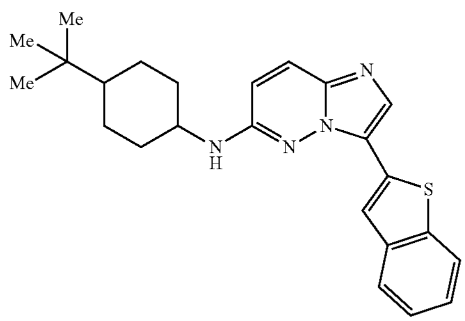 [SMILES: CC(C)(C)C1CCC(Nc2ccc3ncc(-c4cc5ccccc5s4)n3n2)CC1] | N-(4-tert-butylcyclohexyl)-3-(benzo[b]thiophen-2-yl)imidazo[1,2-b]pyridazin-6-amine | 405.7 |
| 135 | 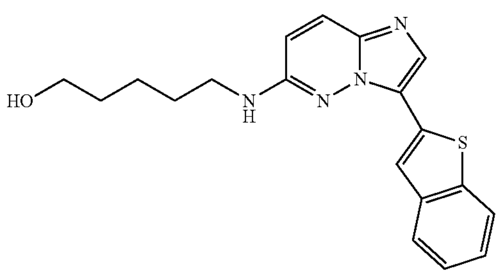 [SMILES: OCCCCCNc1ccc2ncc(-c3cc4ccccc4s3)n2n1] | 5-(3-(benzo[b]thiophen-2-yl)imidazo[1,2-b]pyridazin-6-ylamino)pentan-1-ol | 353.6 |
| 136 | 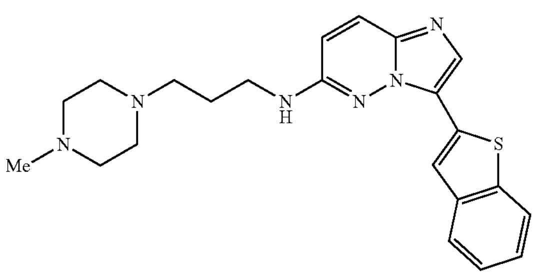 [SMILES: CN1CCN(CCCNc2ccc3ncc(-c4cc5ccccc5s4)n3n2)CC1] | 3-(benzo[b]thiophen-2-yl)-N-(3-(4-methylpiperazin-1-yl)propyl)imidazo[1,2-b]pyridazin-6-amine | 407.5 |
| 137 | 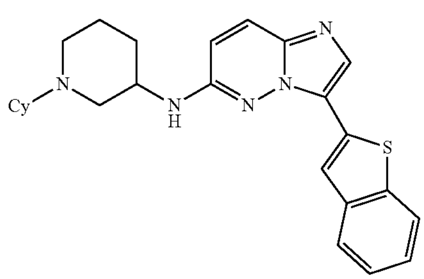 | 3-(benzo[b]thiophen-2-yl)-N-(1-cyclohexylpiperidin-3-yl)imidazo[1,2-b]pyridazin-6-amine | 432.5 |

TABLE 9-b-continued

| Cd. | Structure | IUPAC Name | [M + H]+ |
|---|---|---|---|
| 138 | 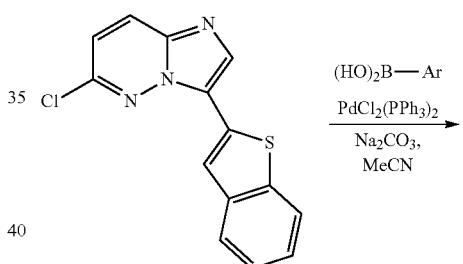 | 4-(3-(benzo[b]thiophen-2-yl)imidazo[1,2-b]pyridazin-6-ylamino)-2-methylbutan-1-ol | 353.6 |
| 139 | 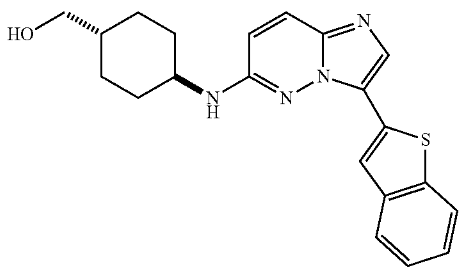 | trans-4-(3-(benzo[b]thiophen-2-yl)imidazo[1,2-b]pyridazin-6-ylamino)cyclohexyl)methanol | 379.7 |

EXAMPLE 10

Synthesis of Compounds 39-40

Scheme 10

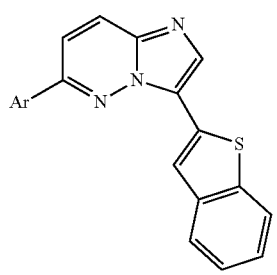

Preparation of 3-(benzo[b]thiophen-2-yl)-6-arylimidazo[1,2-b]pyridazine

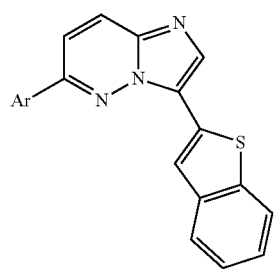

3-(benzo[b]thiophen-2-yl)-6-chloroimidazo[1,2-b]pyridazine (50 mg, 0.175 mmol, 1.0 equiv), in acetonitrile (1.9 mL), was added the boronic ester (0.263 mmol, 1.5 equiv), bis(triphenylphosphine)palladium(II) chloride (12 mg, 0.018 mmol, 0.1 equiv), then sodium carbonate (1.0 M aqueous solution, 10 equiv). The reaction mixture was irradiated at 150° C. for 10 min. Purification by column chromatography gave of the product.

TABLE 10-a

| Cd. | Boronic Ester | Purified Compound Isolated |
|---|---|---|
| 39 | 1-(4-(4,4,5,5-tetramethyl-1,3,2-dioxaborolan-2-yl)benzyl)-4-methylpiperazine | 3-(benzo[b]thiophen-2-yl)-6-(4-((4-methylpiperazin-1-yl)methyl)phenyl)imidazo[1,2-b]pyridazine |
| 40 | 1-(3-(4,4,5,5-tetramethyl-1,3,2-dioxaborolan-2-yl)benzyl)-4-methylpiperazine | 3-(benzo[b]thiophen-2-yl)-6-(3-((4-methylpiperazin-1-yl)methyl)phenyl)imidazo[1,2-b]pyridazine |

Compounds 39-40 were physically characterized by electrospray ionization mass spectrometry. Structures and molecular masses are given below in Table 10-b.

TABLE 10-b

| Cd. | Structure | IUPAC Name | [M + H]+ |
|---|---|---|---|
| 39 | 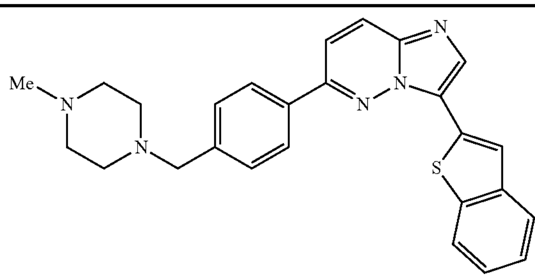 | 3-(benzo[b]thiophen-2-yl)-6-(4-((4-methylpiperazin-1-yl)methyl)phenyl)imidazo[1,2-b]pyridazine | 440.7 |
| 40 | 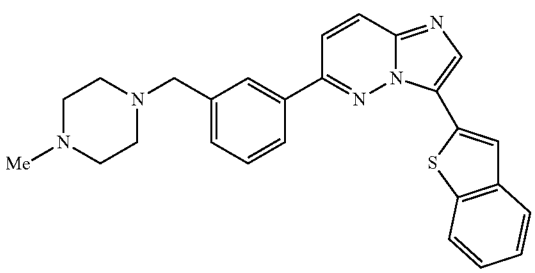 [SMILES: CN1CCN(Cc2cccc(-c3ccc4ncc(-c5cc6ccccc6s5)n4n3)c2)CC1] | 3-(benzo[b]thiophen-2-yl)-6-(3-((4-methylpiperazin-1-yl)methyl)phenyl)imidazo[1,2-b]pyridazine | 440.7 |

EXAMPLE 11

Synthesis of Compound 46

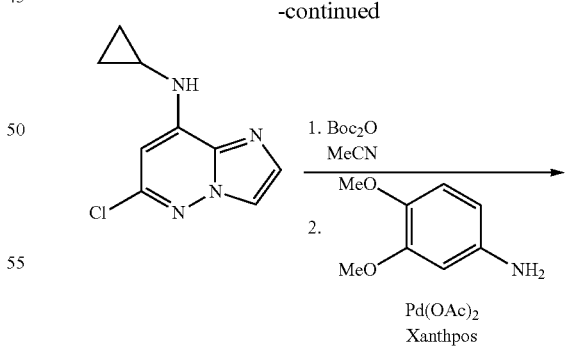

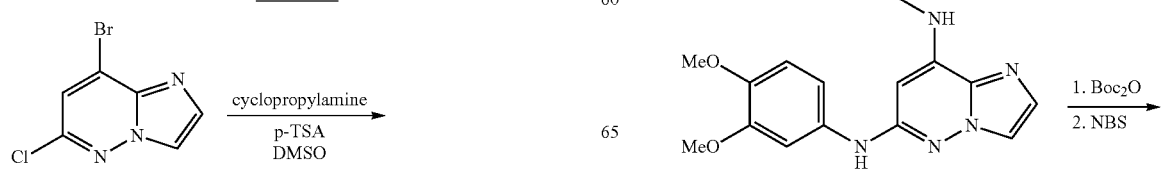

-continued

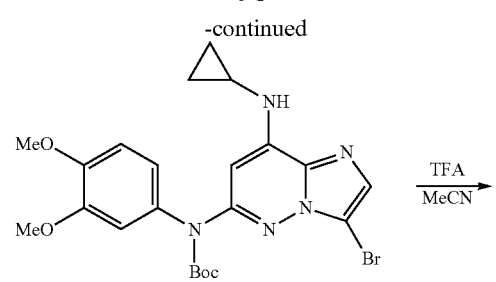

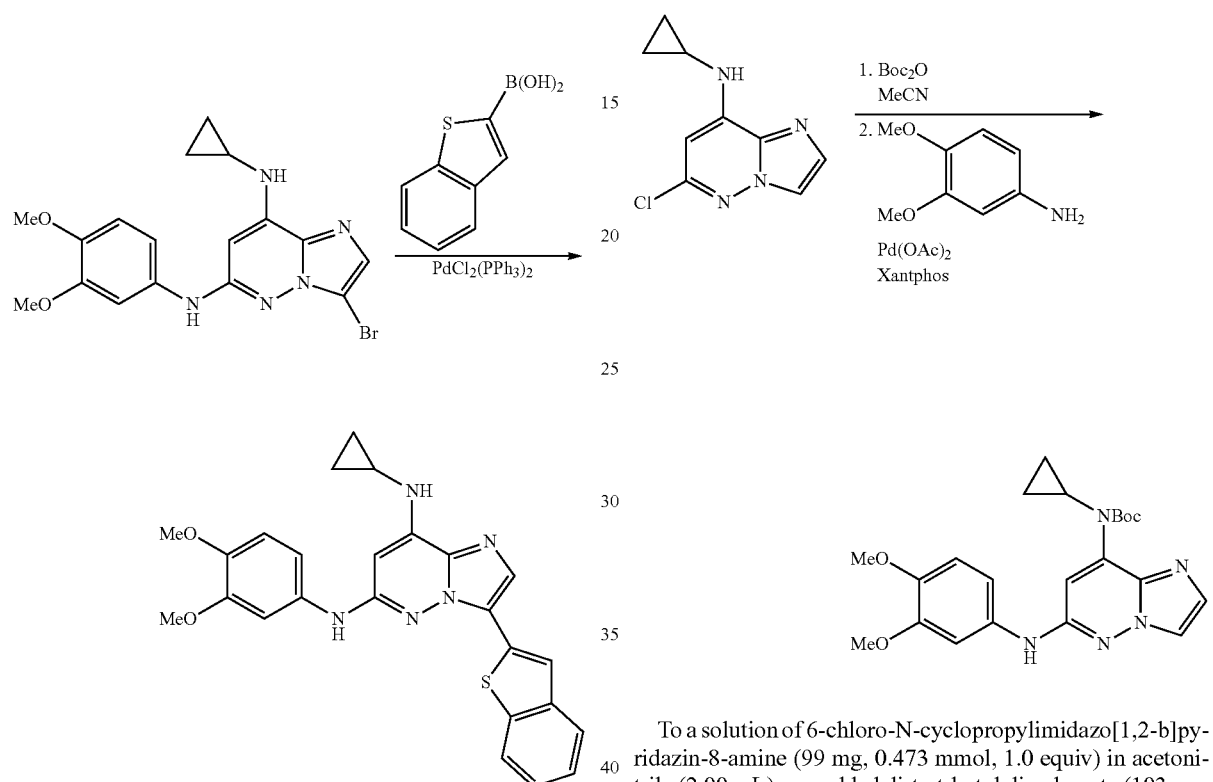

Preparation of 6-chloro-N-cyclopropylimidazo[1,2-b]pyridazin-8-amine

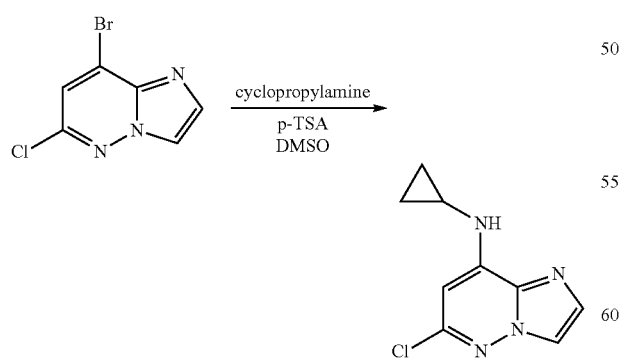

To a solution of 8-bromo-6-chloroimidazo[1,2-b]pyridazine (1.00 g, 3.21 mmol, 1.0 equiv) and p-TSA (611 mg, 3.21 mmol, 1.0 equiv) in DMSO (10.0 mL) was added cyclopropylamine (1.13 mL, 16.1 mmol, 5.0 equiv) and heated to 100° C. for 24 h. Purification by column chromatography using 50% ethyl acetate in hexanes elution gave 536 mg of the white solid, 80%.

Preparation of tert-butyl 6-(3,4-dimethoxyphenylamino)imidazo[1,2-b]pyridazin-8-ylcyclopropylcarbamate To a solution of 6-chloro-N-cyclopropylimidazo[1,2-b]pyridazin-8-amine (99 mg, 0.473 mmol, 1.0 equiv) in acetonitrile (2.00 mL) was added di-tert-butyl dicarbonate (103 mg, 0.473 mmol, 1.0 equiv) and stirred at room temperature for 15 h. The reaction mixture was diluted with water and extracted with ethyl acetate and concentrated in vacuo. The crude material was diluted in dioxane (5.00 mL) and 3,4-dimethoxyaniline (109 mg, 0.709 mmol, 1.3 equiv), xantphos (55 mg, 0.0946 mmol, 0.2 equiv), palladium acetate (11 mg, 0.0473 mmol, 0.1 equiv) and potassium carbonate (1.31 g, 9.46 mmol, 20 equiv) was added. The reaction mixture was heated in the microwave at 150° C. for 10 minutes. Purification by column chromatography using 2% methanol in hexanes elution gave 173 mg of the brown solid, 86%.

Preparation of bis-Boc-protected pyridazine

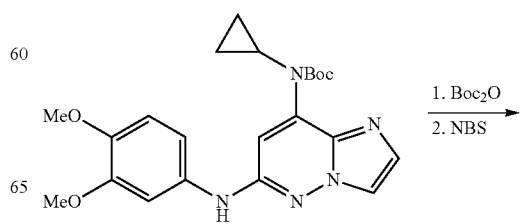

-continued

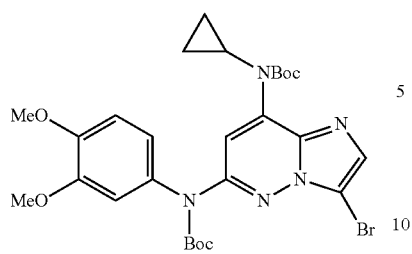

To a solution of tert-butyl 6-(3,4-dimethoxyphenylamino) imidazo[1,2-b]pyridazin-8-ylcyclopropylcarbamate (173 mg, 0.407 mmol, 1.0 equiv) in acetonitrile (5.00 mL) was added di-tert-butyl dicarbonate (177 mg, 0.813 mmol, 2.0 equiv) and catalytic 4-dimethylaminopyridine. After 15 h, the reaction was diluted with water and extracted with ethyl acetate. The crude material was diluted in chloroform (10.0 mL) and N-bromosuccinimide (72 mg, 0.407 mmol, 1.0 equiv) and heated to 70° C. for 20 minutes. Purification by column chromatography using 50% ethyl acetate in hexanes elution gave 214 mg of the yellow solid, 87%

Preparation of 3-bromo-$N_8$-cyclopropyl-$N_6$-(3,4-dimethoxyphenyl)imidazo[1,2-b]pyridazine-6,8-diamine

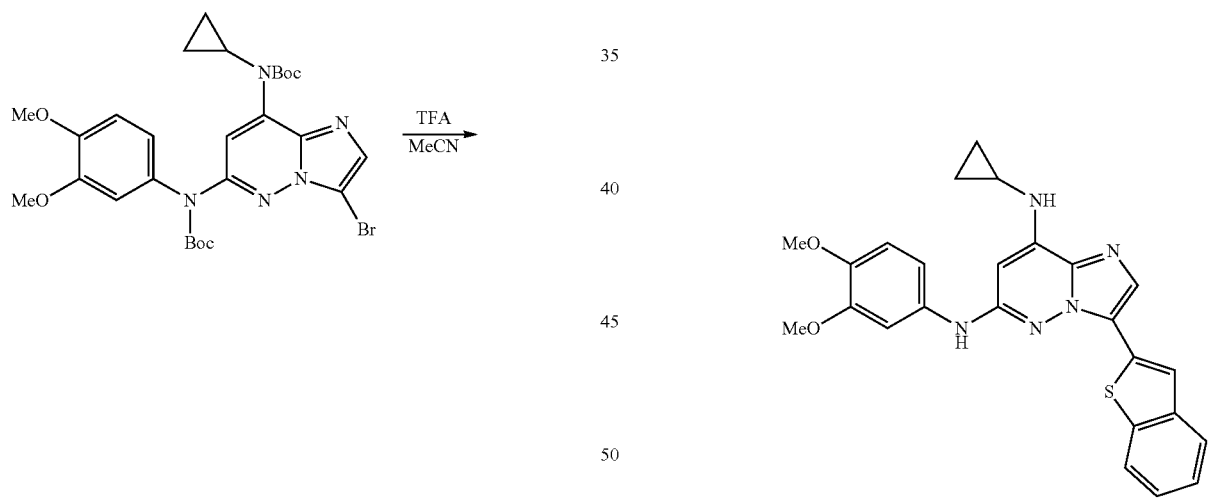

To the bis-Boc-protected pyridazine (99 mg, 0.163 mmol, 1.0 equiv) in dichloromethane (5.00 mL) was added excess trifluoroacetic acid (1.00 mL) and stirred for 3 h. The reaction was diluted with water and extracted with ethyl acetate. Purification by column chromatography using 2% methanol in hexanes elution gave 66 mg of the brown solid, 100%.

Preparation of 3-(benzo[b]thiophen-2-yl)-$N_8$-cyclopropyl-$N_6$-(3,4-dimethoxyphenyl)imidazo[1,2-b]pyridazine-6,8-diamine

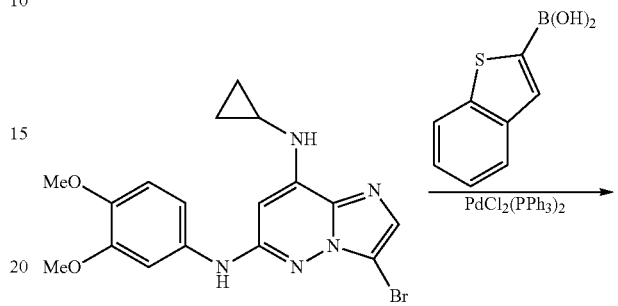

To a solution of 3-bromo-$N_8$-cyclopropyl-$N_6$-(3,4-dimethoxyphenyl)imidazo[1,2-b]pyridazine-6,8-diamine (66 mg, 0.163 mmol, 1.0 equiv) in acetonitrile (1.63 mL), was added benzo[b]thiophen-2-yl-2-boronic acid (58 mg, 0.327 mmol, 2.0 equiv), bis(triphenylphosphine)palladium(II) chloride (11 mg, 0.0163 mmol, 0.1 equiv), then sodium carbonate (1.63 mL, 1.0 M aqueous solution, 10 equiv). The reaction mixture was irradiated at 150° C. for 10 min. Purification by column chromatography gave 26 mg of the brown solid, 34%.

Compound 46 was physically characterized by electrospray ionization mass spectrometry. Structures and molecular masses are given below in Table 11-b.

TABLE 11-b

| Cd. | Structure | IUPAC Name | [M + H]+ |
|---|---|---|---|
| 46 | 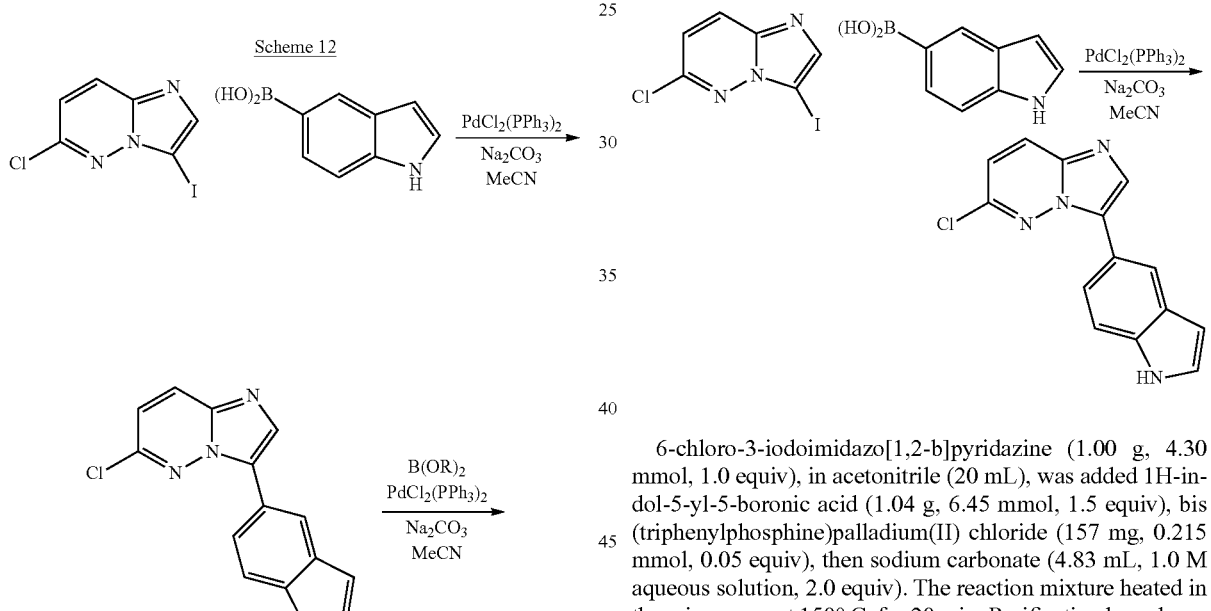 | 3-(benzo[b]thiophen-2-yl)-N$_8$-cyclopropyl-N$_6$-(3,4-dimethoxyphenyl)imidazo[1,2-b]pyridazine-6,8-diamine | 458.8 |

EXAMPLE 12

Synthesis of Compounds 49-50, 59

Scheme 12

Preparation of 6-chloro-3-(1H-indol-5-yl)imidazo[1,2-b]pyridazine 6-chloro-3-iodoimidazo[1,2-b]pyridazine (1.00 g, 4.30 mmol, 1.0 equiv), in acetonitrile (20 mL), was added 1H-indol-5-yl-5-boronic acid (1.04 g, 6.45 mmol, 1.5 equiv), bis(triphenylphosphine)palladium(II) chloride (157 mg, 0.215 mmol, 0.05 equiv), then sodium carbonate (4.83 mL, 1.0 M aqueous solution, 2.0 equiv). The reaction mixture heated in the microwave at 150° C. for 20 min. Purification by column chromatography using 2% methanol in dichloromethane elutions gave 1.04 g of the white solid, 60%.

Preparation of 3-(1H-indol-5-yl)-6-arylimidazo[1,2-b]pyridazine

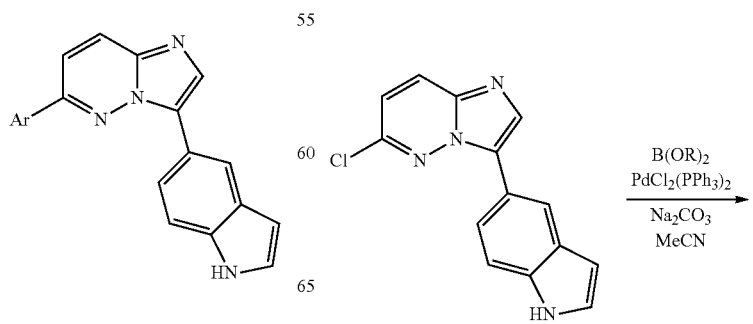

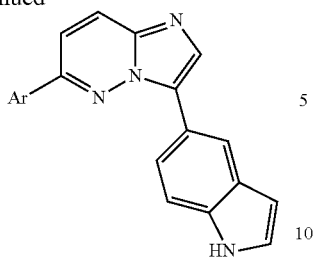

6-chloro-3-(1H-indol-5-yl)imidazo[1,2-b]pyridazine (60 mg, 0.223 mmol, 1.0 equiv), in acetonitrile (1.00 mL), was added boronic acid (0.241 mmol, 1.3 equiv), bis(triphenylphosphine)palladium(II) chloride (2 mg, 0.002, 0.01 equiv), then sodium carbonate (1.00 mL, 1.0 M aqueous solution). The reaction mixture heated in the microwave at 150° C. for 10 min. Purification by column chromatography using 5% methanol in hexanes elution gave the product.

TABLE 12-a

| Cd. | Boronic Ester | Purified Compound Isolated |
|---|---|---|
| 49 | 1-(4-(4,4,5,5-tetramethyl-1,3,2-dioxaborolan-2-yl)benzyl)-4-methylpiperazine | 3-(1H-indol-5-yl)-6-(4-((4-methylpiperazin-1-yl)methyl)phenyl)imidazo[1,2-b]pyridazine |
| 50 | 1H-indol-5-yl-5-boronic acid | 3,6-di(1H-indol-5-yl)imidazo[1,2-b]pyridazine |
| 59 | 3,4,5-trimethoxyphenyl-boronic acid | 3-(1H-indol-5-yl)-6-(3,4,5-trimethoxyphenyl)imidazo[1,2-b]pyridazine |

Compounds 49-50, 59 were physically characterized by electrospray ionization mass spectrometry. Structures and molecular masses are given below in Table 12-b.

TABLE 12-b

| Cd. | Structure | IUPAC Name | [M + H]⁺ |
|---|---|---|---|
| 49 | 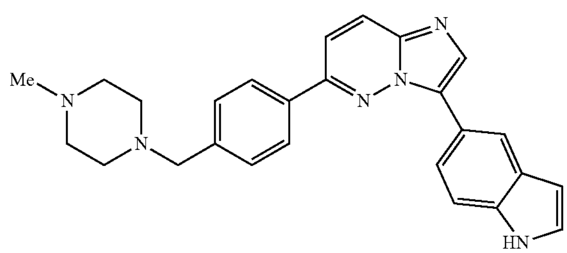 [SMILES: CN1CCN(Cc2ccc(-c3ccc4ncc(-c5ccc6[nH]ccc6c5)n4n3)cc2)CC1] | 3-(1H-indol-5-yl)-6-(4-((4-methylpiperazin-1-yl)methyl)phenyl)imidazo[1,2-b]pyridazine | 423.6 |
| 50 | 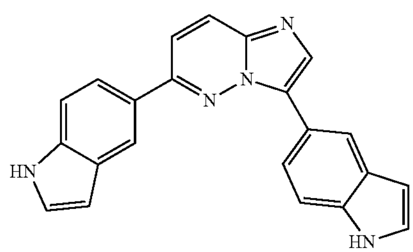 [SMILES: c1cc2cc(-c3ccc4ncc(-c5ccc6[nH]ccc6c5)n4n3)ccc2[nH]1] | 3,6-di(1H-indol-5-yl)imidazo[1,2-b]pyridazine | 350.6 |
| 59 | 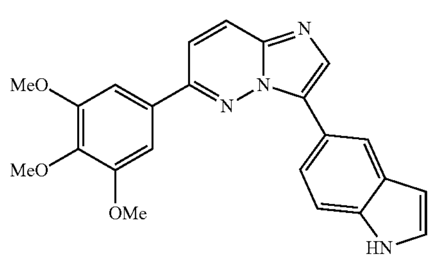 [SMILES: COc1cc(-c2ccc3ncc(-c4ccc5[nH]ccc5c4)n3n2)cc(OC)c1OC] | 3-(1H-indol-5-yl)-6-(3,4,5-trimethoxyphenyl)imidazo[1,2-b]pyridazine | 401.6 |

EXAMPLE 13

Synthesis of Compounds 52-58, 60-61

Scheme 13

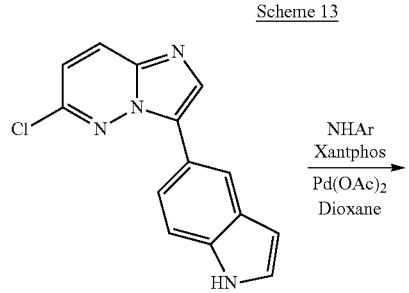

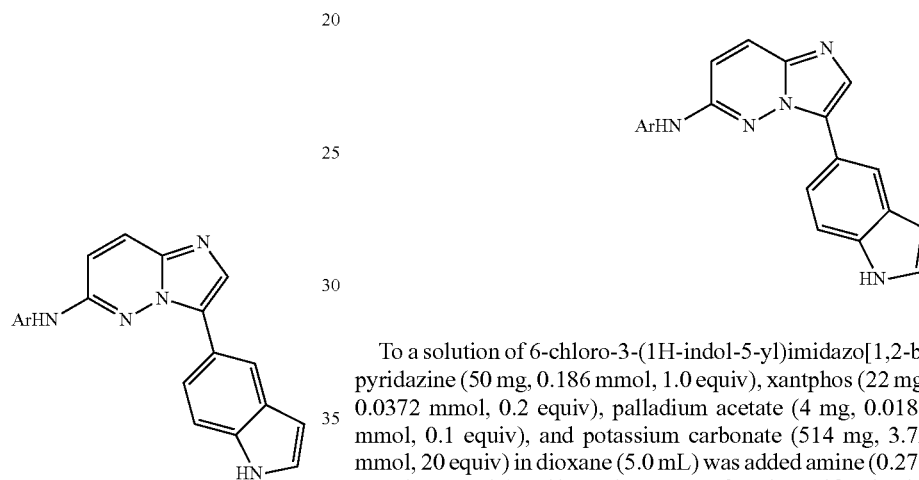

Preparation of 3-(1H-indol-5-yl)-N-arylimidazo[1,2-b]pyridazin-6-amine

To a solution of 6-chloro-3-(1H-indol-5-yl)imidazo[1,2-b]pyridazine (50 mg, 0.186 mmol, 1.0 equiv), xantphos (22 mg, 0.0372 mmol, 0.2 equiv), palladium acetate (4 mg, 0.0186 mmol, 0.1 equiv), and potassium carbonate (514 mg, 3.72 mmol, 20 equiv) in dioxane (5.0 mL) was added amine (0.279 mmol, 1.5 equiv) and heated to 100° C. for 2 h. Purification by column chromatography using 2% methanol in dichloromethane elution gave the product.

TABLE 13-a

| Cd. | Amine | Purified Compound Isolated |
|---|---|---|
| 52 | 4-methoxybenzenamine | 3-(1H-indol-5-yl)-N-(4-methoxyphenyl)imidazo[1,2-b]pyridazin-6-amine |
| 53 | 3,4-dimethoxyaniline | 3-(1H-indol-5-yl)-N-(3,4-dimethoxyphenyl)imidazo[1,2-b]pyridazin-6-amine |
| 54 | 3-methoxybenzenamine | 3-(1H-indol-5-yl)-N-(3-methoxyphenyl)imidazo[1,2-b]pyridazin-6-amine |
| 55 | 4-(4-methylpiperazin-1-yl)benzenamine | 3-(1H-indol-5-yl)-N-(4-(4-methylpiperazin-1-yl)phenyl)imidazo[1,2-b]pyridazin-6-amine |
| 56 | 3-(4-methylpiperazin-1-yl)benzenamine | 3-(1H-indol-5-yl)-N-(3-(4-methylpiperazin-1-yl)phenyl)imidazo[1,2-b]pyridazin-6-amine |
| 57 | 4-((4-methylpiperazin-1-yl)methyl)benzenamine | 3-(1H-indol-5-yl)-N-(4-((4-methylpiperazin-1-yl)methyl)phenyl)imidazo[1,2-b]pyridazin-6-amine |
| 58 | 3-((4-methylpiperazin-1-yl)methyl)benzenamine | 3-(1H-indol-5-yl)-N-(3-((4-methylpiperazin-1-yl)methyl)phenyl)imidazo[1,2-b]pyridazin-6-amine |
| 60 | methyl 4-aminobenzoate | methyl 4-(3-(1H-indol-5-yl)imidazo[1,2-b]pyridazin-6-ylamino)benzoate |
| 61 | methyl 3-aminobenzoate | methyl 3-(3-(1H-indol-5-yl)imidazo[1,2-b]pyridazin-6-ylamino)benzoate |

Compounds 52-58, 60-61 were physically characterized by electrospray ionization mass spectrometry. Structures and molecular masses are given below in Table 13-b.

TABLE 13-b

| Cd. | Structure | IUPAC Name | [M + H]+ |
|---|---|---|---|
| 52 | 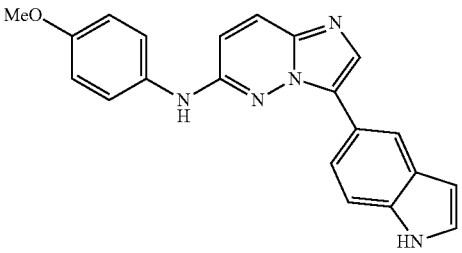 [SMILES: COc1ccc(Nc2ccc3ncc(-c4ccc5[nH]ccc5c4)n3n2)cc1] | 3-(1H-indol-5-yl)-N-(4-methoxyphenyl)imidazo[1,2-b]pyridazin-6-amine | 356.7 |
| 53 | 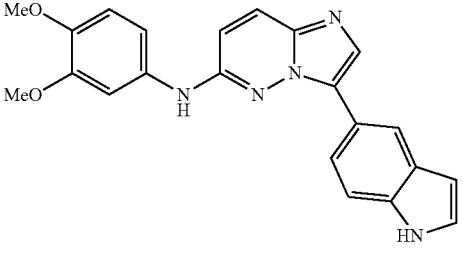 [SMILES: COc1ccc(Nc2ccc3ncc(-c4ccc5[nH]ccc5c4)n3n2)cc1OC] | 3-(1H-indol-5-yl)-N-(3,4-dimethoxyphenyl)imidazo[1,2-b]pyridazin-6-amine | 386.6 |
| 54 | 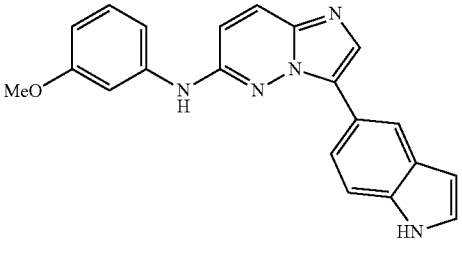 [SMILES: COc1cccc(Nc2ccc3ncc(-c4ccc5[nH]ccc5c4)n3n2)c1] | 3-(1H-indol-5-yl)-N-(3-methoxyphenyl)imidazo[1,2-b]pyridazin-6-amine | 356.7 |
| 55 | 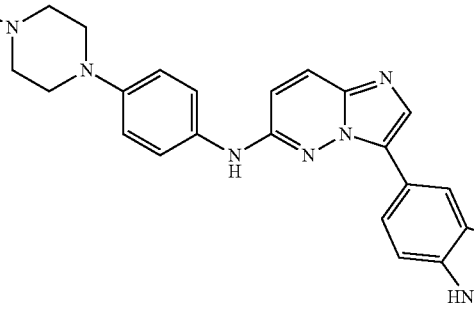 | 3-(1H-indol-5-yl)-N-(4-(4-methylpiperazin-1-yl)phenyl)imidazo[1,2-b]pyridazin-6-amine | 424.8 |
| 56 | 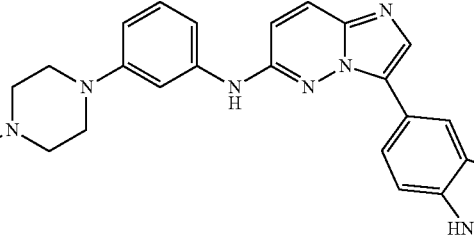 | 3-(1H-indol-5-yl)-N-(3-(4-methylpiperazin-1-yl)phenyl)imidazo[1,2-b]pyridazin-6-amine | 424.8 |
| 57 | 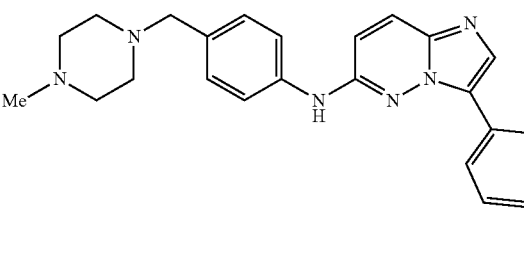 | 3-(1H-indol-5-yl)-N-(4-((4-methylpiperazin-1-yl)methyl)phenyl)imidazo[1,2-b]pyridazin-6-amine | 438.8 |

TABLE 13-b-continued

| Cd. | Structure | IUPAC Name | [M + H]+ |
|---|---|---|---|
| 58 | 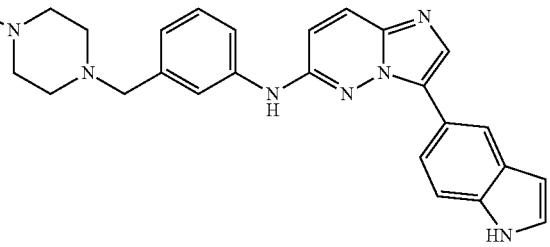 | 3-(1H-indol-5-yl)-N-(3-((4-methylpiperazin-1-yl)methyl)phenyl)imidazo[1,2-b]pyridazin-6-amine | 438.8 |
| 60 | 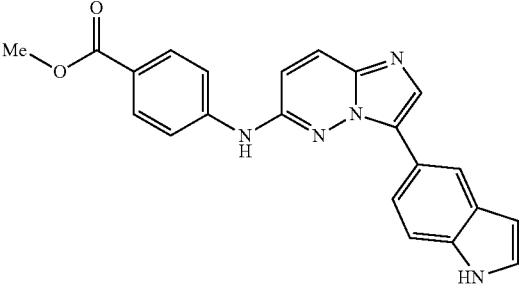 [SMILES: COC(=O)c1ccc(Nc2ccc3ncc(-c4ccc5[nH]ccc5c4)n3n2)cc1] | methyl 4-(3-(1H-indol-5-yl)imidazo[1,2-b]pyridazin-6-ylamino)benzoate | 398.6 |
| 61 | 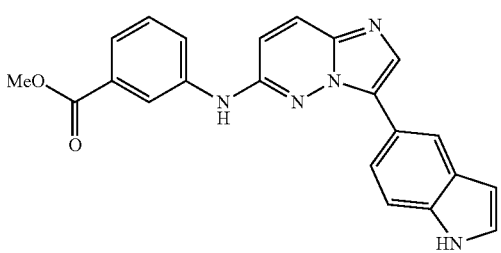 [SMILES: COC(=O)c1cccc(Nc2ccc3ncc(-c4ccc5[nH]ccc5c4)n3n2)c1] | methyl 3-(3-(1H-indol-5-yl)imidazo[1,2-b]pyridazin-6-ylamino)benzoate | 384.7 |

EXAMPLE 14

Synthesis of Compounds 140-143, 148-150, 158

Preparation of 3-(1H-indol-5-yl)-N-arylimidazo[1,2-b]pyridazin-6-amine

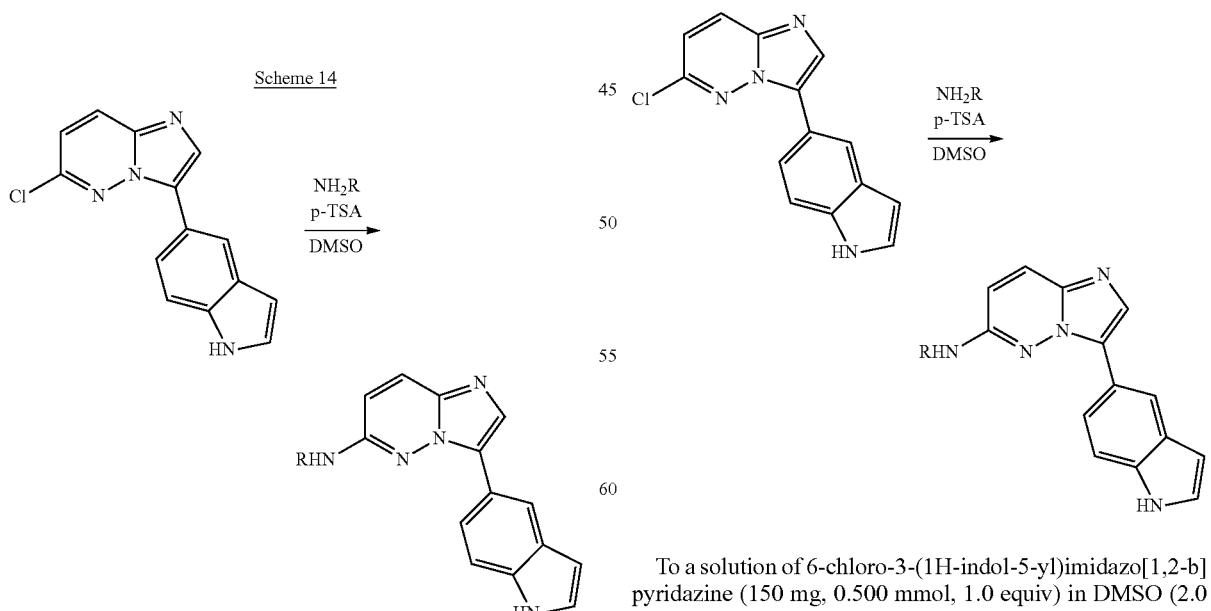

To a solution of 6-chloro-3-(1H-indol-5-yl)imidazo[1,2-b]pyridazine (150 mg, 0.500 mmol, 1.0 equiv) in DMSO (2.0 mL) was added p-toluene sulfonic acid monohydrate (95 mg, 0.500 mmol, 1.0 equiv) and amine (1.95 mmol, 4.0 equiv) and heated to 100° C. for 24 h. The reaction mixture was diluted with water and extracted with ethyl acetate. Purification by column chromatography using 5% methanol in dichloromethane elution gave the product.

TABLE 14-a

| Cd. | Amine | Purified Isolated Compound |
| --- | --- | --- |
| 140 | propan-1-amine | 3-(1H-indol-5-yl)-N-propylimidazo[1,2-b]pyridazin-6-amine |
| 141 | trans-4-aminocyclohexanol | trans-4-(3-(1H-indol-5-yl)imidazo[1,2-b]pyridazin-6-ylamino)cyclohexanol |
| 142 | 2-methylpropan-1-amine | 3-(1H-indol-5-yl)-N-isobutylimidazo[1,2-b]pyridazin-6-amine |
| 143 | 2-aminoethanol | 2-(3-(1H-indol-5-yl)imidazo[1,2-b]pyridazin-6-ylamino)ethanol |
| 148 | cyclopropanamine | N-cyclopropyl-3-(1H-indol-5-yl)imidazo[1,2-b]pyridazin-6-amine |
| 149 | (R)-butan-2-amine | N-sec-butyl-3-(1H-indol-5-yl)imidazo[1,2-b]pyridazin-6-amine |
| 150 | cyclopropylmethanamine | N-(cyclopropylmethyl)-3-(1H-indol-5-yl)imidazo[1,2-b]pyridazin-6-amine |
| 158 | N-methylpropan-1-amine | 3-(1H-indol-5-yl)-N-methyl-N-propylimidazo[1,2-b]pyridazin-6-amine |

Compounds 140-143, 148-150, 158 were physically characterized by electrospray ionization mass spectrometry. Structures and molecular masses are given below in Table 14-b.

TABLE 14-b

| Cd. | Structure | IUPAC Name | [M + H]+ |
| --- | --- | --- | --- |
| 140 | 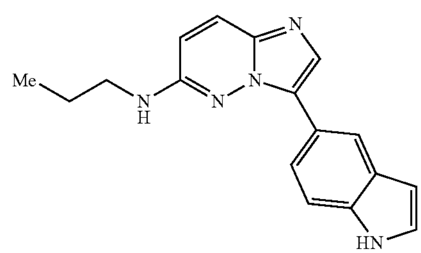 [SMILES: CCCNc1ccc2ncc(-c3ccc4[nH]ccc4c3)n2n1] | 3-(1H-indol-5-yl)-N-propylimidazo[1,2-b]pyridazin-6-amine | 292.5 |
| 141 | 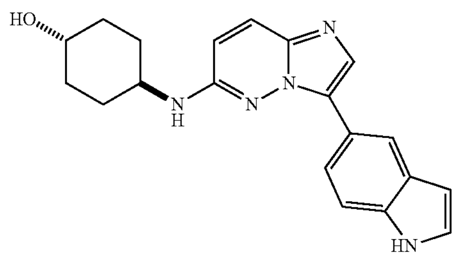 | trans-4-(3-(1H-indol-5-yl)imidazo[1,2-b]pyridazin-6-ylamino)cyclohexanol | 348.7 |
| 142 | 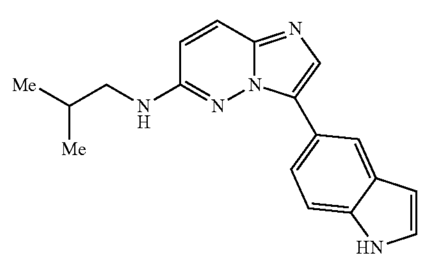 [SMILES: CC(C)CNc1ccc2ncc(-c3ccc4[nH]ccc4c3)n2n1] | 3-(1H-indol-5-yl)-N-isobutylimidazo[1,2-b]pyridazin-6-amine | 306.7 |
| 143 | 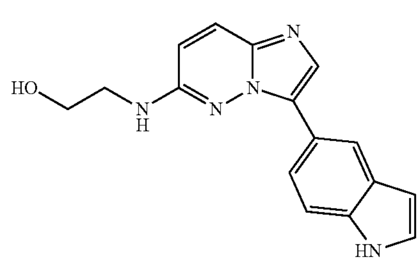 [SMILES: OCCNc1ccc2ncc(-c3ccc4[nH]ccc4c3)n2n1] | 2-(3-(1H-indol-5-yl)imidazo[1,2-b]pyridazin-6-ylamino)ethanol | 294.6 |

TABLE 14-b-continued

| Cd. | Structure | IUPAC Name | [M + H]+ |
|---|---|---|---|
| 148 | 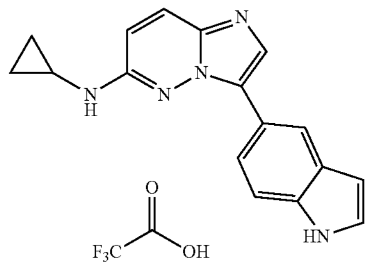 [SMILES: c1cc2cc(-c3cnc4ccc(NC5CC5)nn34)ccc2[nH]1 ; O=C(O)C(F)(F)F] | N-cyclopropyl-3-(1H-indol-5-yl)imidazo[1,2-b]pyridazin-6-amine | 290.6 |
| 149 | 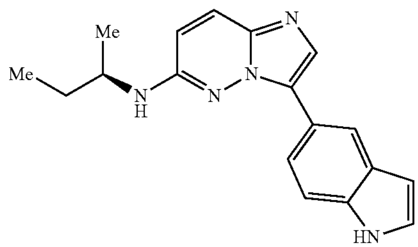 [SMILES: CC[C@@H](C)Nc1ccc2ncc(-c3ccc4[nH]ccc4c3)n2n1] | N-sec-butyl-3-(1H-indol-5-yl)imidazo[1,2-b]pyridazin-6-amine | 306.7 |
| 150 | 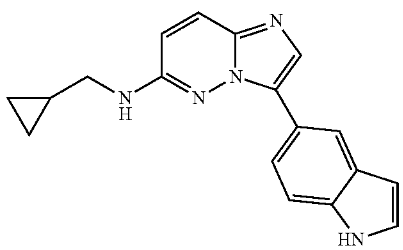 [SMILES: c1cc2cc(-c3cnc4ccc(NCC5CC5)nn34)ccc2[nH]1] | N-(cyclopropylmethyl)-3-(1H-indol-5-yl)imidazo[1,2-b]pyridazin-6-amine | 304.6 |
| 158 | 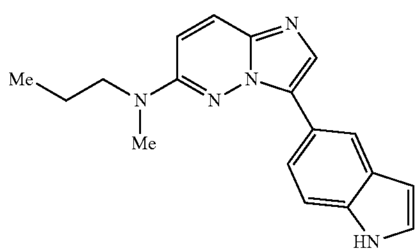 [SMILES: CCCN(C)c1ccc2ncc(-c3ccc4[nH]ccc4c3)n2n1] | 3-(1H-indol-5-yl)-N-methyl-N-propylimidazo[1,2-b]pyridazin-6-amine | 306.7 |

EXAMPLE 15

Synthesis of Compounds 62-65

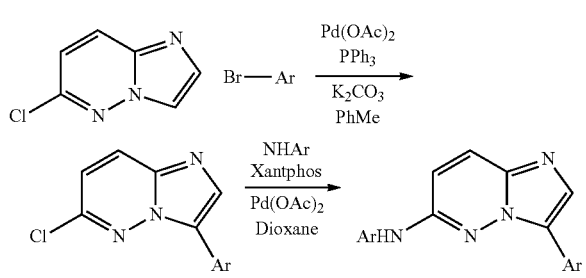

Scheme 15

Preparation of 6-chloro-3-arylimidazo[1,2-b]pyridazine

To a stirred solution of 6-chloroimidazo[1,2-b]pyridazine (404 mg, 2.63 mmol, 1.0 equiv) in 10.0 mL of toluene was added aryl bromide (1.00 g, 3.95 mmol, 1.5 equiv), potassium carbonate (728 mg, 5.27 mmol, 2.0 equiv), triphenylphosphine (138 mg, 0.527 mmol, 0.2 equiv) and palladium acetate (59 mg, 0.263 mmol, 0.1 equiv). The solution was stirred to reflux for 24 h. Purification by column chromatography using 50% ethyl acetate in hexanes elution gave the product.

Preparation of N,3-bisarylimidazo[1,2-b]pyridazin-6-amine

To a solution of 6-chloro-3-arylimidazo[1,2-b]pyridazine (50 mg, 0.179 mmol, 1.0 equiv), xantphos (21 mg, 0.0358 mmol, 0.2 equiv), palladium acetate (4 mg, 0.0179 mmol, 0.1 equiv), and potassium carbonate (495 mg, 3.58 mmol, 20 equiv) in dioxane (5.0 mL) was added amine (0.179 mmol, 1.0 equiv) and heated to 100° C. for 2 h. Purification by column chromatography using 2% methanol in dichloromethane elution gave the product.

TABLE 15-a

| Cd. | Arylbromide | Amine | Purified Isolated Compound |
|---|---|---|---|
| 62 | 2-bromonaphthalene | 3,4-dimethoxyaniline | N-(3,4-dimethoxyphenyl)-3-(naphthalen-3-yl)imidazo[1,2-b]pyridazin-6-amine |
| 63 | 2-bromonaphthalene | methyl 3-aminobenzoate | 3-(3-(naphthalen-3-yl)imidazo[1,2-b]pyridazin-6-ylamino)benzoic acid |
| 64 | 2-bromo-6-fluoronaphthalene | 3,4-dimethoxyaniline | 3-(2-fluoronaphthalen-6-yl)-N-(3,4-dimethoxyphenyl)imidazo[1,2-b]pyridazin-6-amine |
| 65 | 2-bromo-6-methoxynaphthalene | 3,4-dimethoxyaniline | 3-(2-methoxynaphthalen-6-yl)-N-(3,4-dimethoxyphenyl)imidazo[1,2-b]pyridazin-6-amine |

Compounds 62-65 were physically characterized by electrospray ionization mass spectrometry. Structures and molecular masses are given below in Table 15-b.

TABLE 15-b

| Cd. | Structure | IUPAC Name | [M + H]+ |
|---|---|---|---|
| 62 | (structure) | N-(3,4-dimethoxyphenyl)-3-(naphthalen-3-yl)imidazo[1,2-b]pyridazin-6-amine | 397.6 |
| 63 | (structure) | 3-(3-(naphthalen-3-yl)imidazo[1,2-b]pyridazin-6-ylamino)benzoic acid | 381.7 |
| 64 | (structure) | 3-(2-fluoronaphthalen-6-yl)-N-(3,4-dimethoxyphenyl)imidazo[1,2-b]pyridazin-6-amine | 415.8 |

TABLE 15-b-continued

| Cd. | Structure | IUPAC Name | [M + H]+ |
|---|---|---|---|
| 65 | MeO, MeO-C6H3-NH-[imidazo[1,2-b]pyridazine]-naphthalen-OMe | 3-(2-methoxynaphthalen-6-yl)-N-(3,4-dimethoxyphenyl)imidazo[1,2-b]pyridazin-6-amine | 427.7 |

EXAMPLE 16

Synthesis of Compounds 160-163

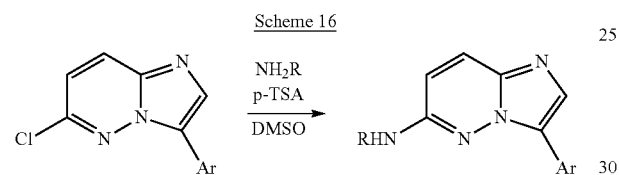

Scheme 16

Preparation of N-alkyl-3-arylimidazo[1,2-b]pyridazin-6-amine

To a solution of 6-chloro-2-methyl-3-arylimidazo[1,2-b]pyridazine (150 mg, 0.500 mmol, 1.0 equiv) in DMSO (2.0 mL) was added p-toluene sulfonic acid monohydrate (95 mg, 0.500 mmol, 1.0 equiv) and amine (1.95 mmol, 4.0 equiv) and heated to 100° C. for 24 h. The reaction mixture was diluted with water and extracted with ethyl acetate. Purification by column chromatography using 5% methanol in dichloromethane elution gave the product.

TABLE 16-a

| Cd. | Arylbromide | Amine | Purified Isolated Compound |
|---|---|---|---|
| 160 | 2-bromonaphthalene | 4-aminobutan-1-ol | 4-(3-(naphthalen-3-yl)imidazo[1,2-b]pyridazin-6-ylamino)butan-1-ol |
| 161 | 2-bromonaphthalene | trans-4-aminocyclohexanol | trans-4-(3-(naphthalen-3-yl)imidazo[1,2-b]pyridazin-6-ylamino)cyclohexanol |
| 162 | 2-bromo-6-fluoronaphthalene | trans-4-aminocyclohexanol | trans-4-(3-(2-fluoronaphthalen-6-yl)imidazo[1,2-b]pyridazin-6-ylamino)cyclohexanol |
| 163 | 2-bromo-6-methoxynaphthalene | trans-4-aminocyclohexanol | trans-4-(3-(2-methoxynaphthalen-6-yl)imidazo[1,2-b]pyridazin-6-ylamino)cyclohexanol |

Compounds 160-163 were physically characterized by electrospray ionization mass spectrometry. Structures and molecular masses are given below in Table 16-b.

TABLE 16-b
| Cd. | Structure | IUPAC Name | [M + H]+ |
|---|---|---|---|
| 160 | 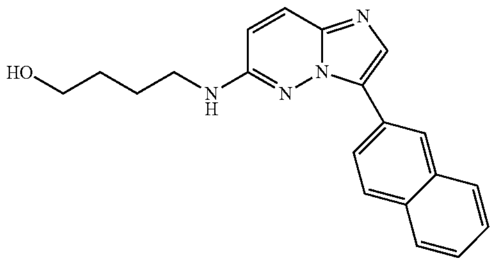 [SMILES: OCCCCNc1ccc2ncc(-c3ccc4ccccc4c3)n2n1] | 4-(3-(naphthalen-3-yl)imidazo[1,2-b]pyridazin-6-ylamino)butan-1-ol | 333.7 |
| 161 | 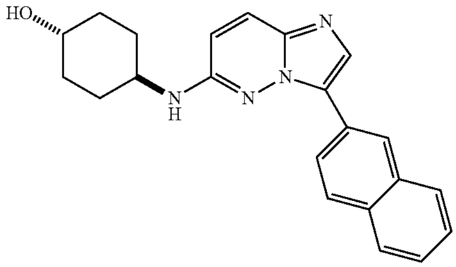 | trans-4-(3-(naphthalen-3-yl)imidazo[1,2-b]pyridazin-6-ylamino)cyclohexanol | 359.8 |
| 162 | 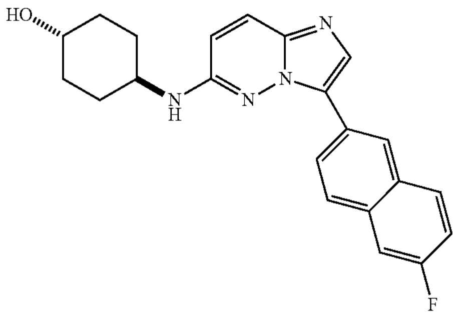 | trans-4-(3-(2-fluoronaphthalen-6-yl)imidazo[1,2-b]pyridazin-6-ylamino)cyclohexanol | 377.8 |
| 163 | 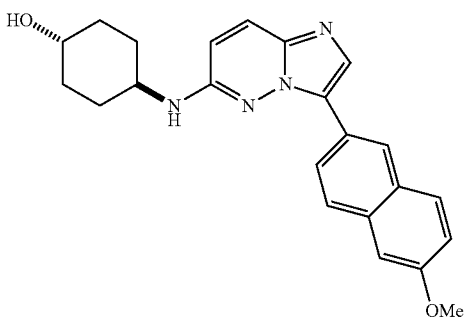 | trans-4-(3-(2-methoxynaphthalen-6-yl)imidazo[1,2-b]pyridazin-6-ylamino)cyclohexanol | 389.9 |
EXAMPLE 17
Synthesis of Compound 68, 181-185
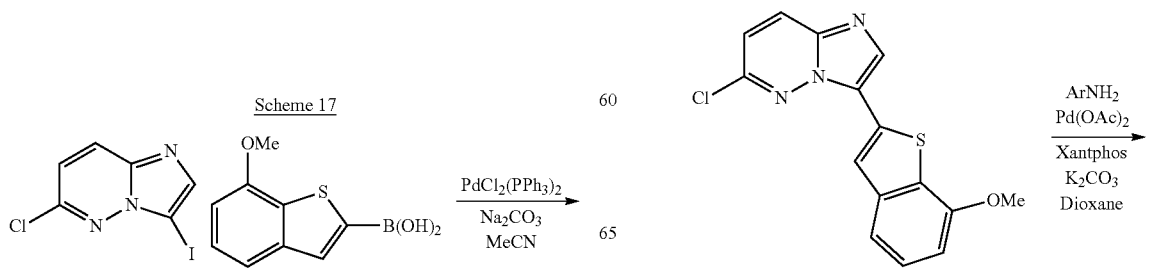

-continued

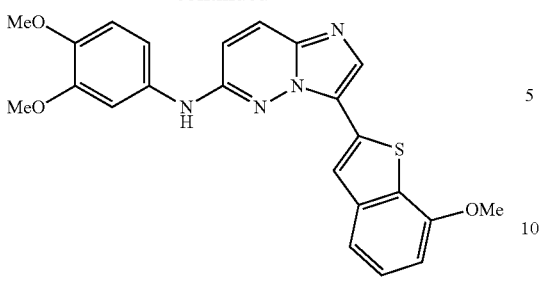

Preparation of 6-chloro-3-(7-methoxybenzo[b]thiophen-2-yl)imidazo[1,2-b]pyridazine

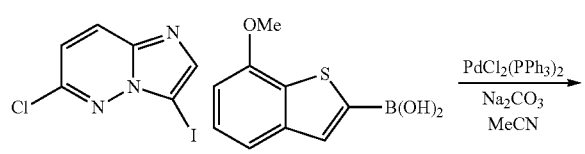

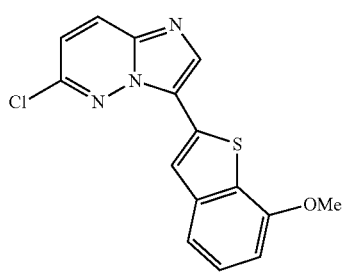

To a solution of 7-methoxybenzo[b]thiophen-2-yl-2-boronic acid (49 mg, 0.237 mmol, 1.1 equiv) in acetonitrile (2.15 mL) was added 6-chloro-3-iodoimidazo[1,2-b]pyridazine (50 mg, 0.215 mmol, 1.0 equiv), palladium catalyst (8 mg, 0.0108 mmol, 0.05 equiv) and sodium carbonate (2.15 mL, 1.0 M, 10.0 equiv). The solution was stirred at 150° C. in the microwave for 10 minutes. Purification using column chromatography gave 48 mg of the yellow solid, 70%.

Preparation of 3-(7-methoxybenzo[b]thiophen-2-yl)-N-arylimidazo[1,2-b]pyridazin-6-amine

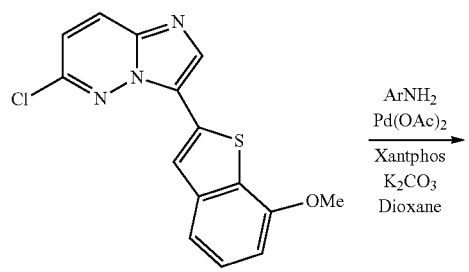

-continued

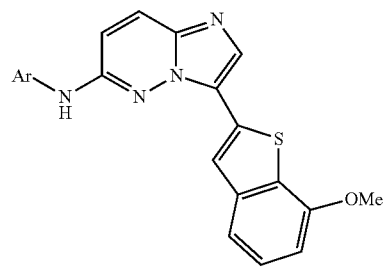

To a solution of 6-chloro-3-(7-methoxybenzo[b]thiophen-2-yl)imidazo[1,2-b]pyridazine (82 mg, 0.260 mmol, 1.0 equiv), xantphos (30 mg, 0.0519 mmol, 0.2 equiv), palladium acetate (6 mg, 0.0260 mmol, 0.1 equiv), and potassium carbonate (718 mg, 5.19 mmol, 20 equiv) in dioxane (5.0 mL) was added substituted aniline (48 mg, 0.312 mmol, 1.1 equiv) and heated to 110° C. for 2 h. Purification by column chromatography using 2% methanol in dichloromethane elution gave the product.

TABLE 17A

| Cd. | Amine | Purified Isolated Compound |
|---|---|---|
| 68 | 3,4-dimethoxyaniline | 3-(7-methoxybenzo[b]thiophen-2-yl)-N-(3,4-dimethoxyphenyl)imidazo[1,2-b]pyridazin-6-amine |
| 181 | 4-ethoxy-3-methoxybenzenamine | N-(4-ethoxy-3-methoxyphenyl)-3-(7-methoxybenzo[b]thiophen-2-yl)imidazo[1,2-b]pyridazin-6-amine |
| 182 | 3-methoxy-4-propoxybenzenamine | N-(3-methoxy-4-propoxyphenyl)-3-(7-methoxybenzo[b]thiophen-2-yl)imidazo[1,2-b]pyridazin-6-amine |
| 183 | 4-(difluoromethoxy)-3-methoxybenzenamine | N-(4-(difluoromethoxy)-3-methoxyphenyl)-3-(7-methoxybenzo[b]thiophen-2-yl)imidazo[1,2-b]pyridazin-6-amine |
| 184 | 3-methoxy-4-(trifluoromethoxy)benzenamine | N-(3-methoxy-4-(trifluoromethoxy)phenyl)-3-(7-methoxybenzo[b]thiophen-2-yl)imidazo[1,2-b]pyridazin-6-amine |
| 185 | 4-methoxy-3-(trifluoromethoxy)benzenamine | N-(4-methoxy-3-(trifluoromethoxy)phenyl)-3-(7-methoxybenzo[b]thiophen-2-yl)imidazo[1,2-b]pyridazin-6-amine |

Compound 68, 181-185 was physically characterized by electrospray ionization mass spectrometry. Structures and molecular masses are given below in Table x-x.

TABLE 17-b

| Cd. | Structure | IUPAC Name | [M + H]+ |
|---|---|---|---|
| 68 | 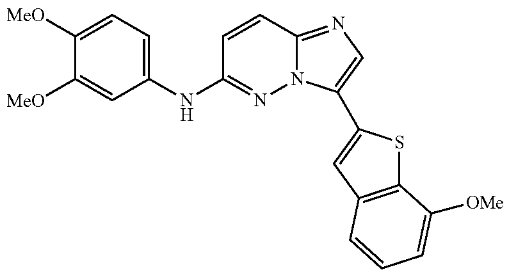 [SMILES: COc1ccc(Nc2ccc3ncc(-c4cc5cccc(OC)c5s4)n3n2)cc1OC] | 3-(7-methoxybenzo[b]thiophen-2-yl)-N-(3,4-dimethoxyphenyl)imidazo[1,2-b]pyridazin-6-amine | 433.2 |
| 181 | 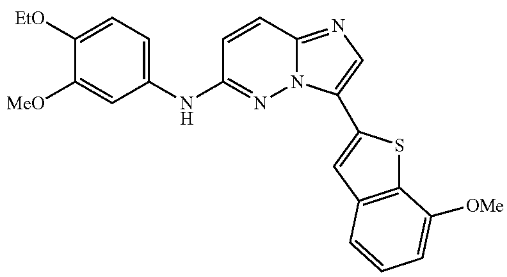 | N-(4-ethoxy-3-methoxyphenyl)-3-(7-methoxybenzo[b]thiophen-2-yl)imidazo[1,2-b]pyridazin-6-amine | 447.1 |
| 182 | 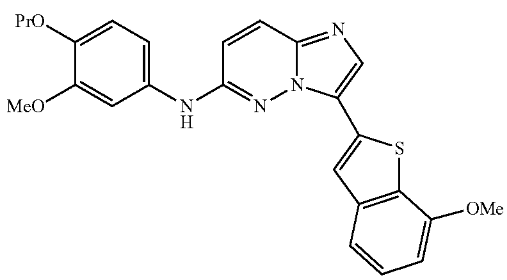 | N-(3-methoxy-4-propoxyphenyl)-3-(7-methoxybenzo[b]thiophen-2-yl)imidazo[1,2-b]pyridazin-6-amine | 461.3 |
| 183 | 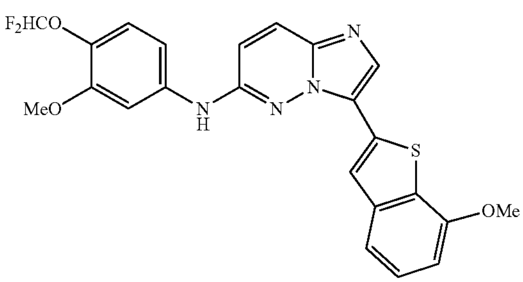 [SMILES: COc1cc(Nc2ccc3ncc(-c4cc5cccc(OC)c5s4)n3n2)ccc1OC(F)F] | N-(4-(difluoromethoxy)-3-methoxyphenyl)-3-(7-methoxybenzo[b]thiophen-2-yl)imidazo[1,2-b]pyridazin-6-amine | 469.1 |
| 184 | 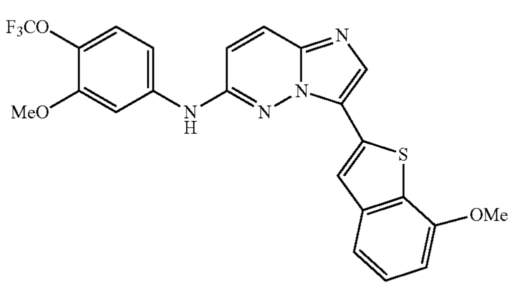 [SMILES: COc1cc(Nc2ccc3ncc(-c4cc5cccc(OC)c5s4)n3n2)ccc1OC(F)(F)F] | N-(3-methoxy-4-(trifluoromethoxy)phenyl)-3-(7-methoxybenzo[b]thiophen-2-yl)imidazo[1,2-b]pyridazin-6-amine | 487.1 |

TABLE 17-b-continued

| Cd. | Structure | IUPAC Name | [M + H]+ |
|---|---|---|---|
| 185 | (structure shown) | N-(4-methoxy-3-(trifluoromethoxy)phenyl)-3-(7-methoxybenzo[b]thiophen-2-yl)imidazo[1,2-b]pyridazin-6-amine | 487.4 |

EXAMPLE 18

Synthesis of Compounds 170 and 200

Preparation of trans-4-(3-(7-methoxybenzo[b]thiophen-2-yl)imidazo[1,2-b]pyridazin-6-ylamino)cyclohexanol

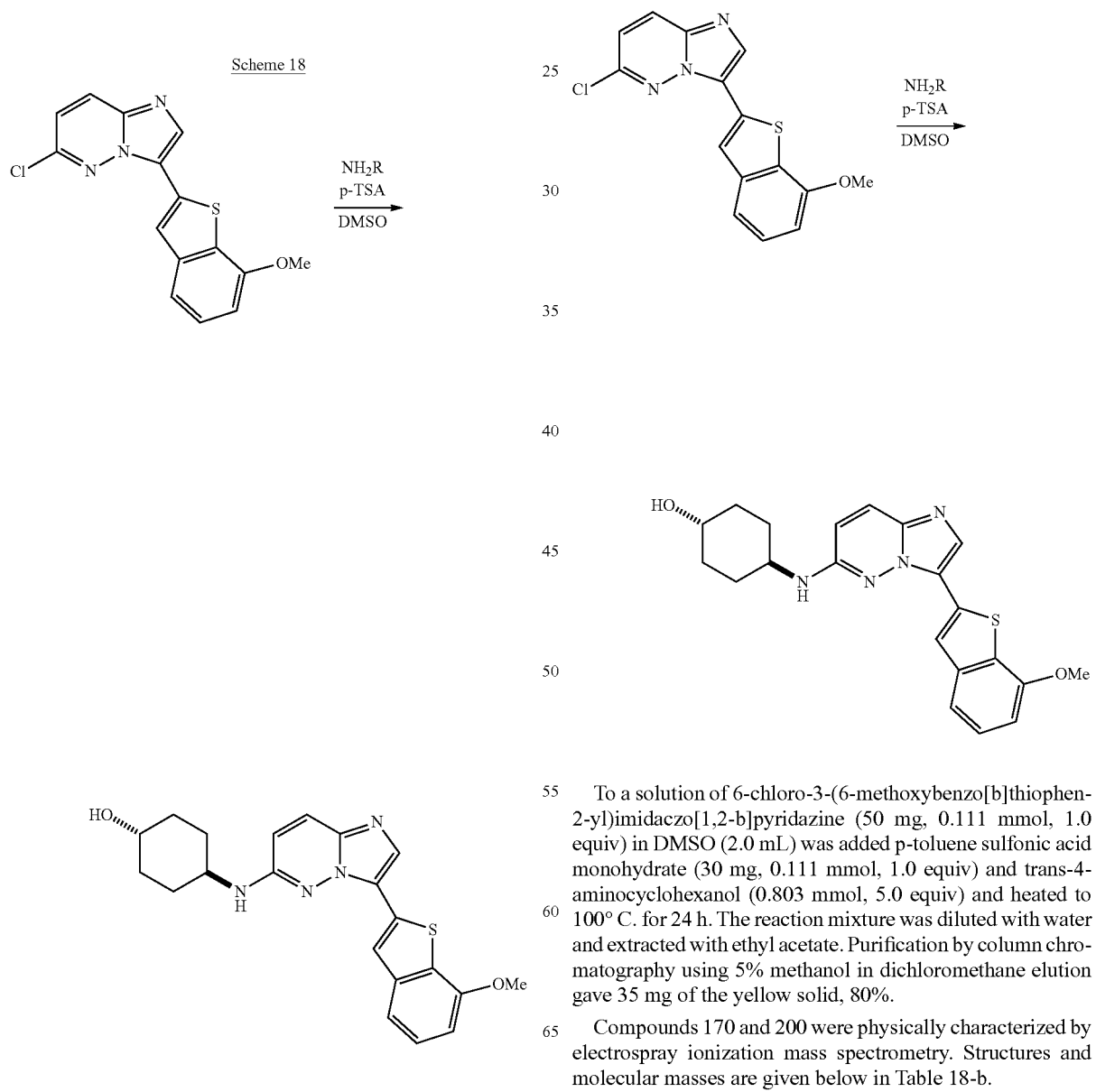

To a solution of 6-chloro-3-(6-methoxybenzo[b]thiophen-2-yl)imidaczo[1,2-b]pyridazine (50 mg, 0.111 mmol, 1.0 equiv) in DMSO (2.0 mL) was added p-toluene sulfonic acid monohydrate (30 mg, 0.111 mmol, 1.0 equiv) and trans-4-aminocyclohexanol (0.803 mmol, 5.0 equiv) and heated to 100° C. for 24 h. The reaction mixture was diluted with water and extracted with ethyl acetate. Purification by column chromatography using 5% methanol in dichloromethane elution gave 35 mg of the yellow solid, 80%.

Compounds 170 and 200 were physically characterized by electrospray ionization mass spectrometry. Structures and molecular masses are given below in Table 18-b.

TABLE 18-b

| Cd. | Amine | Structure | IUPAC Name | [M +H]+ |
|---|---|---|---|---|
| 170 | trans-4-aminocyclo-hexanol | 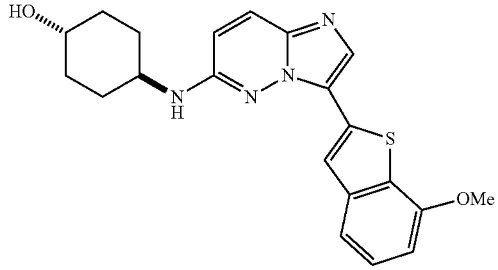 | trans-4-(3-(7-methoxybenzo[b]thiophen-2-yl)imidazo[1,2-b]pyridazin-6-ylamino)cyclohexanol | 395.5 |
| 200 | trans-4-methoxycyclo-hexan amine | 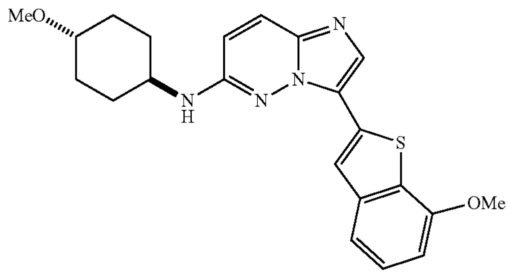 | trans-3-(7-methoxybenzo[b]thiophen-2-yl)-N-(4-methoxycyclohexyl)imidazo[1,2-b]pyridazin-6-amine | 409.1 |

EXAMPLE 19A

Synthesis of Compounds 78-81 and 186-188

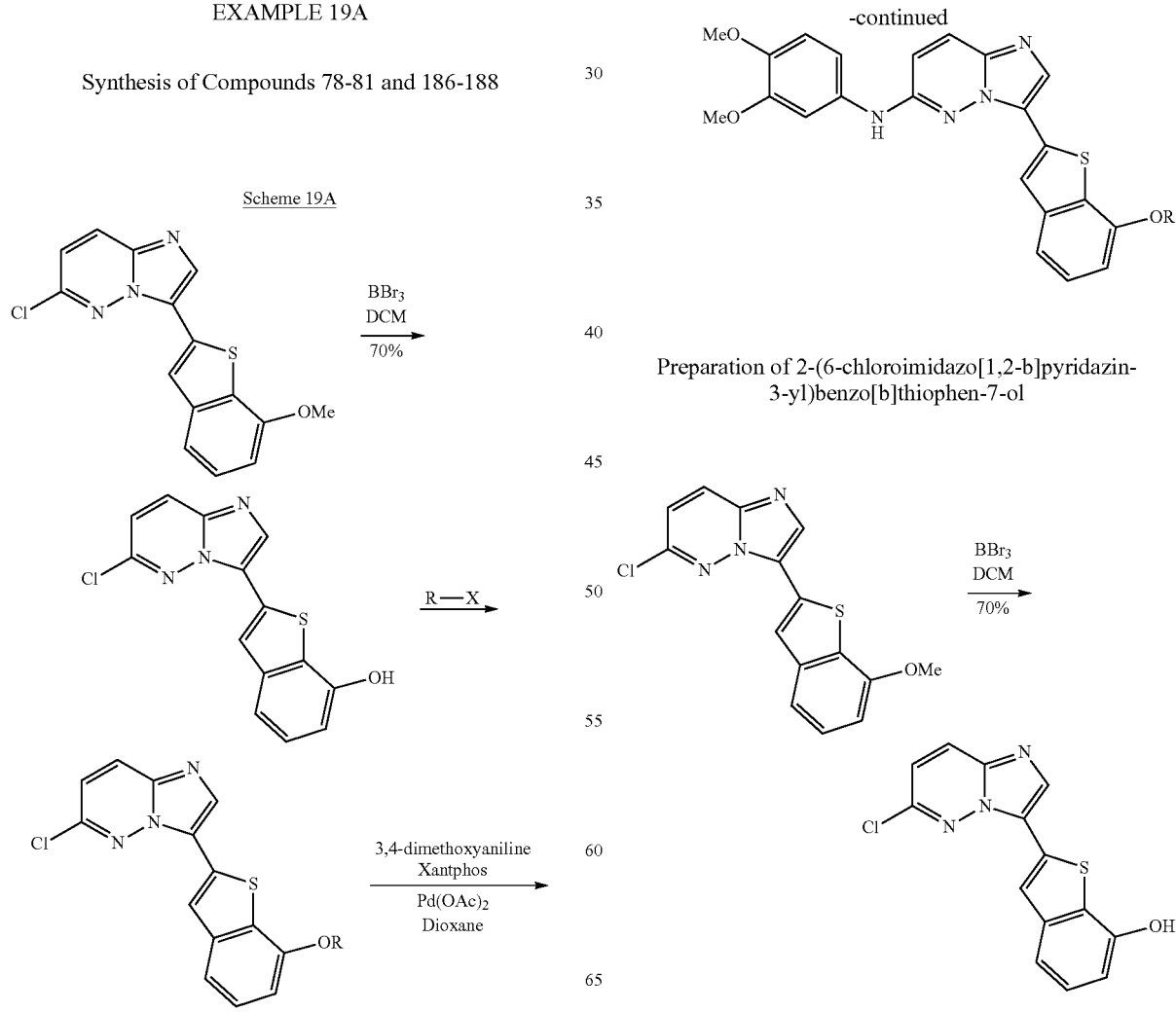

Preparation of 2-(6-chloroimidazo[1,2-b]pyridazin-3-yl)benzo[b]thiophen-7-ol

To a solution of 6-chloro-3-(7-methoxybenzo[b]thiophen-2-yl)imidazo[1,2-b]pyridazine (103 mg, 0.326 mmol, 1.0 equiv) in dichloromethane at −78° C. was added boron tribromide (2.27 mL, 1.0 M solution in dichloromethane, 7.0 equiv). The reaction mixture was stirred at the reduced temperature for 10 min then warmed to room temperature and stirred for 15 h. Methanol (2 mL) was added to quench the reaction and extracted with dichloromethane. Purification by column chromatography using 5% methanol in dichloromethane elution gave 70 mg of the yellow solid, 70%.

Preparation of 6-chloro-3-(7-alkoxybenzo[b]thiophen-2-yl)imidazo[1,2-b]pyridazine

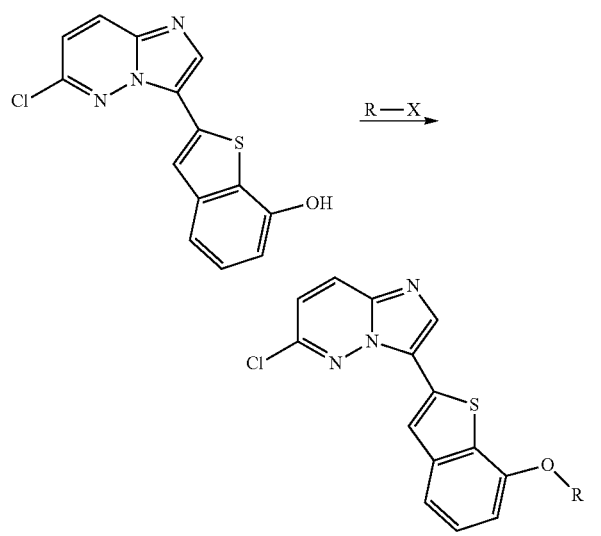

To a solution of 2-(6-chloroimidazo[1,2-b]pyridazin-3-yl)benzo[b]thiophen-7-ol (33 mg, 0.109 mmol, 1.0 equiv) in acetone (2 mL) was added potassium carbonate (30 mg, 0.219 mmol, 2.0 equiv) and alkyl halide (0.219 mmol, 2.0 equiv) and heated to reflux for 15 h. Purification by column chromatography using 2% methanol in dichloromethane elution gave the product.

Preparation of 3-(7-alkoxybenzo[b]thiophen-2-yl)-N-arylimidazo[1,2-b]pyridazin-6-amine

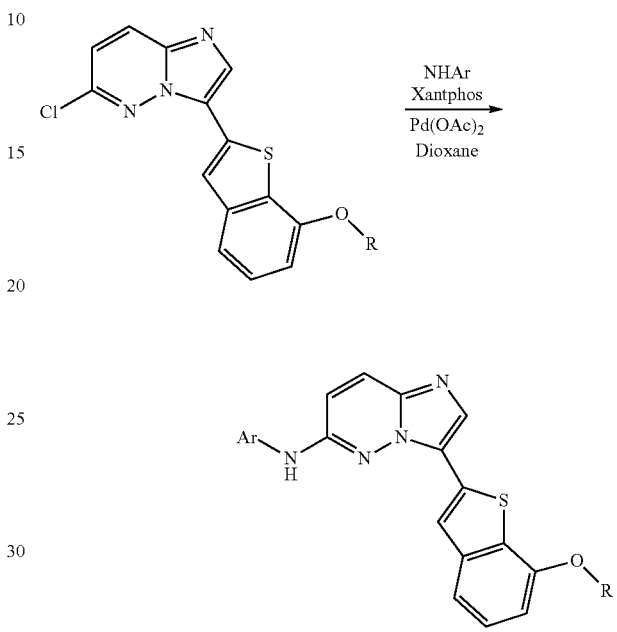

To a solution of 6-chloro-3-(7-alkoxybenzo[b]thiophen-2-yl)imidazo[1,2-b]pyridazine (38 mg, 0.109 mmol, 1.0 equiv), xantphos (0.022 mmol, 0.2 equiv), palladium acetate (0.011 mmol, 0.1 equiv), and potassium carbonate (2.19 mmol, 20 equiv) in dioxane (5.0 mL) was added 3,4-dimethoxyaniline (0.164 mmol, 1.5 equiv) and heated to 100° C. for 2 h. Purification by column chromatography using 2% methanol in dichloromethane elution gave the product.

TABLE 19-a

| Cd. | Alkyl halide | Purified Isolated Compound |
|---|---|---|
| 78 | acetyl chloride | 2-(6-(3,4-dimethoxyphenylamino)imidazo[1,2-b]pyridazin-3-yl)benzo[b]thiophen-7-yl acetate |
| 79 |  | 2-(6-(3,4-dimethoxyphenylamino)imidazo[1,2-b]pyridazin-3-yl)benzo[b]thiophen-7-ol |
| 80 | 2-iodopropane | 3-(7-isopropoxybenzo[b]thiophen-2-yl)-N-(3,4-dimethoxyphenyl)imidazo[1,2-b]pyridazin-6-amine |
| 81 | 1-iodopropane | N-(3,4-dimethoxyphenyl)-3-(7-propoxybenzo[b]thiophen-2-yl)imidazo[1,2-b]pyridazin-6-amine |
| 186 | Ethyliodide | 3-(7-ethoxybenzo[b]thiophen-2-yl)-N-(3,4-dimethoxyphenyl)imidazo[1,2-b]pyridazin-6-amine |
| 187 | sodium 2-chloro-2,2-difluoroacetate | 3-(7-(difluoromethoxy)benzo[b]thiophen-2-yl)-N-(3,4-dimethoxyphenyl)imidazo[1,2-b]pyridazin-6-amine |
| 188 | trifluoroiodomethane | N-(3,4-dimethoxyphenyl)-3-(7-(trifluoromethoxy)benzo[b]thiophen-2-yl)imidazo[1,2-b]pyridazin-6-amine |

Compounds 78-81, 186-188 were physically characterized by electrospray ionization mass spectrometry. Structures and molecular masses are given below in Table 19-A.

TABLE 19-B

| Cd. | Structure | IUPAC Name | [M + H]+ |
|---|---|---|---|
| 78 | 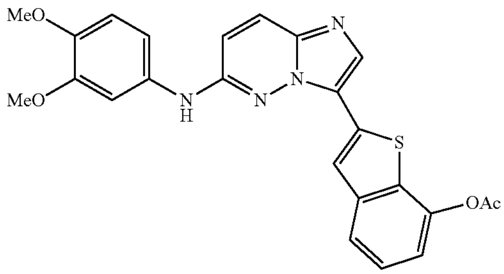 [SMILES: COc1ccc(Nc2ccc3ncc(-c4cc5cccc(OC(C)=O)c5s4)n3n2)cc1OC] | 2-(6-(3,4-dimethoxyphenylamino)imidazo[1,2-b]pyridazin-3-yl)benzo[b]thiophen-7-yl acetate | 461.3 |
| 79 | 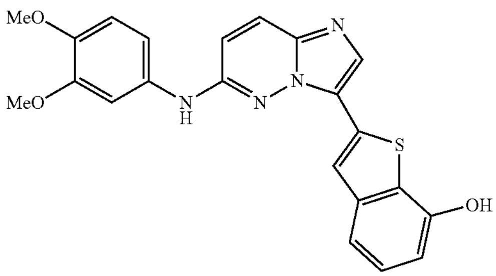 [SMILES: COc1ccc(Nc2ccc3ncc(-c4cc5cccc(O)c5s4)n3n2)cc1OC] | 2-(6-(3,4-dimethoxyphenylamino)imidazo[1,2-b]pyridazin-3-yl)benzo[b]thiophen-7-ol | 419.4 |
| 80 | 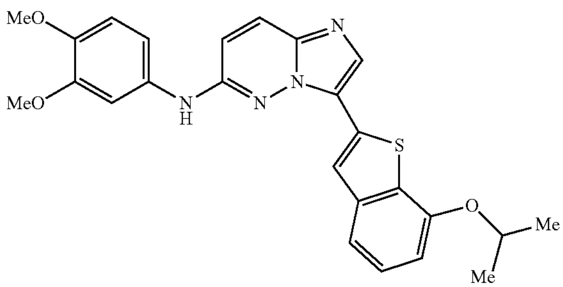 [SMILES: COc1ccc(Nc2ccc3ncc(-c4cc5cccc(OC(C)C)c5s4)n3n2)cc1OC] | 3-(7-isopropoxybenzo[b]thiophen-2-yl)-N-(3,4-dimethoxyphenyl)imidazo[1,2-b]pyridazin-6-amine | 461.4 |
| 81 | 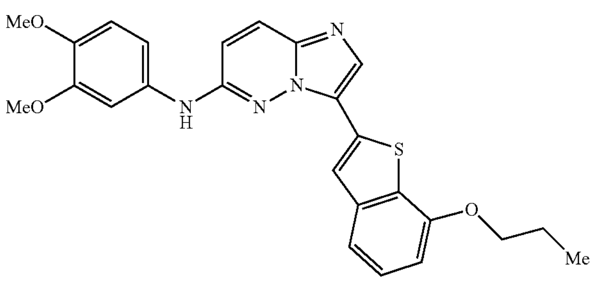 [SMILES: CCCOc1cccc2cc(-c3cnc4ccc(Nc5ccc(OC)c(OC)c5)nn34)sc12] | N-(3,4-dimethoxyphenyl)-3-(7-propoxybenzo[b]thiophen-2-yl)imidazo[1,2-b]pyridazin-6-amine | 461.5 |
| 186 | 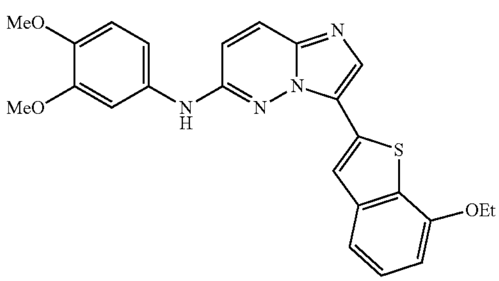 [SMILES: CCOc1cccc2cc(-c3cnc4ccc(Nc5ccc(OC)c(OC)c5)nn34)sc12] | 3-(7-ethoxybenzo[b]thiophen-2-yl)-N-(3,4-dimethoxyphenyl)imidazo[1,2-b]pyridazin-6-amine | 447.2 |

TABLE 19-B-continued

| Cd. | Structure | IUPAC Name | [M + H]⁺ |
|---|---|---|---|
| 187 | 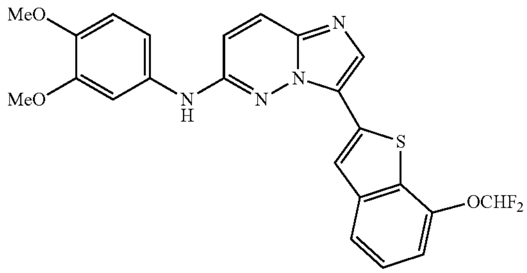 [SMILES: COc1ccc(Nc2ccc3ncc(-c4cc5cccc(OC(F)F)c5s4)n3n2)cc1OC] | 3-(7-(difluoromethoxy)benzo[b]thiophen-2-yl)-N-(3,4-dimethoxyphenyl)imidazo[1,2-b]pyridazin-6-amine | 469.3 |
| 188 | 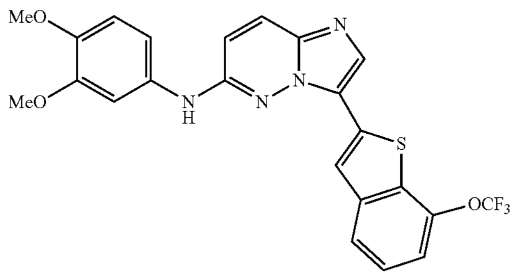 [SMILES: COc1ccc(Nc2ccc3ncc(-c4cc5cccc(OC(F)(F)F)c5s4)n3n2)cc1OC] | N-(3,4-dimethoxyphenyl)-3-(7-(trifluoromethoxy)benzo[b]thiophen-2-yl)imidazo[1,2-b]pyridazin-6-amine | 487.3 |

EXAMPLE 19B

Synthesis of Compounds 189-190

Preparation of N-aryl-3-(7-(trifluoromethoxy)benzo[b]thiophen-2-yl)imidazo[1,2-b]pyridazin-6-amine

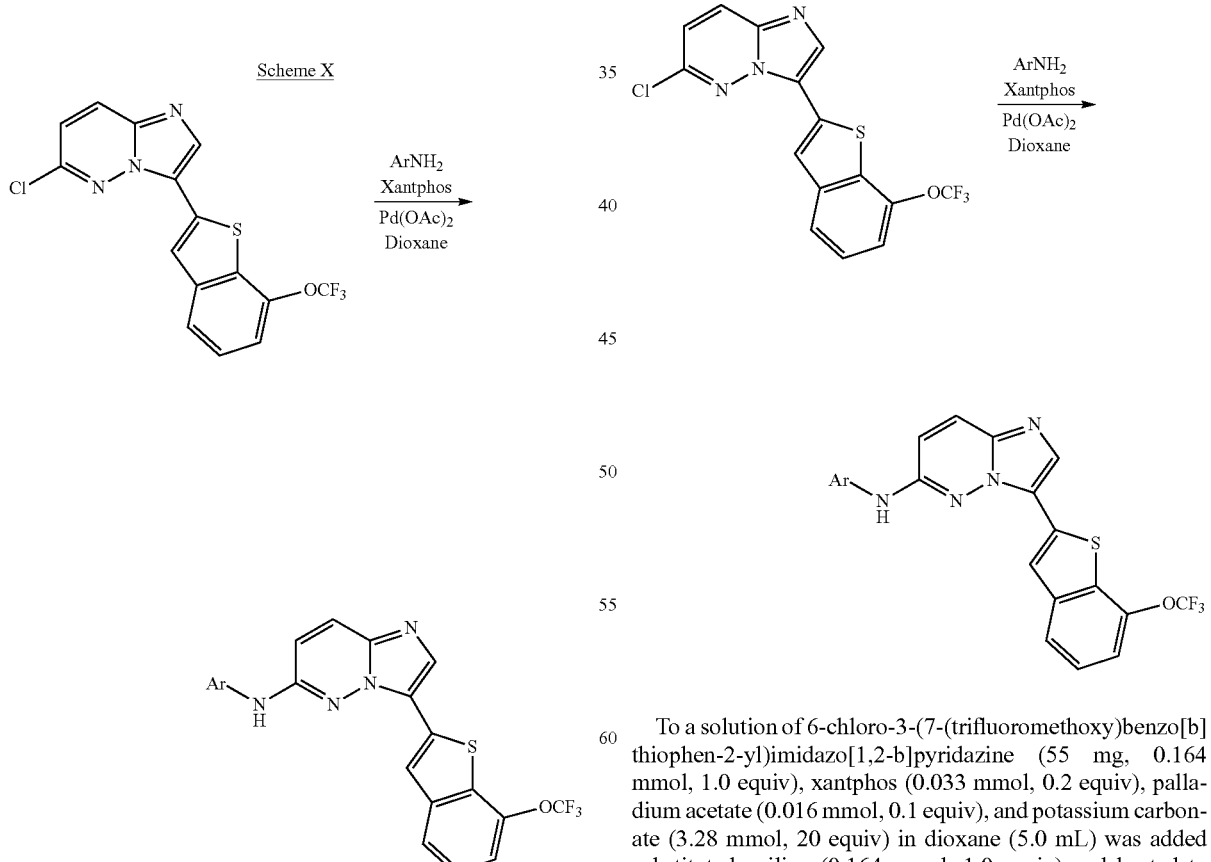

To a solution of 6-chloro-3-(7-(trifluoromethoxy)benzo[b]thiophen-2-yl)imidazo[1,2-b]pyridazine (55 mg, 0.164 mmol, 1.0 equiv), xantphos (0.033 mmol, 0.2 equiv), palladium acetate (0.016 mmol, 0.1 equiv), and potassium carbonate (3.28 mmol, 20 equiv) in dioxane (5.0 mL) was added substituted aniline (0.164 mmol, 1.0 equiv) and heated to 100° C. for 2 h. Purification by column chromatography using 2% methanol in dichloromethane elution gave the product.

TABLE 19C

| Cd. | Amine | Purified Isolated Compound |
|---|---|---|
| 189 | 4-(difluoromethoxy)-3-methoxybenzenamine | N-(4-(difluoromethoxy)-3-methoxyphenyl)-3-(7-(trifluoromethoxy)benzo[b]thiophen-2-yl)imidazo[1,2-b]pyridazin-6-amine |
| 190 | N-(3-methoxy-4-(trifluoromethoxy)phenyl)-3-(7-(trifluoromethoxy)benzo[b]thiophen-2-yl)imidazo[1,2-b]pyridazin-6-amine | N-(3-methoxy-4-(trifluoromethoxy)phenyl)-3-(7-(trifluoromethoxy)benzo[b]thiophen-2-yl)imidazo[1,2-b]pyridazin-6-amine |

Compounds 189-190 were physically characterized by electrospray ionization mass spectrometry. Structures and molecular masses are given below in Table 19D.

TABLE 19D

| Cd. | Structure | IUPAC Name | [M +H]⁺ |
|---|---|---|---|
| 189 | 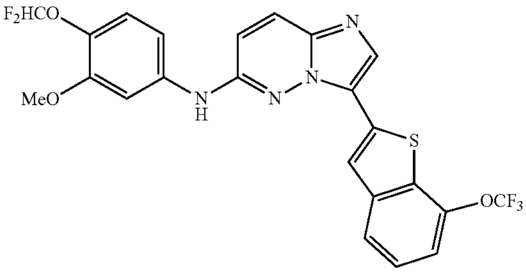 [SMILES: COc1cc(Nc2ccc3ncc(-c4cc5cccc(OC(F)(F)F)c5s4)n3n2)ccc1OC(F)F] | N-(4-(difluoromethoxy)-3-methoxyphenyl)-3-(7-(trifluoromethoxy)benzo[b]thiophen-2-yl)imidazo[1,2-b]pyridazin-6-amine | 523.1 |
| 190 | 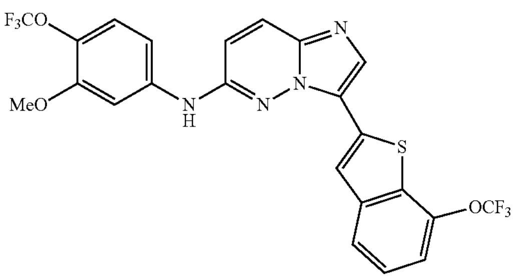 [SMILES: COc1cc(Nc2ccc3ncc(-c4cc5cccc(OC(F)(F)F)c5s4)n3n2)ccc1OC(F)(F)F] | N-(3-methoxy-4-(trifluoromethoxy)phenyl)-3-(7-(trifluoromethoxy)benzo[b]thiophen-2-yl)imidazo[1,2-b]pyridazin-6-amine | 541.4 |

EXAMPLE 20

Synthesis of Compound 77

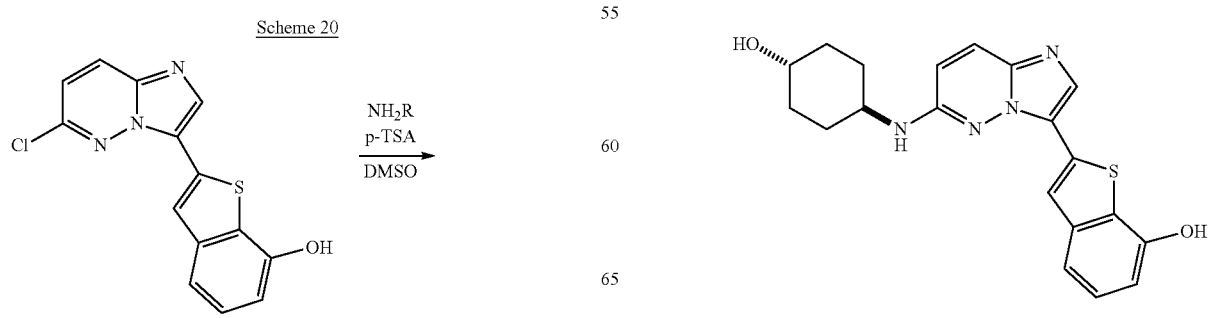

Scheme 20

135

Preparation of 2-(6-trans-4-hydroxycyclohexylamino)imidazo[1,2-b]pyridazin-3-yl)benzo[b]thiophen-7-ol

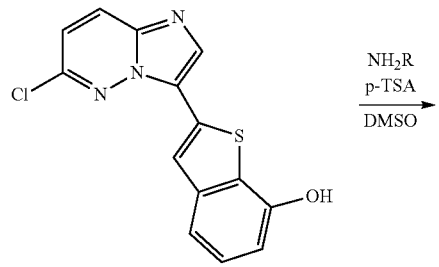

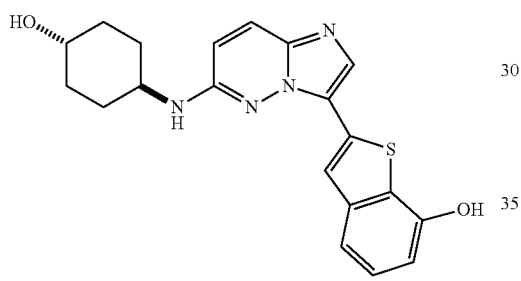

To a solution of 2-(6-chloroimidazo[1,2-b]pyridazin-3-yl)benzo[b]thiophen-7-ol (50 mg, 0.166 mmol, 1.0 equiv) in DMSO (2.0 mL) was added p-toluene sulfonic acid monohydrate (32 mg, 0.167 mmol, 1.0 equiv) and trans-4-aminocyclohexanol (95 mg, 0.830 mmol, 5.0 equiv) and heated to 100° C. for 24 h. The reaction mixture was diluted with water and extracted with ethyl acetate. Purification by column chromatography using 5% methanol in dichloromethane elution gave 40 mg of the yellow solid, 79%.

Compound 77 was physically characterized by electrospray ionization mass spectrometry. Structures and molecular masses are given below in Table 20-b.

136

EXAMPLE 21A

Synthesis of Compound 178

Scheme 21

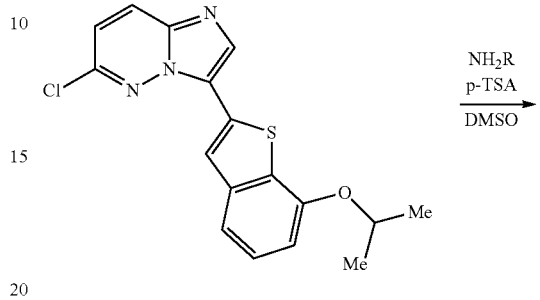

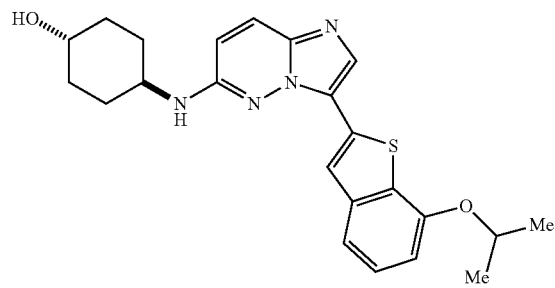

TABLE 20-b

| Cd. | Structure | IUPAC Name | [M +H]+ |
|---|---|---|---|
| 77 | 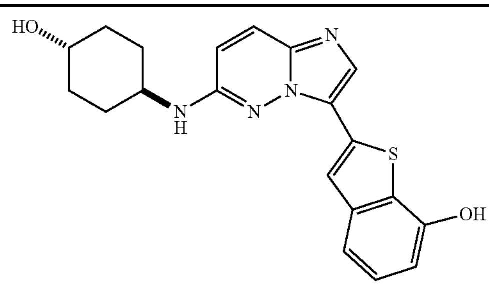 | 2-(6-trans-4-hydroxycyclohexylamino)imidazo[1,2-b]pyridazin-3-yl)benzo[b]thiophen-7-ol | 381.3 |

Preparation of trans-4-(3-(7-isopropoxybenzo[b]thiophen-2-yl)imidazo[1,2-b]pyridazin-6-ylamino)cyclohexanol

EXAMPLE 21A

Synthesis of Compound 202

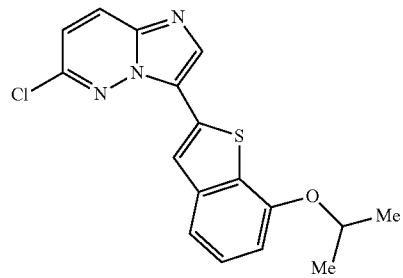

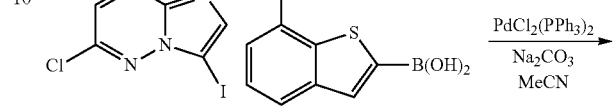

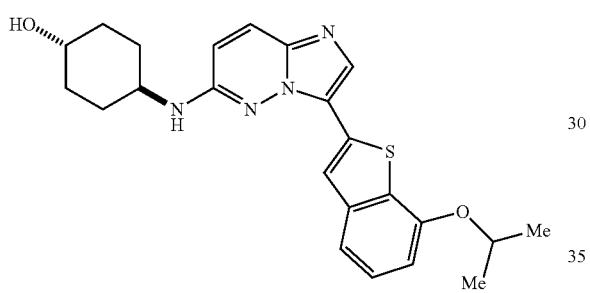

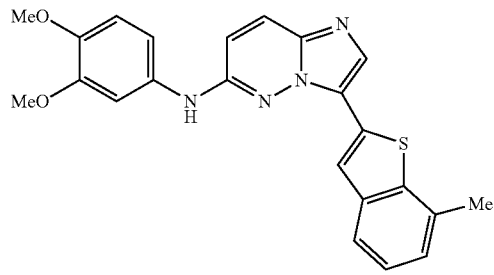

To a solution of 6-chloro-3-(7-isopropoxybenzo[b]thiophen-2-yl)imidaczo[1,2-b]pyridazine (56 mg, 0.167 mmol, 1.0 equiv) in DMSO (2.0 mL) was added p-toluene sulfonic acid monohydrate (32 mg, 0.167 mmol, 1.0 equiv) and trans-4-aminocyclohexanol (0.828 mmol, 5.0 equiv) and heated to 100° C. for 24 h. The reaction mixture was diluted with water and extracted with ethyl acetate. Purification by column chromatography using 5% methanol in dichloromethane elution gave 25 mg of the yellow solid, 36%.

Compound 178 was physically characterized by electrospray ionization mass spectrometry. Structures and molecular masses are given below in Table 21-b.

TABLE 21-b

| Cd. | Structure | IUPAC Name | [M + H]⁺ |
|---|---|---|---|
| 178 | (structure shown) | trans-4-(3-(7-isopropoxybenzo[b]thiophen-2-yl)imidazo[1,2-b]pyridazin-6-ylamino)cyclohexanol | 423.2 |

139
Preparation of 6-chloro-3-(7-methylbenzo[b]thiophen-2-yl)imidazo[1,2-b]pyridazine

140
Preparation of N-(3,4-dimethoxyphenyl)-3-(7-methylbenzo[b]thiophen-2-yl)imidazo[1,2-b]pyridazin-6-amine

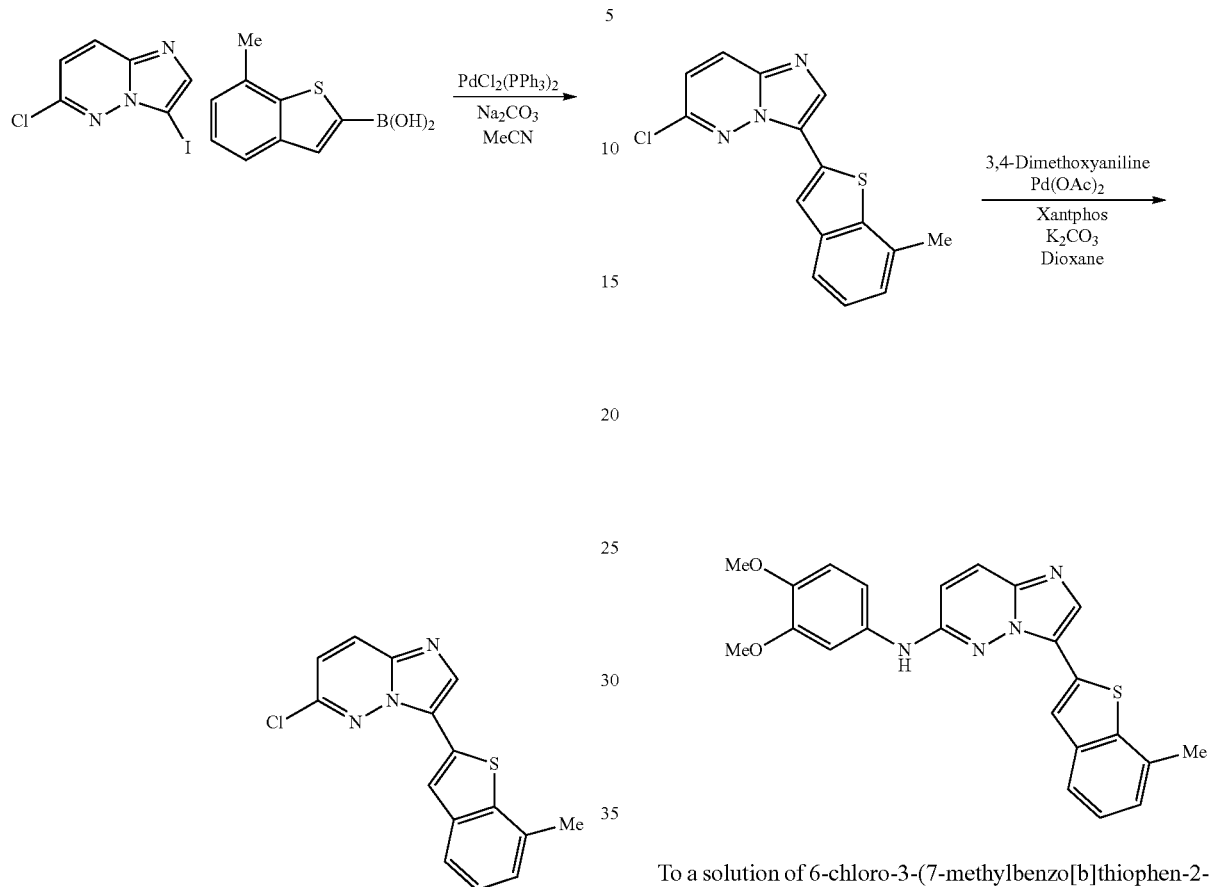

To a solution of 6-methylbenzo[b]thiophen-2-yl-2-boronic acid (100 mg, 0.521 mmol, 1.1 equiv) in acetonitrile (4.73 mL) was added 6-chloro-3-iodoimidazo[1,2-b]pyridazine (132 mg, 0.473 mmol, 1.0 equiv), palladium catalyst (35 mg, 0.0473 mmol, 0.1 equiv) and sodium carbonate (4.73 mL, 1.0 M, 10.0 equiv). The solution was stirred at 150° C. in the microwave for 10 minutes. Purification using column chromatography gave 110 mg of the yellow solid, 78%.

To a solution of 6-chloro-3-(7-methylbenzo[b]thiophen-2-yl)imidazo[1,2-b]pyridazine (50 mg, 0.167 mmol, 1.0 equiv), xantphos (19 mg, 0.0334 mmol, 0.2 equiv), palladium acetate (4 mg, 0.0167 mmol, 0.1 equiv), and potassium carbonate (461 mg, 3.34 mmol, 20 equiv) in dioxane (5.0 mL) was added 3,4-dimethoxyaniline (21 mg, 0.184 mmol, 1.1 equiv) and heated to 110° C. for 2 h. Purification by column chromatography using 2% methanol in dichloromethane elution gave 40 mg, 0.195 mmol of the yellow solid, 58%.

Compound 202 was physically characterized by electrospray ionization mass spectrometry. Structures and molecular masses are given below in Table 21C.

TABLE 21C

| Cd. | Structure | IUPAC Name | [M + H]$^+$ |
| --- | --- | --- | --- |
| 202 | 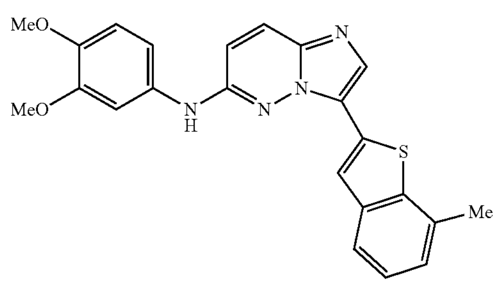 [SMILES: COc1ccc(Nc2ccc3ncc(-c4cc5cccc(C)c5s4)n3n2)cc1OC] | N-(3,4-dimethoxyphenyl)-3-(7-methylbenzo[b]thiophen-2-yl)imidazo[1,2-b]pyridazin-6-amine | 416.7 |

EXAMPLE 21B

Synthesis of Compound 203

Scheme X

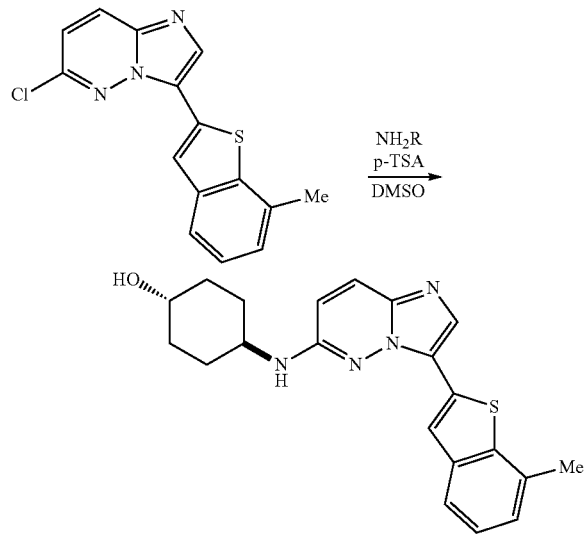

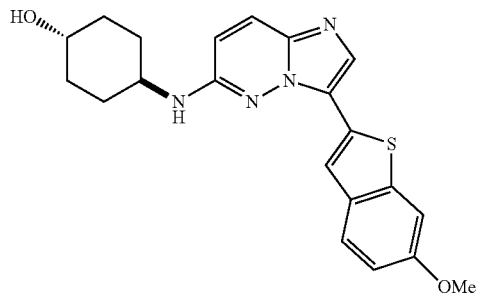

To a solution of -chloro-3-(7-methylbenzo[b]thiophen-2-yl)imidazo[1,2-b]pyridazine (50 mg, 0.168 mmol, 1.0 equiv) in DMSO (2.0 mL) was added p-toluene sulfonic acid monohydrate (23 mg, 0.168 mmol, 1.0 equiv) and trans-4-aminocyclohexanol (0.840 mmol, 5.0 equiv) and heated to 100° C. for 24 h. The reaction mixture was diluted with water and extracted with ethyl acetate. Purification by column chromatography using 5% methanol in dichloromethane elution gave 32 mg of the yellow solid, 48%.

Compound 203 was physically characterized by electrospray ionization mass spectrometry. Structures and molecular masses are given below in Table 21D.

TABLE 21D

| Cd. | Structure | IUPAC Name | [M + H]+ |
|---|---|---|---|
| 203 | 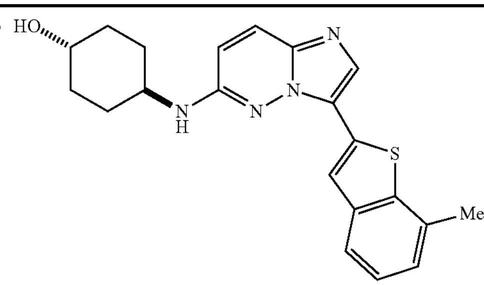 | trans-4-(3-(7-methylbenzo[b]thiophen-2-yl)imidazo[1,2-b]pyridazin-6-ylamino)cyclohexanol | 379.4 |

Preparation of trans-4-(3-(7-methylbenzo[b]thiophen-2-yl)imidazo[1,2-b]pyridazin-6-ylamino)cyclohexanol

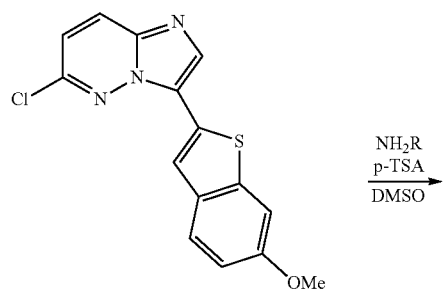

EXAMPLE 22

Synthesis of Compound 72

Scheme 22

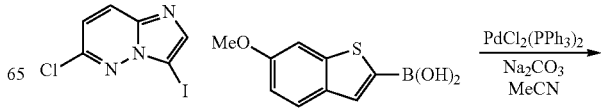

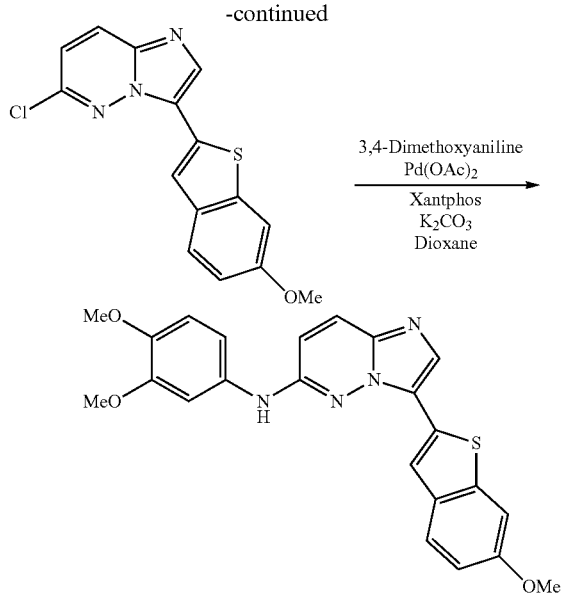

Preparation of 6-chloro-3-(6-methoxybenzo[b]thiophen-2-yl)imidazo[1,2-b]pyridazine

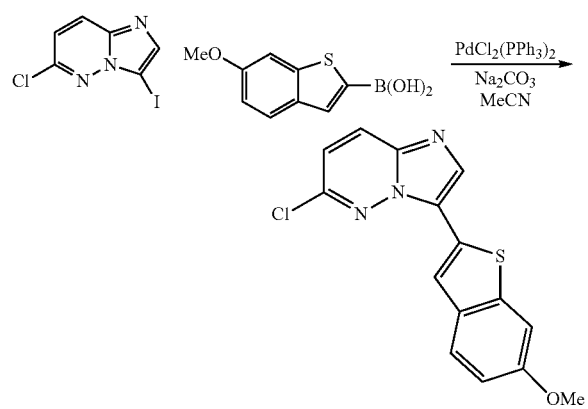

To a solution of 6-methoxybenzo[b]thiophen-2-yl-2-boronic acid (49 mg, 0.237 mmol, 1.1 equiv) in acetonitrile (2.15 mL) was added 6-chloro-3-iodoimidazo[1,2-b]pyridazine (50 mg, 0.215 mmol, 1.0 equiv), palladium catalyst (8 mg, 0.0108 mmol, 0.05 equiv) and sodium carbonate (2.15 mL, 1.0 M, 10.0 equiv). The solution was stirred at 150° C. in the microwave for 10 minutes. Purification using column chromatography gave 50 mg of the yellow solid, 75%.

Preparation of 3-(6-methoxybenzo[b]thiophen-2-yl)-N-(3,4-dimethoxyphenyl)imidazo[1,2-b]pyridazin-6-amine

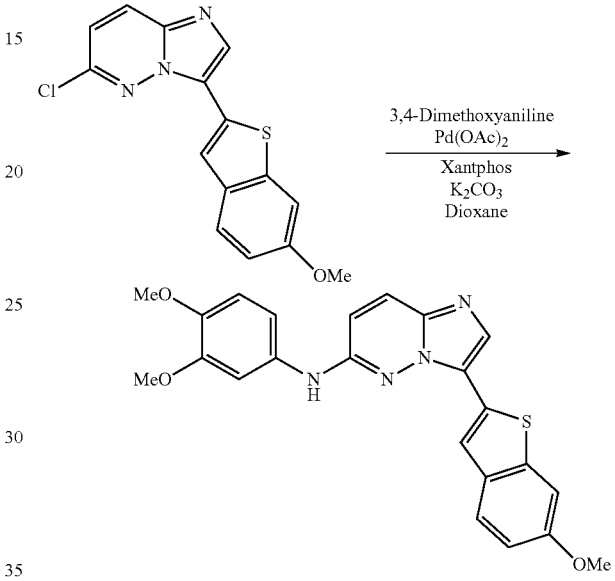

To a solution of 6-chloro-3-(6-methoxybenzo[b]thiophen-2-yl)imidazo[1,2-b]pyridazine (82 mg, 0.260 mmol, 1.0 equiv), xantphos (30 mg, 0.0519 mmol, 0.2 equiv), palladium acetate (6 mg, 0.0260 mmol, 0.1 equiv), and potassium carbonate (718 mg, 5.19 mmol, 20 equiv) in dioxane (5.0 mL) was added 3,4-dimethoxyaniline (48 mg, 0.312 mmol, 1.1 equiv) and heated to 110° C. for 2 h. Purification by column chromatography using 2% methanol in dichloromethane elution gave 77 mg, 0.195 mmol of the yellow solid, 75%.

Compound 72 was physically characterized by electrospray ionization mass spectrometry. Structures and molecular masses are given below in Table 22-b.

TABLE 22-b

| Cd. | Structure | IUPAC Name | [M + H]+ |
|---|---|---|---|
| 72 | 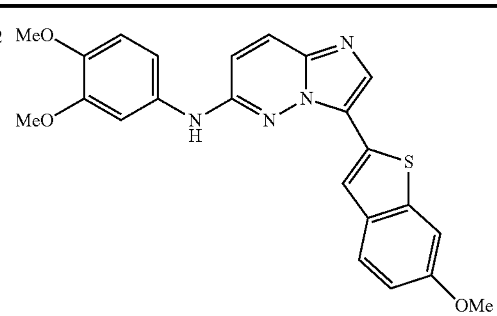 | 3-(6-methoxybenzo[b]thiophen-2-yl)-N-(3,4-dimethoxyphenyl)imidazo[1,2-b]pyridazin-6-amine | 395.1 |

EXAMPLE 23

Synthesis of Compound 172

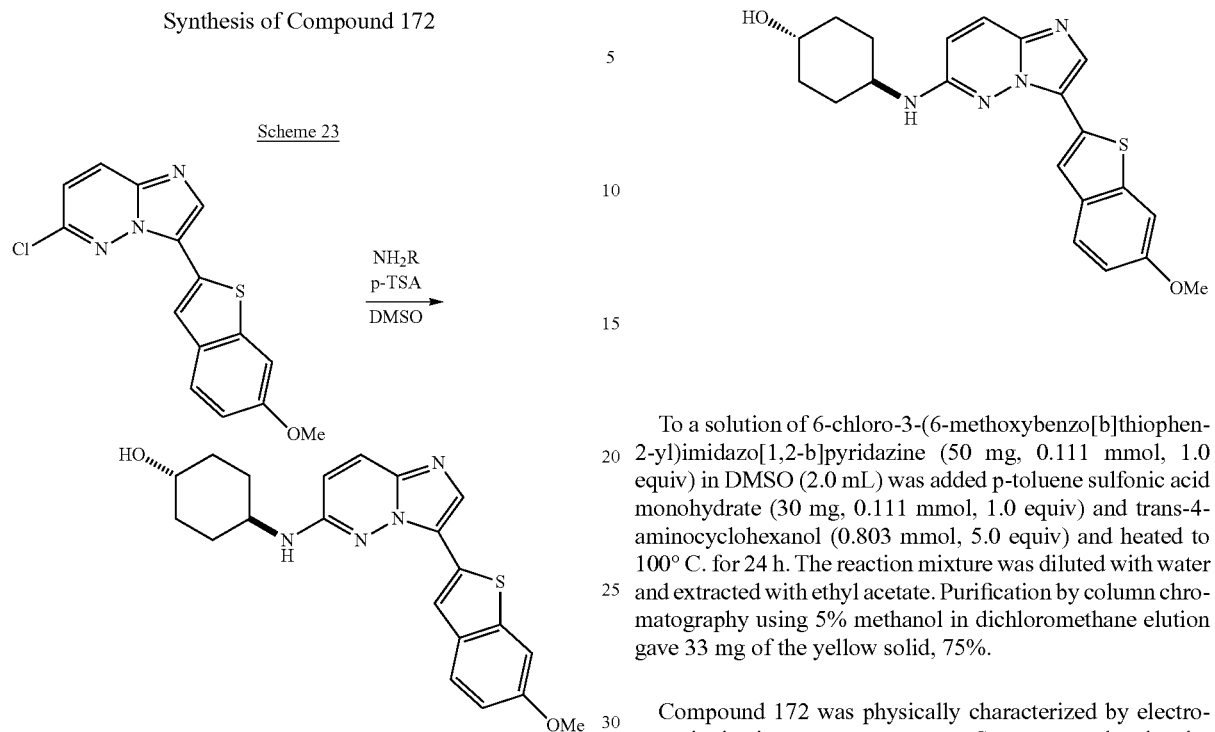

Scheme 23

Preparation of trans-4-(3-(6-methoxybenzo[b]thiophen-2-yl)imidazo[1,2-b]pyridazin-6-ylamino)cyclohexanol To a solution of 6-chloro-3-(6-methoxybenzo[b]thiophen-2-yl)imidazo[1,2-b]pyridazine (50 mg, 0.111 mmol, 1.0 equiv) in DMSO (2.0 mL) was added p-toluene sulfonic acid monohydrate (30 mg, 0.111 mmol, 1.0 equiv) and trans-4-aminocyclohexanol (0.803 mmol, 5.0 equiv) and heated to 100° C. for 24 h. The reaction mixture was diluted with water and extracted with ethyl acetate. Purification by column chromatography using 5% methanol in dichloromethane elution gave 33 mg of the yellow solid, 75%.

Compound 172 was physically characterized by electrospray ionization mass spectrometry. Structures and molecular masses are given below in Table 23-b.

TABLE 23-b

| Cd. | Structure | IUPAC Name | [M + H]⁺ |
|---|---|---|---|
| 172 | (structure shown) | trans-4-(3-(6-methoxybenzo[b]thiophen-2-yl)imidazo[1,2-b]pyridazin-6-ylamino)cyclohexanol | 395.1 |

EXAMPLE 24

Synthesis of Compound 167

Scheme 24

-continued

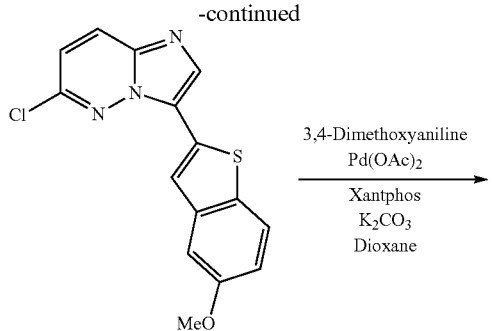

Preparation of 6-chloro-3-(5-methoxybenzo[b]thiophen-2-yl)imidazo[1,2-b]pyridazine

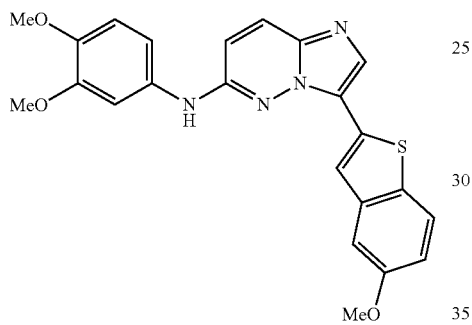

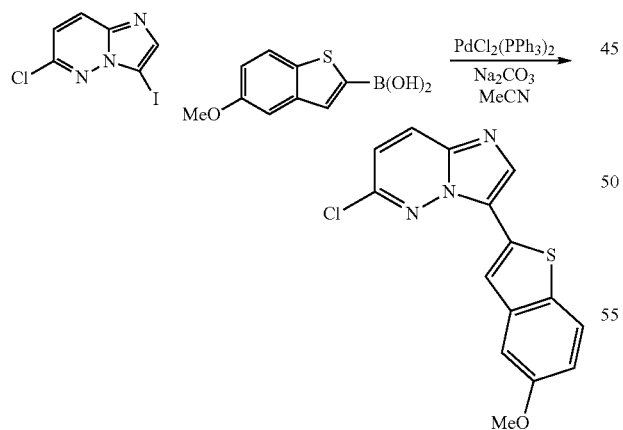

To a solution of 6-methoxybenzo[b]thiophen-2-yl-2-boronic acid (50 mg, 0.242 mmol, 1.1 equiv) in acetonitrile (2.15 mL) was added 6-chloro-3-iodoimidazo[1,2-b]pyridazine (56 mg, 0.220 mmol, 1.0 equiv), palladium catalyst (8 mg, 0.0121 mmol, 0.05 equiv) and sodium carbonate (2.42 mL, 1.0 M, 10.0 equiv). The solution was stirred at 150° C. in the microwave for 10 minutes. Purification using column chromatography gave 50 mg of the yellow solid, 77%.

Preparation of 3-(5-methoxybenzo[b]thiophen-2-yl)-N-(3,4-dimethoxyphenyl)imidazo[1,2-b]pyridazin-6-amine

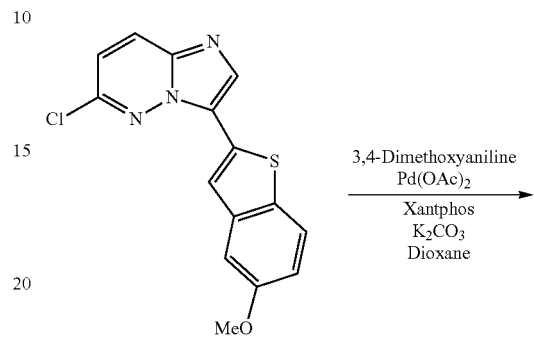

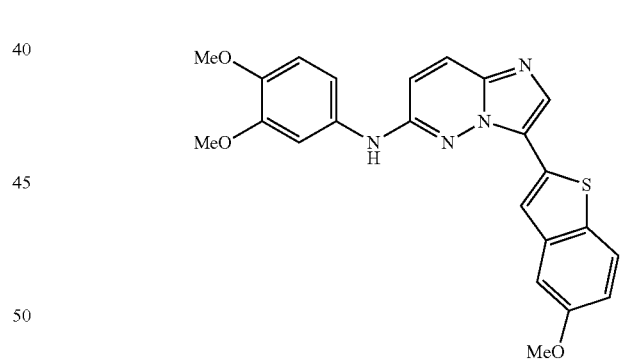

To a solution of 6-chloro-3-(5-methoxybenzo[b]thiophen-2-yl)imidazo[1,2-b]pyridazine (80 mg, 0.254 mmol, 1.0 equiv), xantphos (29 mg, 0.0506 mmol, 0.2 equiv), palladium acetate (6 mg, 0.0254 mmol, 0.1 equiv), and potassium carbonate (700 mg, 5.06 mmol, 20 equiv) in dioxane (5.0 mL) was added 3,4-dimethoxyaniline (47 mg, 0.304 mmol, 1.1 equiv) and heated to 110° C. for 2 h. Purification by column chromatography using 2% methanol in dichloromethane elution gave 62 mg, 0.152 mmol of the yellow solid, 60%.

Compound 167 was physically characterized by electrospray ionization mass spectrometry. Structures and molecular masses are given below in Table 24-b.

TABLE 24-b

| Cd. | Structure | IUPAC Name | [M + H]+ |
|---|---|---|---|
| 167 | 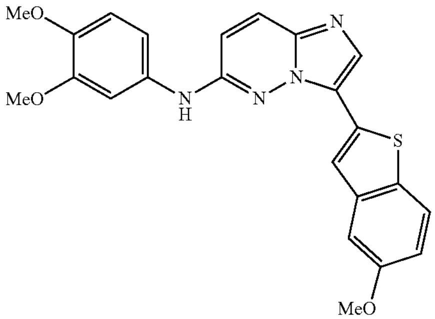 [SMILES: COc1ccc2sc(-c3cnc4ccc(Nc5ccc(OC)c(OC)c5)nn34)cc2c1] | 3-(5-methoxybenzo[b]thiophen-2-yl)-N-(3,4-dimethoxyphenyl)imidazo[1,2-b]pyridazin-6-amine | 433.7 |

EXAMPLE 25A

Synthesis of Compound 168

Preparation of trans-4-(3-(5-methoxybenzo[b]thiophen-2-yl)imidazo[1,2-b]pyridazin-6-ylamino)cyclohexanol

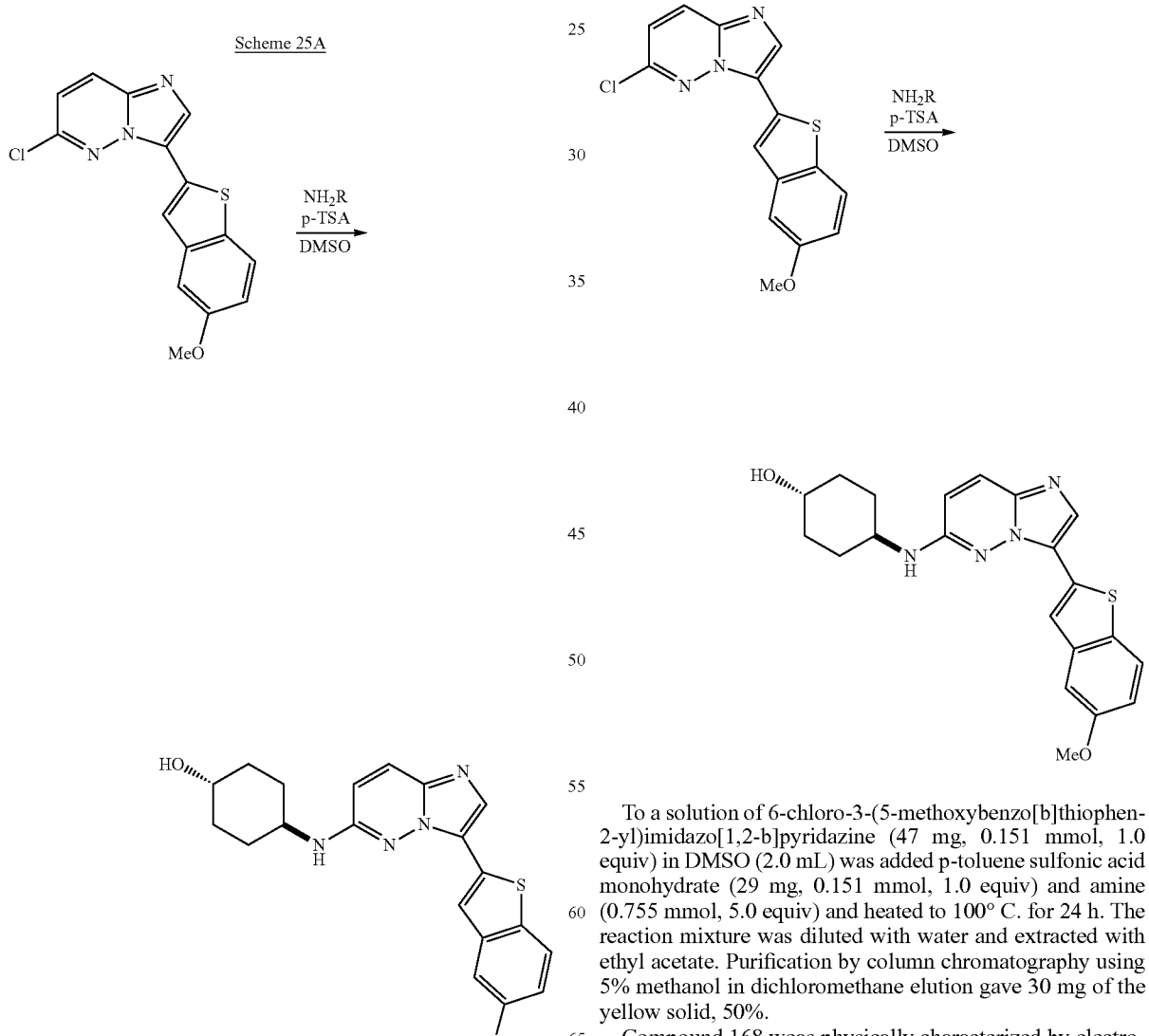

Scheme 25A

To a solution of 6-chloro-3-(5-methoxybenzo[b]thiophen-2-yl)imidazo[1,2-b]pyridazine (47 mg, 0.151 mmol, 1.0 equiv) in DMSO (2.0 mL) was added p-toluene sulfonic acid monohydrate (29 mg, 0.151 mmol, 1.0 equiv) and amine (0.755 mmol, 5.0 equiv) and heated to 100° C. for 24 h. The reaction mixture was diluted with water and extracted with ethyl acetate. Purification by column chromatography using 5% methanol in dichloromethane elution gave 30 mg of the yellow solid, 50%.

Compound 168 weas physically characterized by electrospray ionization mass spectrometry. Structures and molecular masses are given below in Table 25A.

TABLE 25A

| Cd. | Structure | IUPAC Name | [M + H]+ |
|---|---|---|---|
| 168 | 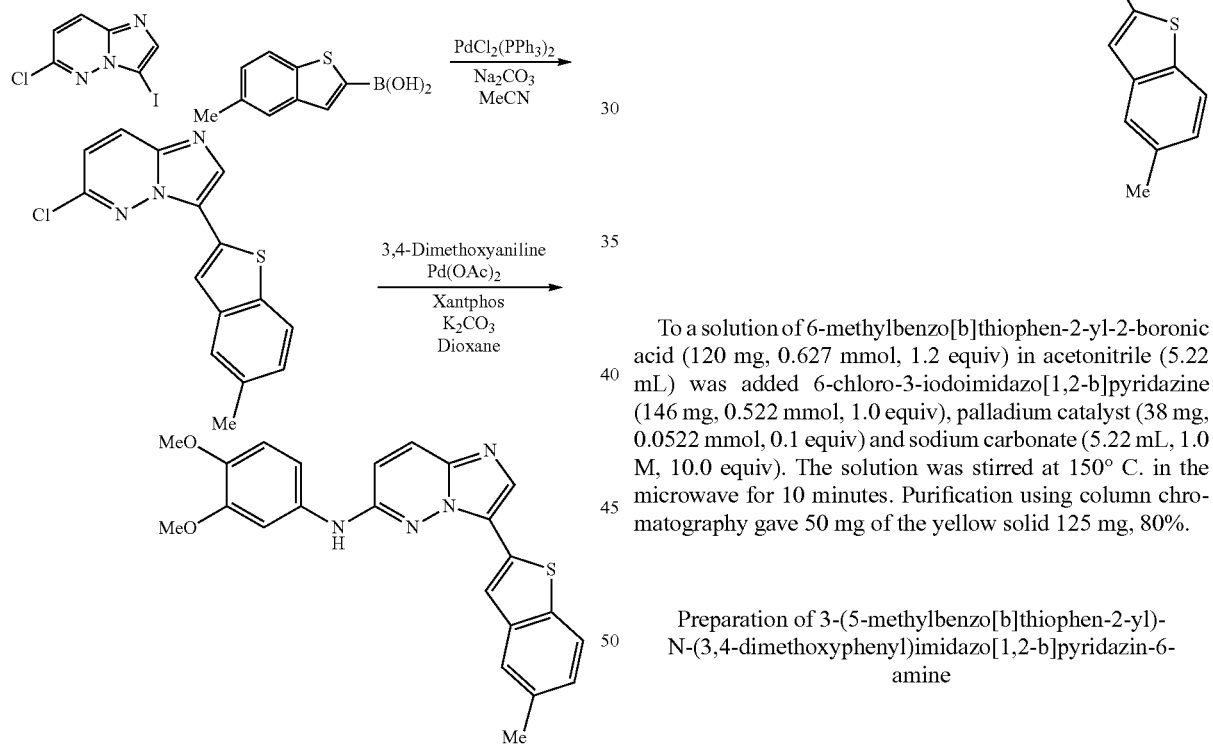 | trans-4-(3-(5-methoxybenzo[b]thiophen-2-yl)imidazo[1,2-b]pyridazin-6-ylamino)cyclohexanol | 395.7 |

EXAMPLE 25B

Synthesis of Compound 191

Scheme 25B

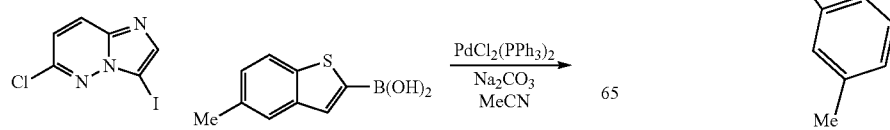

Preparation of 6-chloro-3-(5-methylbenzo[b]thiophen-2-yl)imidazo[1,2-b]pyridazine

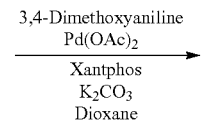

To a solution of 6-methylbenzo[b]thiophen-2-yl-2-boronic acid (120 mg, 0.627 mmol, 1.2 equiv) in acetonitrile (5.22 mL) was added 6-chloro-3-iodoimidazo[1,2-b]pyridazine (146 mg, 0.522 mmol, 1.0 equiv), palladium catalyst (38 mg, 0.0522 mmol, 0.1 equiv) and sodium carbonate (5.22 mL, 1.0 M, 10.0 equiv). The solution was stirred at 150° C. in the microwave for 10 minutes. Purification using column chromatography gave 50 mg of the yellow solid 125 mg, 80%.

Preparation of 3-(5-methylbenzo[b]thiophen-2-yl)-N-(3,4-dimethoxyphenyl)imidazo[1,2-b]pyridazin-6-amine

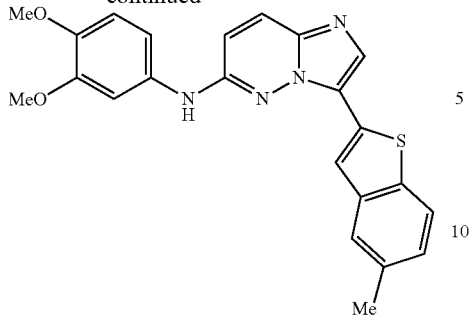

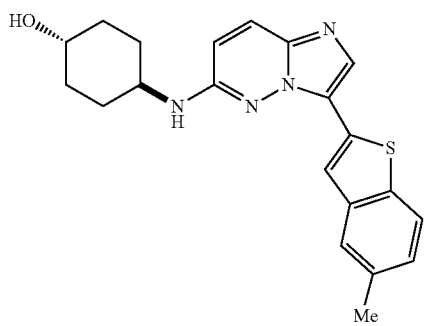

To a solution of 6-chloro-3-(5-methylbenzo[b]thiophen-2-yl)imidazo[1,2-b]pyridazine (50 mg, 0.168 mmol, 1.0 equiv), xantphos (19 mg, 0.0334 mmol, 0.2 equiv), palladium acetate (4 mg, 0.0167 mmol, 0.1 equiv), and potassium carbonate (461 mg, 3.34 mmol, 20 equiv) in dioxane (5.0 mL) was added 3,4-dimethoxyaniline (28 mg, 0.167 mmol, 1.1 equiv) and heated to 110° C. for 2 h. Purification by column chromatography using 2% methanol in dichloromethane elution gave 42 mg, 0.152 mmol of the yellow solid, 60%.

Compound 191 was physically characterized by electrospray ionization mass spectrometry. Structures and molecular masses are given below in Table 25B.

TABLE 25B

| Cd. | Structure | IUPAC Name | [M + H]⁺ |
|---|---|---|---|
| 191 | 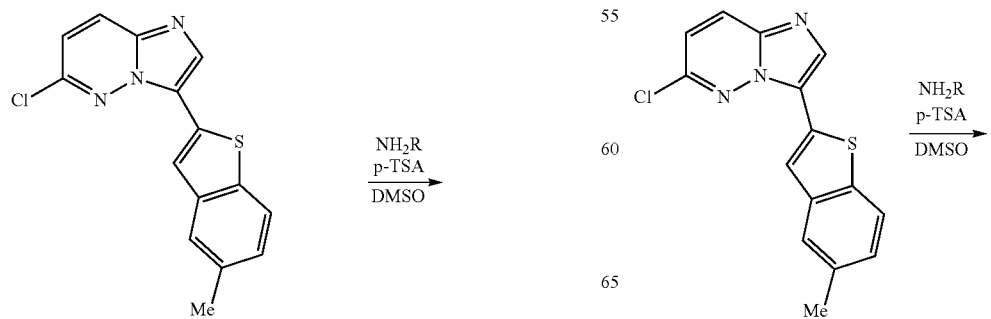 | N-(3,4-dimethoxyphenyl)-3-(5-methylbenzo[b]thiophen-2-yl)imidazo[1,2-b]pyridazin-6-amine | 417.1 |

EXAMPLE 25C

Synthesis of Compound 192

Preparation of trans-4-(3-(5-methylbenzo[b]thiophen-2-yl)imidazo[1,2-b]pyridazin-6-ylamino)cyclohexanol Scheme 25C

155

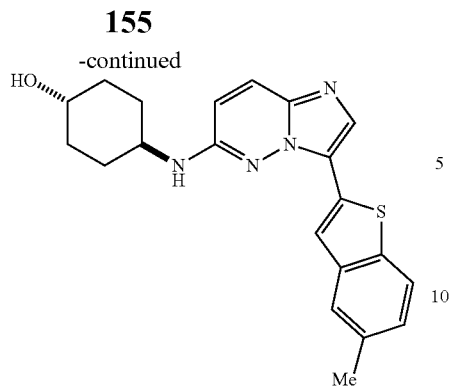

To a solution of 6-chloro-3-(5-methylbenzo[b]thiophen-2-yl)imidazo[1,2-b]pyridazine (50 mg, 0.168 mmol, 1.0 equiv) in DMSO (2.0 mL) was added p-toluene sulfonic acid monohydrate (30 mg, 0.168 mmol, 1.0 equiv) and amine (0.840 mmol, 5.0 equiv) and heated to 100° C. for 24 h. The reaction mixture was diluted with water and extracted with ethyl acetate. Purification by column chromatography using 5% methanol in dichloromethane elution gave 30 mg of the yellow solid, 47%.

Compound 192 weas physically characterized by electrospray ionization mass spectrometry. Structures and molecular masses are given below in Table 25C.

TABLE 25C

| Cd. | Structure | IUPAC Name | [M + H]+ |
|---|---|---|---|
| 192 | 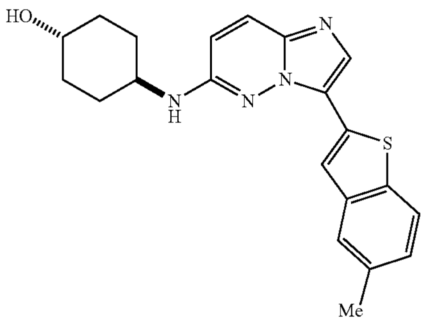 | trans-4-(3-(5-methylbenzo[b]thiophen-2-yl)imidazo[1,2-b]pyridazin-6-ylamino)cyclohexanol | 379.5 |

156

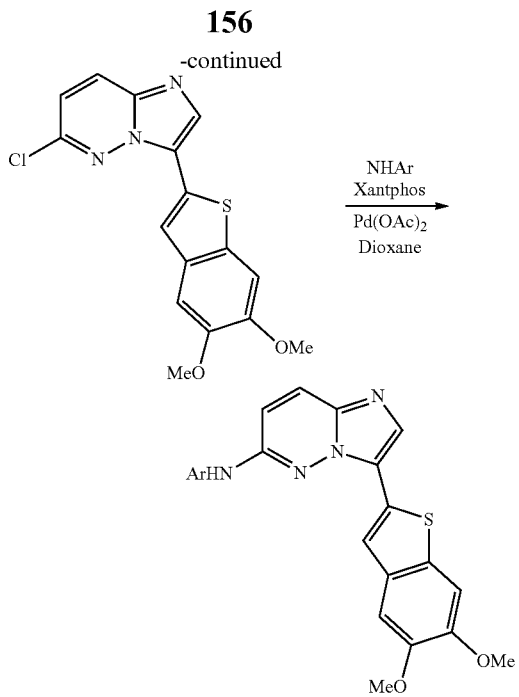

EXAMPLE 26

Synthesis of Compounds 67, 70-71

Preparation of 6-chloro-3-(5,6-dimethoxybenzo[b]thiophen-2-yl)imidazo[1,2-b]pyridazine

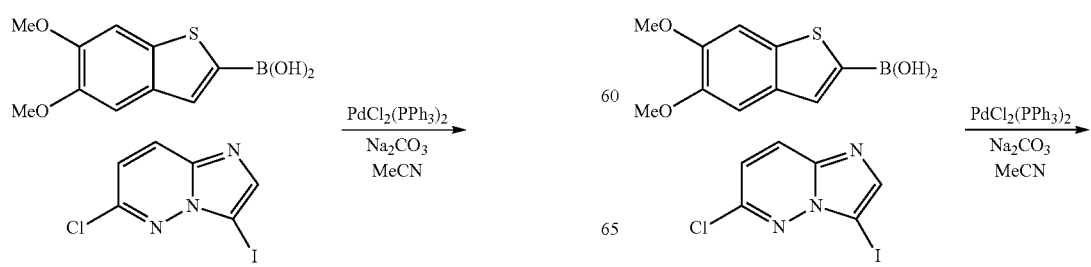

Scheme 26

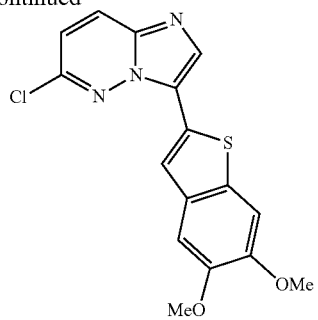

To a solution of 5,6-dimethoxybenzo[b]thiophen-2-yl-2-boronic acid (471 mg, 1.98 mmol, 1.3 equiv) in acetonitrile (10.0 mL) was added 6-chloro-3-iodoimidazo[1,2-b]pyridazine (425 mg, 1.52 mmol, 1.0 equiv), palladium catalyst (56 mg, 0.0760 mmol, 0.05 equiv) and sodium carbonate (10.0 mL, 1.0 M, 10.0 equiv). The solution was stirred at rt overnight. Purification using column chromatography gave 368 mg of the product, 70%: $^1$H NMR (400 MHz, DMSO) δ 8.35 (s, 1H), 8.32 (d, J=7.6 Hz, 1H), 8.06 (s, 1H), 7.63 (s, 1H), 7.47 (s, 1H), 7.44 (d, J=7.6 Hz, 1H), 3.85 (s, 3H), 3.84 (s, 3H).

Preparation of 3-(5,6-dimethoxybenzo[b]thiophen-2-yl)-N-arylimidazo[1,2-b]pyridazin-6-amine

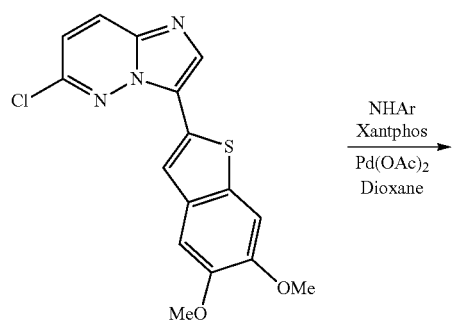

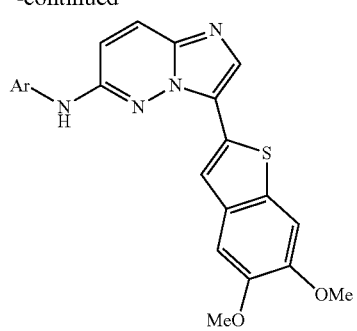

To a solution of 6-chloro-3-(5,6-dimethoxybenzo[b]thiophen-2-yl)imidazo[1,2-b]pyridazine (69 mg, 0.20 mmol, 1.0 equiv), xantphos (23 mg, 0.04 mmol, 0.2 equiv), palladium acetate (4 mg, 0.02 mmol, 0.1 equiv), and potassium carbonate (553 mg, 4.00 mmol, 20 equiv) in dioxane (5.0 mL) was added amine (0.20 mmol, 1.0 equiv) and heated to 110° C. for 2 h. Purification by column chromatography using 2% methanol in dichloromethane elution gave the product.

TABLE 26-a

| Cd. | Amine | Pure Isolated Compound |
|---|---|---|
| 67 | 3,4-dimethoxyaniline | 3-(5,6-dimethoxybenzo[b]thiophen-2-yl)-N-(3,4-dimethoxyphenyl)imidazo[1,2-b]pyridazin-6-amine |
| 70 | 3-(4-amino-2-methoxyphenoxy)propan-1-ol | 3-(4-(3-(5,6-dimethoxybenzo[b]thiophen-2-yl)imidazo[1,2-b]pyridazin-6-ylamino)-2-methoxyphenoxy)propan-1-ol |
| 71 | methyl 3-aminobenzoate | 3-(3-(5,6-dimethoxybenzo[b]thiophen-2-yl)imidazo[1,2-b]pyridazin-6-ylamino)benzoic acid |

Compounds 67, 70-71 were physically characterized by electrospray ionization mass spectrometry. Structures and molecular masses are given below in Table 26-b.

TABLE 26-b

| Cd. | Structure | IUPAC Name | [M + H]$^+$ |
|---|---|---|---|
| 67 | 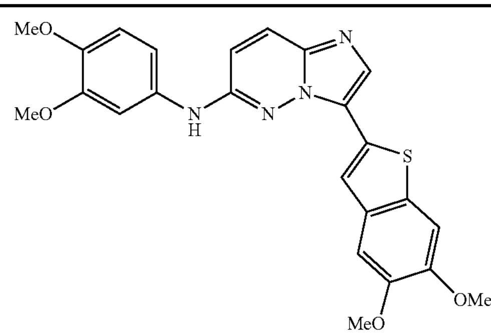 | 3-(5,6-dimethoxybenzo[b]thiophen-2-yl)-N-(3,4-dimethoxyphenyl)imidazo[1,2-b]pyridazin-6-amine | 463.5 |

TABLE 26-b-continued

| Cd. | Structure | IUPAC Name | [M + H]⁺ |
|---|---|---|---|
| 70 | 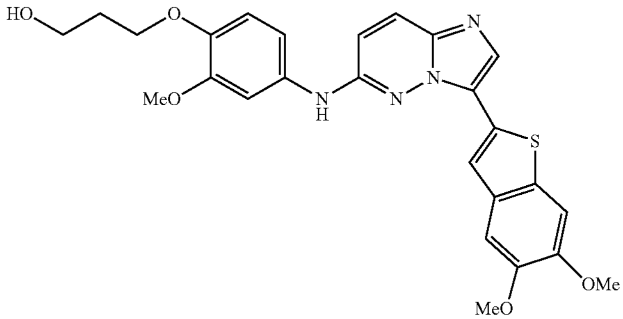 [SMILES: COc1cc2cc(-c3cnc4ccc(Nc5ccc(OCCCO)c(OC)c5)nn34)sc2cc1OC] | 3-(4-(3-(5,6-dimethoxybenzo[b]thiophen-2-yl)imidazo[1,2-b]pyridazin-6-ylamino)-2-methoxyphenoxy)propan-1-ol | 507.3 |
| 71 | 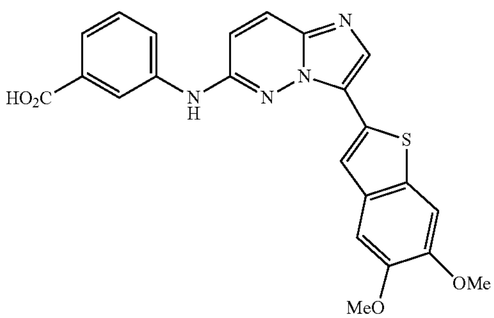 [SMILES: COc1cc2cc(-c3cnc4ccc(Nc5cccc(C(=O)O)c5)nn34)sc2cc1OC] | 3-(3-(5,6-dimethoxybenzo[b]thiophen-2-yl)imidazo[1,2-b]pyridazin-6-ylamino)benzoic acid | 447.1 |

EXAMPLE 27

Synthesis of Compound 75

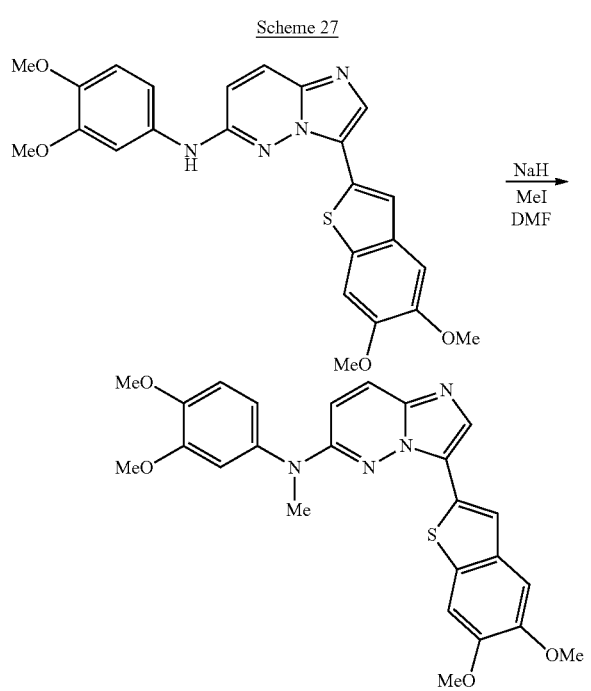

Scheme 27

Preparation of 3-(5,6-dimethoxybenzo[b]thiophen-2-yl)-N-(3,4-dimethoxyphenyl)-N-methylimidazo[1,2-b]pyridazin-6-amine To a solution of 3-(5,6-dimethoxybenzo[b]thiophen-2-yl)-N-(3,4-dimethoxyphenyl)imidazo[1,2-b]pyridazin-6-amine (50 mg, 0.108 mmol, 1.0 equiv) in DMF (5.0 mL) was added NaH (13 mg, 0.324 mmol, 3.0 equiv) followed by iodomethane (0.07 mL, 0.541 mmol, 5.0 equiv). After 1 h, the reaction was quenched with saturated aqueous solution of ammonium chloride then extracted with ethyl acetate. Purification by column chromatography using 2% methanol in dichloromethane elution gave 30 mg of the brown solid, 58%.

Compound 75 was physically characterized by electrospray ionization mass spectrometry. Structure and molecular mass is given below in Table 27-b.

TABLE 27-b

| Cd. | Structure | IUPAC Name | [M + H]+ |
|---|---|---|---|
| 75 | 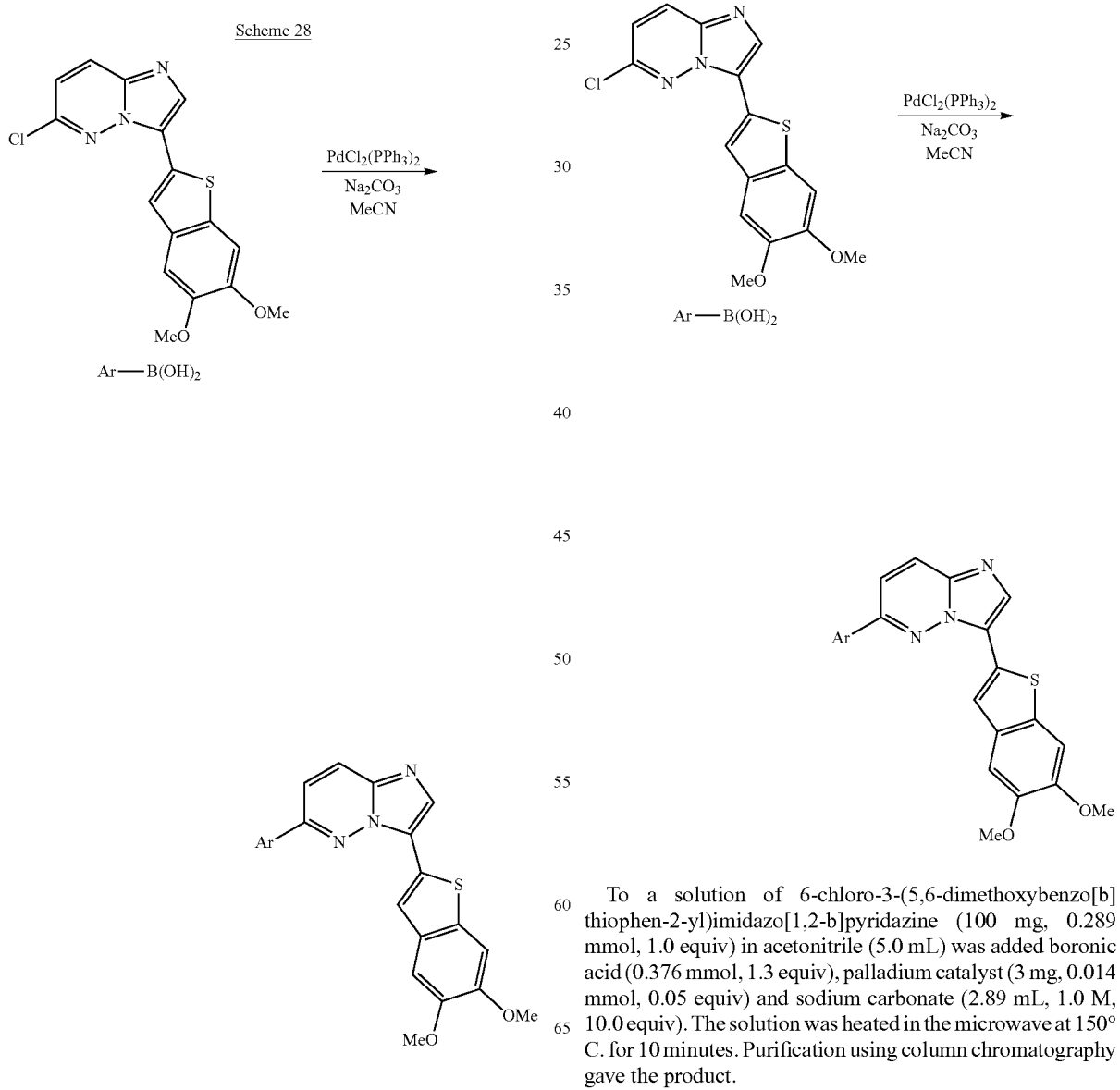 | 3-(5,6-dimethoxybenzo[b]thiophen-2-yl)-N-(3,4-dimethoxyphenyl)-N-methylimidazo[1,2-b]pyridazin-6-amine | 477.1 |

EXAMPLE 28

Synthesis of Compounds 69, 73-74

Preparation of 3-(5,6-dimethoxybenzo[b]thiophen-2-yl)-6-arylimidazo[1,2-b]pyridazine To a solution of 6-chloro-3-(5,6-dimethoxybenzo[b]thiophen-2-yl)imidazo[1,2-b]pyridazine (100 mg, 0.289 mmol, 1.0 equiv) in acetonitrile (5.0 mL) was added boronic acid (0.376 mmol, 1.3 equiv), palladium catalyst (3 mg, 0.014 mmol, 0.05 equiv) and sodium carbonate (2.89 mL, 1.0 M, 10.0 equiv). The solution was heated in the microwave at 150° C. for 10 minutes. Purification using column chromatography gave the product.

TABLE 28-a

| Cd. | Boronic Acid | Pure Isolated Compound |
|---|---|---|
| 69 | 1H-indol-5-yl-5-boronic acid | 6-(1H-indol-5-yl)-3-(5,6-dimethoxybenzo[b]thiophen-2-yl)imidazo[1,2-b]pyridazine |
| 73 | 4-((4-methylpiperazin-1-yl)methyl)phenylboronic acid | 3-(5,6-dimethoxybenzo[b]thiophen-2-yl)-6-(4-((4-methylpiperazin-1-yl)methyl)phenyl)imidazo[1,2-b]pyridazine |
| 74 | 3-((4-methylpiperazin-1-yl)methyl)phenylboronic acid | 3-(5,6-dimethoxybenzo[b]thiophen-2-yl)-6-(3-((4-methylpiperazin-1-yl)methyl)phenyl)imidazo[1,2-b]pyridazine |

Compounds 69, 73-74 were physically characterized by electrospray ionization mass spectrometry. Structures and molecular masses are given below in Table 28-b.

TABLE 28-b

| Cd. | Structure | IUPAC Name | [M + H]+ |
|---|---|---|---|
| 69 | 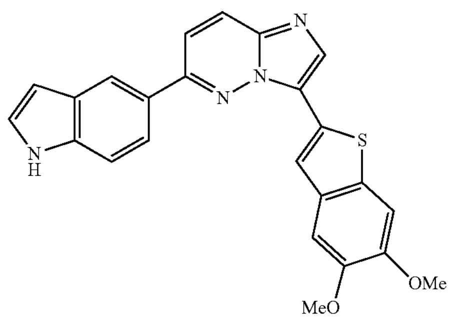 [SMILES: COc1cc2cc(-c3cnc4ccc(-c5ccc6[nH]ccc6c5)nn34)sc2cc1OC] | 6-(1H-indol-5-yl)-3-(5,6-dimethoxybenzo[b]thiophen-2-yl)imidazo[1,2-b]pyridazine | 427.0 |
| 73 | 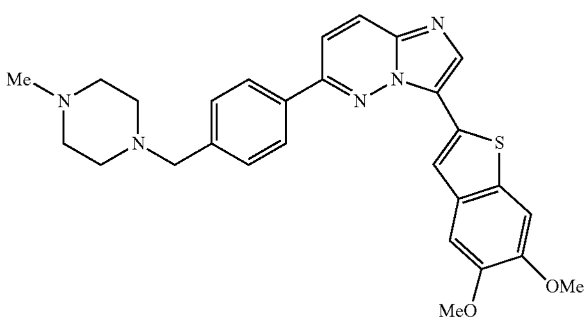 [SMILES: COc1cc2cc(-c3cnc4ccc(-c5ccc(CN6CCN(C)CC6)cc5)nn34)sc2cc1OC] | 3-(5,6-dimethoxybenzo[b]thiophen-2-yl)-6-(4-((4-methylpiperazin-1-yl)methyl)phenyl)imidazo[1,2-b]pyridazine | 500.2 |
| 74 | 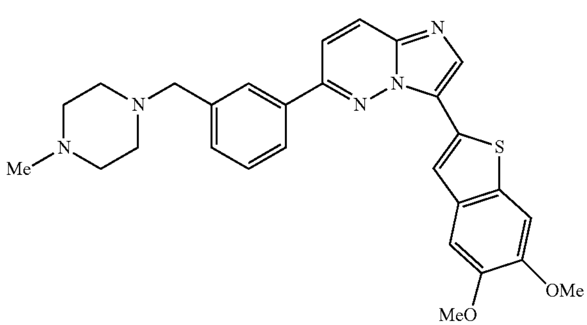 [SMILES: COc1cc2cc(-c3cnc4ccc(-c5cccc(CN6CCN(C)CC6)c5)nn34)sc2cc1OC] | 3-(5,6-dimethoxybenzo[b]thiophen-2-yl)-6-(3-((4-methylpiperazin-1-yl)methyl)phenyl)imidazo[1,2-b]pyridazine | 500.3 |

EXAMPLE 29

Synthesis of Compounds 169, 171, 173-174

Scheme 29

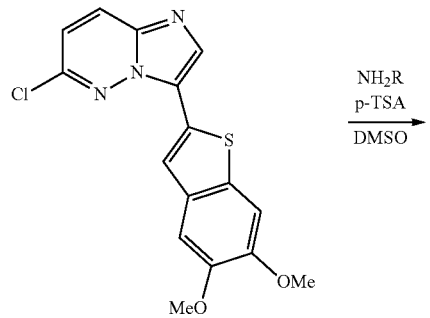

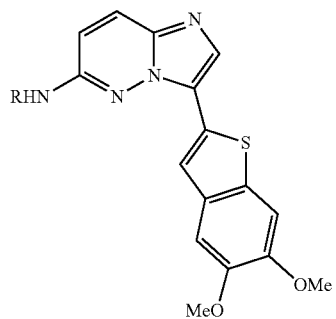

To a solution of 6-chloro-3-(5,6-dimethoxybenzo[b]thiophen-2-yl)imidazo[1,2-b]pyridazine (311 mg, 0.899 mmol, 1.0 equiv) in DMSO (5.0 mL) was added p-toluene sulfonic acid monohydrate (171 mg, 0.899 mmol, 1.0 equiv) and amine (4.50 mmol, 5.0 equiv) and heated to 100° C. for 24 h. The reaction mixture was diluted with water and extracted with ethyl acetate. Purification by column chromatography using 5% methanol in dichloromethane elution gave the product.

Preparation of 3-(5,6-dimethoxybenzo[b]thiophen-2-yl)-N-alkylimidazo[1,2-b]pyridazin-6-amine

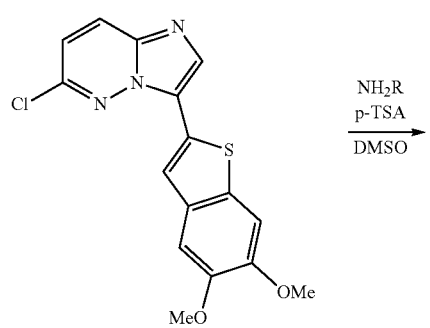

TABLE 29-a

| Cd. | Amine | Pure Isolated Compound |
|---|---|---|
| 169 | trans-4-aminocyclohexanol | trans-4-(3-(5,6-dimethoxybenzo[b]thiophen-2-yl)imidazo[1,2-b]pyridazin-6-ylamino)cyclohexanol |
| 171 | 4-amino-2-methylbutan-1-ol | 4-(3-(5,6-dimethoxybenzo[b]thiophen-2-yl)imidazo[1,2-b]pyridazin-6-ylamino)-2-methylbutan-1-ol |
| 173 | trans-4-amino-1-methylcyclohexanol | (1r,4r)-4-(3-(5,6-dimethoxybenzo[b]thiophen-2-yl)imidazo[1,2-b]pyridazin-6-ylamino)-1-methylcyclohexanol |
| 174 | 3-aminocyclohexanol | 3-(3-(5,6-dimethoxybenzo[b]thiophen-2-yl)imidazo[1,2-b]pyridazin-6-ylamino)cyclohexanol |
| 201 | trans-4-methoxycyclohexanamine | trans-3-(5,6-dimethoxybenzo[b]thiophen-2-yl)-N-(4-methoxycyclohexyl)imidazo[1,2-b]pyridazin-6-amine |

Compounds 169, 171, 173-174, 201 were physically characterized by electrospray ionization mass spectrometry. Structures and molecular masses are given below in Table 29-b.

TABLE 29-b

| Cd. | Structure | IUPAC Name | [M + H]⁺ |
|---|---|---|---|
| 169 | 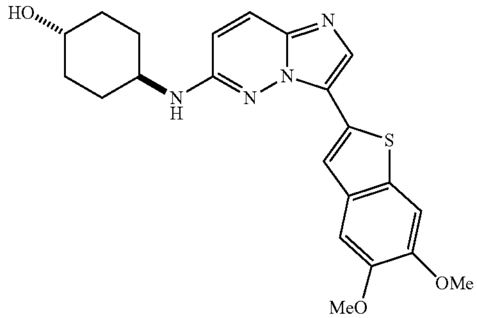 | trans-4-(3-(5,6-dimethoxybenzo[b]thiophen-2-yl)imidazo[1,2-b]pyridazin-6-ylamino)cyclohexanol | 425.5 |
| 171 | 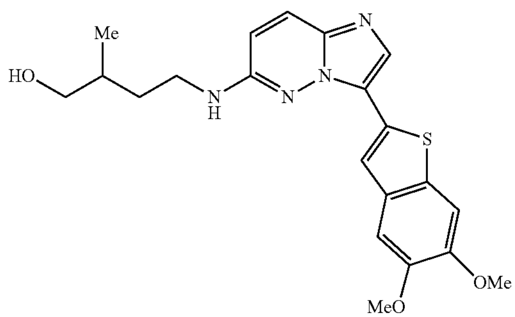 [SMILES: COc1cc2cc(-c3cnc4ccc(NCCC(C)CO)nn34)sc2cc1OC] | 4-(3-(5,6-dimethoxybenzo[b]thiophen-2-yl)imidazo[1,2-b]pyridazin-6-ylamino)-2-methylbutan-1-ol | 413.3 |
| 173 | 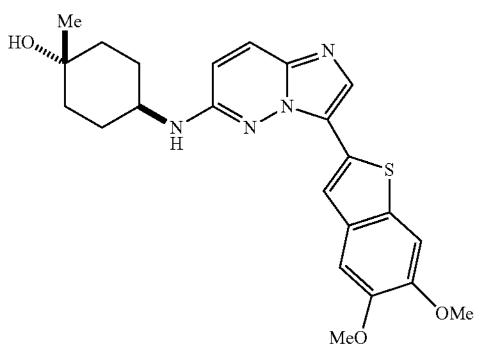 | (1r,4r)-4-(3-(5,6-dimethoxybenzo[b]thiophen-2-yl)imidazo[1,2-b]pyridazin-6-ylamino)-1-methylcyclohexanol | 439.2 |
| 174 | 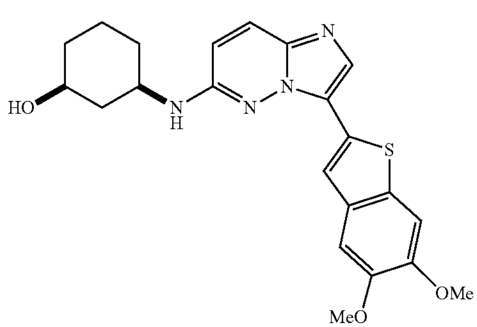 | 3-(3-(5,6-dimethoxybenzo[b]thiophen-2-yl)imidazo[1,2-b]pyridazin-6-ylamino)cyclohexanol | 425.1 |

TABLE 29-b-continued

| Cd. | Structure | IUPAC Name | [M + H]⁺ |
|---|---|---|---|
| 201 | 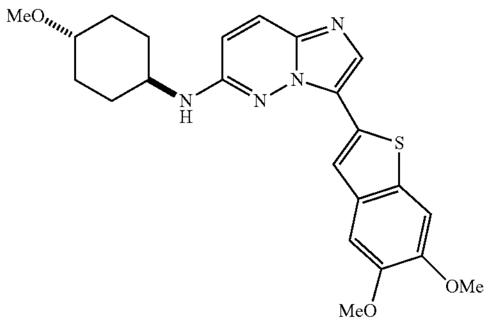 | trans-3-(5,6-dimethoxybenzo[b]thiophen-2-yl)-N-(4-methoxycyclohexyl)imidazo[1,2-b]pyridazin-6-amine | 439.4 |

EXAMPLE 30

Synthesis of Compounds 175 and 177

Preparation of 3-(5,6-dimethoxybenzo[b]thiophen-2-yl)-N-(trans-4-methoxycyclohexyl)-N-methylimidazo[1,2-b]pyridazin-6-amine and trans-4-(N-(3-(5,6-dimethoxybenzo[b]thiophen-2-yl)imidazo[1,2-b]pyridazin-6-yl)-N-methylamino)cyclohexanol

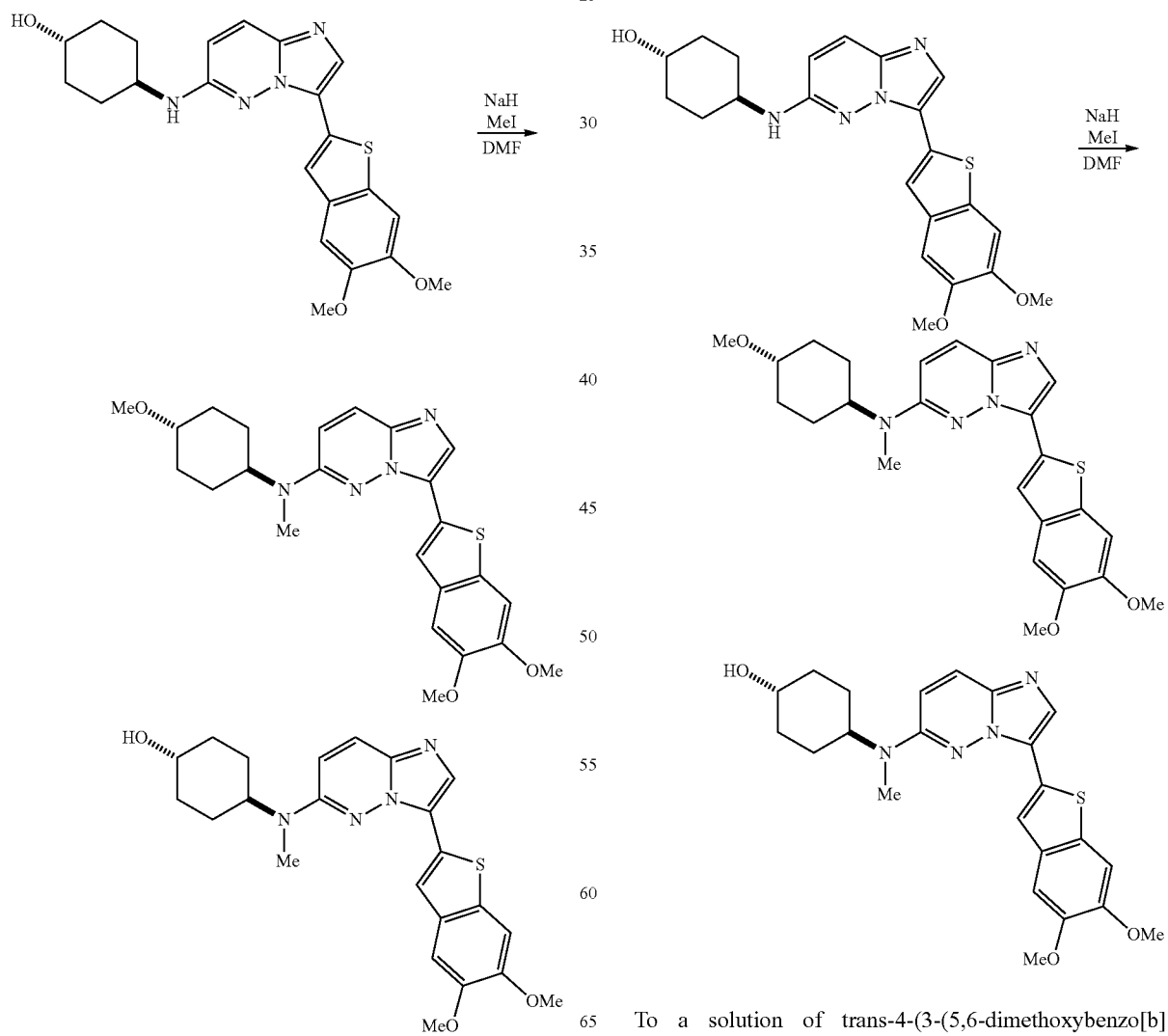

Scheme 30

To a solution of trans-4-(3-(5,6-dimethoxybenzo[b]thiophen-2-yl)imidazo[1,2-b]pyridazin-6-ylamino)cyclohexanol (100 mg, 0.236 mmol, 1.0 equiv) in DMF (2.00 mL)

was added sodium hydride (28 mg, 0.707 mmol, 3.0 equiv) and methyl iodide (167 mg, 1.18 mmol, 5.0 equiv). After 2 h, the reaction mixture was quenched with water and extracted with ethyl acetate. Purification by column chromatography gave 30 mg (28%) of 3-(5,6-dimethoxybenzo[b]thiophen-2-yl)-N-(trans-4-methoxycyclohexyl)-N-methylimidazo[1,2-b]pyridazin-6-amine as the less polar product and 21 mg (20%) of trans-4-(N-(3-(5,6-dimethoxybenzo[b]thiophen-2-yl)imidazo[1,2-b]pyridazin-6-yl)-N-methylamino)cyclohexanol as the more polar product.

Compounds 175 and 177 were physically characterized by electrospray ionization mass spectrometry. Structures and molecular masses are given below in Table 30-b.

TABLE 30-b

| Cd. | Structure | IUPAC Name | [M + H]+ |
|---|---|---|---|
| 175 | 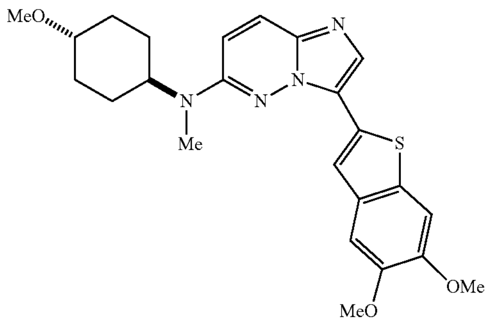 | 3-(5,6-dimethoxybenzo[b]thiophen-2-yl)-N-(trans-4-methoxycyclohexyl)-N-methylimidazo[1,2-b]pyridazin-6-amine | 453.3 |
| 177 | 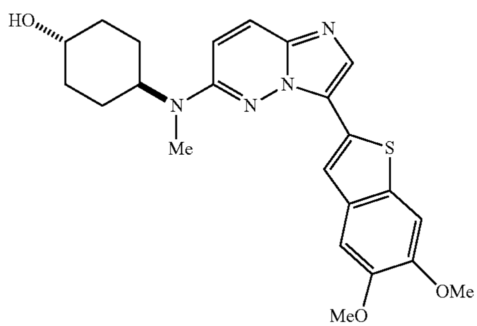 | trans-4-(N-(3-(5,6-dimethoxybenzo[b]thiophen-2-yl)imidazo[1,2-b]pyridazin-6-yl)-N-methylamino)cyclohexanol | 439.4 |

EXAMPLE 31

Synthesis of Compound 76

Scheme 31

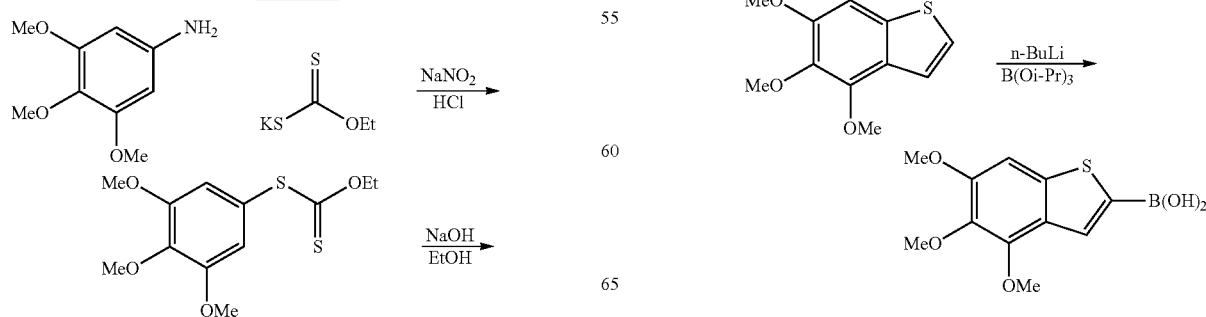

Preparation of O-ethyl S-3,4,5-trimethoxyphenyl carbonodithioate

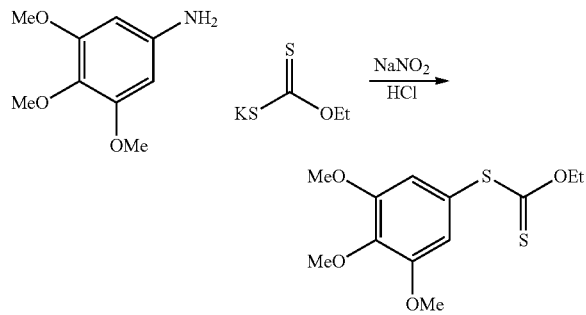

Aniline (2.00 g, 10.9 mmol, 1.0 equiv) at 0° C. was added hydrochloric acid (3 mL) and water (10 mL) followed by sodium nitrite (932 mg, 13.5 mmol, 1.25 equiv). The resulting solution was poured over potassium ethyl xanthogenate (5.35 g, 33.4 mmol, 3.0 equiv) in water (10 mL) and stirred at 50° C. for 40 minutes. Purification by column chromatography using 5% ethyl acetate in hexanes elution gave the yellow solid.

Preparation of 3,4,5-trimethoxybenzenethiol

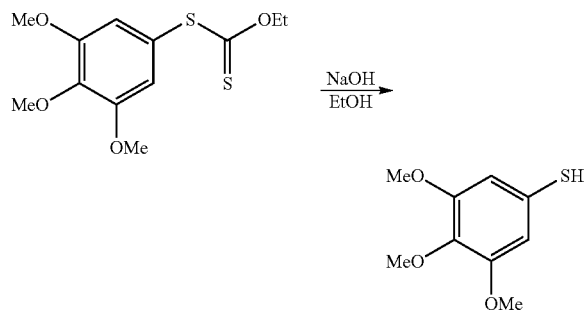

To a solution of O-ethyl S-3,4,5-trimethoxyphenyl carbonodithioate (3.45 g, 10.9 mmol, 1.0 equiv) in methanol (30 mL) was added sodium hydroxide (1.44 g, 32.8 mmol, 3.0 equiv) and heated to 60 C for 3 h. Purification by column chromatography using 5% ethyl acetate in hexanes elution gave 1.75 g, 8.73 mmol of the yellow solid, 80% over 2 steps.

Preparation of (2,2-diethoxyethyl)(3,4,5-trimethoxyphenyl)sulfane

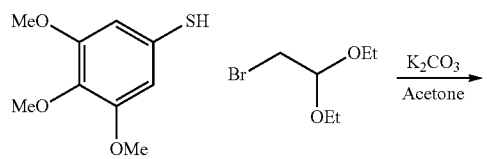

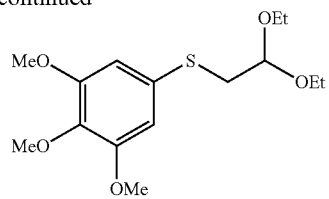

To a solution of thiophenol (1.3 g, 6.49 mmol, 1.0 equiv) in acetone (20 mL) was added potassium carbonate (1.79 g, 13.0 mmol, 2.0 equiv) and bromoacetaldehyde diethylacetal (2.56 g, 13.0 mmol, 2.0 equiv). After 15 h, the reaction mixture was filtered and concentrated. Purification by column chromatography using 5% ethyl acetate in hexanes elution gave the product.

Preparation of 4,5,6-trimethoxybenzo[b]thiophene

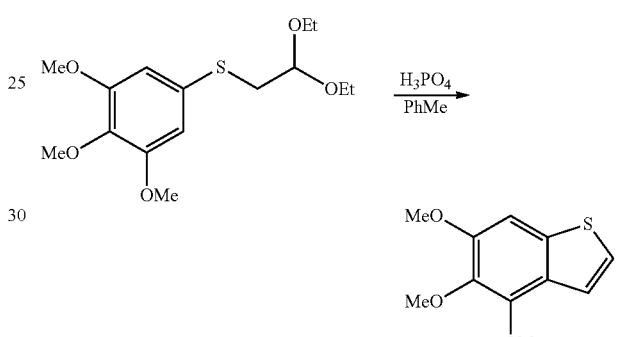

To a solution of thioether (1.00 g, 3.16 mmol, 1.0 equiv) in toluene (20 mL) was added phosphoric acid (10 mL) and heated to 110° C. After 2 h, the reaction mixture was diluted with a saturated aqueous solution of sodium bicarbonate and extracted with ethyl acetate then concentrated. Purification by column chromatography using 5% ethyl acetate in hexanes elution gave 230 g of the white product, 32% yield.

Preparation of 4,5,6-trimethoxybenzo[b]thiophen-2-yl-2-boronic acid

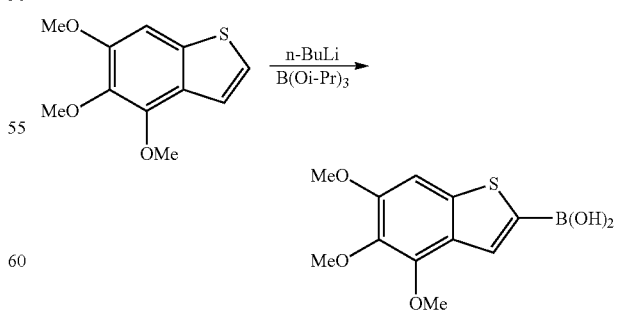

To a solution of 4,5,6-trimethoxybenzo[b]thiophene (200 mg, 0.892 mmol, 1.0 equiv) in THF (10.0 mL) at −78° C. was added n-BuLi (0.84 mL, 1.34 mmol, 1.5 equiv). The reaction was stirred at the reduced temperature for 1 h, then triisopropylborate (0.31 mL, 1.34 mmol, 1.5 equiv) was added and stirred at rt for 2 h. The mixture was quenched with 2N HCl and then extracted with ethyl acetate. Purification by column chromatography using 2% methanol in dichloromethane elution gave 191 mg of white solid, 80%.

Scheme 32

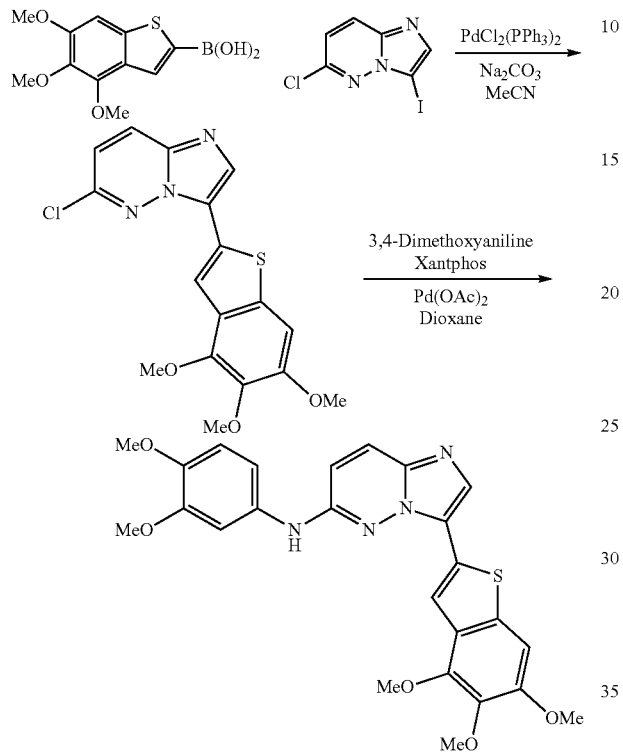

Preparation of 6-chloro-3-(4,5,6-trimethoxybenzo[b]thiophen-2-yl)imidazo[1,2-b]pyridazine

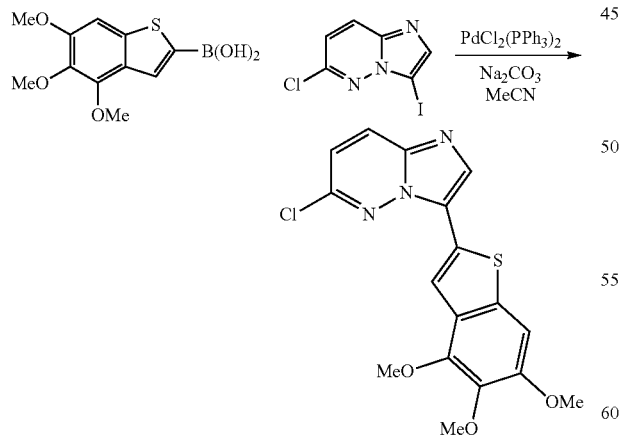

To a solution of 4,5,6-trimethoxybenzo[b]thiophen-2-yl-2-boronic acid (200 mg, 0.746 mmol, 1.3 equiv) in acetonitrile (10.0 mL) was added 6-chloro-3-iodoimidazo[1,2-b]pyridazine (160 mg, 0.574 mmol, 1.0 equiv), palladium catalyst (20 mg, 0.0287 mmol, 0.05 equiv) and sodium carbonate (5.74 mL, 1.0 M, 10.0 equiv). The solution was stirred at rt overnight. Purification using column chromatography gave 151 mg of the yellow product, 70%.

Preparation of 3-(4,5,6-trimethoxybenzo[b]thiophen-2-yl)-N-(3,4-dimethoxyphenyl)imidazo[1,2-b]pyridazin-6-amine

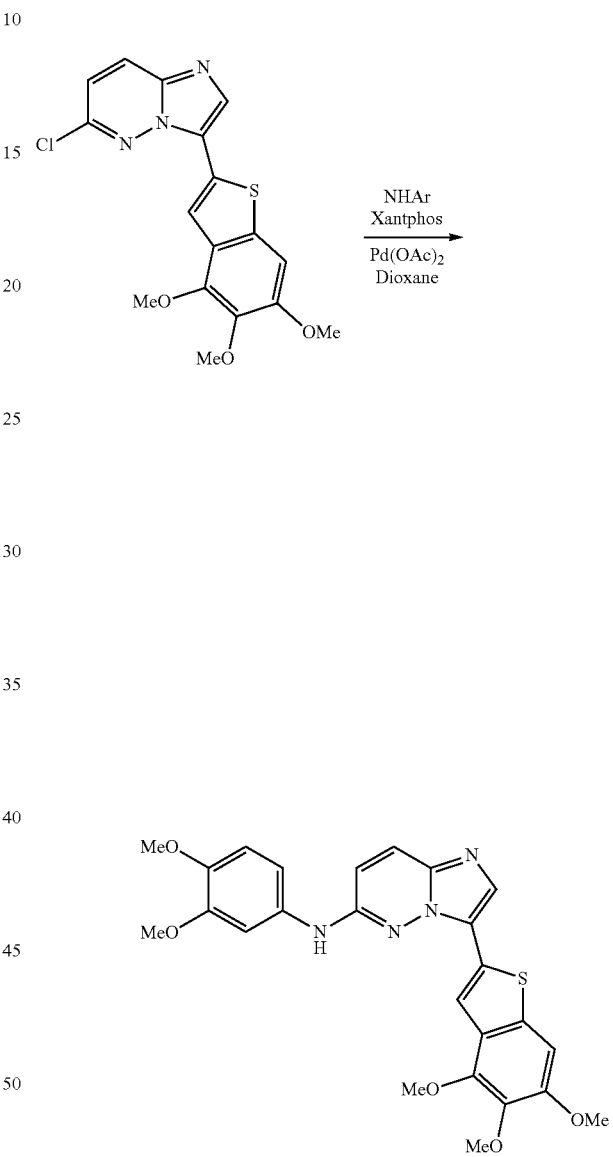

To a solution of 6-chloro-3-(4,5,6-trimethoxybenzo[b]thiophen-2-yl)imidazo[1,2-b]pyridazine (50 mg, 0.133 mmol, 1.0 equiv), xantphos (15 mg, 0.0266 mmol, 0.2 equiv), palladium acetate (2 mg, 0.0133 mmol, 0.1 equiv), and potassium carbonate (367 mg, 2.66 mmol, 20 equiv) in dioxane (5.0 mL) was added 3,4-dimethoxyaniline (20 mg, 0.133 mmol, 1.0 equiv) and heated to 110° C. for 2 h. Purification by column chromatography using 2% methanol in dichloromethane elution gave the product.

Compound 76 was physically characterized by electrospray ionization mass spectrometry. Structures and molecular masses are given below in Table 32-b.

TABLE 32-b

| Cd. | Structure | IUPAC Name | [M +H]+ |
|---|---|---|---|
| 76 | (structure) | 3-(4,5,6-trimethoxybenzo[b]thiophen-2-yl)-N-(3,4-dimethoxyphenyl)imidazo[1,2-b]pyridazin-6-amine | 493.3 |

EXAMPLE 33

Synthesis of Compound 176

Preparation of trans-4-(3-(4,5,6-trimethoxybenzo[b]thiophen-2-yl)imidazo[1,2-b]pyridazin-6-ylamino)cyclohexanol

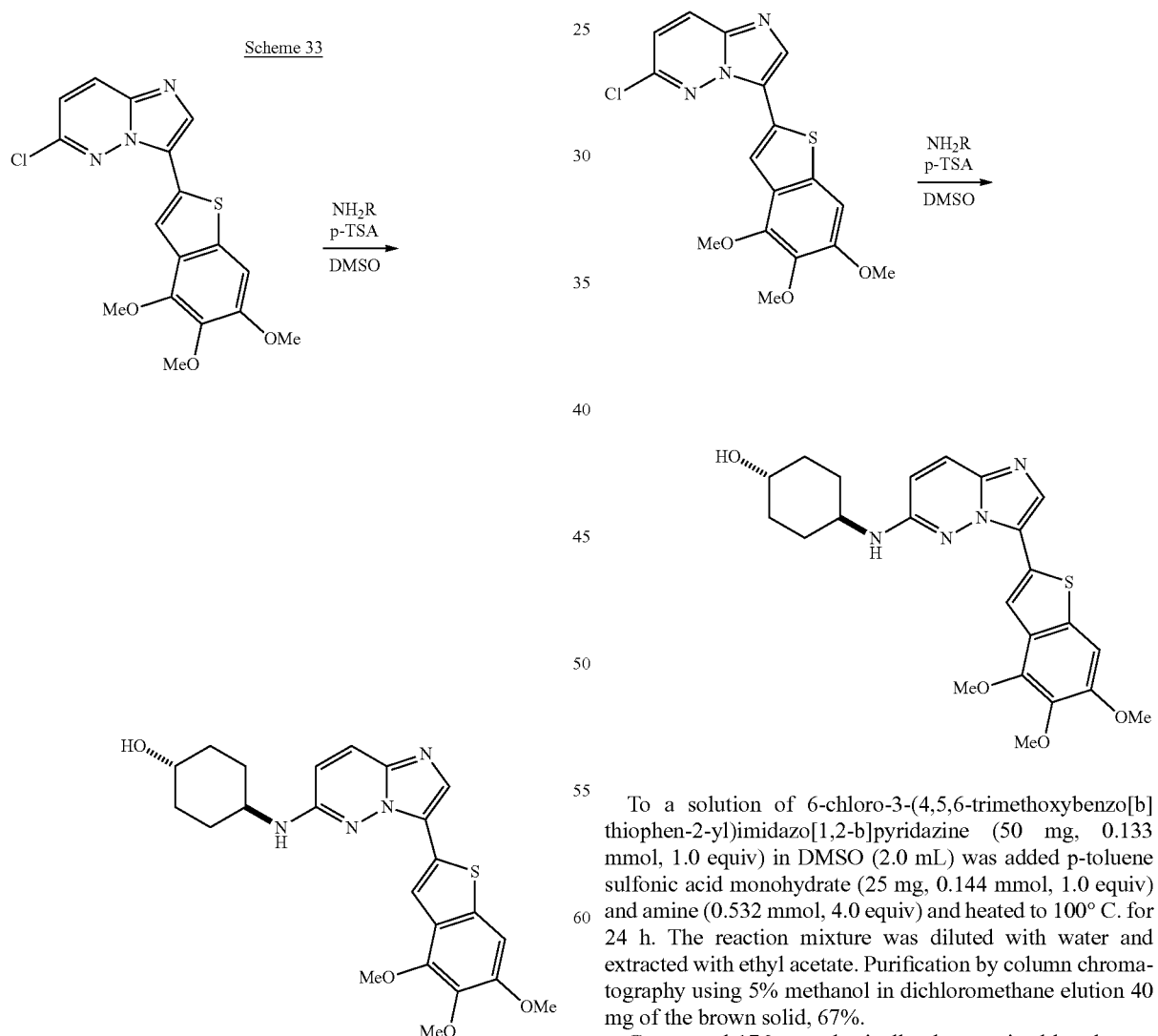

To a solution of 6-chloro-3-(4,5,6-trimethoxybenzo[b]thiophen-2-yl)imidazo[1,2-b]pyridazine (50 mg, 0.133 mmol, 1.0 equiv) in DMSO (2.0 mL) was added p-toluene sulfonic acid monohydrate (25 mg, 0.144 mmol, 1.0 equiv) and amine (0.532 mmol, 4.0 equiv) and heated to 100° C. for 24 h. The reaction mixture was diluted with water and extracted with ethyl acetate. Purification by column chromatography using 5% methanol in dichloromethane elution 40 mg of the brown solid, 67%.

Compound 176 was physically characterized by electrospray ionization mass spectrometry. Structures and molecular masses are given below in Table 33-b.

| Cd. | Structure | IUPAC Name | [M + H]+ |
|---|---|---|---|
| 176 | 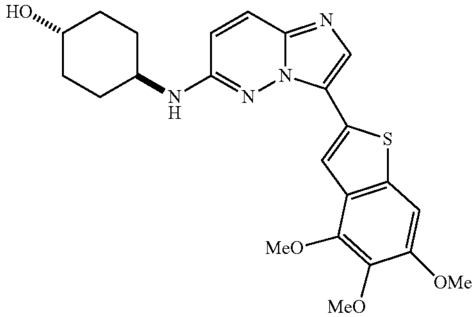 | trans-4-(3-(4,5,6,trimethoxybenzo[b]thiophen-2-yl)imidazo[1,2-b]pyridazin-6-ylamino)cyclohexanol | 455.4 |

EXAMPLE 34

Synthesis of Compound 83

Scheme 34a

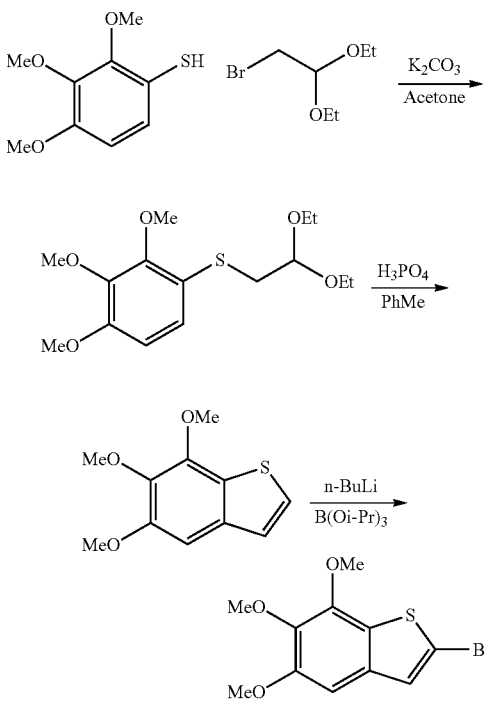

Preparation of O-ethyl S-2,3,4-trimethoxyphenyl carbonodithioate

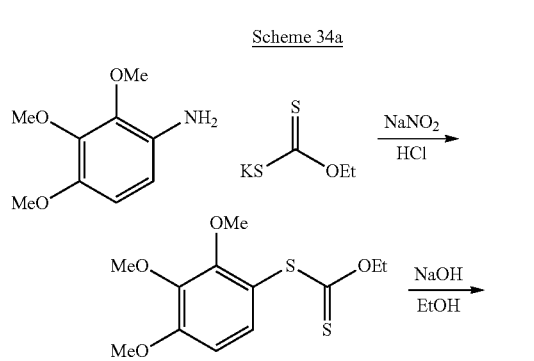

Aniline (482 g, 2.63 mmol, 1.0 equiv) at 0° C. was added hydrochloric acid (0.71 mL) and water (1.86 mL) followed by sodium nitrite (227 mg, 3.29 mmol, 1.25 equiv). The resulting solution was poured over potassium ethyl xanthogenate (1.31 g, 8.06 mmol, 3.0 equiv) in water (1.50 mL) and stirred at 50° C. for 40 minutes. Purification by column chromatography using 5% ethyl acetate in hexanes elution gave the yellow solid.

Preparation of 2,3,4-trimethoxybenzenethiol

To a solution of O-ethyl S-2,3,4-trimethoxyphenyl carbonodithioate (759 mg, 2.63 mmol, 1.0 equiv) in methanol (10 mL) was added sodium hydroxide (347 mg, 7.89 mmol, 3.0 equiv) and heated to 60 C for 3 h. Purification by column chromatography using 5% ethyl acetate in hexanes elution gave 395 mg of the yellow solid, 75% over 2 steps.

Preparation of (2,2-diethoxyethyl)(2,3,4-trimethoxyphenyl)sulfane

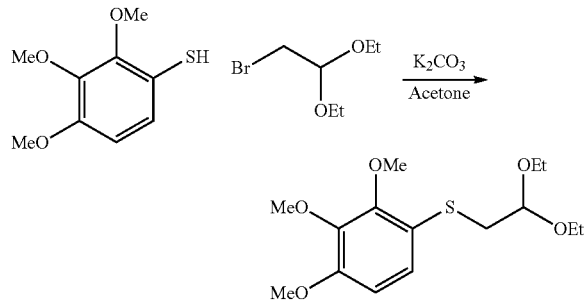

To a solution of thiophenol (1.02 g, 5.09 mmol, 1.0 equiv) in acetone (20 mL) was added potassium carbonate (1.41 g, 10.2 mmol, 2.0 equiv) and bromoacetaldehyde diethylacetal (1.57 g, 10.2 mmol, 2.0 equiv). After 15 h, the reaction mixture was filtered and concentrated. Purification by column chromatography using 5% ethyl acetate in hexanes elution gave the product.

Preparation of 5,6,7-trimethoxybenzo[b]thiophene

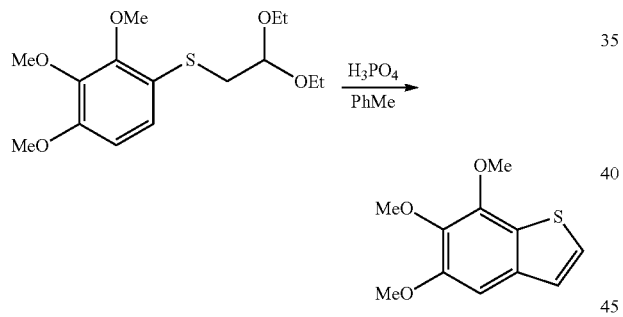

To a solution of thioether (1.03 g, 3.25 mmol, 1.0 equiv) in toluene (20 mL) was added phosphoric acid (10 mL) and heated to 110° C. After 2 h, the reaction mixture was diluted with a saturated aqueous solution of sodium bicarbonate and extracted with ethyl acetate then concentrated. Purification by column chromatography using 5% ethyl acetate in hexanes elution gave 300 mg of the white solid, 41%.

Preparation of 5,6,7-trimethoxybenzo[b]thiophen-2-yl-2-boronic acid

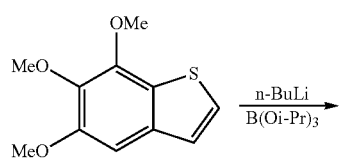

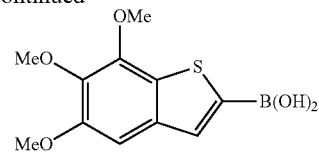

To a solution of 5,6,7-trimethoxybenzo[b]thiophene (365 mg, 1.62 mmol, 1.0 equiv) in THF (10.0 mL) at −78° C. was added n-BuLi (1.53 mL, 2.44 mmol, 1.5 equiv). The reaction was stirred at the reduced temperature for 1 h, then triisopropylborate (0.56 mL, 2.44 mmol, 1.5 equiv) was added and stirred at rt for 2 h. The mixture was quenched with 2N HCl and then extracted with ethyl acetate. Purification by column chromatography using 2% methanol in dichloromethane elution gave 370 mg of white solid, 85%.

Scheme 34b

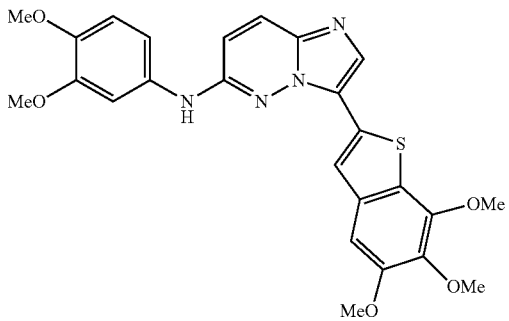 [SMILES: COc1ccc(Nc2ccc3ncc(-c4cc5cc(OC)c(OC)c(OC)c5s4)n3n2)cc1OC]

183

Preparation of 6-chloro-3-(5,6,7-trimethoxybenzo[b]thiophen-2-yl)imidazo[1,2-b]pyridazine

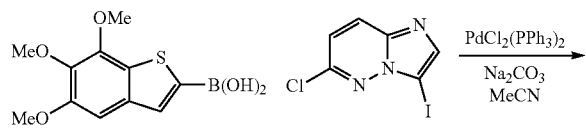

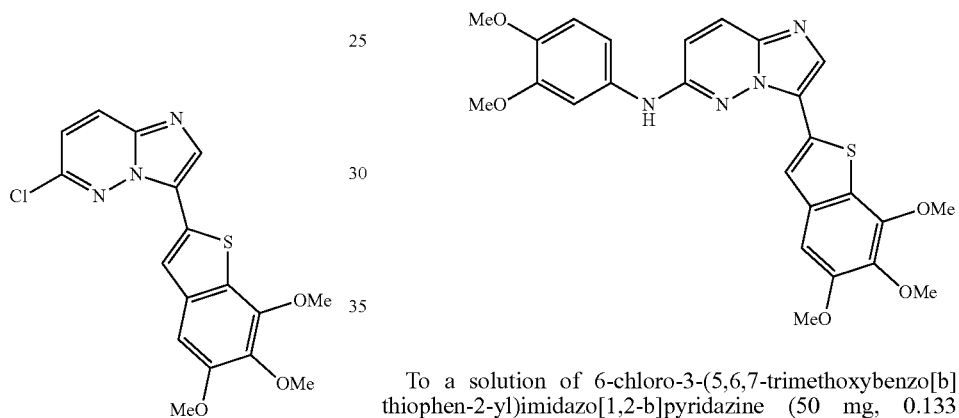

To a solution of 5,6,7-trimethoxybenzo[b]thiophen-2-yl-2-boronic acid (410 mg, 1.53 mmol, 1.3 equiv) in acetonitrile (10 mL) was added 6-chloro-3-iodoimidazo[1,2-b]pyridazine (427 mg, 1.53 mmol, 1.0 equiv), palladium catalyst (56 mg, 0.077 mmol, 0.05 equiv) and sodium carbonate (15.3 mL, 1.0 M, 10.0 equiv). The solution was stirred in the microwave at 150° C. for 10 min. Purification using column chromatography gave 368 mg of the yellow product, 64%.

184

Preparation of 3-(5,6,7-trimethoxybenzo[b]thiophen-2-yl)-N-arylimidazo[1,2-b]pyridazin-6-amine

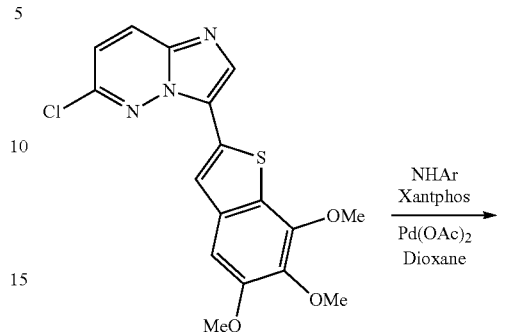

To a solution of 6-chloro-3-(5,6,7-trimethoxybenzo[b]thiophen-2-yl)imidazo[1,2-b]pyridazine (50 mg, 0.133 mmol, 1.0 equiv), xantphos (15 mg, 0.0266 mmol, 0.2 equiv), palladium acetate (2 mg, 0.0133 mmol, 0.1 equiv), and potassium carbonate (367 mg, 2.66 mmol, 20 equiv) in dioxane (5.0 mL) was added 3,4-dimethoxyaniline (20 mg, 0.133 mmol, 1.0 equiv) and heated to 110° C. for 2 h. Purification by column chromatography using 2% methanol in dichloromethane elution gave the product.

Compound 83 was physically characterized by electrospray ionization mass spectrometry. Structures and molecular masses are given below in Table 34-b.

TABLE 34

| Cd. | Structure | IUPAC Name | [M + H]+ |
|---|---|---|---|
| 83 | MeO-phenyl-NH-imidazopyridazine-benzothiophene-(OMe)3 | 3-(5,6,7-trimethoxybenzo[b]thiophen-2-yl)-N-(3,4-dimethoxyphenyl)imidazo[1,2-b]pyridazin-6-amine | 492.9 |

EXAMPLE 35

Synthesis of Compound 179

Scheme 35

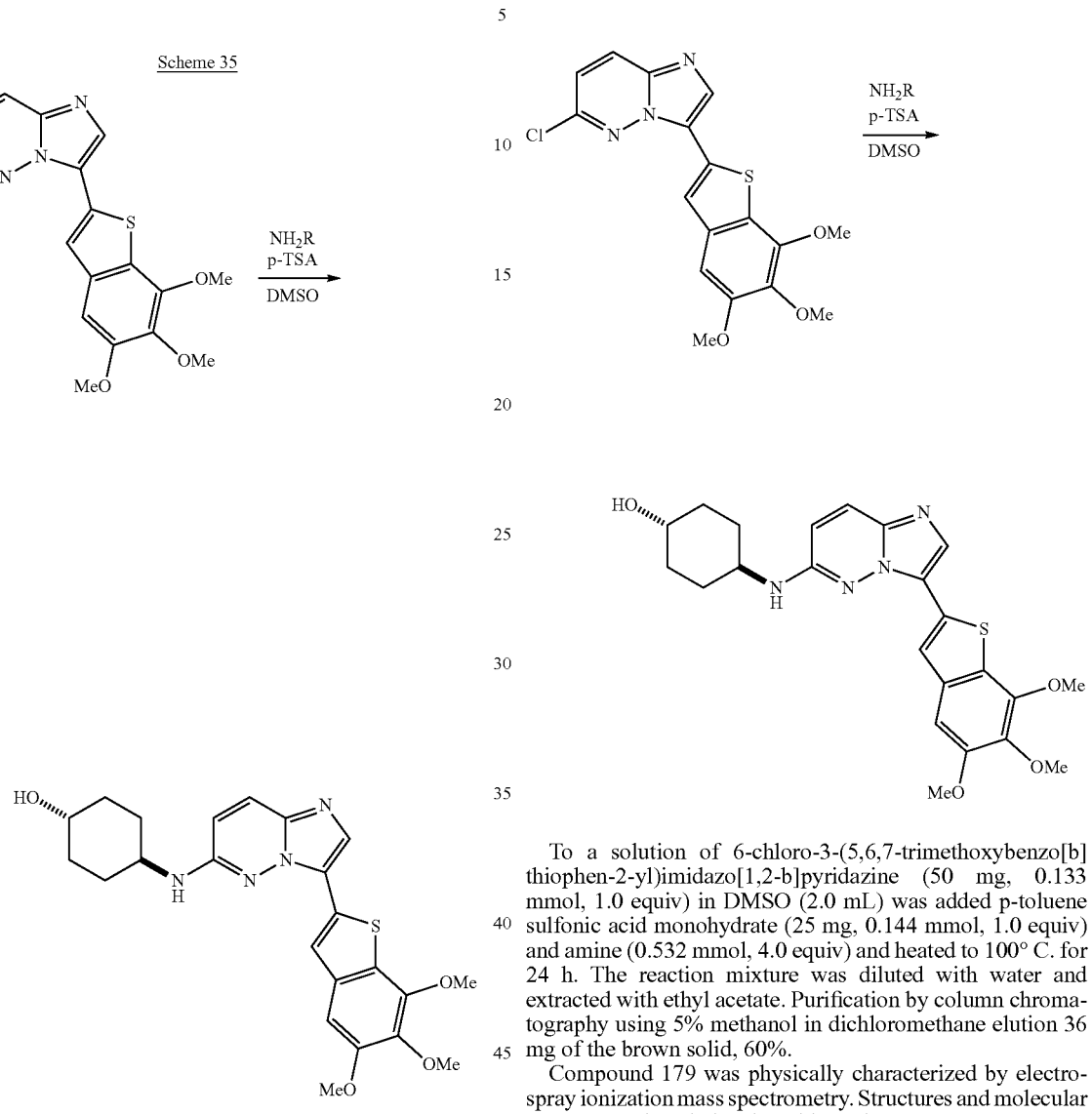

Preparation of trans-4-(3-(5,6,7-trimethoxybenzo[b]thiophen-2-yl)imidazo[1,2-b]pyridazin-6-ylamino)cyclohexanol To a solution of 6-chloro-3-(5,6,7-trimethoxybenzo[b]thiophen-2-yl)imidazo[1,2-b]pyridazine (50 mg, 0.133 mmol, 1.0 equiv) in DMSO (2.0 mL) was added p-toluene sulfonic acid monohydrate (25 mg, 0.144 mmol, 1.0 equiv) and amine (0.532 mmol, 4.0 equiv) and heated to 100° C. for 24 h. The reaction mixture was diluted with water and extracted with ethyl acetate. Purification by column chromatography using 5% methanol in dichloromethane elution 36 mg of the brown solid, 60%.

Compound 179 was physically characterized by electrospray ionization mass spectrometry. Structures and molecular masses are given below in Table 35-b.

TABLE 35-b

| Cd. | Structure | IUPAC Name | [M + H]$^+$ |
|---|---|---|---|
| 179 | 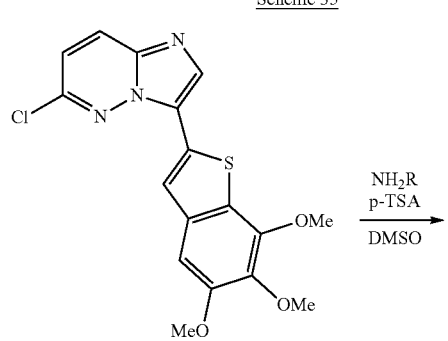 | trans-4-(3-(5,6,7-trimethoxybenzo[b]thiophen-2-yl)imidazo[1,2-b]pyridazin-6-ylamino)cyclohexanol | 455.0 |

EXAMPLE 36

Synthesis of Compounds 94-96, 99, 104

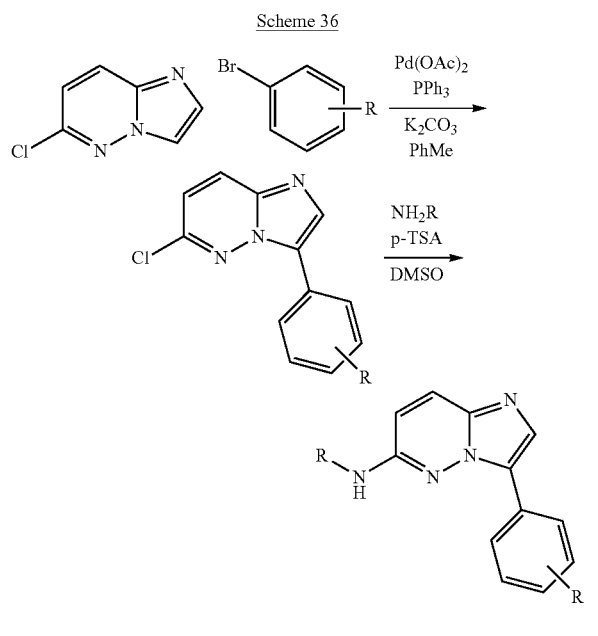

Scheme 36

Preparation of 6-chloro-3-arylimidazo[1,2-b]pyridazine

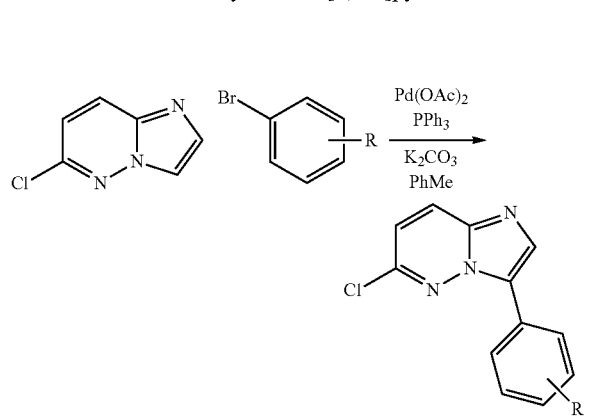

To a stirred solution of 6-chloroimidazo[1,2-b]pyridazine (1.55 g, 10.1 mmol) in 10.0 mL of toluene was added aryl bromide (15.1 mmol, 1.5 equiv), potassium carbonate (2.79 g, 18.2 mmol, 2.0 equiv), triphenylphosphine (529 mg, 2.02 mmol, 0.2 equiv) and palladium acetate (227 mg, 1.01 mmol, 0.1 equiv). The solution was stirred to reflux for 24 h. Purification by column chromatography using 50% ethyl acetate in hexanes elution gave the product.

Preparation of N-alkyl-3-arylimidazo[1,2-b]pyridazin-6-amine

To a solution of 6-chloro-3-arylimidazo[1,2-b]pyridazine (0.500 mmol, 1.0 equiv) in DMSO (2.0 mL) was added p-toluene sulfonic acid monohydrate (95 mg, 0.500 mmol, 1.0 equiv) and amine (1.95 mmol, 4.0 equiv) and heated to 100° C. for 24 h. The reaction mixture was diluted with water and extracted with ethyl acetate. Purification by column chromatography using 5% methanol in dichloromethane elution gave the product.

TABLE 3a

| Cd. | Aryl bromide | Amine | Pure Isolated Compound |
|---|---|---|---|
| 94 | Bromobenzene | Methyl amine | N-methyl-3-phenylimidazo[1,2-b]pyridazin-6-amine |
| 95 | 1-bromo-4-methoxybenzene | Methyl amine | 3-(4-methoxyphenyl)-N-methylimidazo[1,2-b]pyridazin-6-amine |
| 96 | 1-bromo-2-methoxybenzene | Methyl amine | 3-(2-methoxyphenyl)-N-methylimidazo[1,2-b]pyridazin-6-amine |
| 99 | 1-bromo-3-methoxybenzene | Methyl amine | 3-(3-methoxyphenyl)-N-methylimidazo[1,2-b]pyridazin-6-amine |

TABLE 3a-continued

| Cd. | Aryl bromide | Amine | Pure Isolated Compound |
|---|---|---|---|
| 104 | 5-bromo-1,2,3-trimethoxybenzene | trans-4-aminocyclohexanol | trans-4-(3-(3,4,5-trimethoxyphenyl)imidazo[1,2-b]pyridazin-6-ylamino)cyclohexanol |

Compounds 94-96, 99, 104 were physically characterized by electrospray ionization mass spectrometry. Structures and molecular masses are given below in Table 36-b.

TABLE 36-b

| Cd. | Structure | IUPAC Name | [M + H]⁺ |
|---|---|---|---|
| 94 | 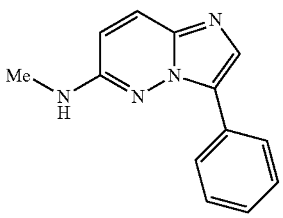 [SMILES: CNc1ccc2ncc(-c3ccccc3)n2n1] | N-methyl-3-phenylimidazo[1,2-b]pyridazin-6-amine | 225.5 |
| 95 | 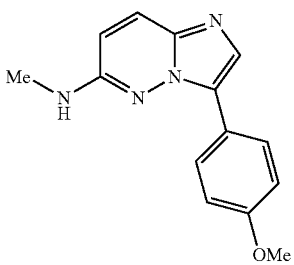 [SMILES: CNc1ccc2ncc(-c3ccc(OC)cc3)n2n1] | 3-(4-methoxyphenyl)-N-methylimidazo[1,2-b]pyridazin-6-amine | 255.6 |
| 96 | 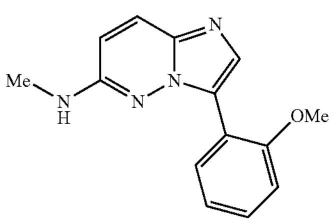 [SMILES: CNc1ccc2ncc(-c3ccccc3OC)n2n1] | 3-(2-methoxyphenyl)-N-methylimidazo[1,2-b]pyridazin-6-amine | 255.5 |
| 99 | 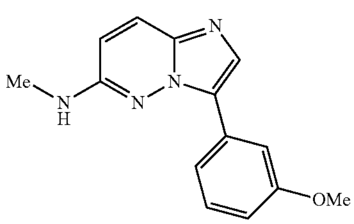 [SMILES: CNc1ccc2ncc(-c3cccc(OC)c3)n2n1] | 3-(3-methoxyphenyl)-N-methylimidazo[1,2-b]pyridazin-6-amine | 255.6 |
| 104 | 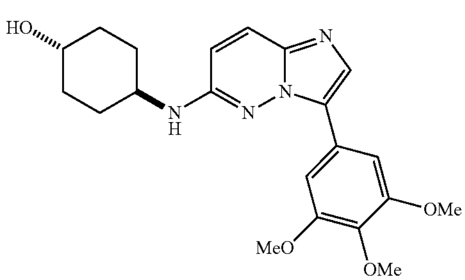 [SMILES: COc1cc(-c2cnc3ccc(N[C@H]4CC[C@H](O)CC4)nn23)cc(OC)c1OC] | trans-4-(3-(3,4,5-trimethoxyphenyl)imidazo[1,2-b]pyridazin-6-ylamino)cyclohexanol | 399.5 |

EXAMPLE 37

Synthesis of Compounds 97-98, 100-102

Scheme 37

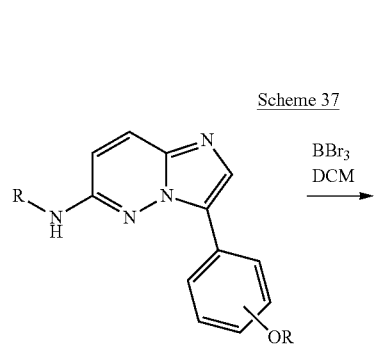

Preparation of 3-(hydroxyphenyl)-N-alkylimidazo[1,2-b]pyridazin-6-amine

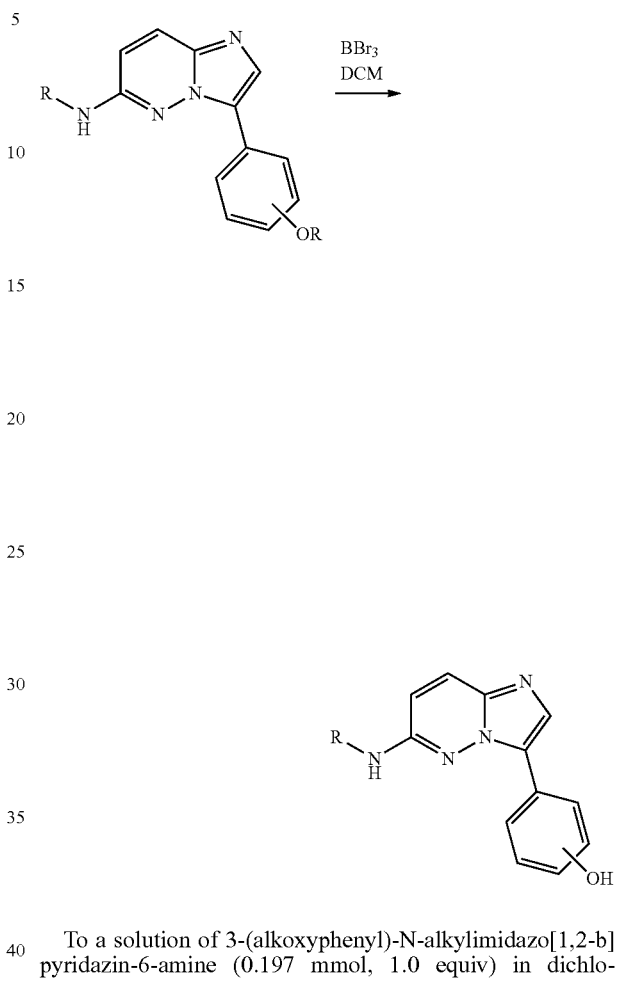

To a solution of 3-(alkoxyphenyl)-N-alkylimidazo[1,2-b]pyridazin-6-amine (0.197 mmol, 1.0 equiv) in dichloromethane at −78° C. was added boron tribromide (0.10 mL, 1.0 M solution in dichloromethane, 5.4 equiv). The reaction mixture was stirred at the reduced temperature for 10 min then warmed to room temperature and stirred for 15 h. Methanol (2 mL) was added to quench the reaction and extracted with dichloromethane. Purification by column chromatography using 5% methanol in dichloromethane elution gave the product.

TABLE 37-a

| Cd. | Aryl bromide | Amine | Pure Isolated Compound |
|---|---|---|---|
| 97 | 1-bromo-4-methoxybenzene | Methyl amine | 4-(6-(methylamino)imidazo[1,2-b]pyridazin-3-yl)phenol |
| 98 | 1-bromo-2-methoxybenzene | Methyl amine | 2-(6-(methylamino)imidazo[1,2-b]pyridazin-3-yl)phenol |
| 100 | 1-bromo-3-methoxybenzene | Methyl amine | 3-(6-(methylamino)imidazo[1,2-b]pyridazin-3-yl)phenol |
| 101 | 1-bromo-3-methoxybenzene | trans-4-aminocyclohexanol | trans-3-(6-(4-hydroxycyclohexylamino)imidazo[1,2-b]pyridazin-3-yl)phenol |
| 102 | 1-bromo-4-methoxybenzene | trans-4-aminocyclohexanol | trans-4-(3-(3,4,5-trimethoxyphenyl)imidazo[1,2-b]pyridazin-6-ylamino)cyclohexanol |

Compounds 97-98, 100-102 were physically characterized by electrospray ionization mass spectrometry. Structures and molecular masses are given below in Table 37-b.

TABLE 37-b

| Cd. | Structure | IUPAC Name | [M + H]+ |
|---|---|---|---|
| 97 | 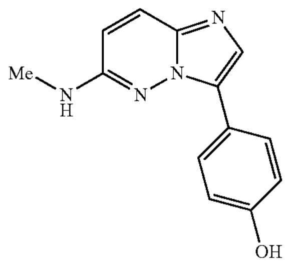 [SMILES: CNc1ccc2ncc(-c3ccc(O)cc3)n2n1] | 4-(6-(methylamino)imidazo[1,2-b]pyridazin-3-yl)phenol | 241.6 |
| 98 | 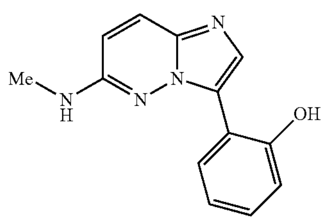 [SMILES: CNc1ccc2ncc(-c3ccccc3O)n2n1] | 2-(6-(methylamino)imidazo[1,2-b]pyridazin-3-yl)phenol | 241.5 |
| 100 | 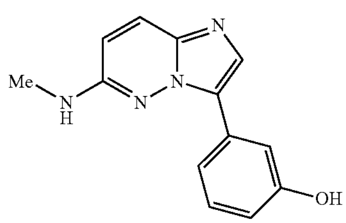 [SMILES: CNc1ccc2ncc(-c3cccc(O)c3)n2n1] | 3-(6-(methylamino)imidazo[1,2-b]pyridazin-3-yl)phenol | 241.6 |
| 101 | 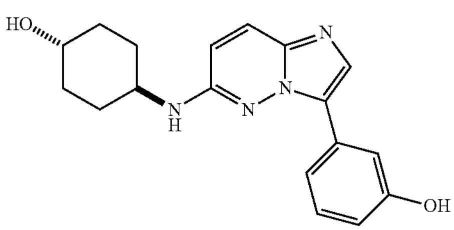 [SMILES: Oc1cccc(-c2cnc3ccc(N[C@H]4CC[C@H](O)CC4)nn23)c1] | trans-3-(6-(4-hydroxycyclohexylamino)imidazo[1,2-b]pyridazin-3-yl)phenol | 325.7 |
| 102 | 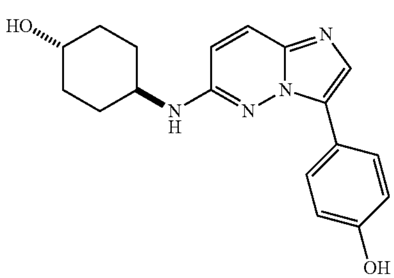 [SMILES: Oc1ccc(-c2cnc3ccc(N[C@H]4CC[C@H](O)CC4)nn23)cc1] | trans-4-(6-(4-hydroxycyclohexylamino)imidazo[1,2-b]pyridazin-3-yl)phenol | 525.7 |

EXAMPLE 38

Synthesis of Compound 66

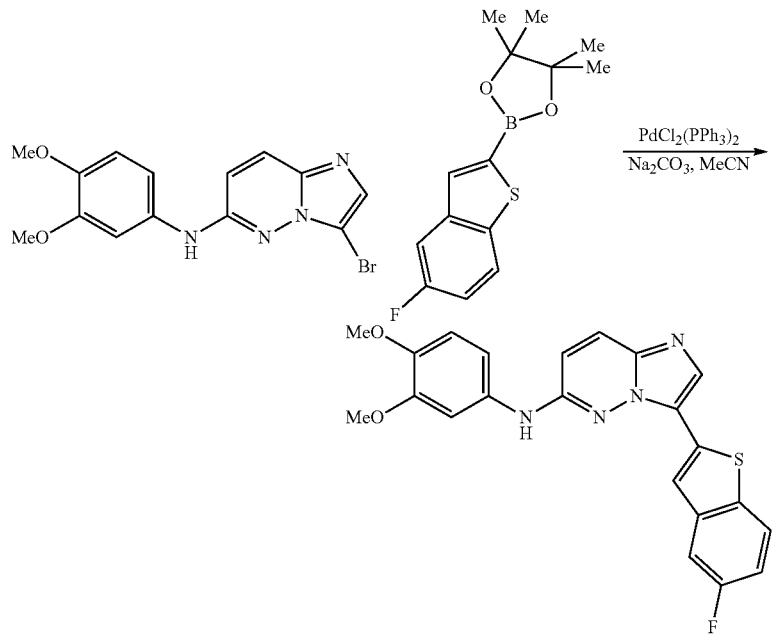

Preparation of 3-(5-fluorobenzo[b]thiophen-2-yl)-N-(3,4-dimethoxyphenyl)imidazo[1,2-b]pyridazin-6-amine

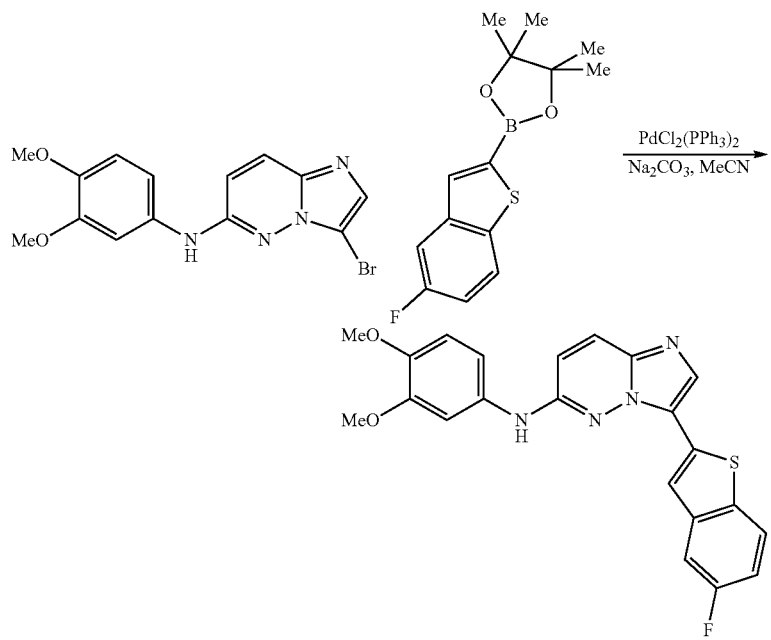

To a solution of 3-bromo-N-(3,4-dimethoxyphenyl)imidazo[1,2-b]pyridazin-6-amine (118 mg, 0.338 mmol, 1.0 equiv) in acetonitrile (3.38 mL) was added 2-(5-fluorobenzo[b]thiophen-2-yl)-4,4,5,5-tetramethyl-1,3,2-dioxaborolane (122 mg, 0.439 mmol, 1.3 equiv), bis(triphenylphosphine)palladium(II)dichloride (24 mg, 0.0338 mmol, 0.1 equiv), then sodium carbonate (3.38 mL, 1.0 M aqueous solution, 10 equiv). The reaction mixture was irradiated in the microwave at 150° C. for 10 min. Purification by column chromatography gave 100 mg of the brown solid, 70%.

Compound 66 was physically characterized by electrospray ionization mass spectrometry. Structures and molecular masses are given below in Table 38-b.

TABLE 38

| Cd. | Structure | IUPAC Name | [M + H]+ |
|---|---|---|---|
| 66 | MeO- structure -F | 3-(5-fluorobenzo[b]thiophen-2-yl)-N-(3,4-dimethoxyphenyl)imidazo[1,2-b]pyridazin-6-amine | 421.8 |

EXAMPLE 39

Synthesis of Compound 166

Scheme 39

Preparation of trans-4-(3-bromoimidazo[1,2-b]pyridazin-6-ylamino)cyclohexanol

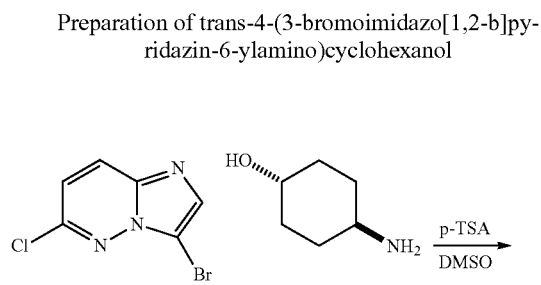

To 6-chloro-3-bromoimidazo[1,2-b]pyridazine (1.00 g, 4.30 mmol, 1.0 equiv) and p-TSA (818 mg, 4.30 mmol, 1.0 equiv) in DMSO (7.00 mL) was added trans-4-aminocyclohexanol (1.49 g, 12.9 mmol, 3.0 equiv). The mixture was heated at 100° C. for 24 h. Purification by column chromatography using 5% methanol in dichloromethane elution gave 1.1 g of the yellow solid, 83%.

Preparation of trans-4-(3-(5-fluorobenzo[b]thiophen-2-yl)imidazo[1,2-b]pyridazin-6-ylamino)cyclohexanol To a solution of 3-bromo-N-(3,4-dimethoxyphenyl)imidazo[1,2-b]pyridazin-6-amine (118 mg, 0.338 mmol, 1.0 equiv) in acetonitrile (3.79 mL) was added 2-(5-fluorobenzo[b]thiophen-2-yl)-4,4,5,5-tetramethyl-1,3,2-dioxaborolane (158 mg, 0.569 mmol, 1.5 equiv), bis(triphenylphosphine) palladium(II)dichloride (27 mg, 0.0379 mmol, 0.1 equiv), then sodium carbonate (3.79 mL, 1.0 M aqueous solution, 10 equiv). The reaction mixture was irradiated in the microwave at 150° C. for 10 min. Purification by column chromatography gave 90 mg of the yellow solid, 62%.

Compound 166 was physically characterized by electrospray ionization mass spectrometry. Structures and molecular masses are given below in Table 39-b.

TABLE 39-b

| Cd. | Structure | IUPAC Name | [M + H]+ |
|---|---|---|---|
| 166 | 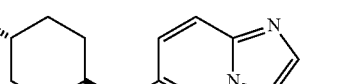 | trans-4-(3-(5-fluorobenzo[b]thiophen-2-yl)imidazo[1,2-b]pyridazin-6-ylamino)cyclohexanol | 383.7 |

EXAMPLE 40

Synthesis of Compound 84

Scheme 40

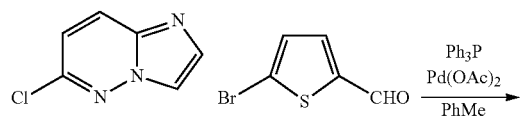

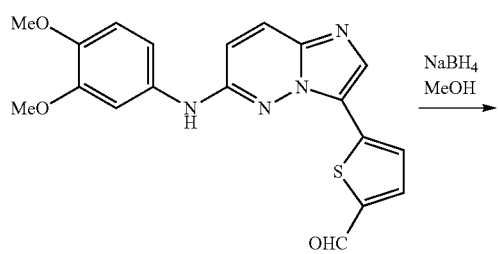

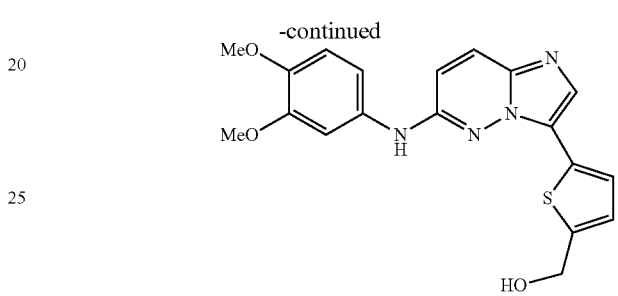

Preparation of 5-(6-chloroimidazo[1,2-b]pyridazin-3-yl)thiophene-2-carbaldehyde

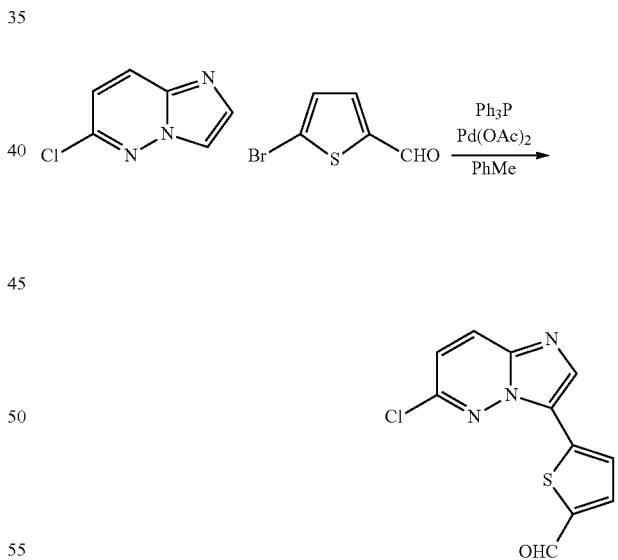

To a solution of 6-chloroimidazo[1,2-b]pyridazine (1.55 g, 10.1 mmol, 1.0 equiv) in toluene (10.0 mL) was added 5-bromothiophene-2-carbaldehyde (1.80 mL, 15.1 mmol, 1.5 equiv), potassium carbonate (2.79 g, 20.2 mmol, 2.0 equiv), triphenyl phosphine (529 mg, 2.02 mmol, 0.2 equiv) and potassium acetate (227 mg, 1.01 mmol, 0.1 equiv). The reaction mixture was heated to reflux for 24 h then diluted with water and extracted with ethyl acetate. Purification by column chromatography using 50% ethyl acetate in hexanes elution gave 1.60 g of the white solid, 60%.

201
Preparation of 5-(6-(3,4-dimethoxyphenylamino) imidazo[1,2-b]pyridazin-3-yl)thiophene-2-carbaldehyde

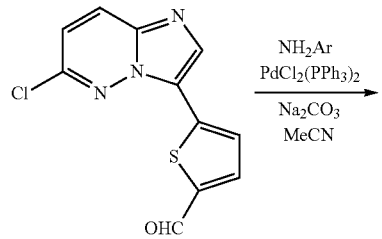

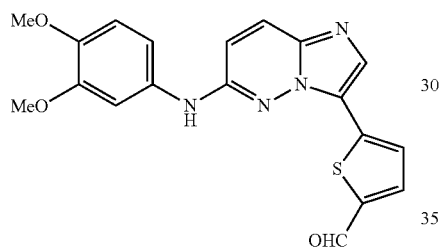

To a solution of 5-(6-chloroimidazo[1,2-b]pyridazin-3-yl) thiophene-2-carbaldehyde (200 mg, 0.758 mmol, 1.0 equiv), xantphos (88 mg, 0.152 mmol, 0.2 equiv), palladium acetate (17 mg, 0.0758 mmol, 0.1 equiv), and potassium carbonate (2.10 g, 1.52 mmol, 20 equiv) in dioxane (6.0 mL) was added 3,4-dimethoxyaniline (116 mg, 0.758 mmol, 1.0 equiv) and heated to 100° C. for 2 h. Purification by column chromatography using 2% methanol in dichloromethane elution gave the 100 mg of the brown solid, 35%.

202
Preparation of (5-(6-chloroimidazo[1,2-b]pyridazin-3-yl)thiophen-2-yl)methanol

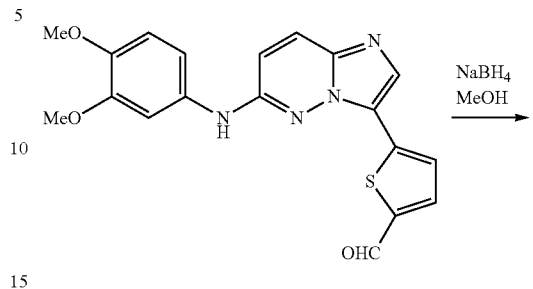

To a solution of 5-(6-(3,4-dimethoxyphenylamino)imidazo[1,2-b]pyridazin-3-yl)thiophene-2-carbaldehyde (34 mg, 0.0894 mmol, 1.0 equiv) in methanol (5.00 mL) was added sodium borohydride (100 mg, 2.64 mmol, 30.0 equiv). After 1 h, the reaction mixture was quenched with water and extracted with ethyl acetate. Purification by column chromatography using 2% methanol in hexanes elution gave 20 mg of the brown solid, 58%.

Compound 84 was physically characterized by electrospray ionization mass spectrometry. Structures and molecular masses are given below in Table 40-b.

TABLE 40-b

| Cd. | Structure | IUPAC Name | [M + H]⁺ |
|---|---|---|---|
| 84 | 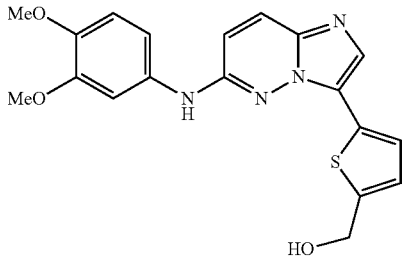 [SMILES: COc1ccc(Nc2ccc3ncc(-c4ccc(CO)s4)n3n2)cc1OC] | (5-(6-(3,4-dimethoxyphenylamino)imidazo[1,2-b]pyridazin-3-yl)thiophen-2-yl)methanol | 383.5 |

EXAMPLE 41

Synthesis of Compound 92

Scheme 41

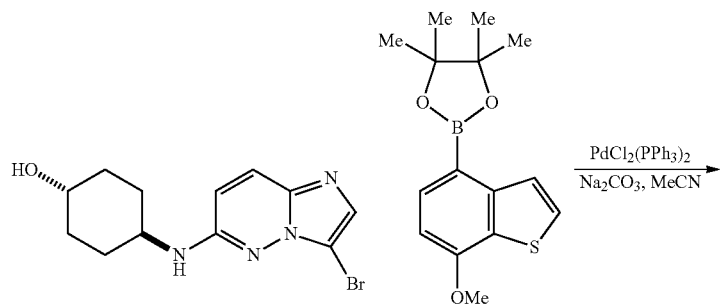

Preparation of trans-4-(3-(7-methoxybenzo[b]thiophen-4-yl)imidazo[1,2-b]pyridazin-6-ylamino)cyclohexanol

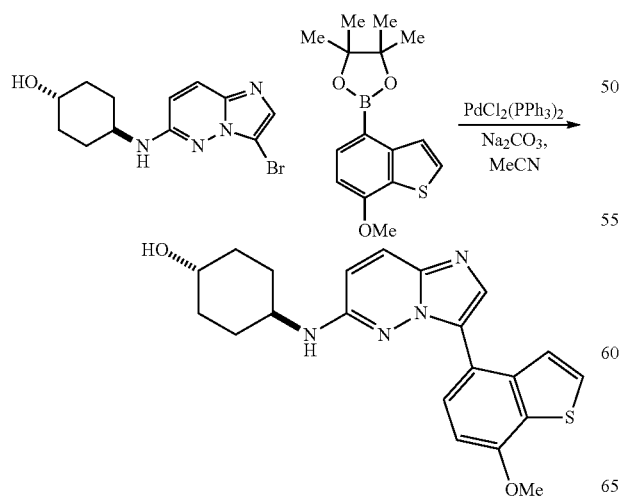

To a solution of trans-4-(3-bromoimidazo[1,2-b]pyridazin-6-ylamino)cyclohexanol (45 mg, 0.145 mmol, 1.0 equiv) in acetonitrile (1.45 mL) was added 2-(7-methoxybenzo[b]thiophen-4-yl)-4,4,5,5-tetramethyl-1,3,2-dioxaborolane (55 mg, 0.188 mmol, 1.3 equiv), bis(triphenylphosphine)palladium(II)dichloride (11 mg, 0.0159 mmol, 0.1 equiv), then sodium carbonate (1.45 mL, 1.0 M aqueous solution, 10 equiv). The reaction mixture was irradiated in the microwave at 150° C. for 10 min. Purification by column chromatography gave 31 mg of the yellow solid, 53%.

Compound 92 was physically characterized by electrospray ionization mass spectrometry. Structures and molecular masses are given below in Table 41-b.

TABLE 41

| Cd. | Structure | IUPAC Name | [M + H]+ |
|---|---|---|---|
| 92 | 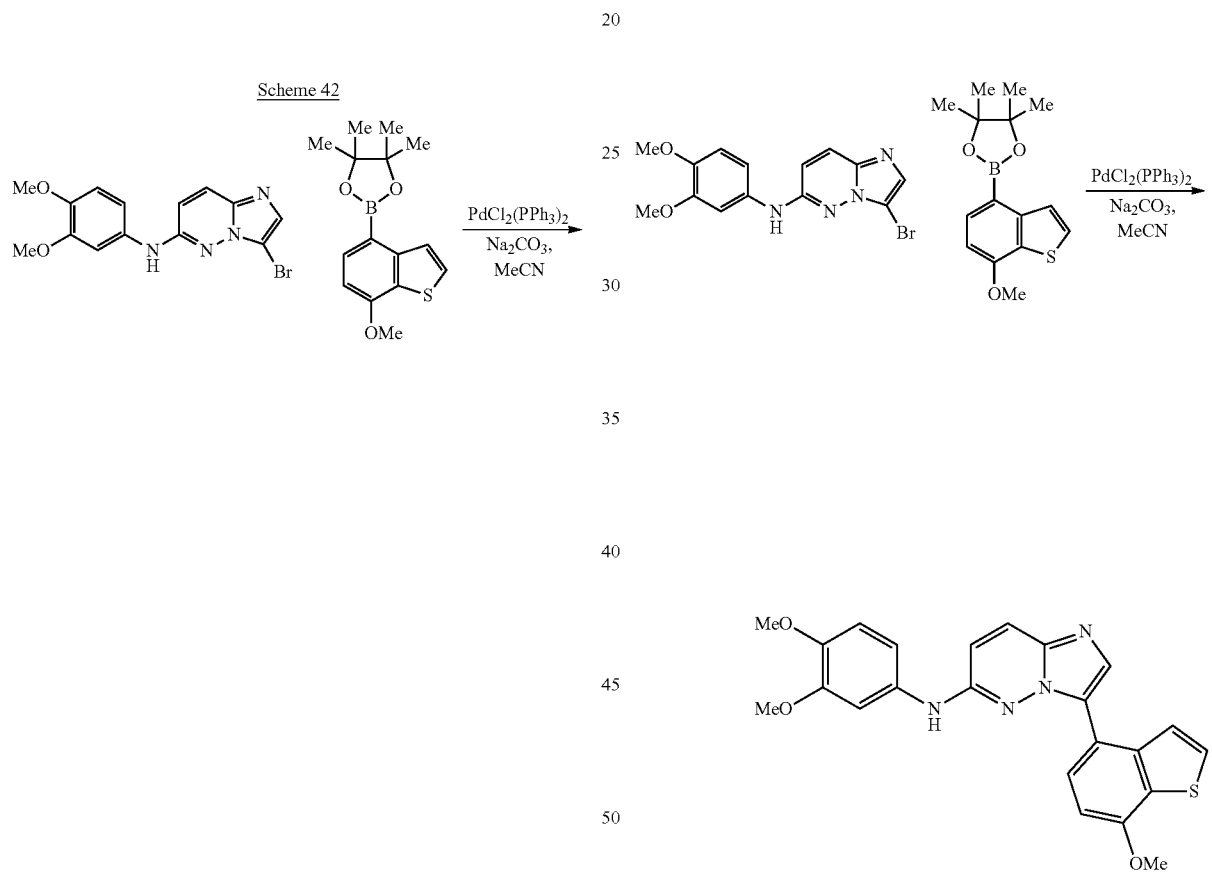 | trans-4-(3-(7-methoxybenzo[b]thiophen-4-yl)imidazo[1,2-b]pyridazin-6-ylamino)cyclohexanol | 395.0 |

EXAMPLE 42

Synthesis of Compound 93

Preparation of 3-(7-methoxybenzo[b]thiophen-4-yl)-N-(3,4-dimethoxyphenyl)imidazo[1,2-b]pyridazin-6-amine

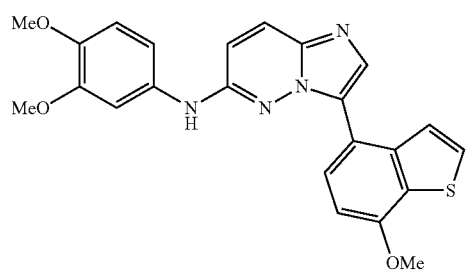 [SMILES: COc1ccc(Nc2ccc3ncc(-c4ccc(OC)c5sccc45)n3n2)cc1OC]

To a solution of 3 3-bromo-N-(3,4-dimethoxyphenyl)imidazo[1,2-b]pyridazin-6-amine (43 mg, 0.123 mmol, 1.0 equiv) in acetonitrile (1.23 mL) was added 2-(7-methoxybenzo[b]thiophen-4-yl)-4,4,5,5-tetramethyl-1,3,2-dioxaborolane (46 mg, 0.160 mmol, 1.3 equiv), bis(triphenylphosphine)palladium(II)dichloride (9 mg, 0.0123 mmol, 0.1 equiv), then sodium carbonate (1.23 mL, 1.0 M aqueous solution, 10 equiv). The reaction mixture was irradiated in the microwave at 150° C. for 10 min. Purification by column chromatography gave 30 mg of the yellow solid, 56%.

Compound 93 was physically characterized by electrospray ionization mass spectrometry. Structures and molecular masses are given below in Table 42-b.

TABLE 42

| Cd. | Structure | IUPAC Name | [M + H]+ |
|---|---|---|---|
| 93 | 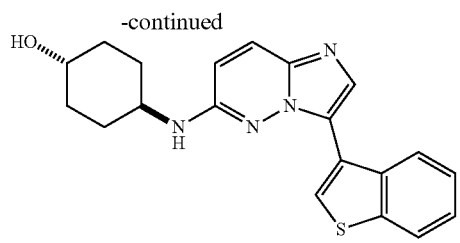 | 3-(7-methoxybenzo[b]thiophen-4-yl)-N-(3,4-dimethoxyphenyl)imidazo[1,2-b]pyridazin-6-amine | 433.1 |

EXAMPLE 43

Synthesis of Compound 90

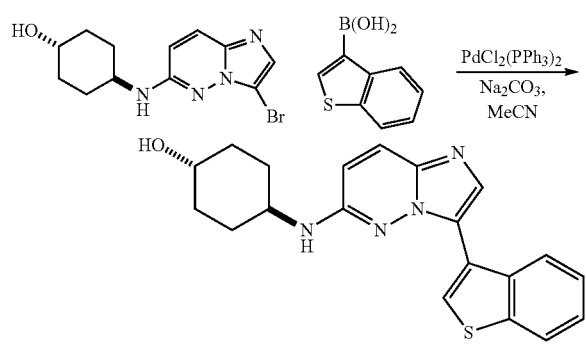

Preparation of trans-4-(3-(benzo[b]thiophen-3-yl)imidazo[1,2-b]pyridazin-6-ylamino)cyclohexanol To a solution of trans-4-(3-bromoimidazo[1,2-b]pyridazin-6-ylamino)cyclohexanol (50 mg, 0.159 mmol, 1.0 equiv) in acetonitrile (1.59 mL) was added benzo[b]thiophen-3-yl-3-boronic acid (117 mg, 0.239 mmol, 1.5 equiv), bis(triphenylphosphine)palladium(II)dichloride (11 mg, 0.0159 mmol, 0.1 equiv), then sodium carbonate (1.59 mL, 1.0 M aqueous solution, 10 equiv). The reaction mixture was irradiated in the microwave at 150° C. for 10 min. Purification by column chromatography gave 20 mg of the yellow solid, 36%.

Compound 90 was physically characterized by electrospray ionization mass spectrometry. Structures and molecular masses are given below in Table 43-b.

TABLE 43-b

| Cd. | Structure | IUPAC Name | [M + H]+ |
|---|---|---|---|
| 90 | 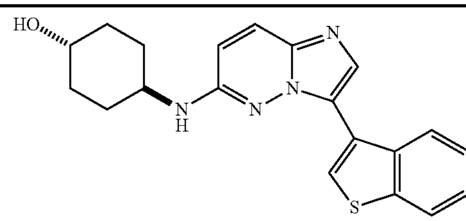 | trans-4-(3-(benzo[b]thiophen-3-yl)imidazo[1,2-b]pyridazin-6-ylamino)cyclohexanol | 365.8 |

EXAMPLE 44

Synthesis of Compound 91 and 180

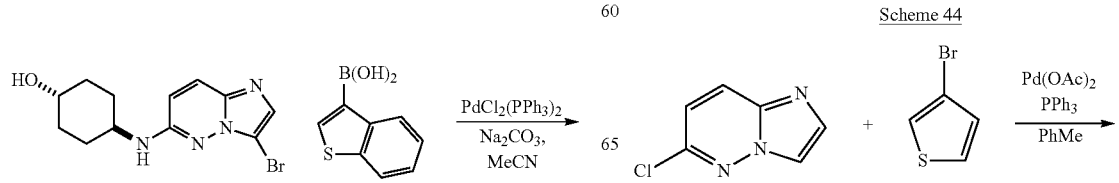

-continued

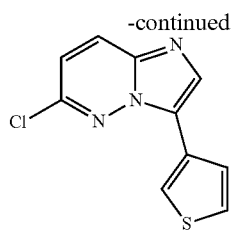

Preparation of 6-chloro-3-(thiophen-3-yl)imidazo[1,2-b]pyridazine

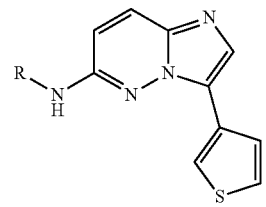

To a solution of 6-chloroimidazo[1,2-b]pyridazine (200 mg, 1.30 mmol, 1.0 equiv) in toluene (5.00 mL) was added 3-bromothiophene (0.18 mL, 1.95 mmol, 1.5 equiv), potassium carbonate (360 mg, 2.60 mmol, 2.0 equiv), triphenyl phosphine (68 mg, 0.260 mmol, 0.20 equiv) and potassium acetate (29 mg, 0.130 mmol, 0.1 equiv). The reaction mixture was heated to reflux for 24 h. Purification by column chromatography using 50% ethyl acetate in hexanes elution gave 201 mg of the white solid, 85%.

Preparation of N-alkyl-3-(thiophen-3-yl)imidazo[1,2-b]pyridazin-6-amine

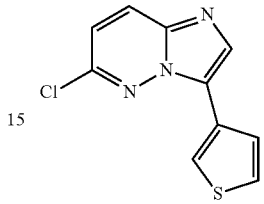

To a solution of 6-chloro-3-(thiophen-3-yl)imidazo[1,2-b]pyridazine (299 mg, 1.30 mmol, 1.0 equiv) in DMSO (5.00 mL) was added p-TSA (247 mg, 1.30 mmol, 1.0 equiv) and amine (6.50 mmol, 5.0 equiv) and heated to 100° C. for 24 h. Purification by column chromatography using 5% methanol in hexanes elution gave the product.

Compounds 91 and 180 were physically characterized by electrospray ionization mass spectrometry. Structures and molecular masses are given below in Table 44-b.

TABLE 44-b

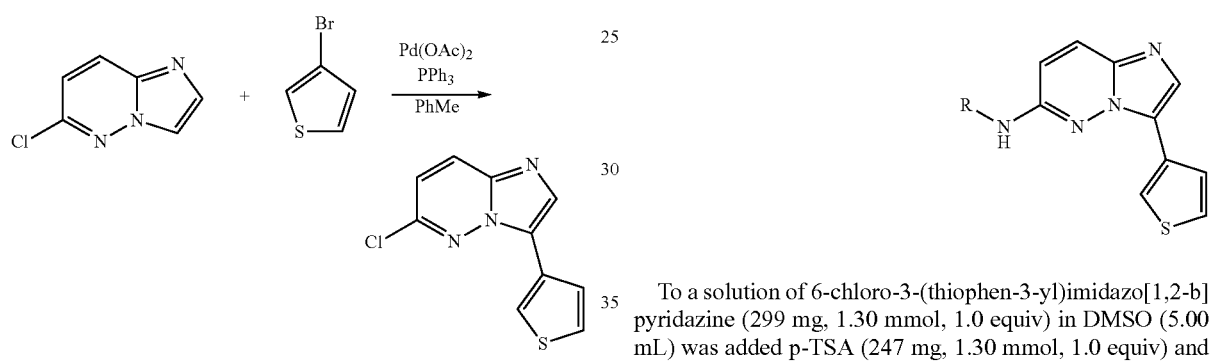

| Cd. | Amine | Structure | IUPAC Name | [M + H]+ |
|---|---|---|---|---|
| 91 | Methylamine | 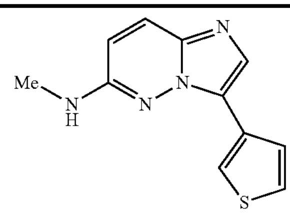 | N-methyl-3-(thiophen-3-yl)imidazo[1,2-b]pyridazin-6-amine | 231.6 |
| 180 | trans-4-aminocyclohexanol | 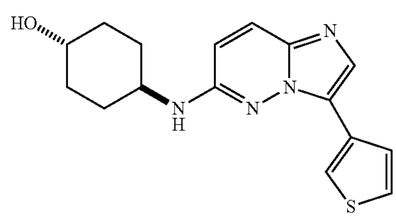 [SMILES: O[C@H]1CC[C@H](Nc2ccc3ncc(-c4ccsc4)n3n2)CC1] | trans-(3-(thiophen-3-yl)imidazo[1,2-b]pyridazin-6-ylamino)cyclohexanol | 315.6 |

EXAMPLE 45

Synthesis of Compound 120

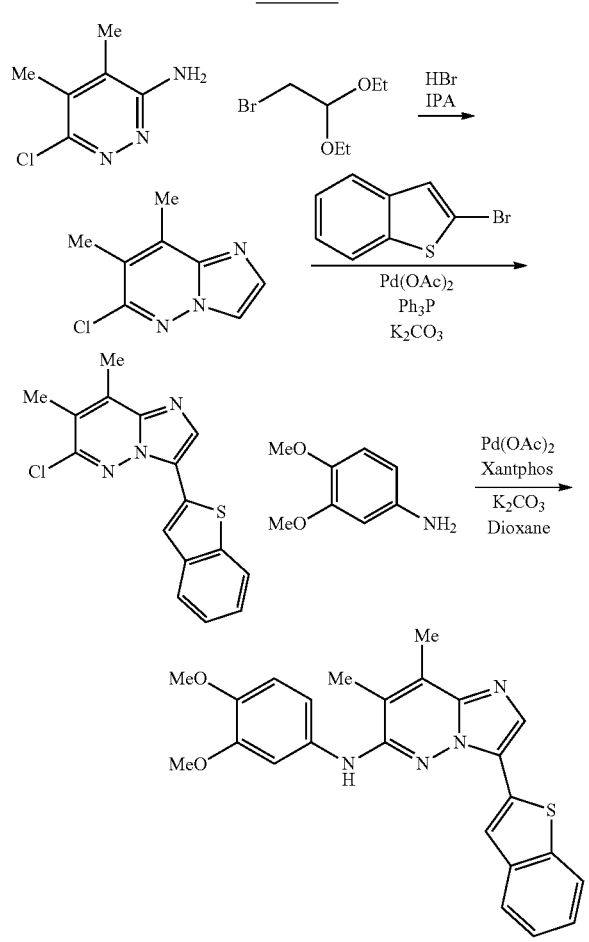

Preparation of 6-chloro-7,8-dimethylimidazo[1,2-b]pyridazine

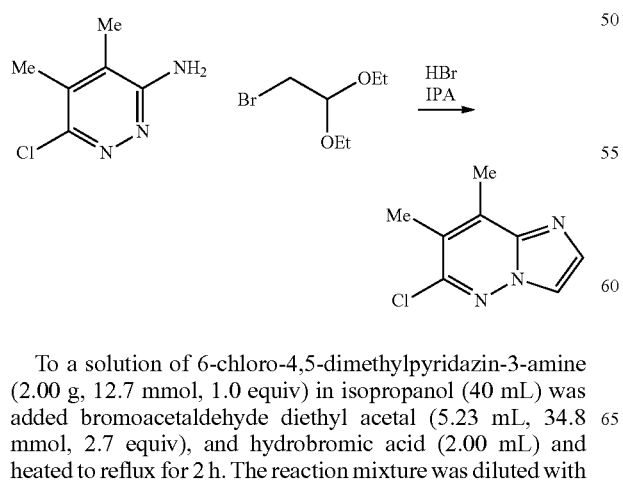

To a solution of 6-chloro-4,5-dimethylpyridazin-3-amine (2.00 g, 12.7 mmol, 1.0 equiv) in isopropanol (40 mL) was added bromoacetaldehyde diethyl acetal (5.23 mL, 34.8 mmol, 2.7 equiv), and hydrobromic acid (2.00 mL) and heated to reflux for 2 h. The reaction mixture was diluted with saturated aqueous sodium bicarbonate and extracted with ethyl acetate. Purification by column chromatography using 20% ethyl acetate in hexanes elution gave 2.07 g of the white solid, 90%.

Preparation of 3-(benzo[b]thiophen-2-yl)-6-chloro-7,8-dimethylimidazo[1,2-b]pyridazine

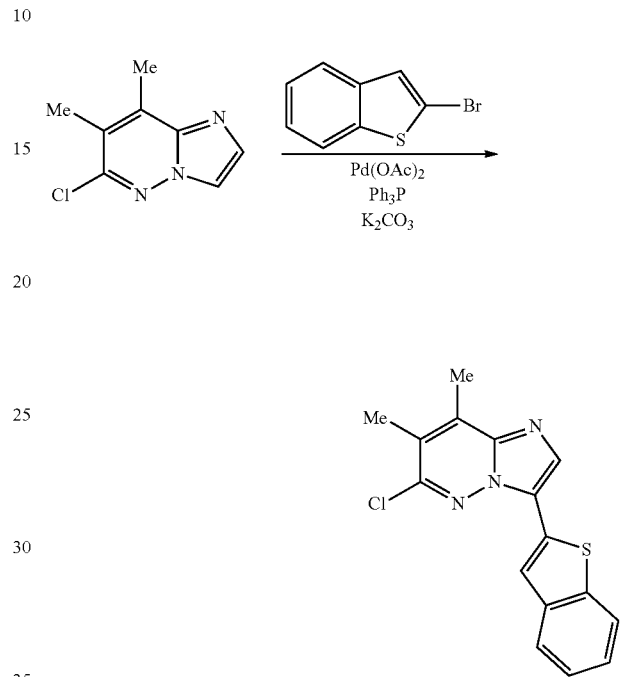

To a solution of 6-chloro-7,8-dimethylimidazo[1,2-b]pyridazine (162 mg, 0.892 mmol, 1.0 equiv) in toluene (5.00 mL) was added 2-bromobenzo[b]thiophene (213 mg, 1.16 mmol, 1.3 equiv), potassium carbonate (247 mg, 1.78 mmol, 2.0 equiv), triphenyl phosphine (47 mg, 0.178 mmol, 0.20 equiv) and potassium acetate (20 mg, 0.0892 mmol, 0.1 equiv). The reaction mixture was heated to reflux for 24 h. Purification by column chromatography using 50% ethyl acetate in hexanes elution gave 105 mg of the white solid, 38%.

Preparation of 3-(benzo[b]thiophen-2-yl)-N-(3,4-dimethoxyphenyl)-7,8-dimethylimidazo[1,2-b]pyridazin-6-amine

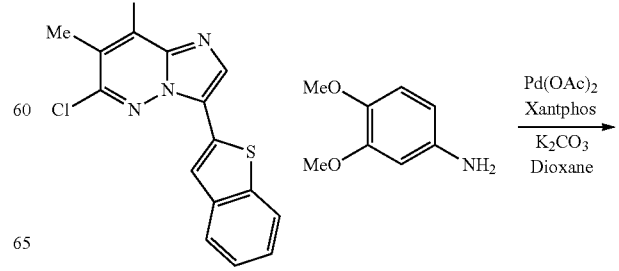

-continued

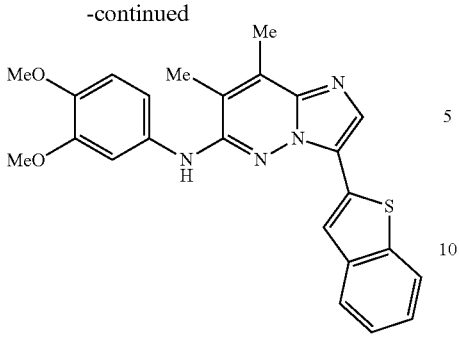

To a solution of 3-(benzo[b]thiophen-2-yl)-6-chloro-7,8-dimethylimidazo[1,2-b]pyridazine (89 mg, 0.284 mmol, 1.0 equiv), xantphos (33 mg, 0.0567 mmol, 0.2 equiv), palladium acetate (6 mg, 0.0284 mmol, 0.1 equiv), and potassium carbonate (784 mg, 5.67 mmol, 20 equiv) in dioxane (5.00 mL) was added 3,4-dimethoxyaniline (52 mg, 0.340 mmol, 1.0 equiv) and heated to 100° C. for 2 h. Purification by column chromatography using 2% methanol in dichloromethane elution gave the 60 mg of the brown solid, 49%.

Compound 120 was physically characterized by electrospray ionization mass spectrometry. Structures and molecular masses are given below in Table 45-b.

TABLE 45-b

| Cd. | Structure | IUPAC Name | [M + H]⁺ |
|---|---|---|---|
| 120 | 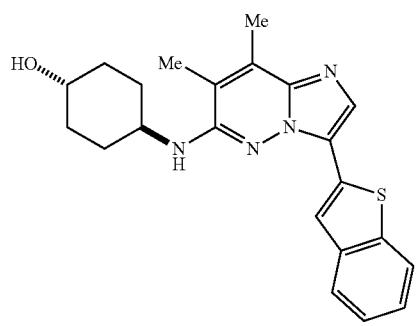 | 3-(benzo[b]thiophen-2-yl)-N-(3,4-dimethoxyphenyl)-7,8-dimethylimidazo[1,2-b]pyridazin-6-amine | 431.7 |

-continued

EXAMPLE 46

Synthesis of Compound 121

Preparation of trans-4-(3-(benzo[b]thiophen-2-yl)-7,8-dimethylimidazo[1,2-b]pyridazin-6-ylamino)cyclohexanol Scheme 46

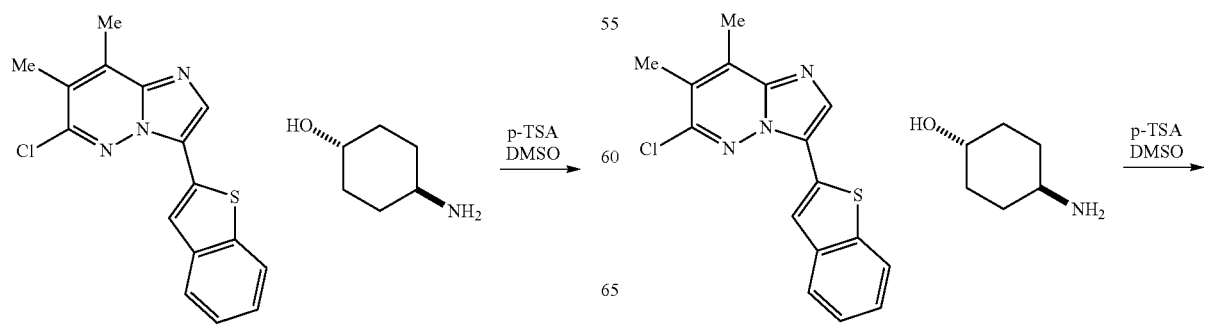

-continued

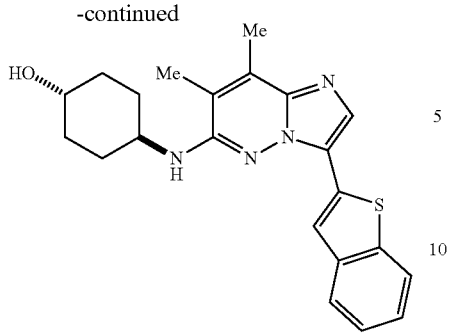

To a solution of 3-(benzo[b]thiophen-2-yl)-6-chloro-7,8-dimethylimidazo[1,2-b]pyridazine (40 mg, 0.128 mmol, 1.0 equiv) in DMSO (1.00 mL) was added p-TSA (24 mg, 0.128 mmol, 1.0 equiv) and trans-4-aminocyclohexanol (73 mg, 0.638 mmol, 5.0 equiv) and heated to 100° C. for 24 h. Purification by column chromatography using 5% methanol in dichloromethane elution gave 31 mg, 62%.

Compound 121 was physically characterized by electrospray ionization mass spectrometry. Structures and molecular masses are given below in Table 46-b.

TABLE 46-b

| Cd. | Structure | IUPAC Name | [M + H]⁺ |
|---|---|---|---|
| 121 | 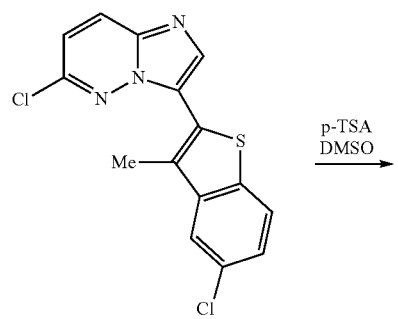 | trans-4-(3-(benzo[b]thiophen-2-yl)-7,8-dimethylimidazo[1,2-b]pyridazin-6-ylamino)cyclohexanol | 393.7 |

EXAMPLE 47

Synthesis of Compounds 118 and 164

Scheme 47

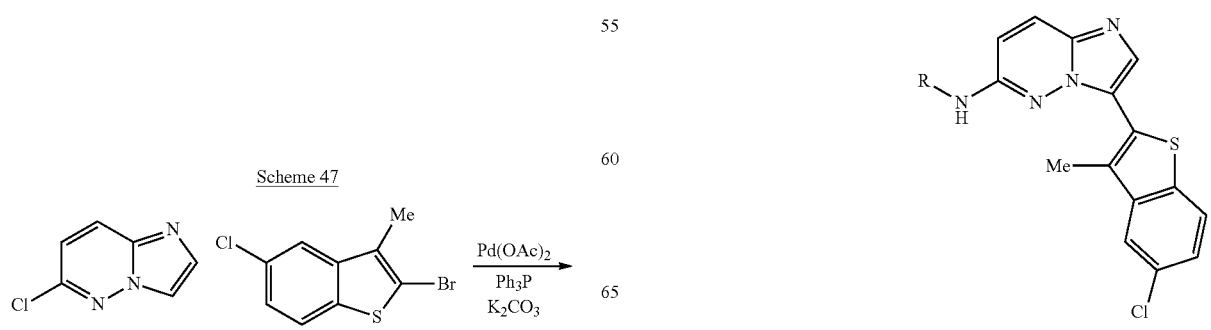

Preparation of 6-chloro-3-(5-chloro-3-methylbenzo[b]thiophen-2-yl)imidazo[1,2-b]pyridazine

Preparation of 3-(5-chloro-3-methylbenzo[b]thiophen-2-yl)-N-alkylimidazo[1,2-b]pyridazin-6-amine

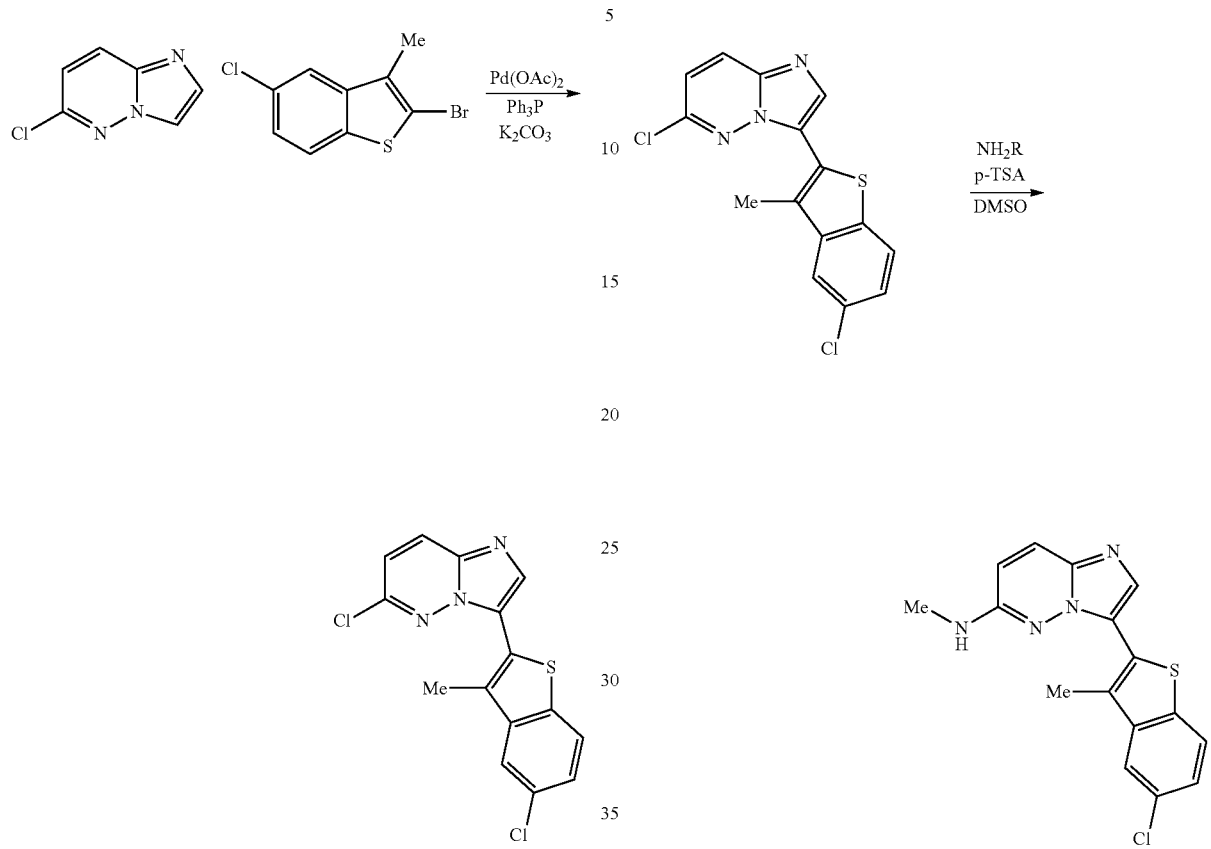

To a solution of 6-chloroimidazo[1,2-b]pyridazine (606 mg, 3.95 mmol, 1.0 equiv) in toluene (10.00 mL) was added 2-bromo-5-chloro-3-methylbenzo[b]thiophene (1.03 g, 3.95 mmol, 1.0 equiv), potassium carbonate (1.09 g, 7.90 mmol, 2.0 equiv), triphenyl phosphine (207 mg, 0.790 mmol, 0.20 equiv) and potassium acetate (89 mg, 0.395 mmol, 0.1 equiv). The reaction mixture was heated to reflux for 24 h. Purification by column chromatography using 50% ethyl acetate in hexanes elution gave 500 mg of the white solid, 38%.

To a solution of 6-chloro-3-(5-chloro-3-methylbenzo[b]thiophen-2-yl)imidazo[1,2-b]pyridazine (40 mg, 0.120 mmol, 1.0 equiv) in DMSO (1.00 mL) was added p-TSA (35 mg, 0.120 mmol, 1.5 equiv) and amine (2.24 mmol, 12.5 equiv) and heated to 100° C. for 24 h. Purification by column chromatography using 5% methanol in dichloromethane elution gave the product.

Compounds 118 and 164 were physically characterized by electrospray ionization mass spectrometry. Structures and molecular masses are given below in Table 47-b.

TABLE 47-b

| Cd. | Amine | Structure | IUPAC | [M + H]$^+$ |
|---|---|---|---|---|
| 118 | 4-aminobutan-1-ol | 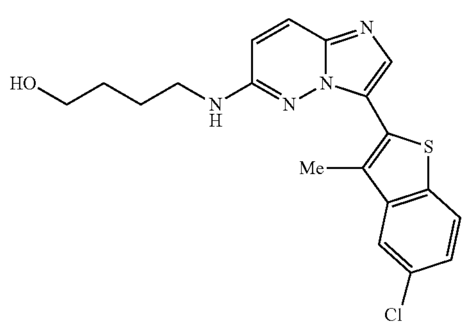 [SMILES: Cc1c(-c2cnc3ccc(NCCCCO)nn23)sc2ccc(Cl)cc12] | 4-(3-(5-chloro-3-methylbenzo[b]thiophen-2-yl)imidazo[1,2-b]pyridazin-6-ylamino)butan-1-ol | 387.6 |

TABLE 47-b-continued

| Cd. | Amine | Structure | IUPAC | [M + H]+ |
|---|---|---|---|---|
| 164 | trans-4-aminocyclohexanol | 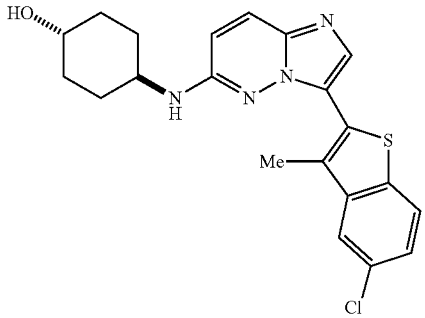 [SMILES: Cc1c(-c2cnc3ccc(N[C@H]4CC[C@H](O)CC4)nn23)sc2ccc(Cl)cc12] | trans-4-(3-(5-chloro-3-methylbenzo[b]thiophen-2-yl)imidazo[1,2-b]pyridazin-6-ylamino)cyclohexanol | 413.8 |

EXAMPLE 48

Synthesis of Compound 165

Preparation of 4-(3-(3-methylbenzo[b]thiophen-2-yl)imidazo[1,2-b]pyridazin-6-ylamino)butan-1-ol

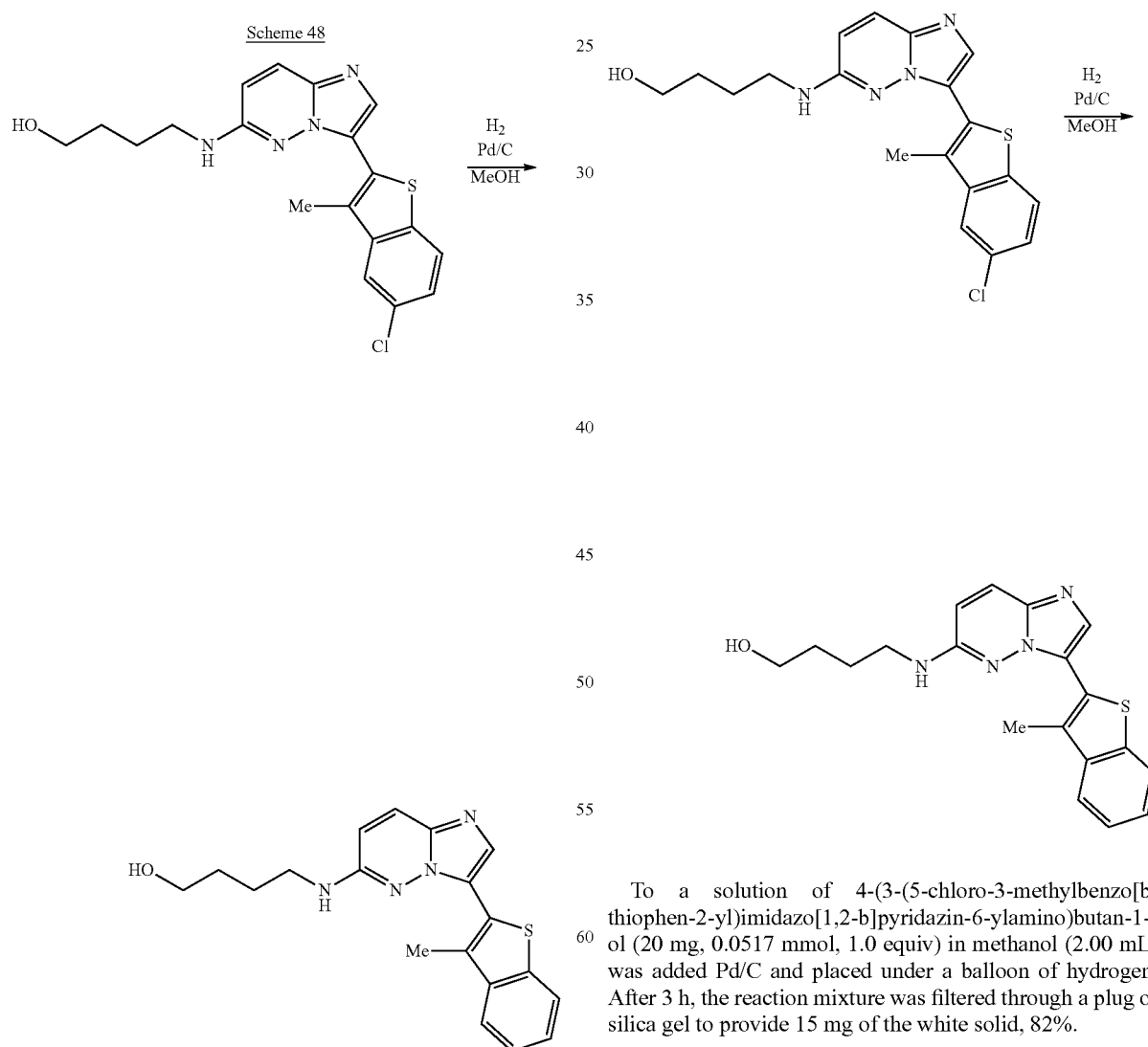

To a solution of 4-(3-(5-chloro-3-methylbenzo[b]thiophen-2-yl)imidazo[1,2-b]pyridazin-6-ylamino)butan-1-ol (20 mg, 0.0517 mmol, 1.0 equiv) in methanol (2.00 mL) was added Pd/C and placed under a balloon of hydrogen. After 3 h, the reaction mixture was filtered through a plug of silica gel to provide 15 mg of the white solid, 82%.

Compound 165 was physically characterized by electrospray ionization mass spectrometry. Structures and molecular masses are given below in Table 48-b.

TABLE 48-b

| Cd. | Structure | IUPAC Name | [M + H]+ |
|---|---|---|---|
| 165 | 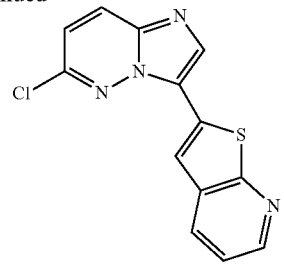 | 4-(3-(3-methylbenzo[b]thiophen-2-yl)imidazo[1,2-b]pyridazin-6-ylamino)butan-1-ol | 355.7 |

EXAMPLE 49

Synthesis of Compound 204

Scheme 49

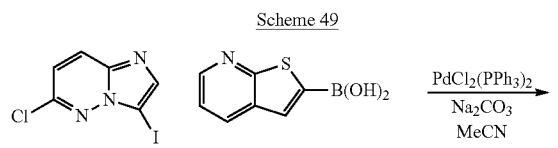

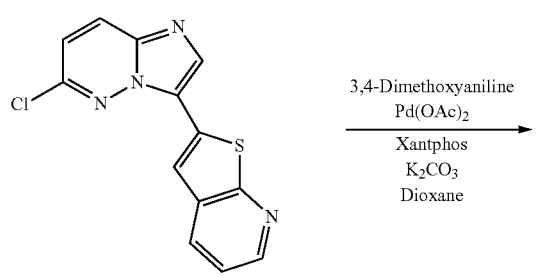

Preparation of 6-chloro-3-(7-methylbenzo[b]thiophen-2-yl)imidazo[1,2-b]pyridazine

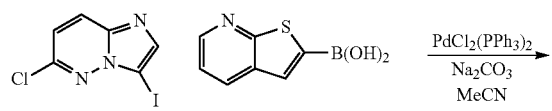

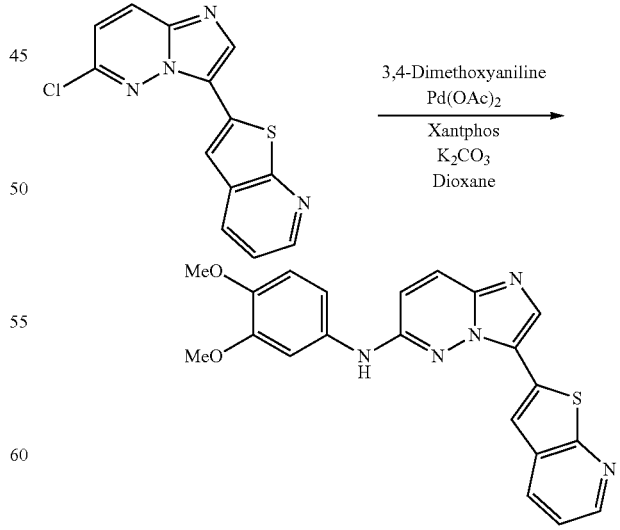

To a solution of thieno[2,3-b]pyridin-2-yl-2-boronic acid (304 mg, 1.70 mmol, 1.1 equiv) in acetonitrile (14.2 mL) was added 6-chloro-3-iodoimidazo[1,2-b]pyridazine (396 mg, 1.42 mmol, 1.0 equiv), palladium catalyst (104 mg, 0.142 mmol, 0.1 equiv) and sodium carbonate (14.2 mL, 1.0 M, 10.0 equiv). The solution was stirred at 150° C. in the microwave for 10 minutes. Purification using column chromatography gave 350 mg of the yellow solid, 86%.

Preparation of N-(3,4-dimethoxyphenyl)-3-(thieno[2,3-b]pyridin-2-yl)imidazo[1,2-b]pyridazin-6-amine

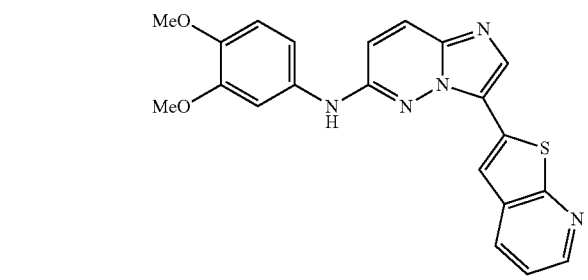

To a solution of 6-chloro-3-(7-methylbenzo[b]thiophen-2-yl)imidazo[1,2-b]pyridazine (58 mg, 0.202 mmol, 1.0 equiv), xantphos (23 mg, 0.0405 mmol, 0.2 equiv), palladium acetate (5 mg, 0.0202 mmol, 0.1 equiv), and potassium carbonate (559 mg, 4.05 mmol, 20 equiv) in dioxane (5.0 mL) was added 3,4-dimethoxyaniline (37 mg, 0.247 mmol, 1.2 equiv) and heated to 110° C. for 2 h. Purification by column chromatography using 2% methanol in dichloromethane elution gave 42 mg, 0.195 mmol of the yellow solid, 52%.

Compound 204 was physically characterized by electrospray ionization mass spectrometry. Structures and molecular masses are given below in Table x.

TABLE 49

| Cd. | Structure | IUPAC Name | [M + H]⁺ |
|---|---|---|---|
| 204 | 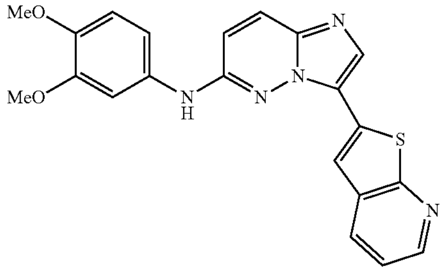 [SMILES: COc1ccc(Nc2ccc3ncc(-c4cc5cccnc5s4)n3n2)cc1OC] | N-(3,4-dimethoxyphenyl)-3-(thieno[2,3-b]pyridin-2-yl)imidazo[1,2-b]pyridazin-6-amine | 404.3 |

EXAMPLE 50

Synthesis of Compound 205

Preparation of trans-4-(3-(thieno[2,3-b]pyridin-2-yl)imidazo[1,2-b]pyridazin-6-ylamino)cyclohexanol

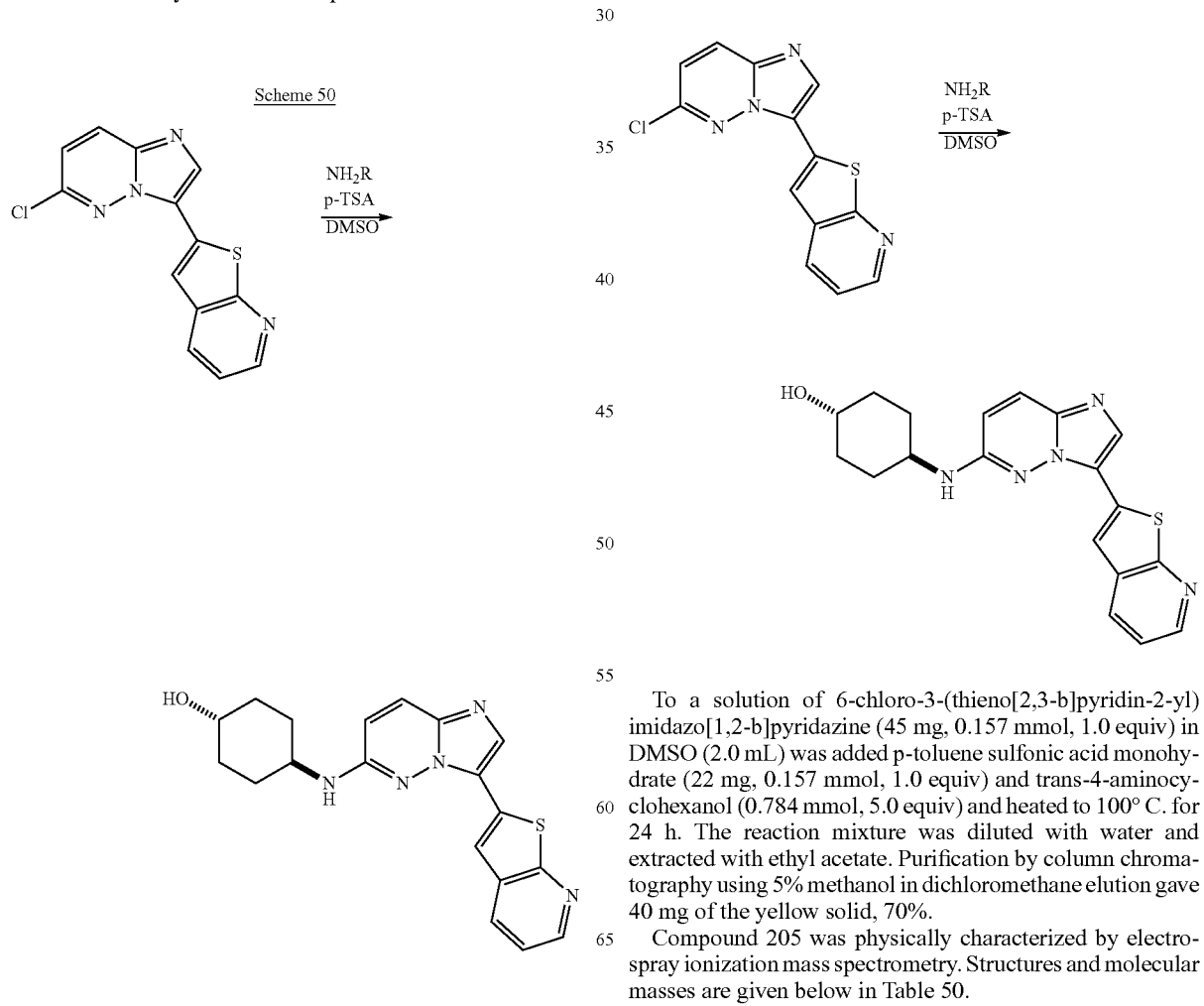

To a solution of 6-chloro-3-(thieno[2,3-b]pyridin-2-yl)imidazo[1,2-b]pyridazine (45 mg, 0.157 mmol, 1.0 equiv) in DMSO (2.0 mL) was added p-toluene sulfonic acid monohydrate (22 mg, 0.157 mmol, 1.0 equiv) and trans-4-aminocyclohexanol (0.784 mmol, 5.0 equiv) and heated to 100° C. for 24 h. The reaction mixture was diluted with water and extracted with ethyl acetate. Purification by column chromatography using 5% methanol in dichloromethane elution gave 40 mg of the yellow solid, 70%.

Compound 205 was physically characterized by electrospray ionization mass spectrometry. Structures and molecular masses are given below in Table 50.

TABLE x

| Cd. | Structure | IUPAC Name | [M + H]+ |
|---|---|---|---|
| 205 | 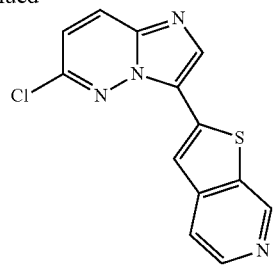 | trans-4-(3-(thieno[2,3-b]pyridin-2-yl)imidazo[1,2-b]pyridazin-6-ylamino)cyclohexanol | 366.2 |

EXAMPLE 51

Synthesis of Compound 218

Scheme 51

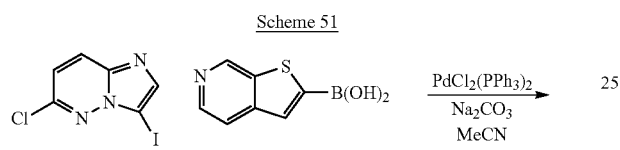

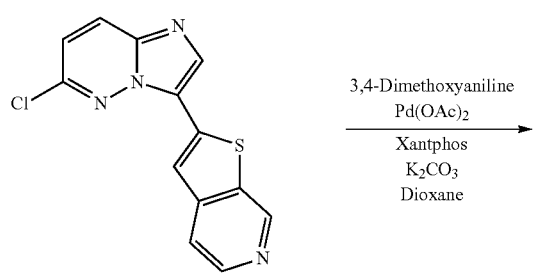

Preparation of 6-chloro-3-(thieno[2,3-c]pyridin-2-yl)imidazo[1,2-b]pyridazine

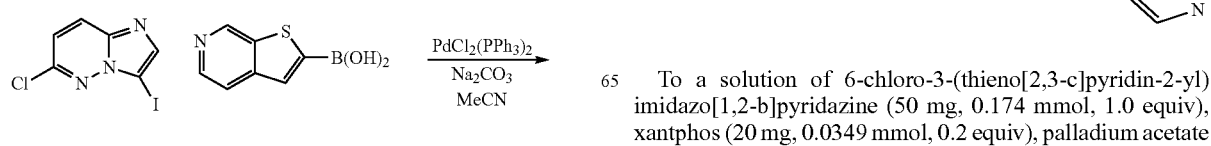

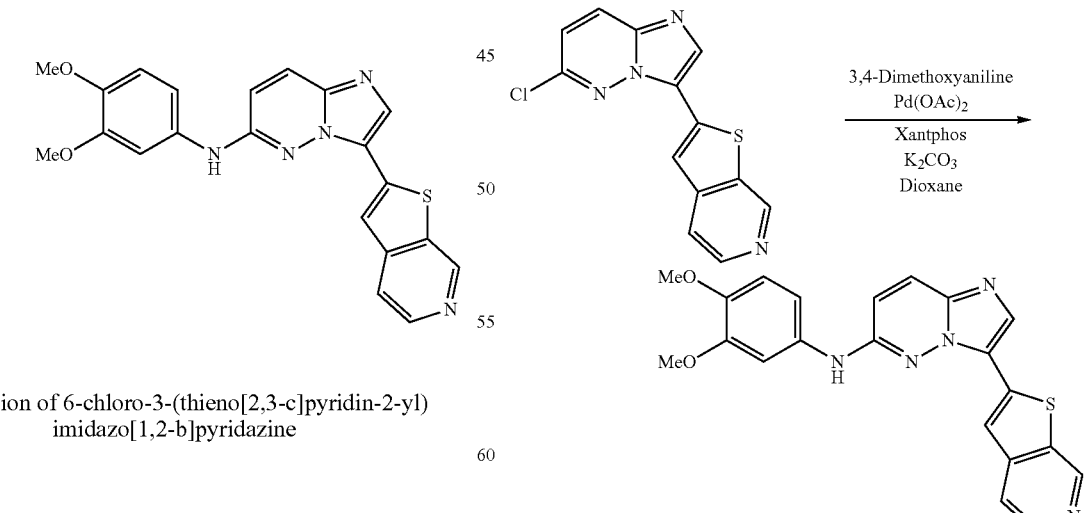

Preparation of N-(3,4-dimethoxyphenyl)-3-(thieno[2,3-c]pyridin-2-yl)imidazo[1,2-b]pyridazin-6-amine To a solution of thieno[2,3-c]pyridin-2-yl-2-boronic acid (265 mg, 1.48 mmol, 1.0 equiv) in acetonitrile (14.8 mL) was added 6-chloro-3-iodoimidazo[1,2-b]pyridazine (414 mg, 1.48 mmol, 1.0 equiv), palladium catalyst (108 mg, 0.148 mmol, 0.1 equiv) and sodium carbonate (14.8 mL, 1.0 M, 10.0 equiv). The solution was stirred at 150° C. in the microwave for 10 minutes. Purification using column chromatography gave 200 mg of the white solid, 47%.

To a solution of 6-chloro-3-(thieno[2,3-c]pyridin-2-yl)imidazo[1,2-b]pyridazine (50 mg, 0.174 mmol, 1.0 equiv), xantphos (20 mg, 0.0349 mmol, 0.2 equiv), palladium acetate (4 mg, 0.0174 mmol, 0.1 equiv), and potassium carbonate (482 mg, 3.49 mmol, 20 equiv) in dioxane (5.0 mL) was added 3,4-dimethoxyaniline (35 mg, 0.227 mmol, 1.3 equiv) and heated to 110° C. for 2 h. Purification by column chromatography using 2% methanol in dichloromethane elution gave 38 mg, of the yellow solid, 54%.

Compound 218 was physically characterized by electrospray ionization mass spectrometry. Structures and molecular masses are given below in Table 51.

TABLE 51

| Cd. | Structure | IUPAC Name | [M + H]+ |
|---|---|---|---|
| 218 | MeO— structure —OMe | N-(3,4-dimethoxyphenyl)-3-(thieno[2,3-c]pyridin-2-yl)imidazo[1,2-b]pyridazin-6-amine | 404.5 |

EXAMPLE 52

Synthesis of Compound 219

Preparation of trans-4-(3-(thieno[2,3-c]pyridin-2-yl)imidazo[1,2-b]pyridazin-6-ylamino)cyclohexanol

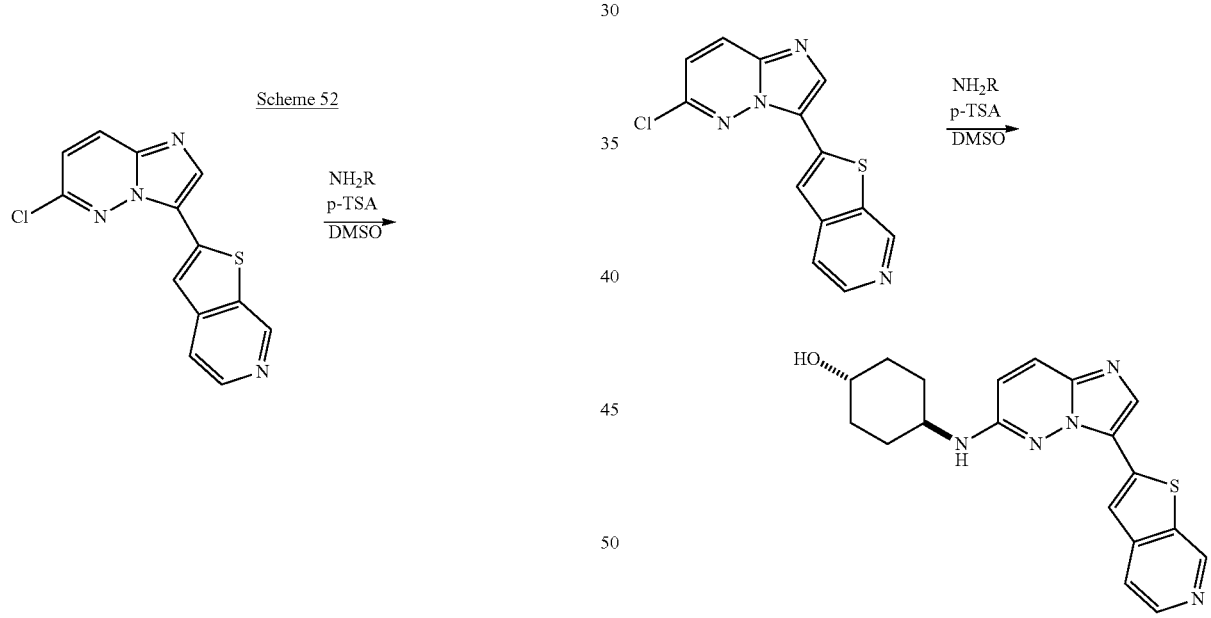

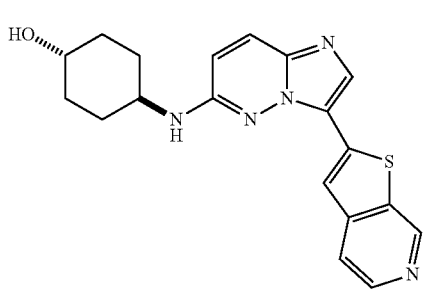

To a solution of 6-chloro-3-(thieno[2,3-c]pyridin-2-yl)imidazo[1,2-b]pyridazine (50 mg, 0.174 mmol, 1.0 equiv) in DMSO (2.0 mL) was added p-toluene sulfonic acid monohydrate (25 mg, 0.174 mmol, 1.0 equiv) and trans-4-aminocyclohexanol (0.870 mmol, 5.0 equiv) and heated to 100° C. for 24 h. The reaction mixture was diluted with water and extracted with ethyl acetate. Purification by column chromatography using 5% methanol in dichloromethane elution gave 42 mg of the yellow solid, 67%.

Compound 219 was physically characterized by electrospray ionization mass spectrometry. Structures and molecular masses are given below in Table 52.

TABLE 52

| Cd. | Structure | IUPAC Name | [M + H]+ |
|---|---|---|---|
| 219 | 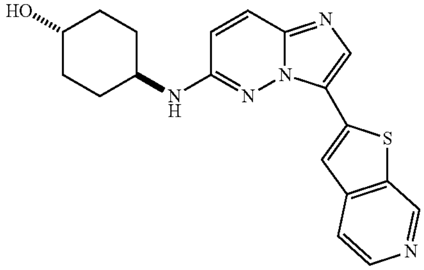 [SMILES: O[C@H]1CC[C@H](Nc2ccc3ncc(-c4cc5ccncc5s4)n3n2)CC1] | trans-4-(3-(thieno[2,3-c]pyridin-2-yl)imidazo[1,2-b]pyridazin-6-ylamino)cyclohexanol | 366.7 |

EXAMPLE X

Synthesis of Compound 206

Scheme 52

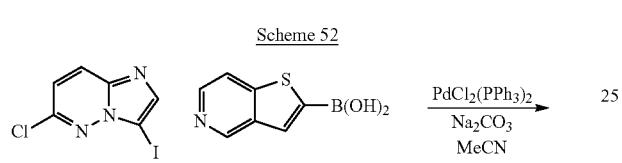

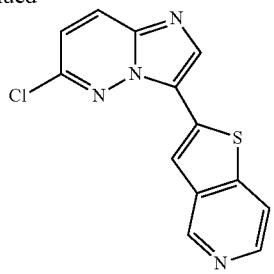

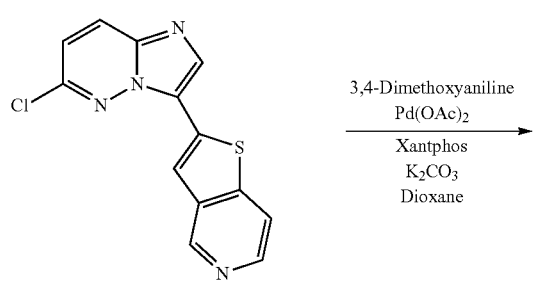

To a solution of thieno[3,2-c]pyridin-2-yl-2-boronic acid (104 mg, 0.580 mmol, 1.1 equiv) in acetonitrile (5.28 mL) was added 6-chloro-3-iodoimidazo[1,2-b]pyridazine (148 mg, 0.528 mmol, 1.0 equiv), palladium catalyst (39 mg, 0.0529 mmol, 0.1 equiv) and sodium carbonate (5.28 mL, 1.0 M, 10.0 equiv). The solution was stirred at 150° C. in the microwave for 10 minutes. Purification using column chromatography gave 101 mg of the yellow solid, 67%.

Preparation of N-(3,4-dimethoxyphenyl)-3-(thieno[2,3-c]pyridin-2-yl)imidazo[1,2-b]pyridazin-6-amine

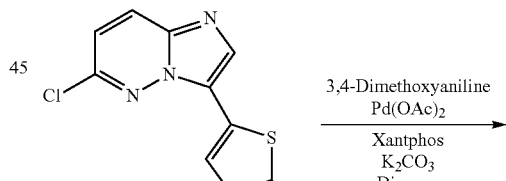

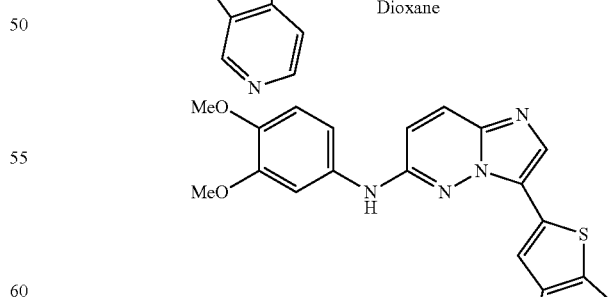

Preparation of 6-chloro-3-(thieno[3,2-c]pyridin-2-yl)imidazo[1,2-b]pyridazine

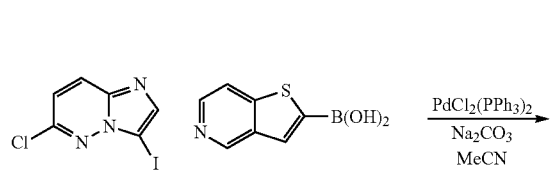

To a solution of N-(3,4-dimethoxyphenyl)-3-(thieno[3,2-c]pyridin-2-yl)imidazo[1,2-b]pyridazin-6-amine (44 mg, 0.153 mmol, 1.0 equiv), xantphos (18 mg, 0.0306 mmol, 0.2 equiv), palladium acetate (3 mg, 0.0153 mmol, 0.1 equiv), and potassium carbonate (424 mg, 3.07 mmol, 20 equiv) in dioxane (5.0 mL) was added 3,4-dimethoxyaniline (28 mg, 0.184 mmol, 1.2 equiv) and heated to 110° C. for 2 h. Purification by column chromatography using 2% methanol in dichloromethane elution gave 38 mg, of the yellow solid, 62%.

Compound 206 was physically characterized by electrospray ionization mass spectrometry. Structures and molecular masses are given below in Table 52.

TABLE 52

| Cd. | Structure | IUPAC Name | [M + H]$^+$ |
|---|---|---|---|
| 206 | 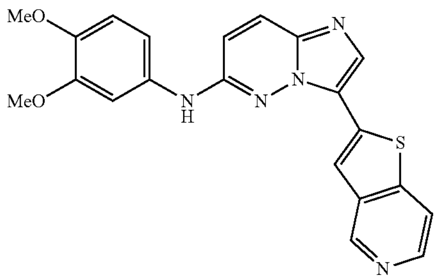 [SMILES: COc1ccc(Nc2ccc3ncc(-c4cc5cnccc5s4)n3n2)cc1OC] | N-(3,4-dimethoxyphenyl)-3-(thieno[3,2-c]pyridin-2-yl)imidazo[1,2-b]pyridazin-6-amine | 404.1 |

EXAMPLE 53

Synthesis of Compound 207

Preparation of trans-(3-(thieno[3,2-c]pyridin-2-yl)imidazo[1,2-b]pyridazin-6-ylamino)cyclohexanol

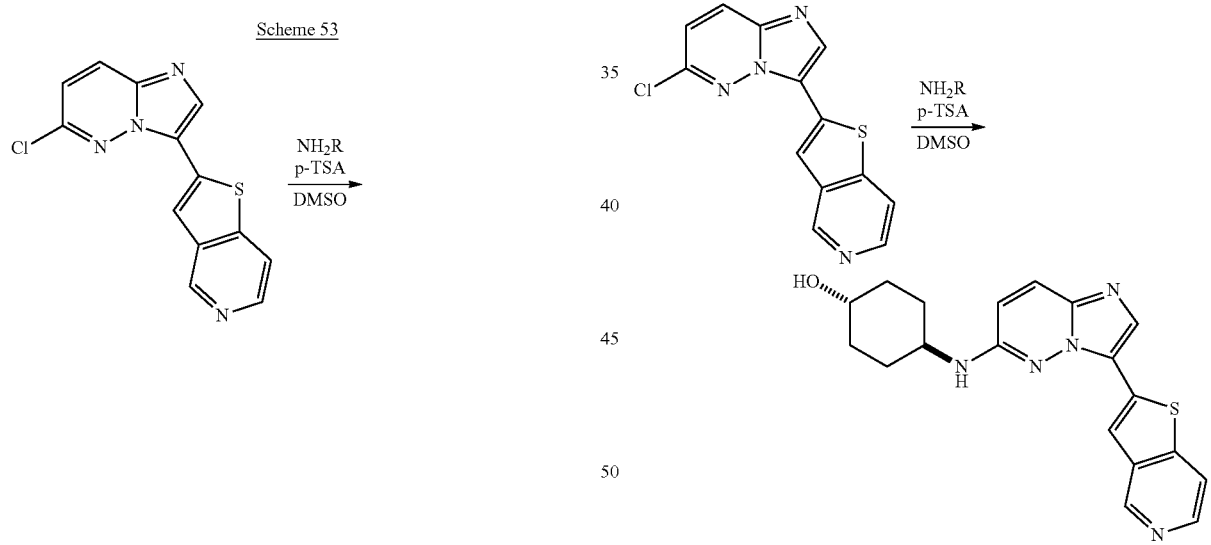

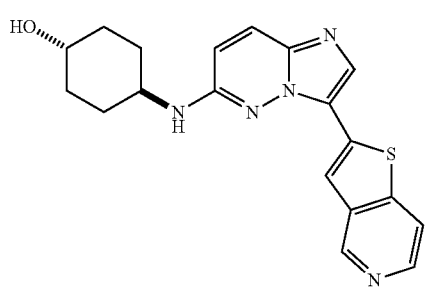 [SMILES: O[C@H]1CC[C@H](Nc2ccc3ncc(-c4cc5cnccc5s4)n3n2)CC1]

To a solution of 6-chloro-3-(thieno[3,2-c]pyridin-2-yl)imidazo[1,2-b]pyridazine (50 mg, 0.174 mmol, 1.0 equiv) in DMSO (2.0 mL) was added p-toluene sulfonic acid monohydrate (25 mg, 0.174 mmol, 1.0 equiv) and trans-4-aminocyclohexanol (0.870 mmol, 5.0 equiv) and heated to 100° C. for 24 h. The reaction mixture was diluted with water and extracted with ethyl acetate. Purification by column chromatography using 5% methanol in dichloromethane elution gave 40 mg of the yellow solid, 63%.

Compound 207 was physically characterized by electrospray ionization mass spectrometry. Structures and molecular masses are given below in Table 53.

TABLE 53

| Cd. | Structure | IUPAC Name | [M + H]+ |
|---|---|---|---|
| 207 | 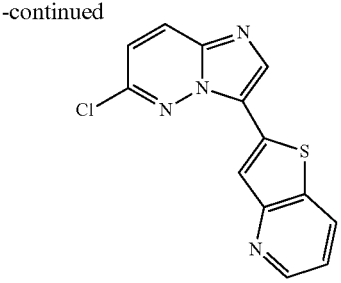 | trans-(3-(thieno[3,2-c]pyridin-2-yl)imidazo[1,2-b]pyridazin-6-ylamino)cyclohexanol | 366.5 |

EXAMPLE 54

Synthesis of Compound 208

Scheme 54

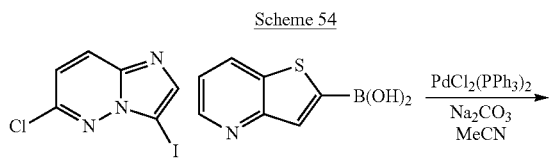

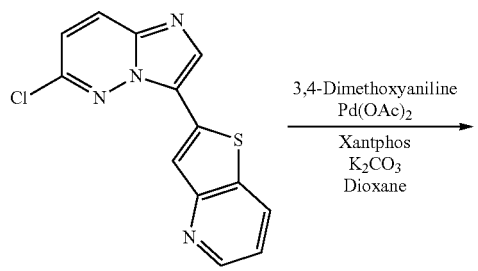

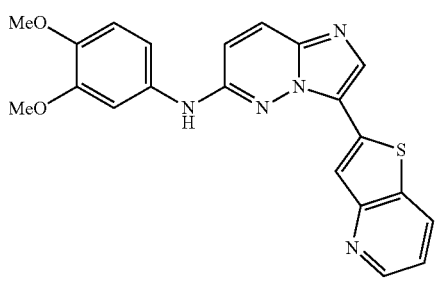 [SMILES: COc1ccc(Nc2ccc3ncc(-c4cc5ncccc5s4)n3n2)cc1OC]

Preparation of 6-chloro-3-(thieno[3,2-b]pyridin-2-yl)imidazo[1,2-b]pyridazine

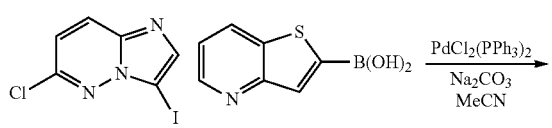

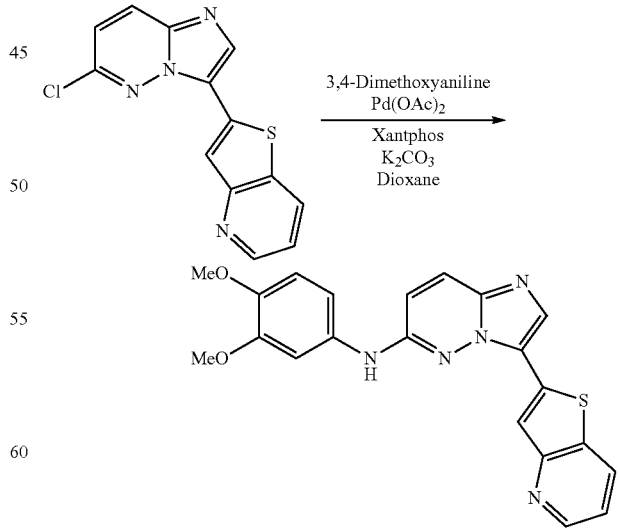

To a solution of thieno[3,2-b]pyridin-2-yl-2-boronic acid (104 mg, 0.580 mmol, 1.1 equiv) in acetonitrile (5.28 mL) was added 6-chloro-3-iodoimidazo[1,2-b]pyridazine (148 mg, 0.528 mmol, 1.0 equiv), palladium catalyst (39 mg, 0.0529 mmol, 0.1 equiv) and sodium carbonate (5.28 mL, 1.0 M, 10.0 equiv). The solution was stirred at 150° C. in the microwave for 10 minutes. Purification using column chromatography gave 95 mg of the yellow solid, 63%.

Preparation of N-(3,4-dimethoxyphenyl)-3-(thieno[3,2-b]pyridin-2-yl)imidazo[1,2-b]pyridazin-6-amine To a solution of 6-chloro-3-(thieno[3,2-b]pyridin-2-yl)imidazo[1,2-b]pyridazine (50 mg, 0.174 mmol, 1.0 equiv), xantphos (20 mg, 0.0348 mmol, 0.2 equiv), palladium acetate (4 mg, 0.0174 mmol, 0.1 equiv), and potassium carbonate (482 mg, 3.49 mmol, 20 equiv) in dioxane (5.0 mL) was added 3,4-dimethoxyaniline (32 mg, 0.209 mmol, 1.2 equiv) and heated to 110° C. for 2 h. Purification by column chromatography using 2% methanol in dichloromethane elution gave 35 mg, of the yellow solid, 50%.

Compound 208 was physically characterized by electrospray ionization mass spectrometry. Structures and molecular masses are given below in Table 54.

TABLE 54

| Cd. | Structure | IUPAC Name | [M + H]+ |
|---|---|---|---|
| 208 | MeO, MeO | N-(3,4-dimethoxyphenyl)-3-(thieno[3,2-b]pyridin-2-yl)imidazo[1,2-b]pyridazin-6-amine | 404.5 |

EXAMPLE 55

Synthesis of Compound 209

Preparation of trans-4-(3-(thieno[3,2-b]pyridin-2-yl)imidazo[1,2-b]pyridazin-6-ylamino)cyclohexanol

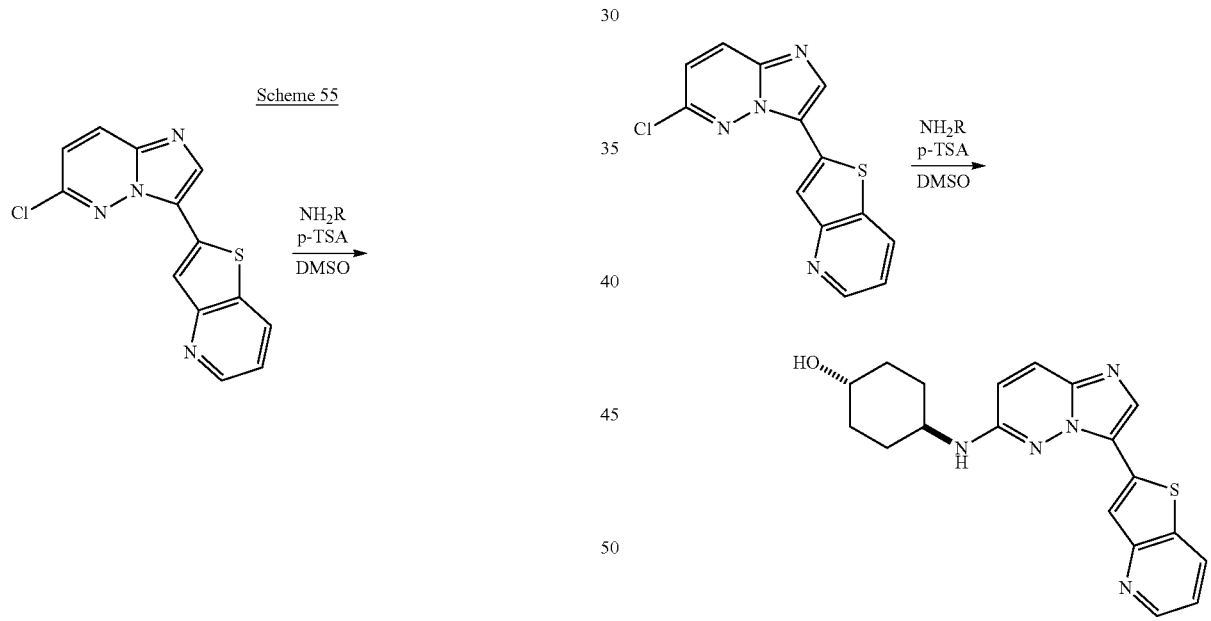

To a solution of 6-chloro-3-(thieno[3,2-b]pyridin-2-yl)imidazo[1,2-b]pyridazine (40 mg, 0.139 mmol, 1.0 equiv) in DMSO (2.0 mL) was added p-toluene sulfonic acid monohydrate (20 mg, 0.139 mmol, 1.0 equiv) and trans-4-aminocyclohexanol (0.695 mmol, 5.0 equiv) and heated to 100° C. for 24 h. The reaction mixture was diluted with water and extracted with ethyl acetate. Purification by column chromatography using 5% methanol in dichloromethane elution gave 40 mg of the yellow solid, 79%.

Compound 209 was physically characterized by electrospray ionization mass spectrometry. Structures and molecular masses are given below in Table 55.

TABLE 55

| Cd. | Structure | IUPAC Name | [M + H]+ |
|---|---|---|---|
| 209 | 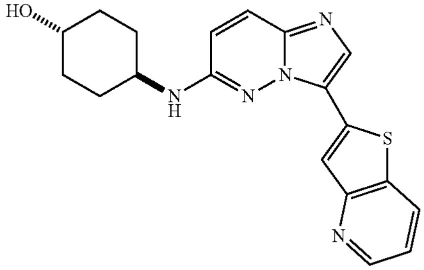 [SMILES: O[C@H]1CC[C@H](Nc2ccc3ncc(-c4cc5ncccc5s4)n3n2)CC1] | trans-4-(3-(thieno[3,2-b]pyridin-2-yl)imidazo[1,2-b]pyridazin-6-ylamino)cyclohexanol | 366.5 |

EXAMPLE 56

Synthesis of Compound 210

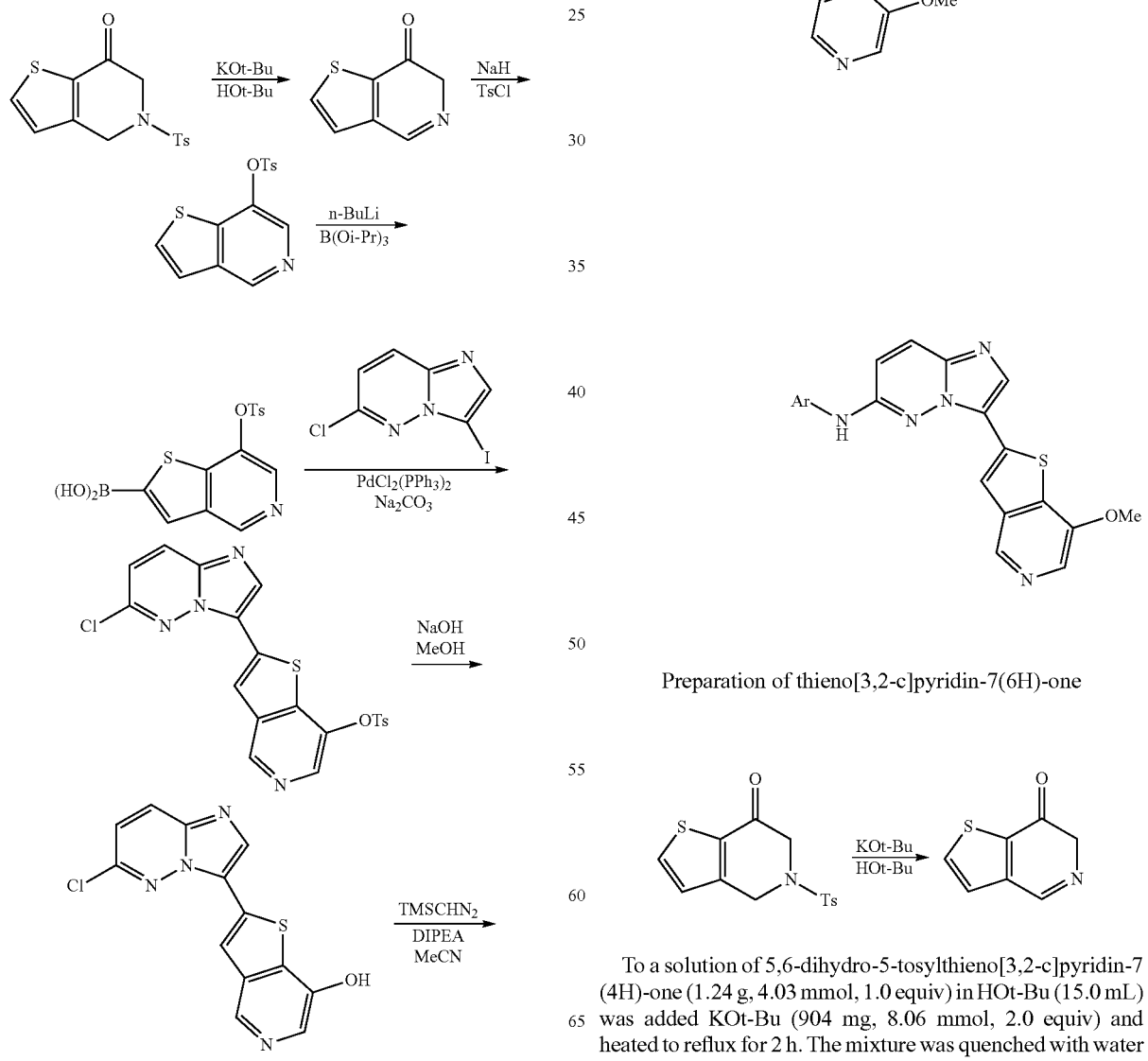

Preparation of thieno[3,2-c]pyridin-7(6H)-one

To a solution of 5,6-dihydro-5-tosylthieno[3,2-c]pyridin-7(4H)-one (1.24 g, 4.03 mmol, 1.0 equiv) in HOt-Bu (15.0 mL) was added KOt-Bu (904 mg, 8.06 mmol, 2.0 equiv) and heated to reflux for 2 h. The mixture was quenched with water and then extracted with ethyl acetate. Purification by column chromatography using 50% ethyl acetate in hexanes elution gave 1.09 g of white solid, 89%.

Preparation of thieno[3,2-c]pyridin-7-yl 4-methylbenzenesulfonate

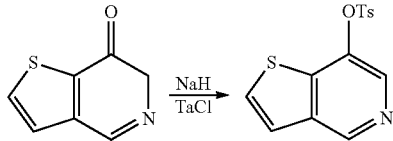

To a solution of thieno[3,2-c]pyridin-7(6H)-one (110 mg, 0.728 mmol, 1.0 equiv) in THF (5.00 mL) was added NaH (35 mg, 0.873 mmol, 1.2 equiv) followed by TsCl (180 mg, 0.946 mmol, 1.3 equiv). The reaction mixture was stirred at rt for 2 h, then quenched with water and extracted with ethyl acetate. Purification by column chromatography using 20% ethyl acetate in hexanes elution gave 180 mg of a white solid, 81%.

Preparation of 7-(4-methylbenzenesulfonyl)thieno[3,2-c]pyridin-2-yl-2-boronic acid

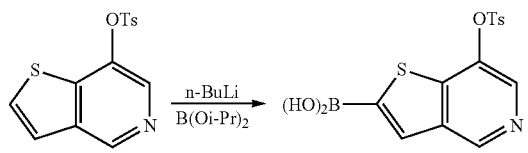

To a solution of thieno[3,2-c]pyridin-7-yl 4-methylbenzenesulfonate (1.18 g, 3.86 mmol, 1.0 equiv) in THF (20.0 mL) at −78° C. was added n-BuLi (3.62 mL, 5.80 mmol, 1.5 equiv). The reaction was stirred at the reduced temperature for 1 h, then triisopropylborate (1.34 mL, 5.80 mmol, 1.5 equiv) was added and stirred at rt for 2 h. The mixture was quenched with 2N HCl and then extracted with ethyl acetate. Purification by column chromatography using 2% methanol in dichloromethane elution gave 800 mg of white solid, 59%.

Preparation of 2-(6-chloroimidazo[1,2-b]pyridazin-3-yl)thieno[3,2-c]pyridin-7-yl 4-methylbenzenesulfonate

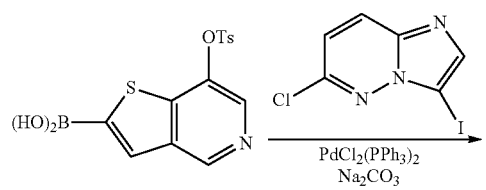

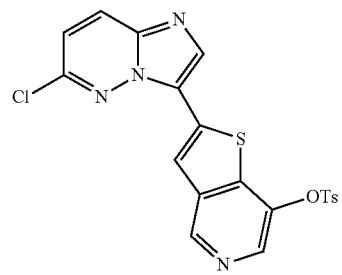

To a solution of 7-(4-methylbenzenesulfonyl)thieno[3,2-c]pyridin-2-yl-2-boronic acid (650 mg, 1.69 mmol, 1.1 equiv) in acetonitrile (16 mL) was added 6-chloro-3-iodoimidazo[1,2-b]pyridazine (473 mg, 1.69 mmol, 1.0 equiv), palladium catalyst (124 mg, 0.169 mmol, 0.1 equiv) and sodium carbonate (16.9 mL, 1.0 M, 10.0 equiv). The solution was stirred in the microwave at 150° C. for 10 min. Purification using column chromatography gave 600 mg of the yellow product, 78%.

Preparation of 2-(6-chloroimidazo[1,2-b]pyridazin-3-yl)thieno[3,2-c]pyridin-7-ol

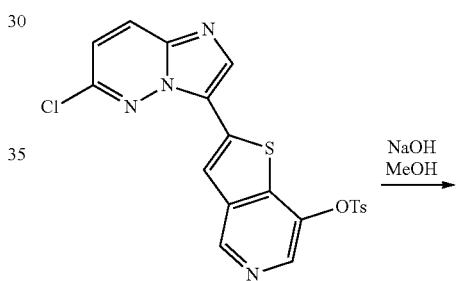

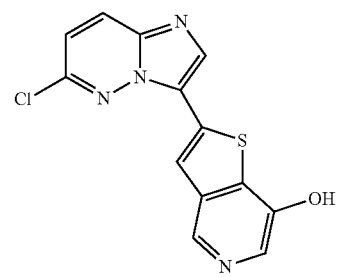

To a solution of 2-(6-chloroimidazo[1,2-b]pyridazin-3-yl) thieno[3,2-c]pyridin-7-yl 4-methylbenzenesulfonate (200 mg, 0.349 mmol, 1.0 equiv) in MeOH (5.0 mL) was added sodium hydroxide (70 microliter, 5.0 M aqueous solution, 1.0 equiv). The reaction mixture was stirred at rt for 3 h, then quenched with water and extracted with ethyl acetate. Purification using column chromatography gave 80 mg of the white product, 76%.

Preparation of 6-chloro-3-(7-methoxythieno[3,2-c]pyridin-2-yl)imidazo[1,2-b]pyridazine

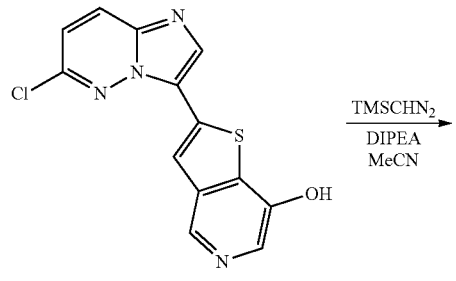

To a solution of 2-(6-chloroimidazo[1,2-b]pyridazin-3-yl)thieno[3,2-c]pyridin-7-ol (38 mg, 0.126 mmol, 1.0 equiv) in DCM (3.0 mL) and MeOH (1.0 mL) was added DIPEA (0.188 mmol, 1.5 equiv) then TMSCHN$_2$ (94 microliter, 0.188 mmol, 1.5 equiv). The reaction mixture was stirred at rt for 3 h, then quenched with water and extracted with ethyl acetate. Purification by column chromatography using 20% ethyl acetate in hexanes elution gave 20 mg of the yellow solid, 50%.

Preparation of 3-(7-methoxythieno[3,2-c]pyridin-2-yl)-N-arylimidazo[1,2-b]pyridazin-6-amine

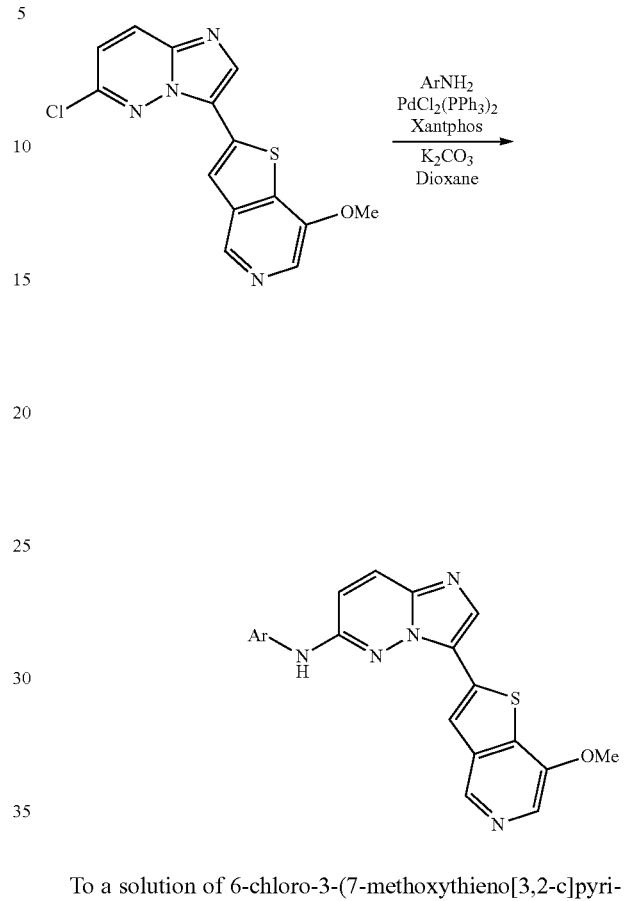

To a solution of 6-chloro-3-(7-methoxythieno[3,2-c]pyridin-2-yl)imidazo[1,2-b]pyridazine (30 mg, 0.095 mmol, 1.0 equiv), xantphos (11 mg, 0.0189 mmol, 0.2 equiv), palladium acetate (2 mg, 0.0947 mmol, 0.1 equiv), and potassium carbonate (261 mg, 1.89 mmol, 20 equiv) in dioxane (5.0 mL) was added 3,4-dimethoxyaniline (22 mg, 0.142 mmol, 1.5 equiv) and heated to 110° C. for 2 h. Purification by column chromatography using 2% methanol in dichloromethane elution gave 28 mg, of the yellow solid, 68%.

Compound 210 was physically characterized by electrospray ionization mass spectrometry. Structures and molecular masses are given below in Table 56.

| Cd. | Structure | IUPAC Name | [M + H]$^+$ |
|---|---|---|---|
| 210 | MeO-phenyl-NH-imidazo[1,2-b]pyridazine-thieno[3,2-c]pyridine-OMe structure | N-(3,4-dimethoxyphenyl)-3-(7-methoxythieno[3,2-c]pyridin-2-yl)imidazo[1,2-b]pyridazin-6-amine | 434.0 |

EXAMPLE 57

Synthesis of Compound 211

Scheme 57

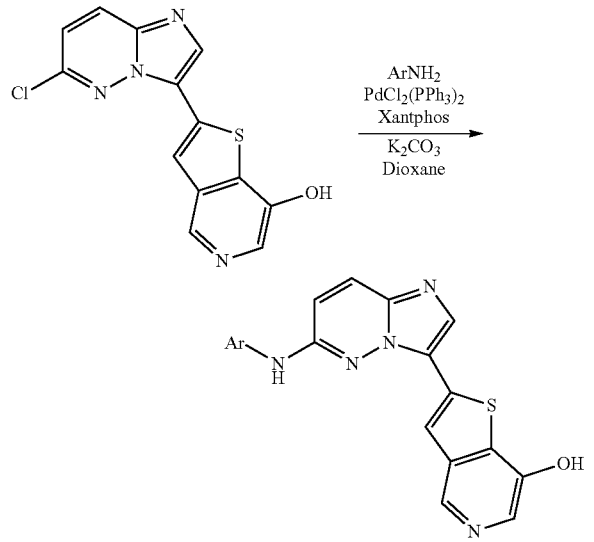

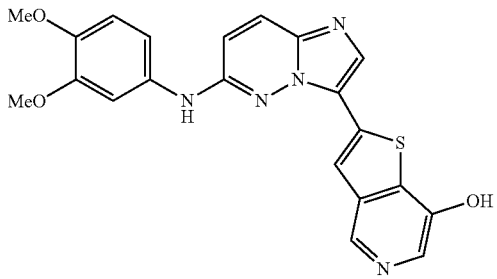 [SMILES: COc1ccc(Nc2ccc3ncc(-c4cc5cncc(O)c5s4)n3n2)cc1OC]

To a solution of 2-(6-chloroimidazo[1,2-b]pyridazin-3-yl)thieno[3,2-c]pyridin-7-ol (50 mg, 0.165 mmol, 1.0 equiv), xantphos (19 mg, 0.0330 mmol, 0.2 equiv), palladium acetate (4 mg, 0.0165 mmol, 0.1 equiv), and potassium carbonate (456 mg, 3.30 mmol, 20 equiv) in dioxane (5.0 mL) was added 3,4-dimethoxyaniline (38 mg, 0.248 mmol, 1.5 equiv) and heated to 110° C. for 2 h. Purification by column chromatography using 2% methanol in dichloromethane elution gave 30 mg, of the brown solid, 43%.

Compound 211 was physically characterized by electrospray ionization mass spectrometry. Structures and molecular masses are given below in Table 57.

| Cd. | Structure | IUPAC Name | [M + H]$^+$ |
|---|---|---|---|
| 211 | 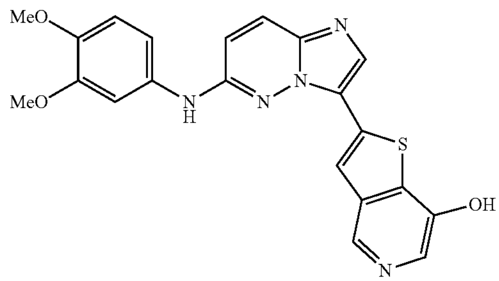 | 2-(6-(3,4-dimethoxyphenylamino)imidazo[1,2-b]pyridazin-3-yl)thieno[3,2-c]pyridin-7-ol | 420.5 |

Preparation of 2-(6-(3,4-dimethoxyphenylamino)imidazo[1,2-b]pyridazin-3-yl)thieno[3,2-c]pyridin-7-ol

EXAMPLE 58

Synthesis of Compound 212

Scheme 58

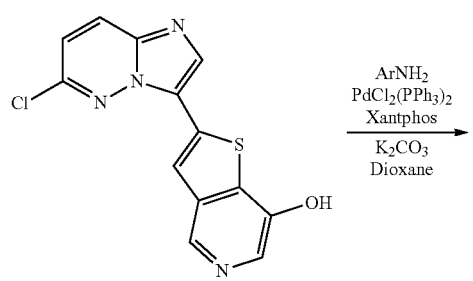

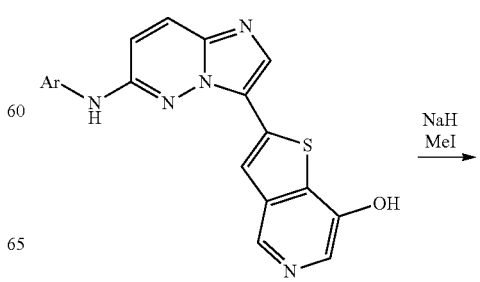

245
-continued

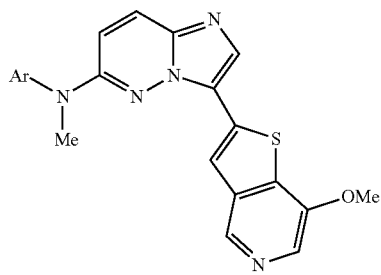

246

To a solution of 2-(6-(3,4-dimethoxyphenylamino)imidazo[1,2-b]pyridazin-3-yl)thieno[3,2-c]pyridin-7-ol (10 mg, 0.0238 mmol, 1.0 equiv) in THF (3.00 mL) was added NaH (30 mg, 0.750 mol, 31.5 equiv) then iodomethane (100 mg, 0.705 mmol, 30.0 equiv). The reaction mixture was stirred at rt for 2 h. Purification by column chromatography using 2% methanol in dichloromethane elution gave 10 mg, of the yellow solid, 94%.

Compound 212 was physically characterized by electrospray ionization mass spectrometry. Structures and molecular masses are given below in Table 58.

| 58. | Structure | IUPAC Name | [M + H]+ |
|---|---|---|---|
| 212 | MeO... | N-(3,4-dimethoxyphenyl)-3-(7-methoxythieno[3,2-c]pyridin-2-yl)-N-methylimidazo[1,2-b]pyridazin-6-amine | 448.1 |

Preparation of N-(3,4-dimethoxyphenyl)-3-(7-methoxythieno[3,2-c]pyridin-2-yl)-N-methylimidazo[1,2-b]pyridazin-6-amine

EXAMPLE X

Synthesis of Compound 213, 217

Scheme 59

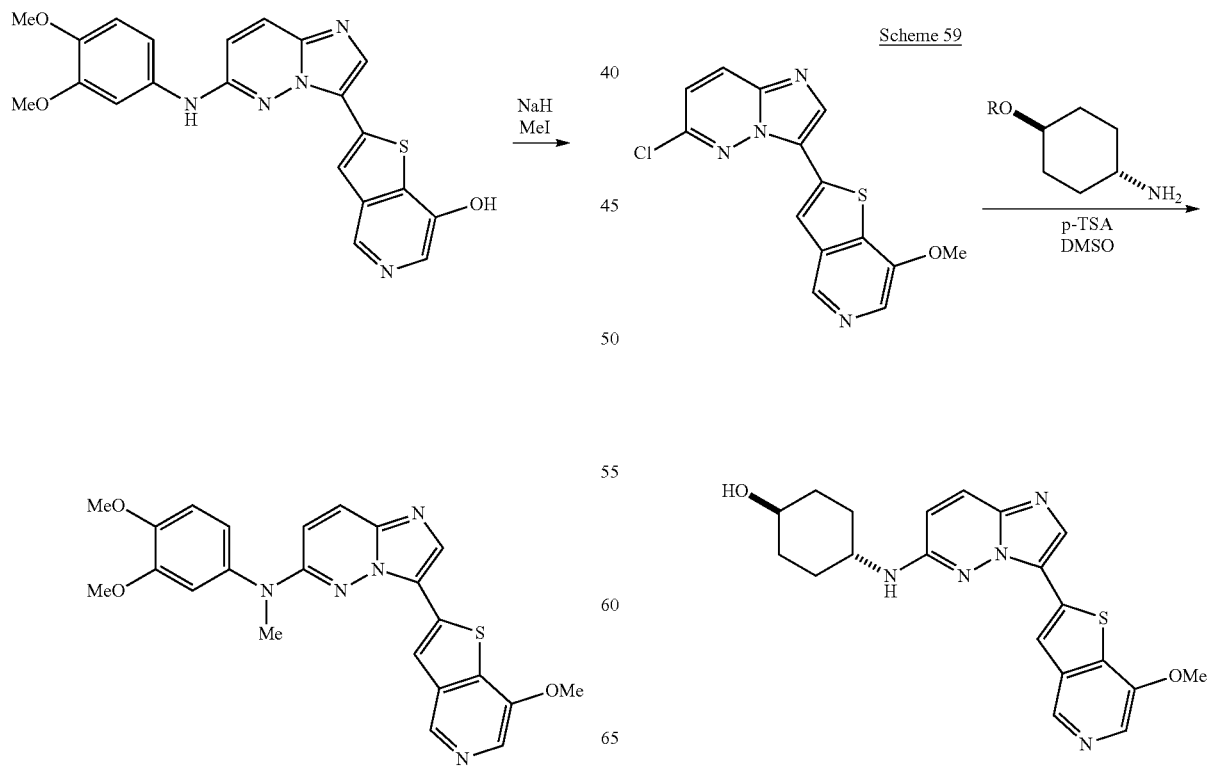

Preparation of N-Alkyl-3-(7-methoxythieno[3,2-c]pyridin-2-yl)imidazo[1,2-b]pyridazin-6-amine

EXAMPLE 60

Synthesis of Compound 215

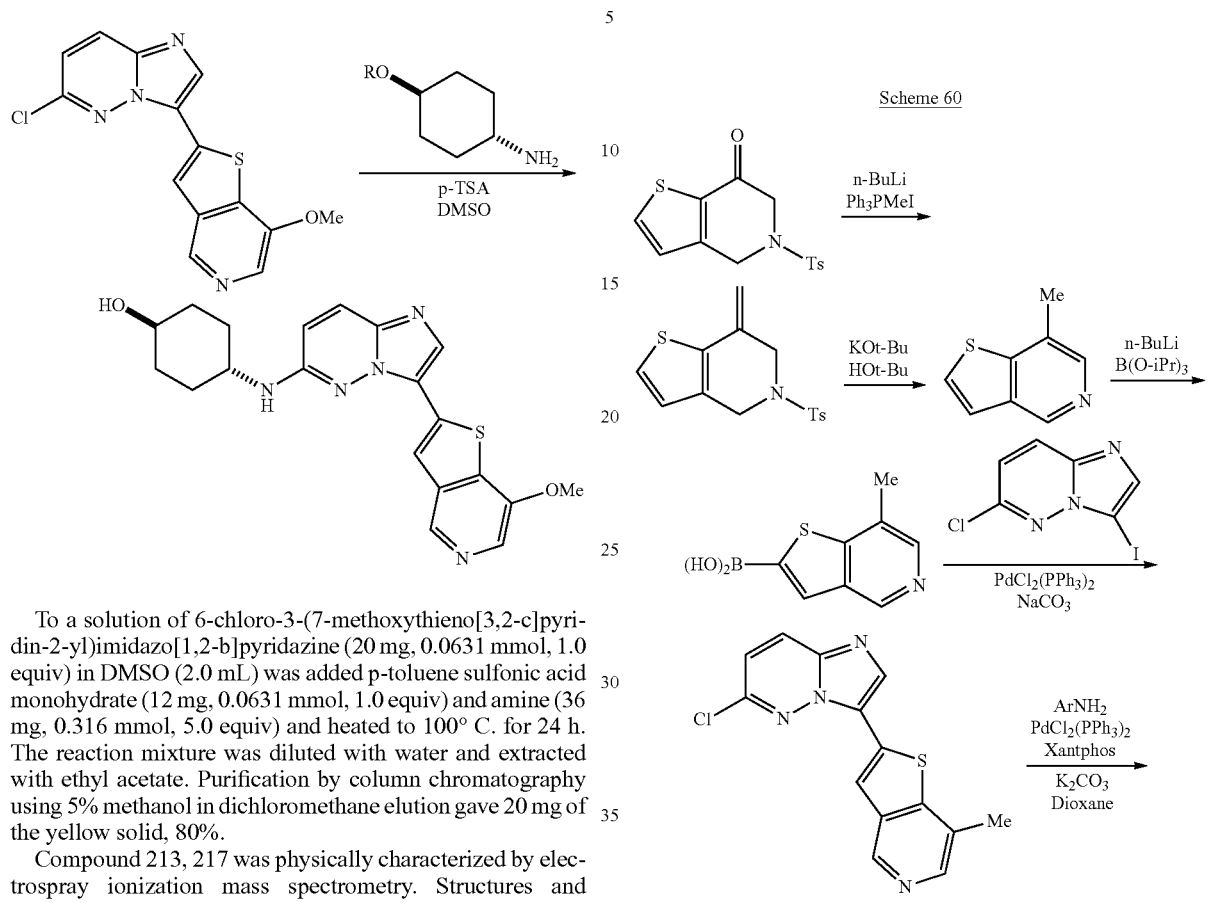

Scheme 60

To a solution of 6-chloro-3-(7-methoxythieno[3,2-c]pyridin-2-yl)imidazo[1,2-b]pyridazine (20 mg, 0.0631 mmol, 1.0 equiv) in DMSO (2.0 mL) was added p-toluene sulfonic acid monohydrate (12 mg, 0.0631 mmol, 1.0 equiv) and amine (36 mg, 0.316 mmol, 5.0 equiv) and heated to 100° C. for 24 h. The reaction mixture was diluted with water and extracted with ethyl acetate. Purification by column chromatography using 5% methanol in dichloromethane elution gave 20 mg of the yellow solid, 80%.

Compound 213, 217 was physically characterized by electrospray ionization mass spectrometry. Structures and molecular masses are given below in Table 59.

TABLE 59

| Cd. | Amine | Structure | IUPAC Name | [M + H]⁺ |
|---|---|---|---|---|
| 213 | trans-4-aminocyclohexanol | 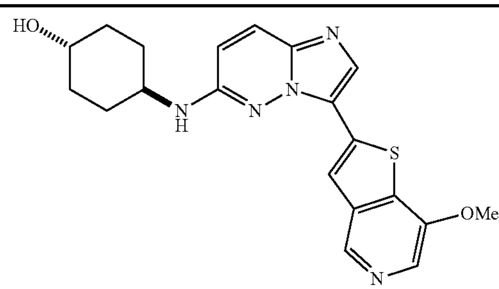 | trans-4-(3-(7-methoxythieno[3,2-c]pyridin-2-yl)imidazo[1,2-b]pyridazin-6-ylamino)cyclohexanol | 396.1 |
| 217 | trans-4-methoxycyclohexanamine | 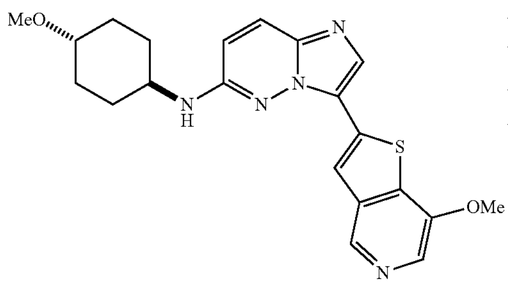 [SMILES: COc1cncc2cc(-c3cnc4ccc(N[C@H]5CC[C@H](OC)CC5)nn34)sc12] | trans-4-methoxycyclohexyl)-3-(7-methoxythieno[3,2-c]pyridin-2-yl)imidazo[1,2-b]pyridazin-6-amine | 410.5 |

-continued

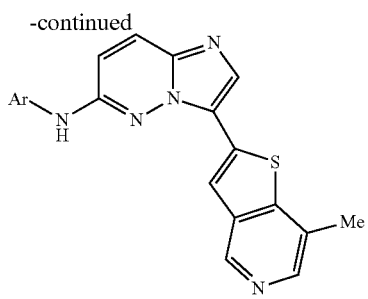

Preparation of 4,5,6,7-tetrahydro-7-methylene-5-tosylthieno[3,2-c]pyridine

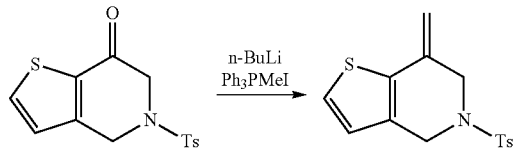 [SMILES: Cc1ccc(S(=O)(=O)N2CC(=O)c3sccc3C2)cc1 ; C=C1CN(S(=O)(=O)c2ccc(C)cc2)Cc2ccsc21]

To a solution of methyltriphenylphosphonium bromide (2.05 g, 5.73 mmol, 2.0 equiv) in THF (10.0 mL) at −78° C. was added n-BuLi (3.58 mL, 1.6 M solution, 2.0 equiv) and stirred for 30 min followed by addition of 5,6-dihydro-5-tosylthieno[3,2-c]pyridin-7(4H)-one (880 mg, 2.86 mmol, 1.0 equiv) in THF (5.00 mL). The reaction mixture was stirred at rt for 1 h, then quenched by the addition of a saturated aqueous solution of ammonium chloride. Purification by column chromatography using 5% ethyl acetate in hexanes elution gave 175 mg of the yellow solid, 20%.

Preparation of 7-methylthieno[3,2-c]pyridine

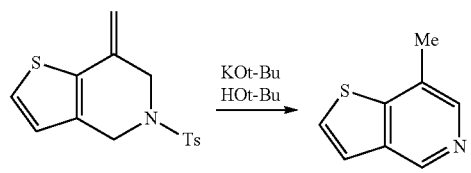 [SMILES: C=C1CN(S(=O)(=O)c2ccc(C)cc2)Cc2ccsc21 ; Cc1cncc2ccsc12]

To a solution of 4,5,6,7-tetrahydro-7-methylene-5-tosylthieno[3,2-c]pyridine (150 mg, 0.491 mmol, 1.0 equiv) in HOt-Bu (5 mL) was added KOt-Bu (110 mg, 0.982 mmol, 2.0 equiv) and heated to reflux for 3 h. Purification by column chromatography using ethyl acetate elution gave 62 mg of the yellow solid, 85%.

Preparation of 7-methylthieno[3,2-c]pyridin-2-yl-2-boronic acid

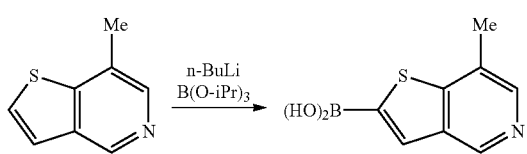 [SMILES: Cc1cncc2ccsc12 ; Cc1cncc2cc(B(O)O)sc12]

To a solution of 7-methylthieno[3,2-c]pyridine (82 mg, 0.550 mmol, 1.0 equiv) in THF (5.0 mL) at −78° C. was added n-BuLi (0.52 mL, 0.824 mmol, 1.5 equiv). The reaction was stirred at the reduced temperature for 1 h, then triisopropylborate (0.19 mL, 0.824 mmol, 1.5 equiv) was added and stirred at rt for 2 h. The mixture was quenched with 2N HCl and then extracted with ethyl acetate. Purification by column chromatography using 2% methanol in dichloromethane elution gave 80 mg of white solid, 75%.

Preparation of 6-chloro-3-(7-methylthieno[3,2-c]pyridin-2-yl)imidazo[1,2-b]pyridazine

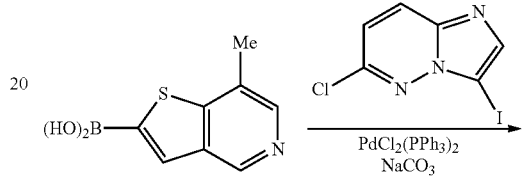

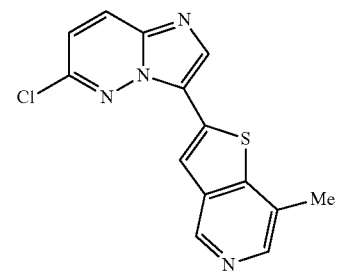

To a solution of 7-methylthieno[3,2-c]pyridin-2-yl-2-boronic acid (71 mg, 0.368 mmol, 1.0 equiv) in acetonitrile (3.68 mL) was added 6-chloro-3-iodoimidazo[1,2-b]pyridazine (103 mg, 0.368 mmol, 1.0 equiv), palladium catalyst (27 mg, 0.0368 mmol, 0.1 equiv) and sodium carbonate (3.68 mL, 1.0 M, 10.0 equiv). The solution was stirred in the microwave at 150° C. for 10 min. Purification using column chromatography gave 60 mg of the yellow product, 54%.

Preparation of N-(3,4-dimethoxyphenyl)-3-(7-methylthieno[3,2-c]pyridin-2-yl)imidazo[1,2-b]pyridazin-6-amine

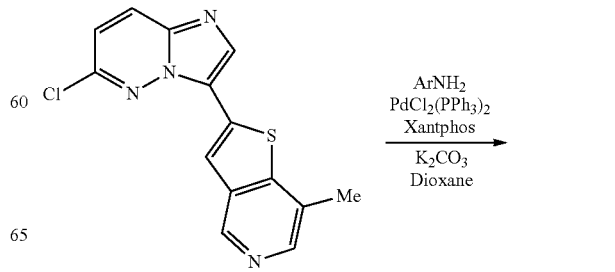

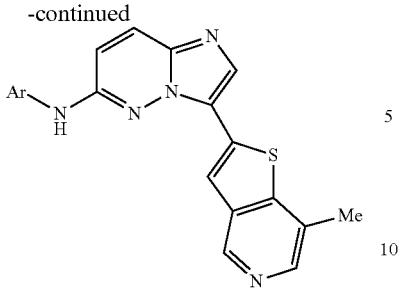

To a solution of 6-chloro-3-(7-methylthieno[3,2-c]pyridin-2-yl)imidazo[1,2-b]pyridazine (31 mg, 0.103 mmol, 1.0 equiv), xantphos (12 mg, 0.0206 mmol, 0.2 equiv), palladium acetate (2 mg, 0.0103 mmol, 0.1 equiv), and potassium carbonate (284 mg, 2.06 mmol, 20 equiv) in dioxane (5.0 mL) was added 3,4-dimethoxyaniline (24 mg, 0.155 mmol, 1.5 equiv) and heated to 110° C. for 2 h. Purification by column chromatography using 2% methanol in dichloromethane elution gave 20 mg, of the brown solid, 47%.

Compound 214 was physically characterized by electrospray ionization mass spectrometry. Structures and molecular masses are given below in Table 60.

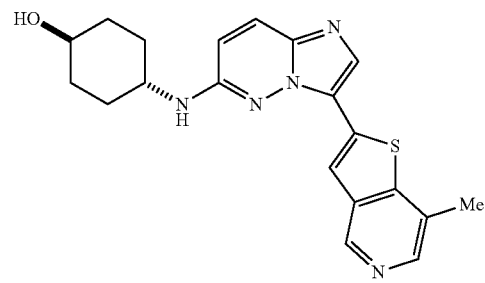

| Cd. | Structure | IUPAC Name | [M + H]$^+$ |
|---|---|---|---|
| 214 | 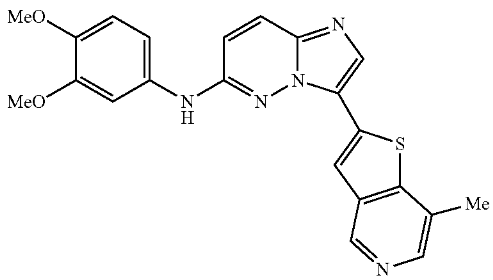 [SMILES: COc1ccc(Nc2ccc3ncc(-c4cc5cncc(C)c5s4)n3n2)cc1OC] | N-(3,4-dimethoxyphenyl)-3-(7-methylthieno[3,2-c]pyridin-2-yl)imidazo[1,2-b]pyridazin-6-amine | 418.0 |

EXAMPLE 61

Synthesis of Compound 215, 216

Preparation of N-alkyl-4-(3-(7-methylthieno[3,2-c]pyridin-2-yl)imidazo[1,2-b]pyridazin-6-ylamino)cyclohexanol Scheme 61

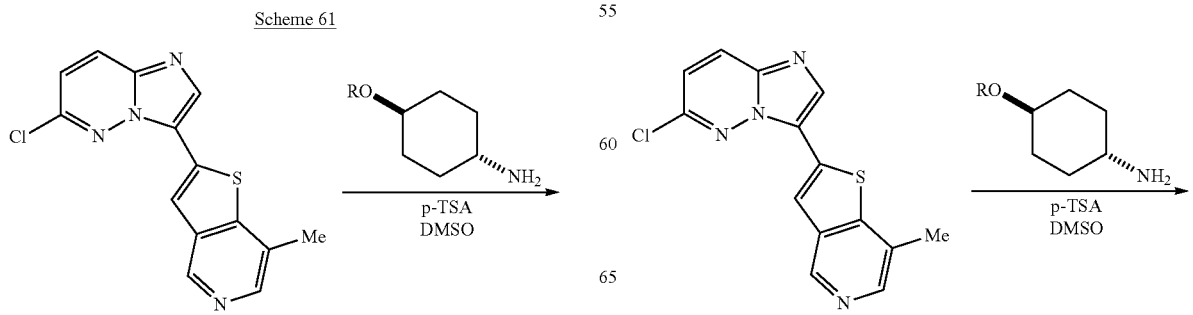

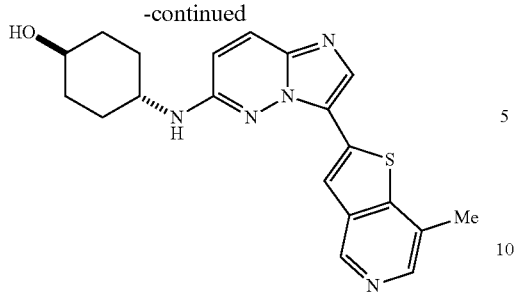

To a solution of 6-chloro-3-(7-methylthieno[3,2-c]pyridin-2-yl)imidazo[1,2-b]pyridazine (20 mg, 0.0665 mmol, 1.0 equiv) in DMSO (2.0 mL) was added p-toluene sulfonic acid monohydrate (13 mg, 0.0665 mmol, 1.0 equiv) and amine (38 mg, 0.333 mmol, 5.0 equiv) and heated to 100° C. for 24 h. The reaction mixture was diluted with water and extracted with ethyl acetate. Purification by column chromatography using 5% methanol in dichloromethane elution gave 22 mg of the yellow solid, 87%.

Compound 215, 216 was physically characterized by electrospray ionization mass spectrometry. Structures and molecular masses are given below in Table 61.

EXAMPLE 62

Synthesis of Compounds 220, 221

Scheme 62

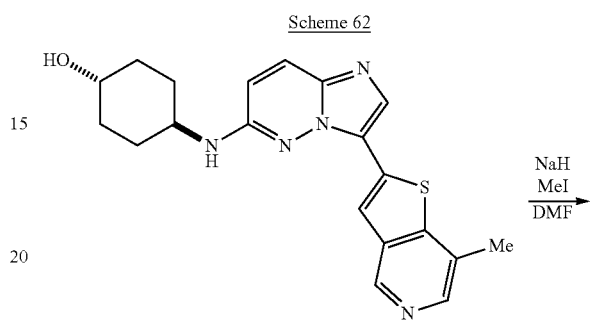

TABLE 61

| Cd. | Structure | IUPAC Name | [M + H]⁺ |
|---|---|---|---|
| 215 | 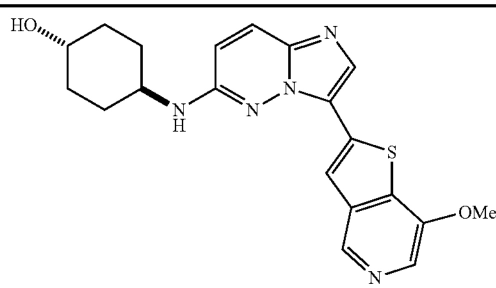 | trans-4-(3-(7-methylthieno[3,2-c]pyridin-2-yl)imidazo[1,2-b]pyridazin-6-ylamino)cyclohexanol | 380.5 |
| 216 | 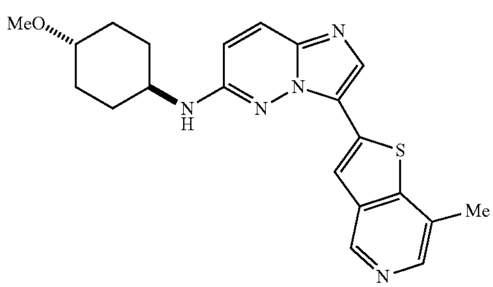 [SMILES: CO[C@H]1CC[C@H](Nc2ccc3ncc(-c4cc5cncc(C)c5s4)n3n2)CC1] | trans-4-methoxycyclohexyl)-3-(7-methylthieno[3,2-c]pyridin-2-yl)imidazo[1,2-b]pyridazin-6-amine | 394.5 |

255
-continued

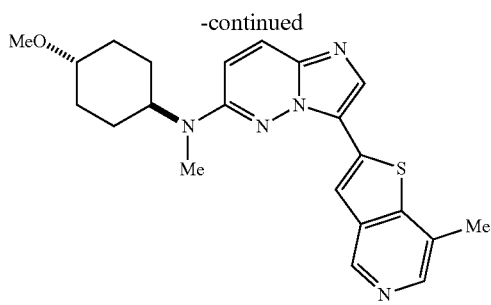

256
-continued

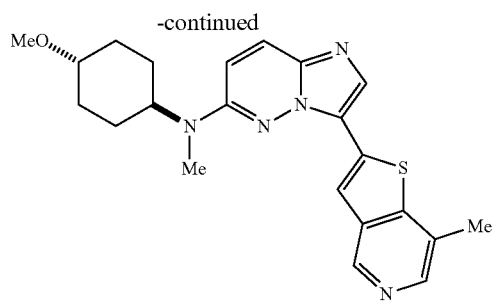

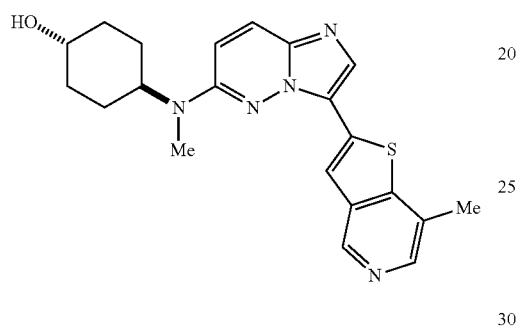

Preparation of N-((1r,4r)-4-methoxycyclohexyl)-N-methyl-3-(7-methylthieno[3,2-c]pyridin-2-yl)imidazo[1,2-b]pyridazin-6-amine and trans-4-(N-methyl-N-(3-(7-methylthieno[3,2-c]pyridin-2-yl)imidazo[1,2-b]pyridazin-6-yl)amino)cyclohexanol

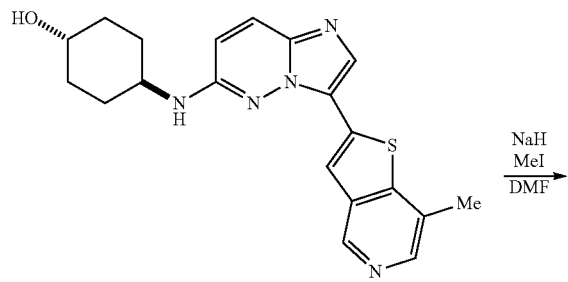

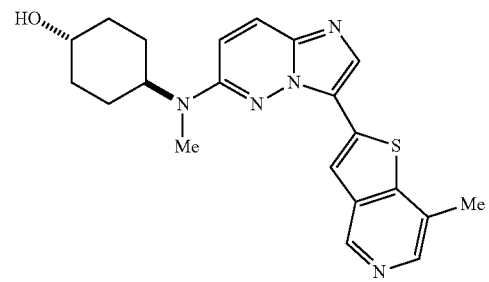 [SMILES: Cc1cncc2cc(-c3cnc4ccc(N(C)[C@H]5CC[C@H](O)CC5)nn34)sc12]

To a solution of trans-4-(3-(7-methylthieno[3,2-c]pyridin-2-yl)imidazo[1,2-b]pyridazin-6-ylamino)cyclohexanol (37 mg, 0.0975 mmol, 1.0 equiv) in DMF (2.00 mL) was added sodium hydride (20 mg, 0.488 mmol, 5.0 equiv) and methyl iodide (68 mg, 0.488 mmol, 5.0 equiv). After 2 h, the reaction mixture was quenched with water and extracted with ethyl acetate. Purification by column chromatography gave 20 mg (50%) of N-((1r,4r)-4-methoxycyclohexyl)-N-methyl-3-(7-methylthieno[3,2-c]pyridin-2-yl)imidazo[1,2-b]pyridazin-6-amine as the less polar product and 10 mg (25%) of trans-4-(N-methyl-N-(3-(7-methylthieno[3,2-c]pyridin-2-yl)imidazo[1,2-b]pyridazin-6-yl)amino)cyclohexanol as the more polar product.

Compounds 220 and 221 were physically characterized by electrospray ionization mass spectrometry. Structures and molecular masses are given below in Table 62.

TABLE 62

| Cd. | Structure | IUPAC Name | [M + H]⁺ |
| --- | --- | --- | --- |
| 220 | (structure shown) | N-((1r,4r)-4-methoxycyclohexyl)-N-methyl-3-(7-methylthieno[3,2-c]pyridin-2-yl)imidazo[1,2-b]pyridazin-6-amine | 407.5 |

TABLE 62-continued

| Cd. | Structure | IUPAC Name | [M + H]+ |
|---|---|---|---|
| 221 | (structure shown) | trans-4-(N-methyl-N-(3-(7-methylthieno[3,2-c]pyridin-2-yl)imidazo[1,2-b]pyridazin-6-yl)amino)cyclohexanol | 394.5 |

Biochemical Assay

Biochemical Assay for the Inhibition of Kinase Activity for MLK-3: Myelin basic protein (20 µM final concentration) is dissolved in 20 mM Hepes (pH 7.5) containing 10 µM $MgCl_2$, 1 µM EGTA, 0.02% Brij35, 0.02 mg/ml BSA, 0.1 µM $Na_3VO_4$, 2 mM DTT, and 1% DMSO. Activated MLK-3 is added and mixed (20 nM final concentration), and inhibitors are added in DMSO. $^{33}$P-ATP (specific activity 500 µCi/µL) is delivered into the reaction mixture to initiate the reaction (ATP concentration is 50 µM) and the mixture is incubated at room temperature for 20 minutes. % Activity is determined using a proprietary HOTSPOT™ microfluidic filter binding technology. See, Expert Opin. Drug Discov. 2008 June; 3(6): 607-621.

Reported MLK-3 Activity

Activity data for selected selected MLK-3 inhibitors is displayed in Table 63. The $IC_{50}$ MLK-3 range is denoted as follows: + denotes activity<5 µM, ++ denotes activity between 0.5 µM to 1 µM, and +++ denotes activity between 0.1 µM to 0.5 µM, and ++++ denotes activity<0.10 µM.

TABLE 63

| COMPOUND # | $IC_{50}$ MLK-3 (µM) |
|---|---|
| 3 | +++ |
| 4 | +++ |
| 5 | ++++ |
| 9 | + |
| 11 | + |
| 12 | +++ |
| 13 | + |
| 14 | ++ |
| 24 | +++ |
| 25 | ++ |
| 26 | +++ |
| 27 | +++ |
| 28 | + |
| 30 | + |
| 31 | + |
| 34 | + |
| 39 | + |
| 40 | + |
| 41 | ++ |
| 43 | ++ |
| 44 | ++ |
| 45 | + |
| 50 | +++ |
| 53 | ++ |
| 54 | + |
| 56 | ++ |
| 61 | + |
| 62 | + |

TABLE 63-continued

| COMPOUND # | $IC_{50}$ MLK-3 (µM) |
|---|---|
| 63 | +++ |
| 67 | ++++ |
| 68 | ++++ |
| 69 | ++++ |
| 70 | ++++ |
| 71 | ++++ |
| 72 | +++ |
| 73 | ++ |
| 74 | ++ |
| 75 | +++ |
| 76 | + |
| 77 | ++++ |
| 78 | +++ |
| 79 | ++++ |
| 80 | +++ |
| 81 | ++ |
| 83 | + |
| 84 | + |
| 85 | ++++ |
| 86 | +++ |
| 87 | ++++ |
| 88 | +++ |
| 90 | ++ |
| 101 | + |
| 102 | + |
| 105 | +++ |
| 107 | + |
| 108 | ++ |
| 109 | +++ |
| 110 | +++ |
| 111 | + |
| 119 | + |
| 122 | +++ |
| 126 | + |
| 127 | + |
| 131 | + |
| 132 | ++ |
| 135 | +++ |
| 136 | + |
| 138 | +++ |
| 139 | +++ |
| 140 | + |
| 142 | + |
| 150 | + |
| 158 | + |
| 160 | ++ |
| 161 | +++ |
| 162 | ++ |
| 163 | ++ |
| 164 | ++ |
| 166 | ++ |
| 167 | +++ |
| 168 | +++ |
| 169 | ++++ |
| 170 | ++++ |
| 171 | ++++ |
| 172 | +++ |
| 173 | ++++ |

TABLE 63-continued

| COMPOUND # | IC$_{50}$ MLK-3 (μM) |
|---|---|
| 174 | ++++ |
| 175 | ++++ |
| 176 | +++ |
| 177 | ++++ |
| 178 | +++ |
| 179 | ++++ |
| 180 | + |
| 181 | +++ |
| 182 | + |
| 183 | + |
| 184 | + |
| 185 | + |
| 186 | +++ |
| 187 | ++ |
| 188 | + |
| 189 | + |
| 190 | + |
| 191 | + |
| 192 | ++ |
| 193 | + |
| 194 | + |
| 195 | + |
| 196 | +++ |
| 197 | +++ |
| 198 | + |
| 199 | + |
| 200 | ++ |
| 201 | +++ |
| 202 | + |
| 203 | +++ |
| 204 | +++ |
| 205 | +++ |
| 206 | ++++ |
| 207 | +++ |
| 208 | + |
| 209 | ++ |
| 210 | + |
| 211 | + |
| 212 | + |
| 213 | ++++ |
| 214 | +++ |
| 215 | ++++ |
| 216 | +++ |
| 217 | +++ |
| 218 | ++++ |
| 219 | + |
| 220 | +++ |
| 221 | +++ |

Blood Brain Barrier Penetration

Compounds disclosed herein may be evaluated in pharmacokinetic assays and models to determine absorption, distribution, metabolism, and excretion parameters. The choice and tailoring of in vitro and ex vivo assays and in vivo models will vary according to the route of administration/formulation, indication under study, properties of test compounds, etc., as well as according to such factors as costs, availability of technology and resources, etc. Such parameters are well known in the fields of pharmacology and drug development. It is within the capacity of one skilled in the art to design and carry out, such work, or to outsource it to a capable third party.

Several compounds disclosed herein were evaluated in a standard murine pharmacokinetic model. Compounds were selected that exhibited reasonable solubility and metabolic stability, and good predicted blood brain barrier penetration, based on low molecular weight, a low number of hydrogen bond donors, logD within a range of from 2 to 5, and low polar surface area. For ease of analysis compounds were dissolved in 5% DMSO, 40% PEG400, and 55% to yield a nominal concentration of 2 mg/mL for intravenous administration. Compounds were administered via a single intravenous (IV) injection in CL57 BL/6 mice at 10 mg/kg in DMSO/PEG400/Saline solution. Three mice in each group were used for blood and brain collection at each time point. Blood samples (300 μL) were collected via the retro-orbital vein predose and at 30, 60 and 180 minutes postdose. Blood samples were placed into tubes containing sodium heparin and centrifuged under refrigerated conditions at 8000 rpm for 6 minutes to separate plasma from the samples. The brain of each animal was collected after the final blood collection. The whole tissue was harvested, excised and rinsed by saline, dried by filter paper, and then placed into one tube per tissue per animal. All samples were stored at −20° C. until bioanalysis. Compound concentrations in plasma and brain homogenate were determined using a high performance liquid chromatography/mass spectrometry (HPLC/MS/MS) methods. Brain concentrations at the three hour time point for several representative compounds are disclosed below in Table 64.

TABLE 64

| Compound # | Cbrain 3 hrs (ng/g) |
|---|---|
| URMC-099 | 950 (Positive Control) |
| CEP-1347 | 67 |
| 12 | 1280 |
| 67 | 566 |
| 175 | 1880 |
| 68 | 1554 |

Protein Kinase Selectivity: MLK-3 inhibitors previously reported in the literature are somewhat promiscuous and inhibit a large number of serine and threonine protein kinases. Compounds of the present invention that show potent inhibition on MLK-3 are very specific for MLK family kinases. For comparison, IC$_{50}$ values for selected compounds from the invention were compared against a diverse set of kinases for inhibition of the MLK-3 potent, brain penetrant compound, URMC-099, which is disclosed in Goodfellow, V. S., et al. A CNS Active, Orally Bioavailable Inhibitor of Mixed Lineage Kinase 3 for Potential Treatment of HIV Associated Neurocognitive Disorder. *Journal of Medicinal Chemistry*, 2013.

TABLE 51

| Kinase/Assay | Compounds | | | | | | |
|---|---|---|---|---|---|---|---|
| | URMC-099 | 105 | 12 | 169 | 67 | 68 | 170 |
| ABL1(T31SI) | 3 | >10,000 | >10,000 | >10,000 | >10,000 | >10,000 | >10,000 |
| CDK2 | 1180 | 1028 | 19,400 | 8,260 | >10,000 | >10,000 | >10,000 |
| IKKa | 591 | >10,000 | >10,000 | >10,000 | >10,000 | >10,000 | >10,000 |
| IKKb | 257 | >10,000 | >10,000 | >10,000 | >10,000 | >10,000 | >10,000 |
| IR | 200 | >10,000 | >10,000 | >10,000 | >10,000 | >10,000 | >10,000 |

Figure 2:
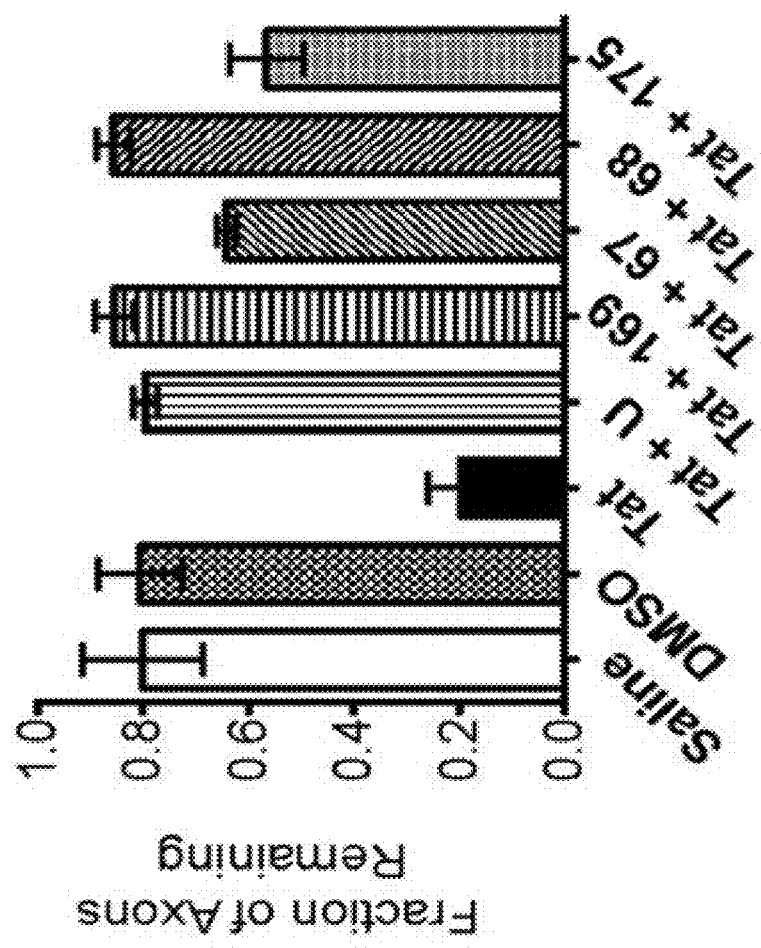
FIG. 2 is a graph illustrating the quantification of axon elimination in the presence of HIV tat and certain inhibitors including compounds of the present disclosure.
Figure 3:
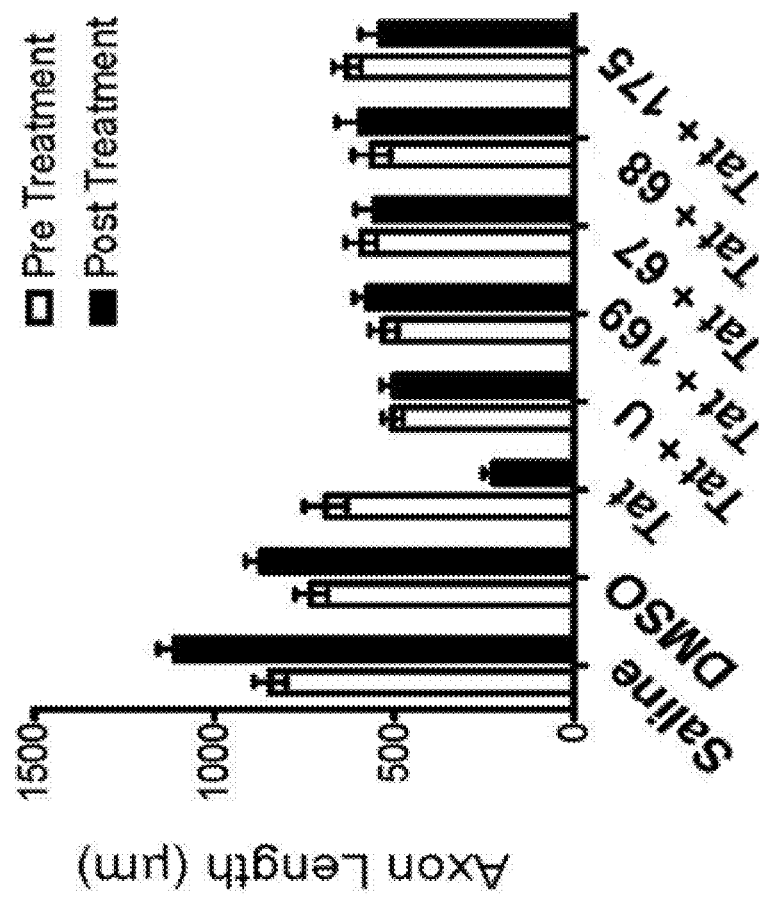
FIG. 3 is a graph illustrating the quantification of axon length in the presence of HIV tat and certain inhibitors including compounds of the present disclosure.

Neuroprotection from HIV-1 Tat: E18 primary hippocampal neurons were plated in microfluidic chambers for 7 days in vitro (DIV). These chambers contain a cell body compartment contiguous with a series of 10 um wide, 3 um high, 400 um long microgrooves through which axons grow into a second compartment, fluidically isolated by a hydrostatic pressure gradient. BV-2 microglial cells treated with 1 μg/ml HIV-1 Tat±test compounds (100 nM) were introduced into the second compartment for 18 hours. Chambers that were exposed to BV-2 microglia treated with Tat alone had almost their entire axonal field destroyed (FIG. 1, brightfield image). Treatment with various example compounds or URMC-099 protected the axon field. The specific MLK3 inhibitor, compound 68, promoted continued axonogenesis in the presence of Tat-activated microglia (FIG. 1, arrows). FIGS. 2 and 3 show quantifications of axon elimination in the presence of HIV tat and Compounds 169, 67, 68 and 175. (U=Control Inhibitor URMC-099, previously shown to protect against effects of HIV-Tat in vitro and in vivo.)

Figure 4:
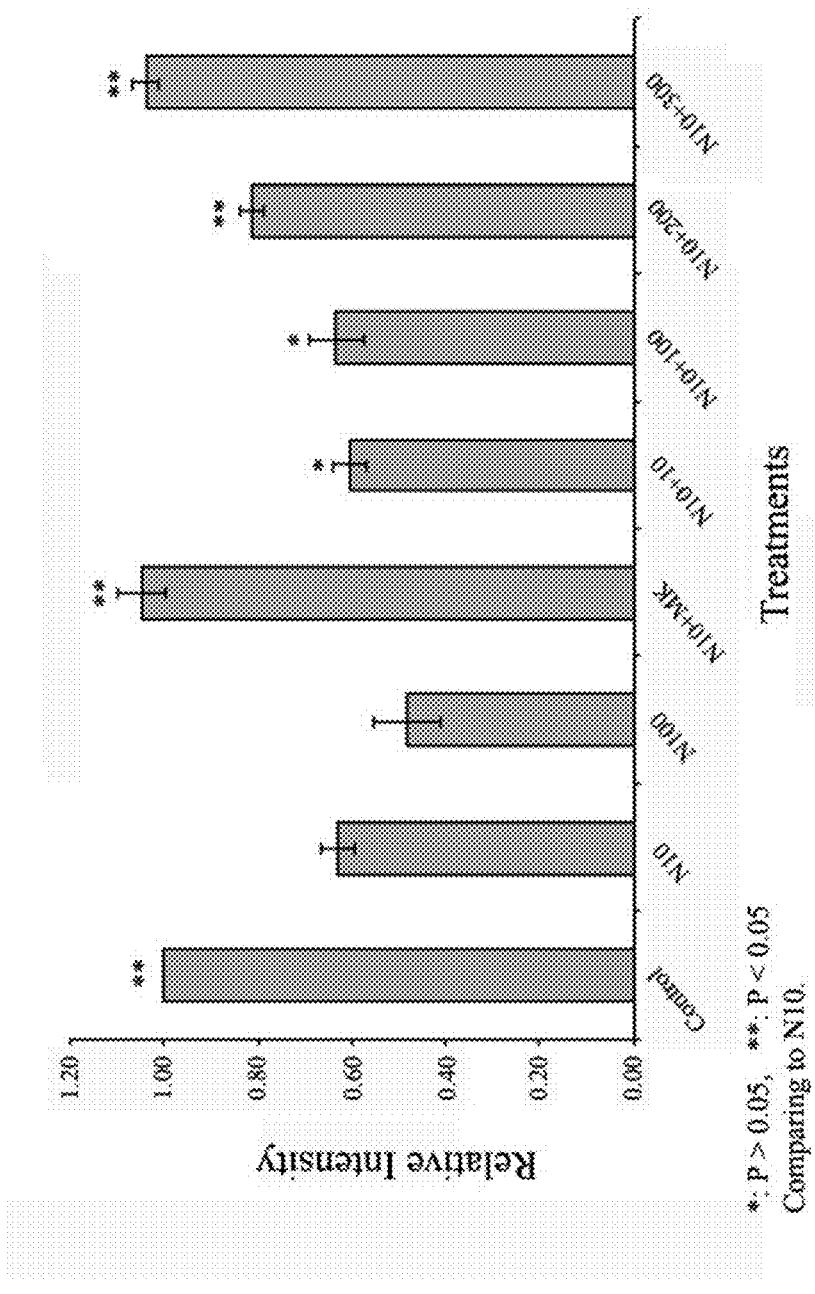
FIG. 4 is a graph illustrating dose-dependent neuroprotection from NMDA excitotoxic activation of matrix metalloproteinases with cleavage of intercellular adhesion molecule type 5 (ICAM-5).

Western blots of ICAM-5 cleavage (FIG. 4): Rat hippocampal neurons were dissected from E18 embryos and plated on 96-well plates in Neurobasal medium supplemented with B27 plus antioxidants (AO) for 24 hours and then maintained in Neurobasal supplemented with B27 minus AO for 12-14 days in vitro before use. Neurons were treated with vehicle or 20 mM of the non-competitive N-methyl-D-aspartate (NMDA) receptor antagonist dizocilpine (MK-801) or increasing doses ranging between 10-300 nM of Compound 68 in 100 ml of modified Locke's buffer (no $Mg^{2+}$) for 20 minutes before adding 10 or 100 mM NMDA for 15 minutes. After NMDA treatment, the modified Locke's Buffer was replaced with Neurobasal Medium supplemented with B27 minus AO and returned to a 37° C. incubator with 5% $CO_2$ overnight. The treated neurons were washed with ice-cold PBS and fixed in 4% PFA+4% Sucrose for 15 minutes and then washed 3 times with PBS. The fixed neurons were then immunostained with rabbit anti-ICAM-5 polyclonal antibody and a specific fluorescent secondary antibody for Odyssey System gel imaging from Licor. Results are from 3 independent experimental replicates. In this paradigm, neurotoxicity was measured as the amount of cleaved (i.e., soluble) ICAM-5 that was released after excitotoxic injury from sublethal doses of NMDA (Guo H, Tong N, Turner T, Epstein L G, McDermott M P, Kilgannon P, Gelbard H A. Release of the neuronal glycoprotein ICAM-5 in serum after hypoxic-ischemic injury. Ann Neurol. 2000 October; 48(4): 590-602. PMID: 11026442; Conant K, Wang Y, Szklarczyk A, Dudak A, Mattson M P, Lim S T. Matrix metalloproteinase-dependent shedding of intercellular adhesion molecule-5 occurs with long-term potentiation. Neuroscience. 2010 Mar. 17; 166(2):508-21. doi: 10.1016/j.neuroscience.2009.12.061. Epub 2010 Jan. 4. PMID: 20045450).

Figure 5:
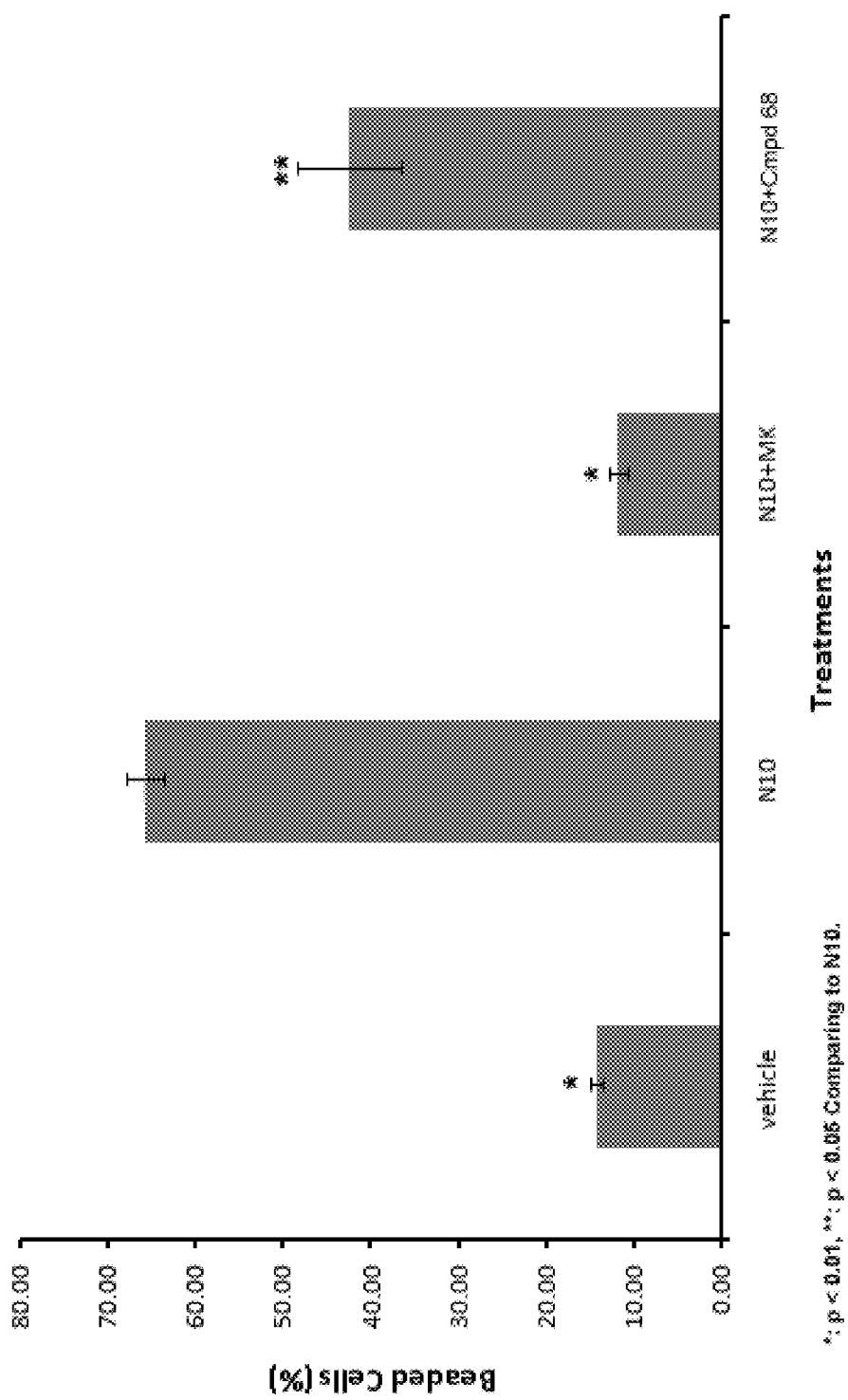
FIG. 5 is a graph illustrating the inhibition of synaptodendritic beading induced by N-methyl-D-aspartate (NMDA) receptor.

Synaptodendritic Beading (FIG. 5.):Rat hippocampal neurons were dissected from E18 embryos and plated on 12 mm glass coverslips in Neurobasal medium supplemented with B27 plus antioxidants (AO) for 24 hours and then maintained in Neurobasal supplemented with B27 minus AO for 12-14 days in vitro (DIV) before use. Neurons cultured for DIV 12-14 were transfected with pMAX-GFP for 12 hours and then treated with vehicle or 20 mM MK-801 and 200 nM of Compound 68 in 0.5 ml of modified Locke's buffer (no $Mg^{2+}$) for 20 minutes before adding 10 mM NMDA for <5 minutes. After NMDA treatment, the neurons were washed with ice-cold PBS and fixed in 4% PFA+4% Sucrose for 15 Minutes and then washed 3 times with PBS. The beaded and unbeaded neurons were identified by GFP expression and quantitated per 20x field using fluorescence microscopy. Results are from three independent experimental replicates. In this paradigm, neurotoxicity is defined as the extent of synaptodendritic beading in each microscopic field (Bellizzi M J, Lu S M, Masliah E, Gelbard H A. Synaptic activity becomes excitotoxic in neurons exposed to elevated levels of platelet-activating factor. J Clin Invest. 2005 November; 115(11):3185-92. PMID: 16276420).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references cited herein are incorporated by reference in their entirety. In case of conflict, the specification, including definitions, will control. As used herein, the singular forms "a", "and," and "the" include plural referents unless the context clearly indicates otherwise. Thus, for example, reference to "a peptide sequence" or a "treatment," includes a plurality of such sequences, treatments, and so forth.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed herein.

Where features or aspects of the invention are described in terms of Markush groups, those skilled in the art will recognize that the invention is also thereby described in terms of any individual member or subgroup of members of the Markush group. For example, if X is described as selected from the group consisting of A, B, C, claims for X being A and claims for X being B and C are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of A, B, and C, and Y is described as selected from the group consisting of D, E, and F, claims for X being A and Y being D are fully described.

We claim:

1. A compound having the structure of Formula I

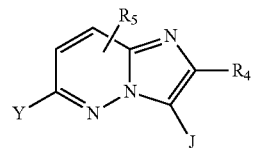

or a pharmaceutically acceptable isomer, isotope, enantiomer, or salt thereof, wherein J has a structure of

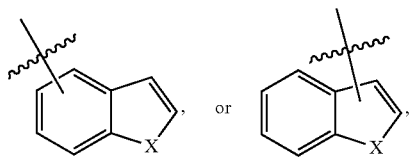

substituted with up to $R_{10}$,
or J has a structure of

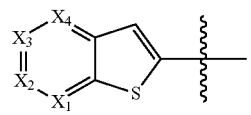

optionally substituted with up to four $R_{10}$,
each $R_{10}$ is independently selected from the group consisting of halo, alkyl, haloalkyl, alkoxy, haloalkoxy, —OH, and —OCOR$_6$;
X is $NR_{12}$ or S;
one of $X_1$, $X_2$, $X_3$, and $X_4$ is N and the other three of $X_1$, $X_2$, $X_3$, and $X_4$ are CH;
Y is —W—(CH$_2$)$_n$—R$_1$,

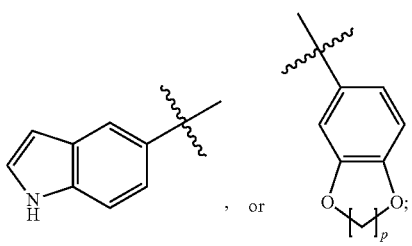

W is null, phenylene, or —NR$_6$-phenylene, where the NR$_6$ is attached to the imidazopyridazine core structure of Formula I;
$R_1$ is —NR$_2$R$_3$, or piperazinyl, where the nitrogen atom of the piperazinyl is optionally substituted with alkyl or alkoxy;
$R_2$ is H or alkyl;
$R_3$ is selected from the group consisting of $C_2$-$C_{10}$ alkyl, aryl, heteroaryl, cycloalkyl, and heterocycloalkyl, where any atom of $R_3$ is optionally substituted with one or more $R_7$; or $R_2$ and $R_3$ taken together with the N atom to which they are attached form a 3- to 7-membered heterocyclic ring optionally substituted with $R_8$;
$R_4$ is H or alkyl;
$R_5$ is H, alkyl, or $NHR_9$;
$R_6$ is H or alkyl;
each $R_7$ is independently alkyl, cycloalkyl, alkoxy, cycloalkoxy, cycloalkylalkoxy, perhaloalkoxy, halo, oxo, —OH, hydroxyalkyl, —COOR$_{11}$, or —O—(CH$_2$)$_m$—OH;
$R_8$ is alkoxy, hydroxyalkyl, or COOR$_{11}$;
$R_9$ is H, alkyl, or cycloalkyl;
$R_{11}$ is H, or alkyl;
$R_{12}$ is H, or alkyl;
n is 0 or 1;
m is 1, 2, or 3; and
p is 1, 2, or 3;

with the proviso that if J is an unsubstituted benzothiophene, then $R_3$ is either aryl or heteroaryl, where any atom of $R_3$ is optionally substituted with one or more $R_7$.

2. The compound of claim 1 wherein J is selected from the group consisting of

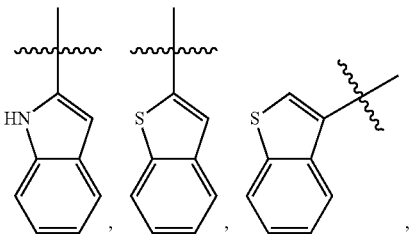

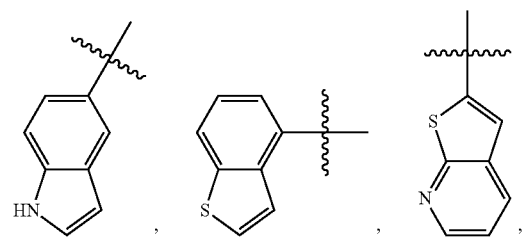

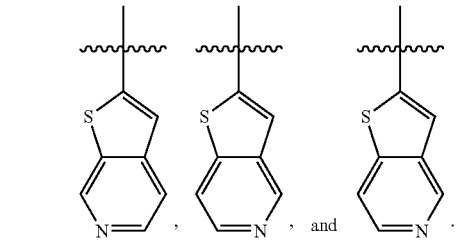

3. The compound of claim 1 wherein J is

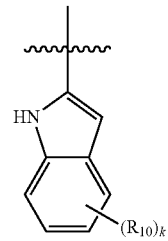

wherein each $R_{10}$ is independently selected from the group consisting of F, Cl, —OH, methyl, methoxy, ethoxy, propoxy, isopropoxy, and —OCOCH$_3$; and k is 0, 1, 2, or 3.

4. The compound of claim 1 wherein J is

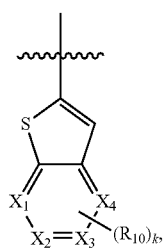

wherein each $R_{10}$ is independently selected from the group consisting of F, Cl, —OH, methyl, methoxy, ethoxy, propoxy, isopropoxy, and —OCOCH$_3$; and k is 0, 1, 2, or 3.

5. The compound of claim 4 wherein $X_1$ is N, and each of $X_2$, $X_3$, and $X_4$ is CH.

6. The compound of claim 4 wherein $X_2$ is N, and each of $X_1$, $X_3$, and $X_4$ is CH.

7. The compound of claim 4 wherein $X_3$ is N, and each of $X_1$, $X_2$, and $X_4$ is CH.

8. The compound of claim 4 wherein $X_4$ is N, and each of $X_1$, $X_2$, and $X_3$ is CH.

9. The compound of claim 1 wherein Y is —W—(CH$_2$)$_n$—R$_1$.

10. The compound of claim 9 wherein R$_1$ is —NR$_2$R$_3$.

11. The compound of claim 10 wherein R$_3$ is selected from the group consisting of C$_2$-C$_{10}$ alkyl, aryl, and cycloalkyl.

12. The compound of claim 11 wherein R$_3$ is phenyl optionally substituted with one or more R$_7$, wherein each R$_7$ is independently selected from the group consisting of hydroxyl, methoxy, —COOH, —O—(CH$_2$)$_m$—OH, cyclopropylmethoxy, cyclopentylmethoxy, and isopropyl.

13. The compound of claim 12 wherein each R$_7$ is independently selected from the group consisting of methoxy, —COOH, and —O—(CH$_2$)$_3$—OH.

14. The compound of claim 10 wherein R$_3$ is C$_2$-C$_{10}$ alkyl, aryl, and cycloalkyl, where any atom of R$_3$ is optionally substituted with one or more R$_7$.

15. The compound of claim 1 wherein the compound is selected from any of:

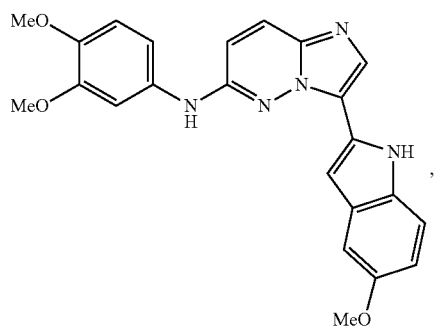

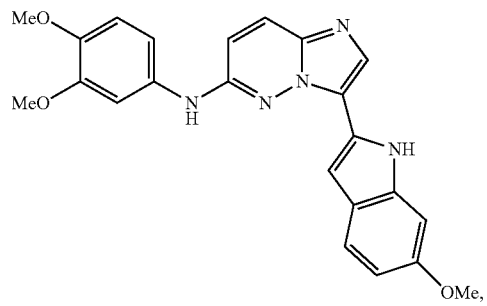

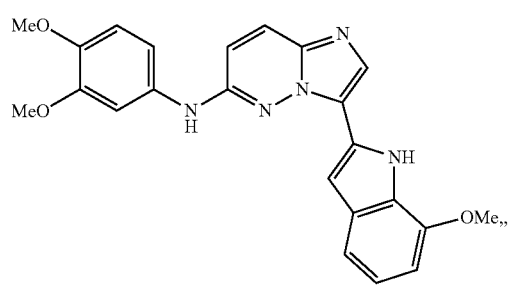

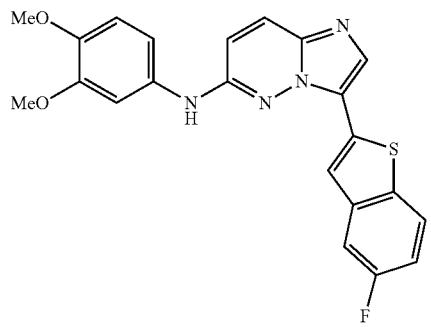

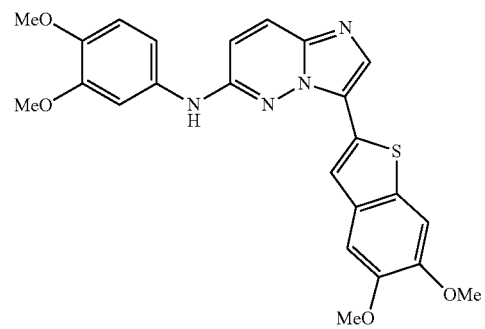

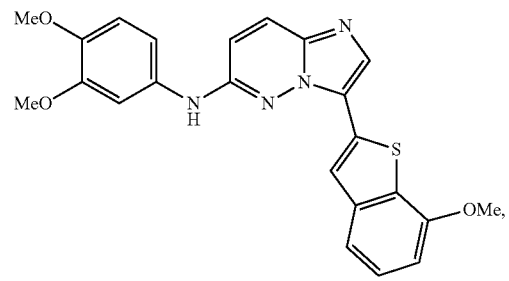

267
-continued
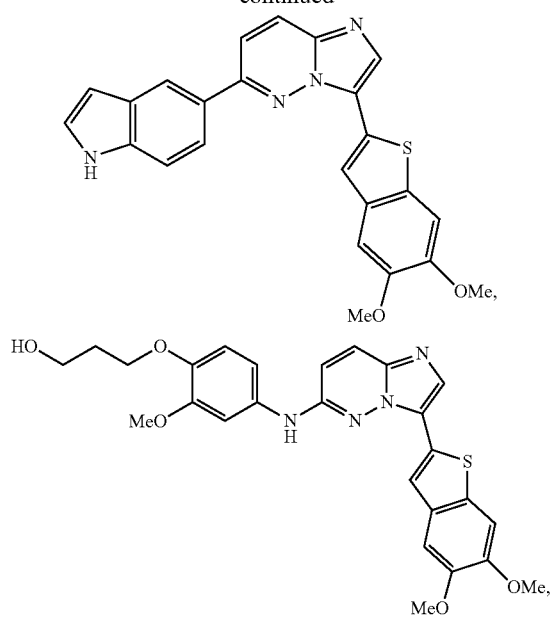
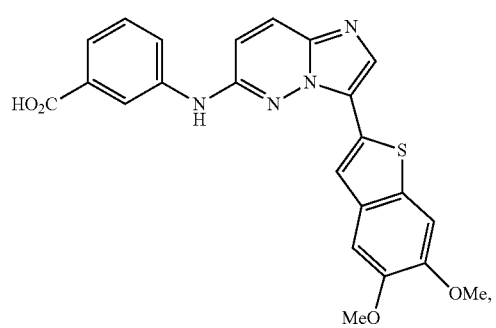
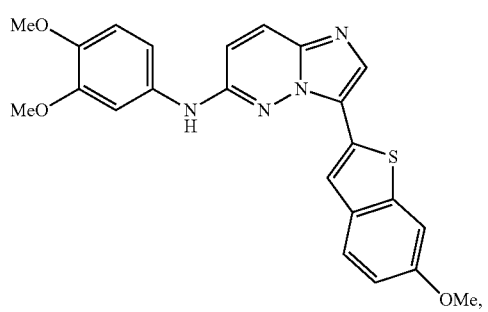
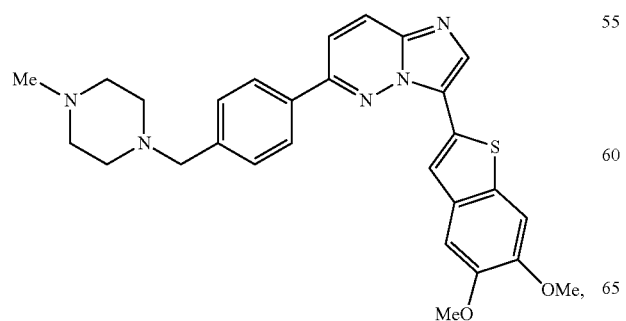
268
-continued
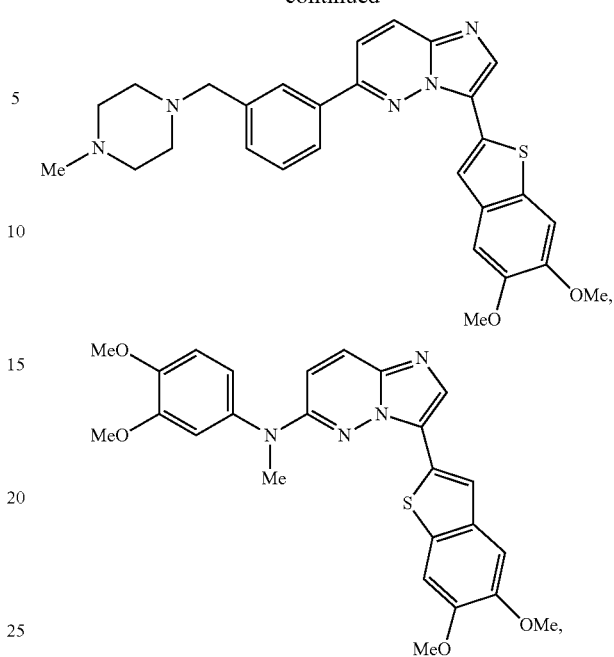
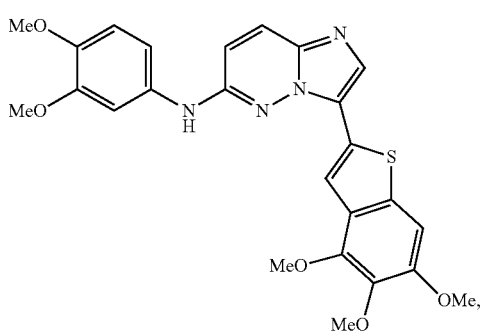
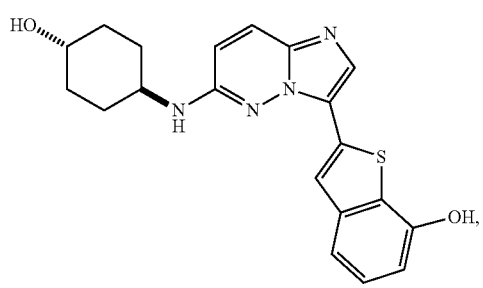
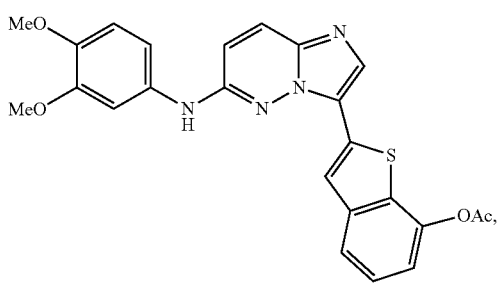

269
-continued
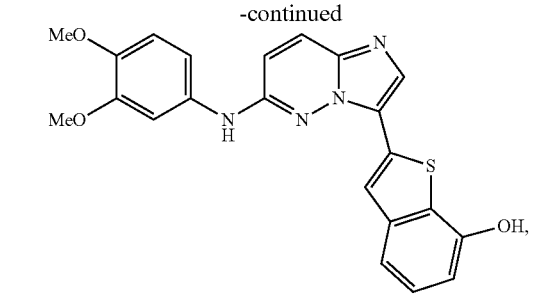
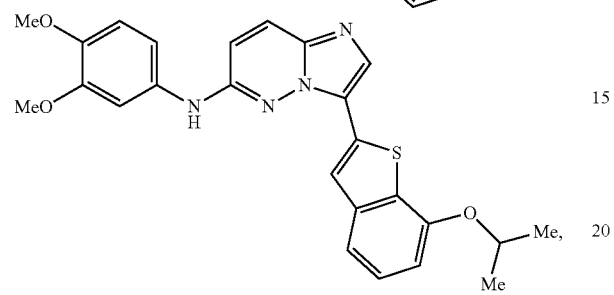
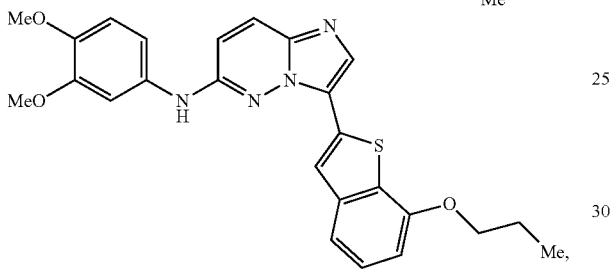
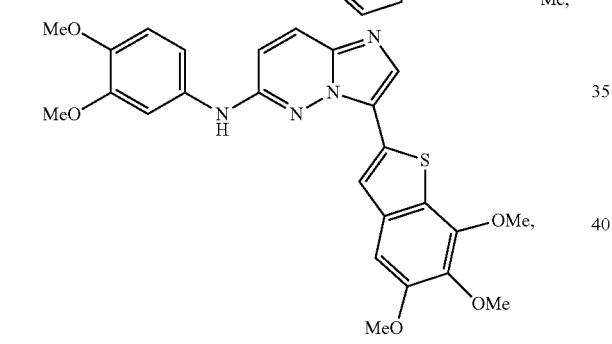
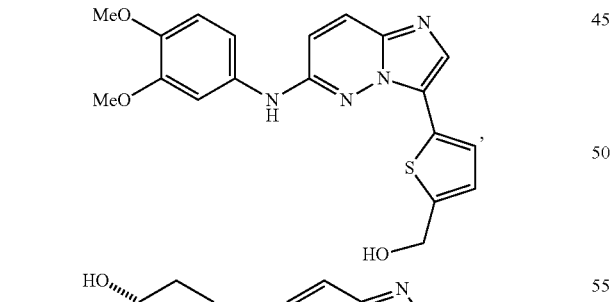
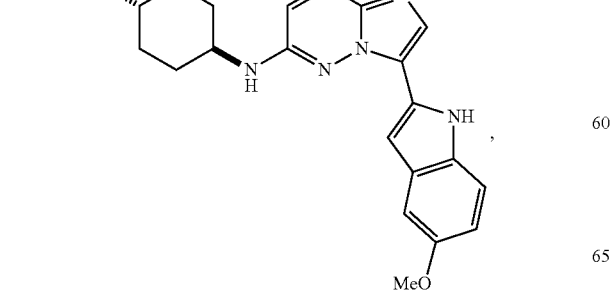
270
-continued
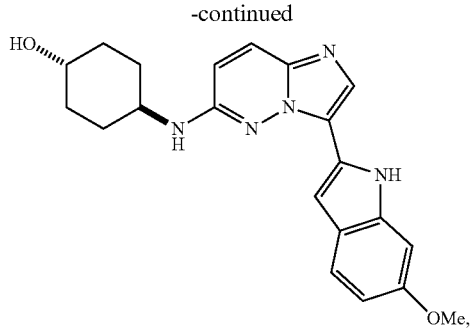
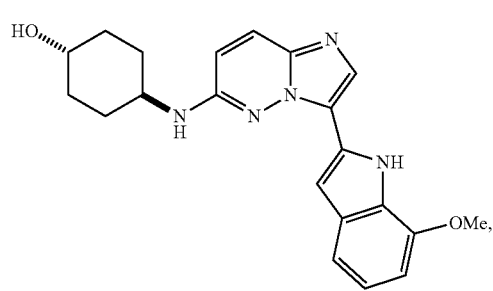
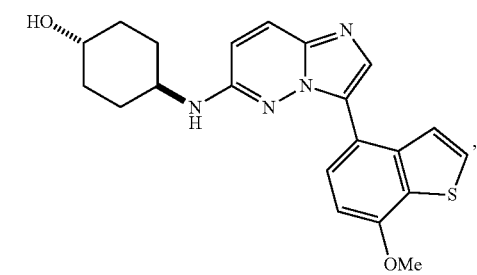
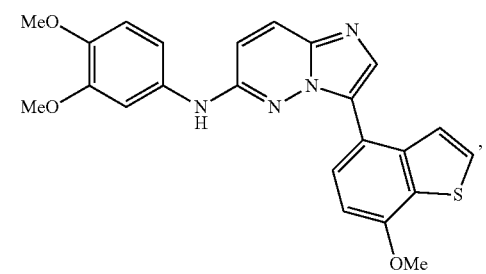
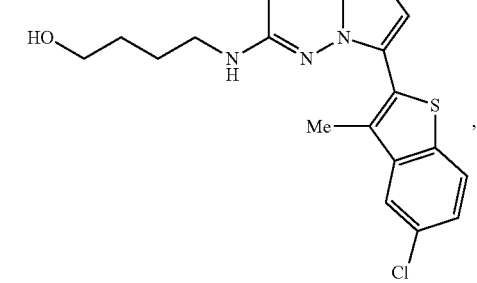

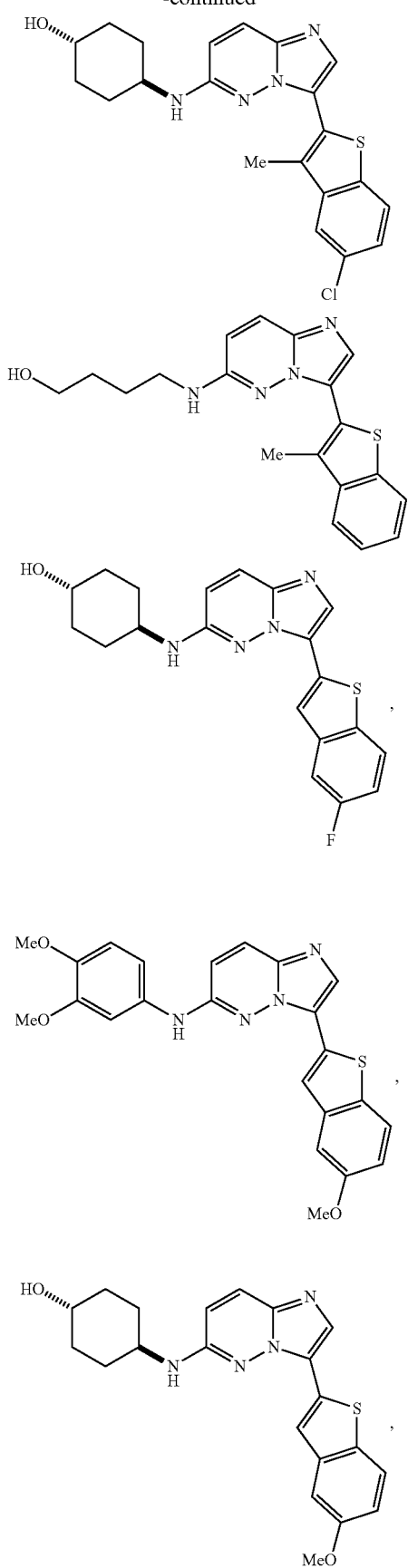
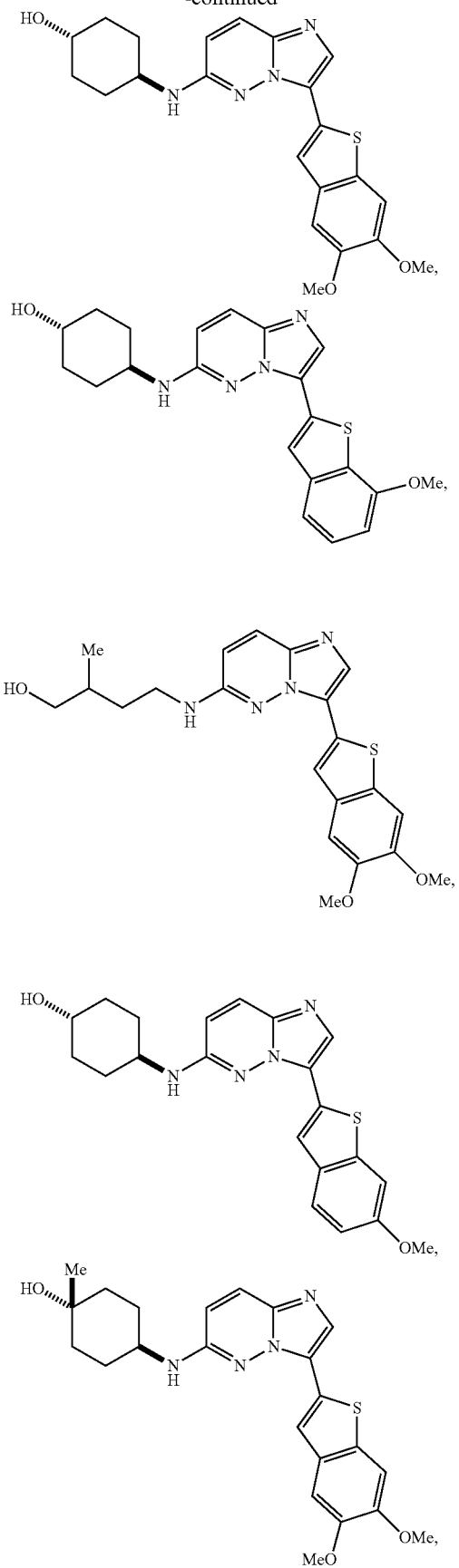

273
-continued
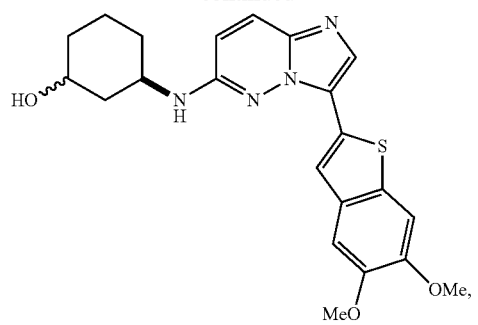
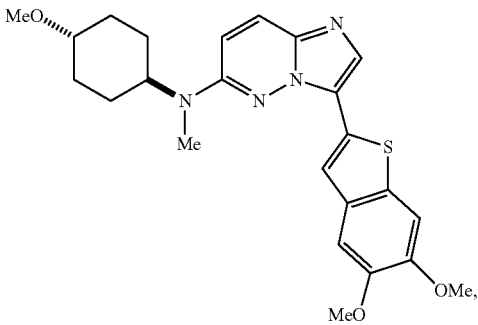
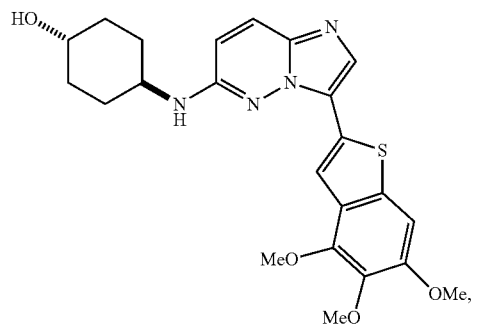
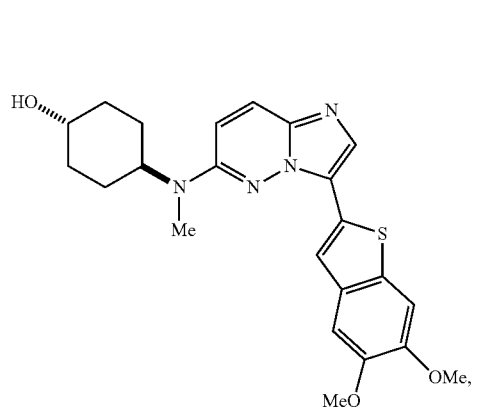
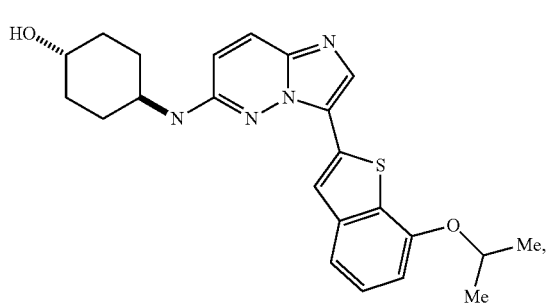
274
-continued
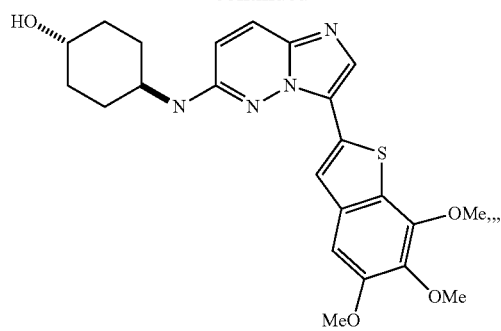
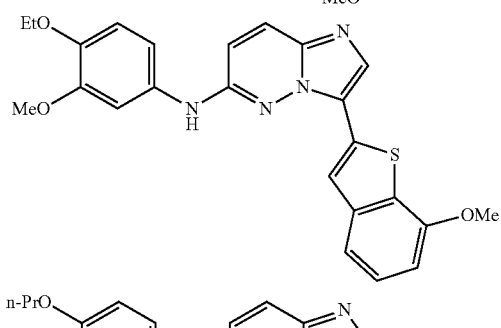
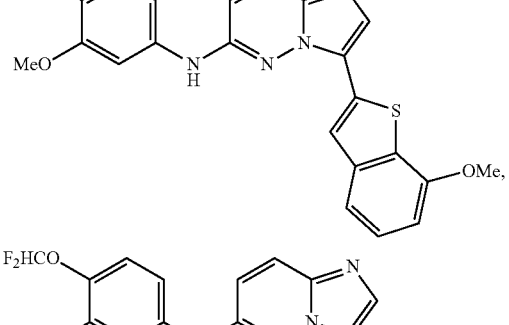
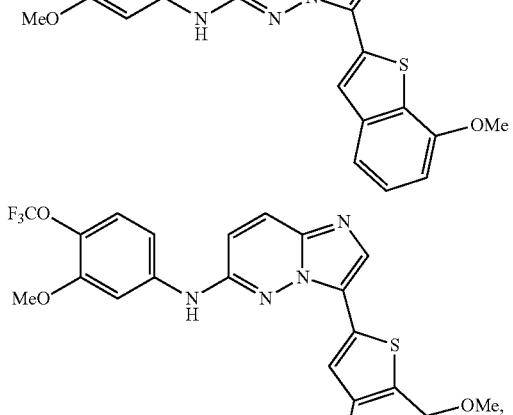
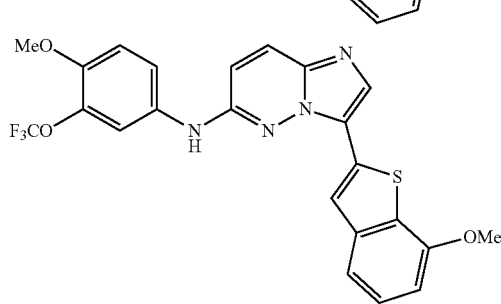

275
-continued
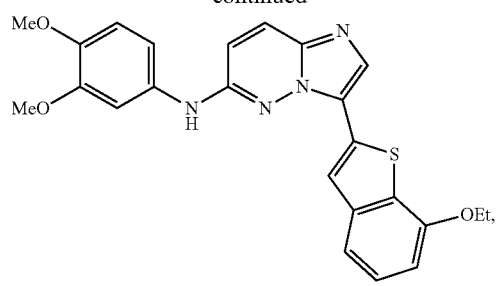
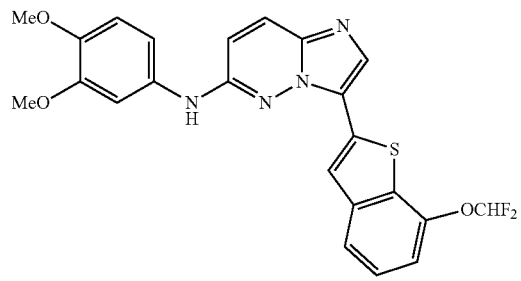
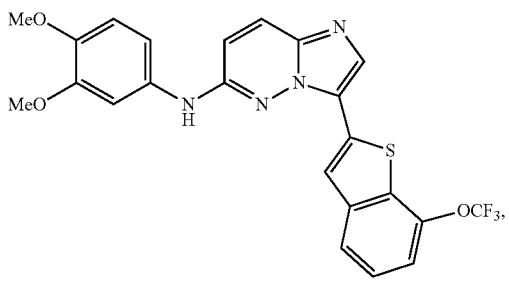
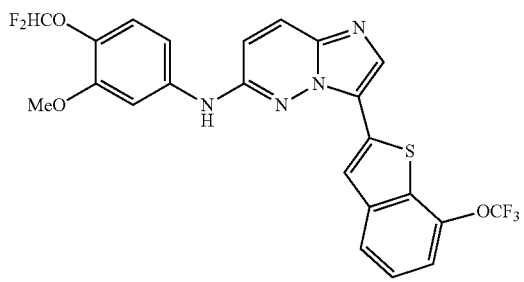
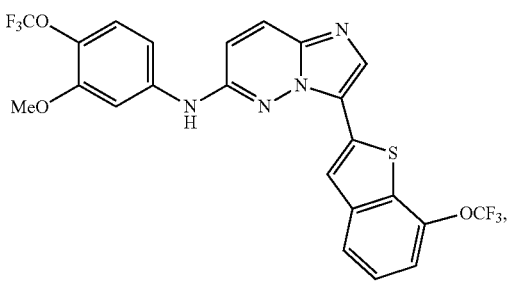
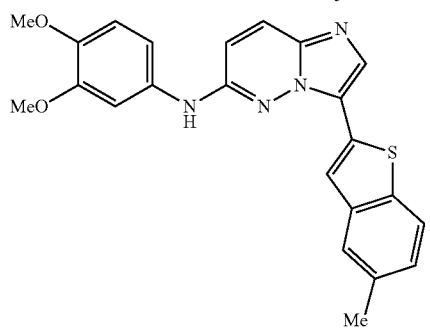
276
-continued
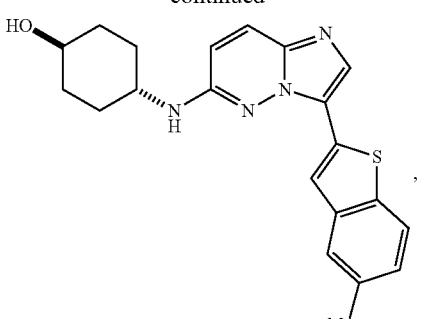
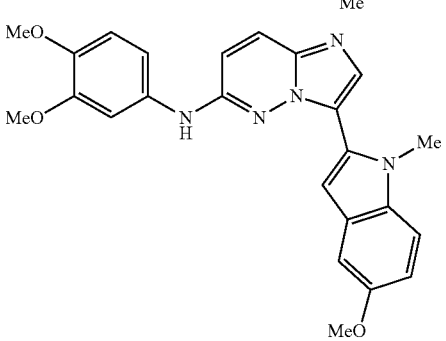
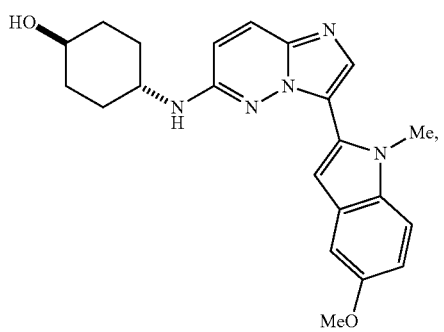
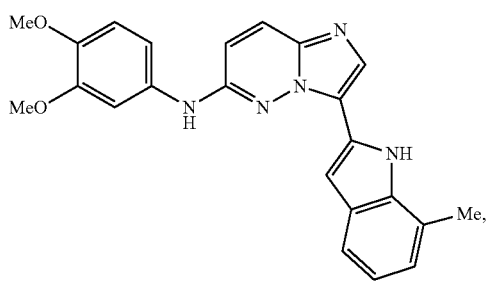

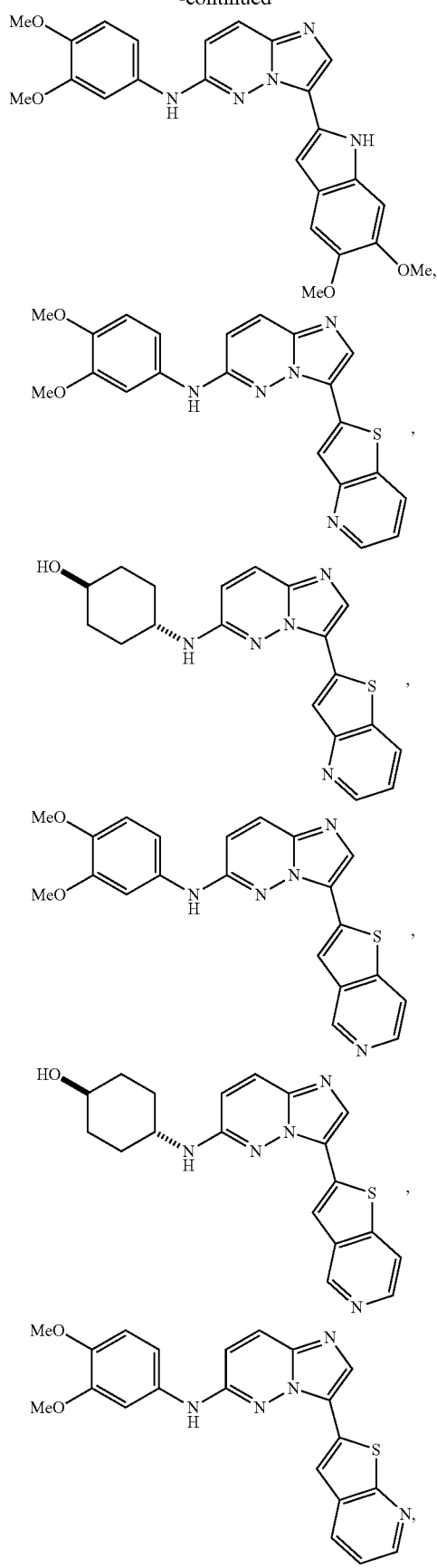
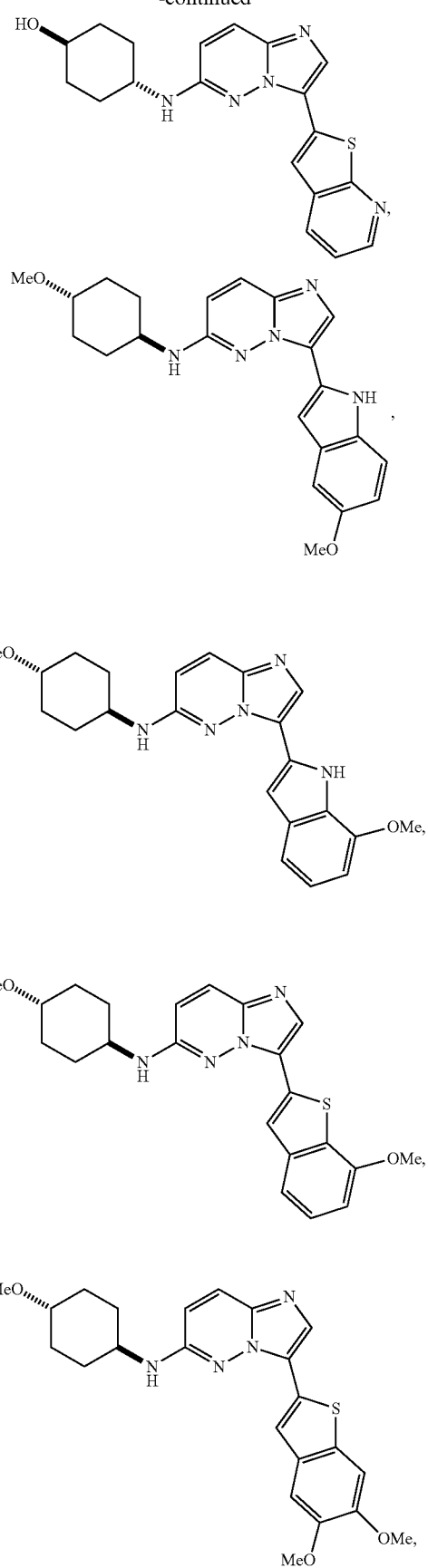

279
-continued
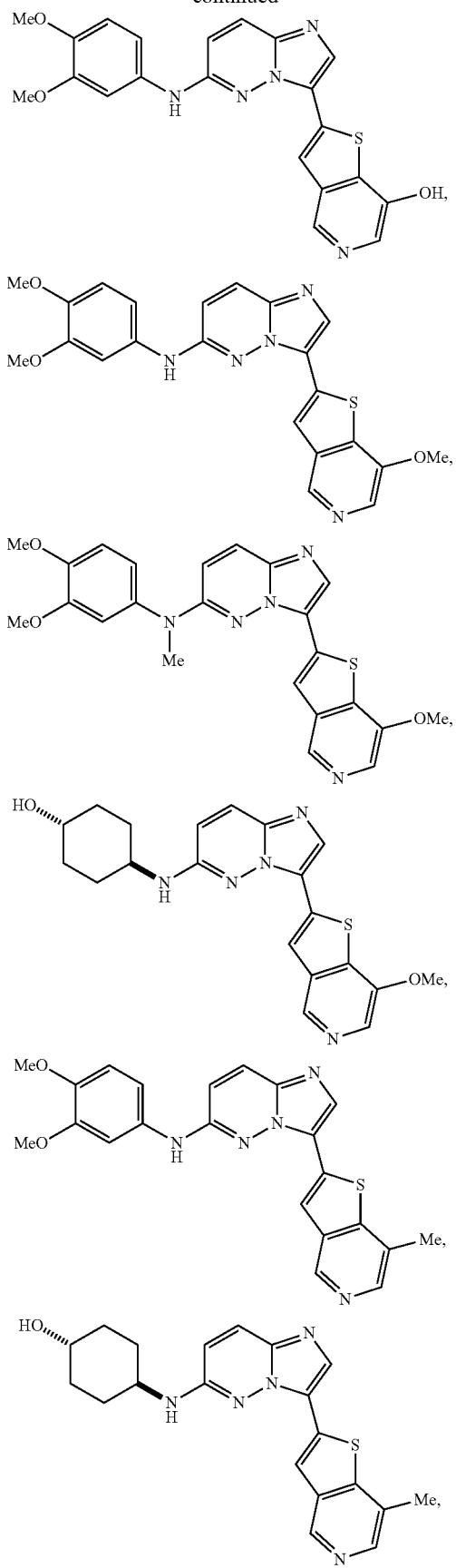
280
-continued
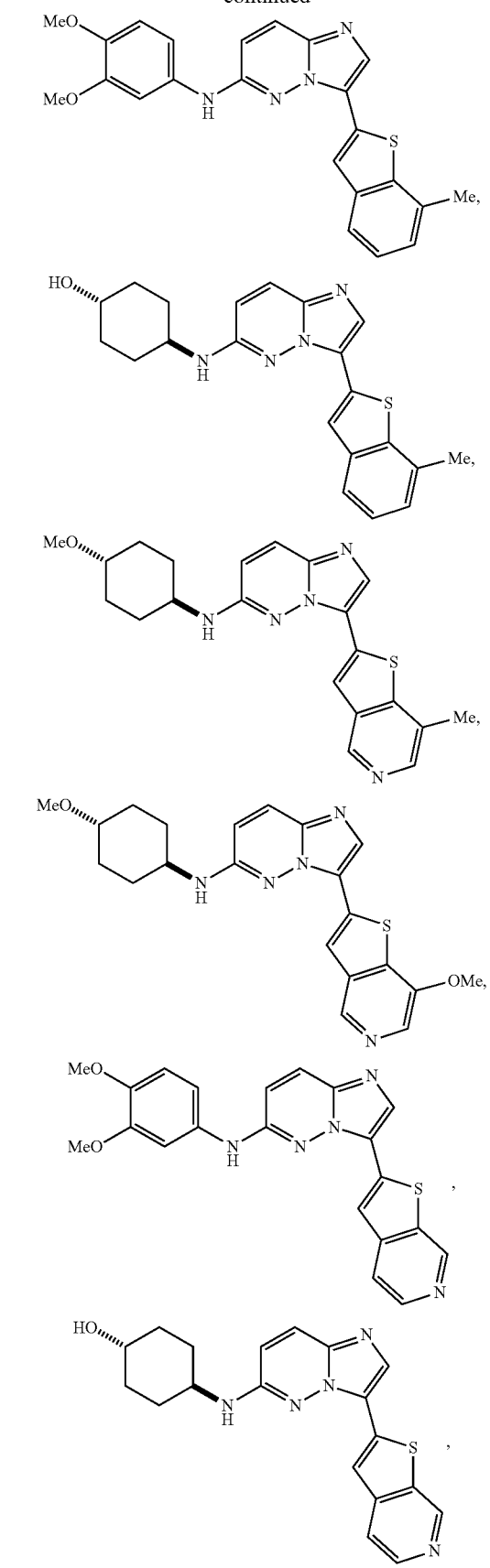

-continued
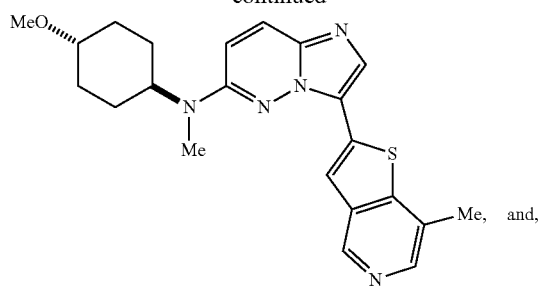
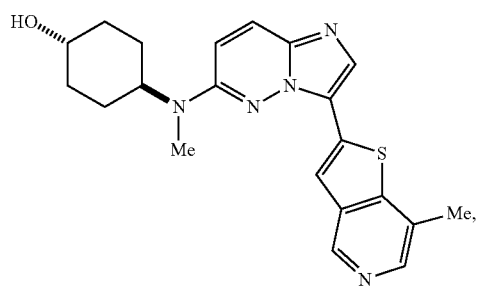
or any pharmaceutically acceptable salt, tautomer, stereoisomer, or isotope thereof.
16. The compound of claim 15 wherein the compound is selected from any of:
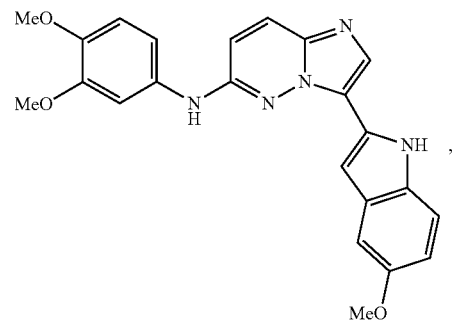
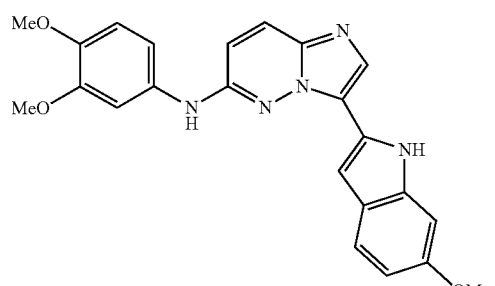
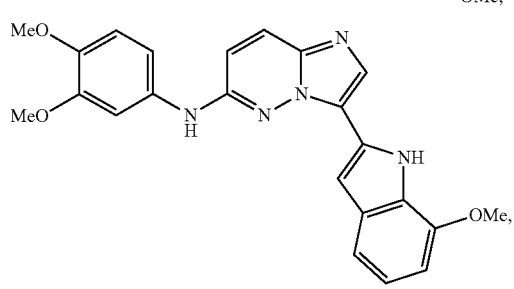
-continued
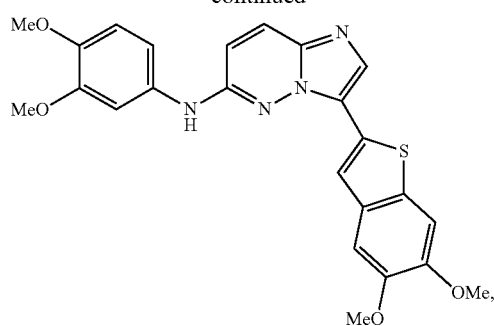
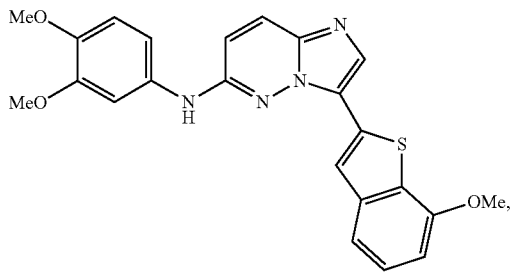
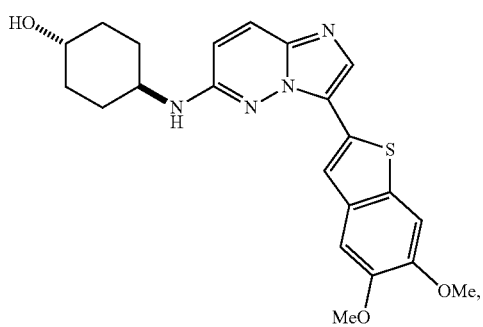
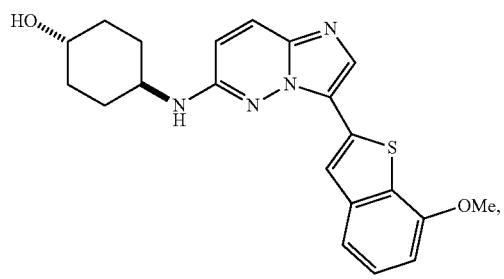
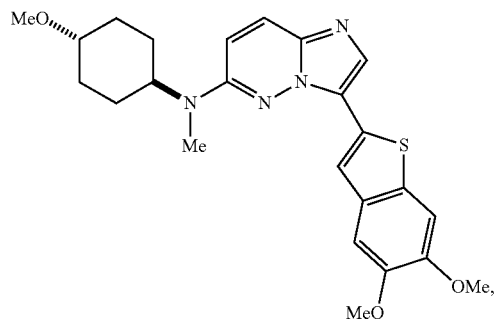

283
-continued

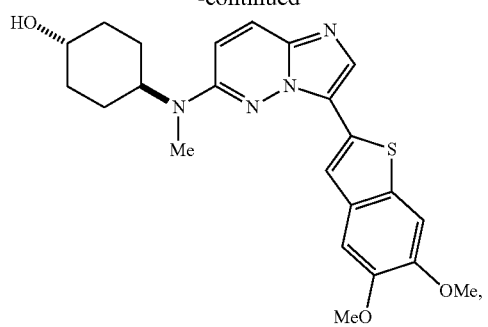

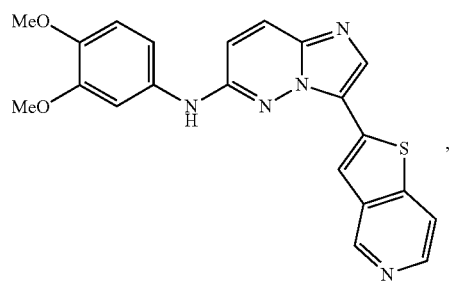

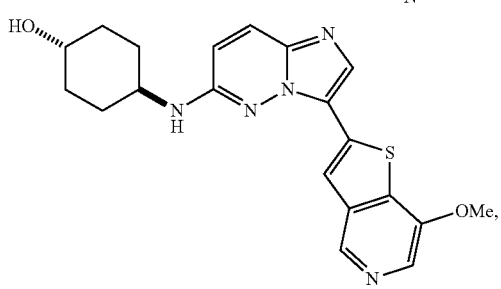

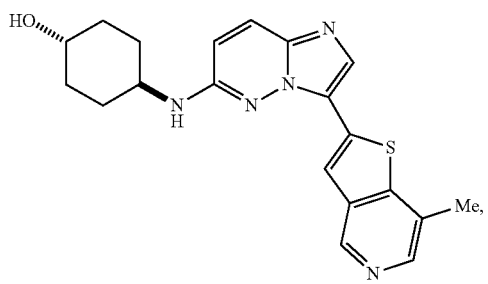

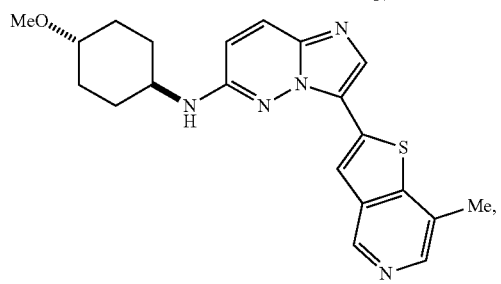

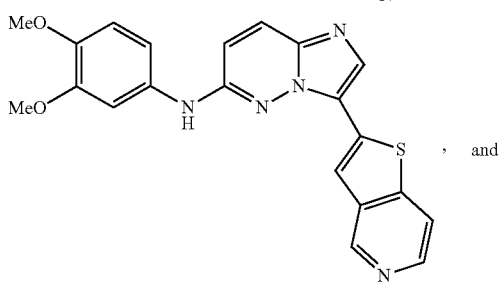, and

284
-continued

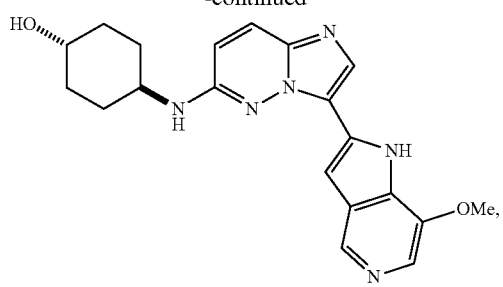

or any pharmaceutically acceptable salt, tautomer, stereoisomer, or isotope thereof.

17. A pharmaceutical composition comprising a compound having the structure of Formula I

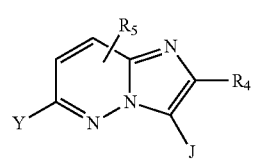

I or a pharmaceutically acceptable isomer, isotope, enantiomer, or salt thereof, wherein J has a structure of

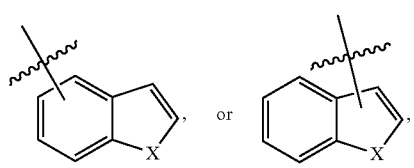

substituted with up to four $R_{10}$, or J has a structure of

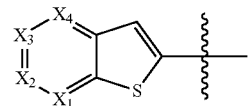

optionally substituted with up to four $R_{10}$, each $R_{10}$ is independently selected from the group consisting of halo, alkyl, haloalkyl, alkoxy, haloalkoxy, —OH, and —OCOR$_6$;

X is NR$_{12}$ or S;

one of $X_1$, $X_2$, $X_3$, and $X_4$ is N and the other three of $X_1$, $X_2$, $X_3$, and $X_4$ are CH;

Y is —W—(CH$_2$)$_n$—R$_1$,

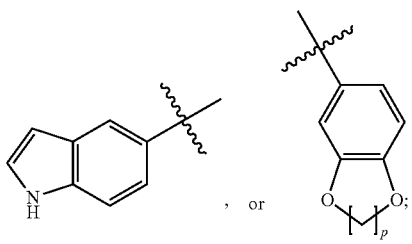

W is null, phenylene, or —NR$_6$-phenylene, where the NR$_6$ is attached to the imidazopyridazine core structure of Formula I;
R$_1$ is —NR$_2$R$_3$, or piperazinyl, where the nitrogen atom of the piperazinyl is optionally substituted with alkyl or alkoxy;
R$_2$ is H or alkyl; R$_3$ is selected from the group consisting of C$_2$-C$_{10}$ alkyl, aryl, heteroaryl, cycloalkyl, and heterocycloalkyl, where any atom of R$_3$ is optionally substituted with one or more R$_7$; or R$_2$ and R$_3$ taken together with the N atom to which they are attached form a 3- to 7-membered heterocyclic ring optionally substituted with R$_8$;
R$_4$ is H or alkyl;
R$_5$ is H, alkyl, or NHR$_9$;
R$_6$ is H or alkyl;
each R$_7$ is independently alkyl, cycloalkyl, alkoxy, cycloalkoxy, cycloalkylalkoxy, perhaloalkoxy, halo, oxo, —OH, hydroxyalkyl, —COOR$_{11}$, or —O—(CH$_2$)$_m$—OH;
R$_8$ is alkoxy, hydroxyalkyl, or COOR$_{11}$;
R$_9$ is H, alkyl, or cycloalkyl;
R$_{11}$ is H, or alkyl;
R$_{12}$ is H, or alkyl;
n is 0 or 1;
m is 1, 2, or 3;
p is 1, 2, or 3; and
together with at least one pharmaceutically acceptable carrier, diluent or excipient.

18. A pharmaceutical composition of claim 17 wherein the compound is selected from any of compounds shown below:

| Compound # | Structure |
|---|---|
| 3 | 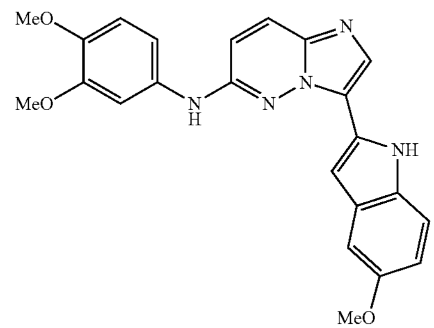 [SMILES: COc1ccc2[nH]c(-c3cnc4ccc(Nc5ccc(OC)c(OC)c5)nn34)cc2c1] |
| 4 | 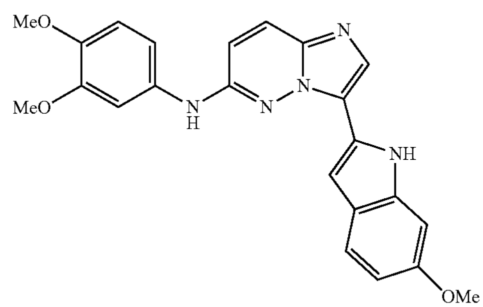 [SMILES: COc1ccc2cc(-c3cnc4ccc(Nc5ccc(OC)c(OC)c5)nn34)[nH]c2c1] |
| 5 | 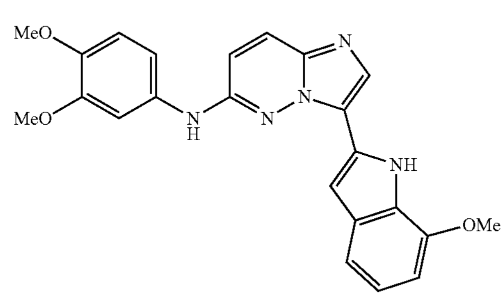 [SMILES: COc1ccc(Nc2ccc3ncc(-c4cc5cccc(OC)c5[nH]4)n3n2)cc1OC] |

| Compound # | Structure |
|---|---|
| 66 | 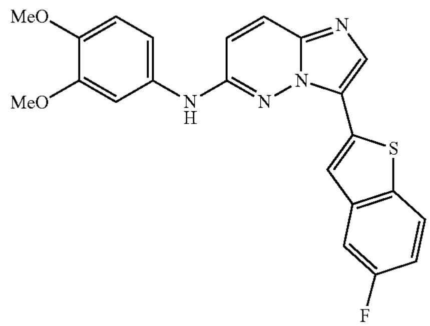 [SMILES: COc1ccc(Nc2ccc3ncc(-c4cc5cc(F)ccc5s4)n3n2)cc1OC] |
| 67 | 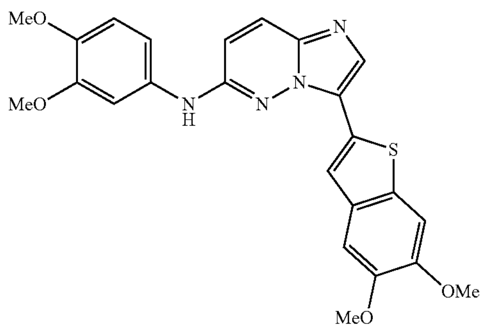 [SMILES: COc1ccc(Nc2ccc3ncc(-c4cc5cc(OC)c(OC)cc5s4)n3n2)cc1OC] |
| 68 | 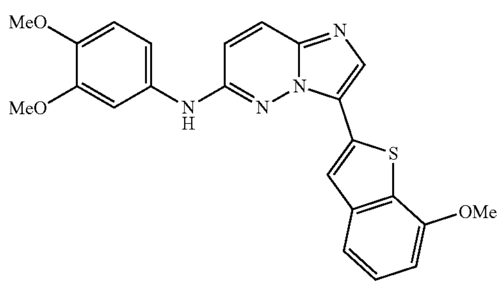 [SMILES: COc1ccc(Nc2ccc3ncc(-c4cc5cccc(OC)c5s4)n3n2)cc1OC] |
| 69 | 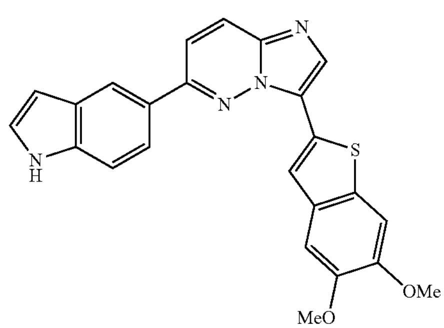 [SMILES: COc1cc2cc(-c3cnc4ccc(-c5ccc6[nH]ccc6c5)nn34)sc2cc1OC] |
| 70 | 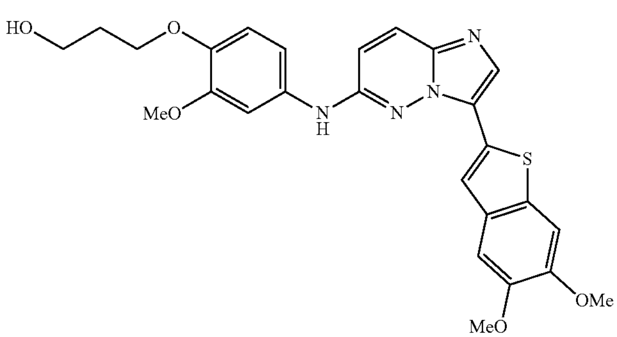 [SMILES: COc1cc2cc(-c3cnc4ccc(Nc5ccc(OCCCO)c(OC)c5)nn34)sc2cc1OC] |

-continued
| Compound # | Structure |
|---|---|
| 71 | 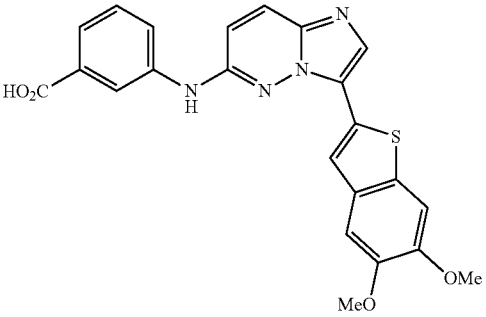 [SMILES: COc1cc2cc(-c3cnc4ccc(Nc5cccc(C(=O)O)c5)nn34)sc2cc1OC] |
| 72 | 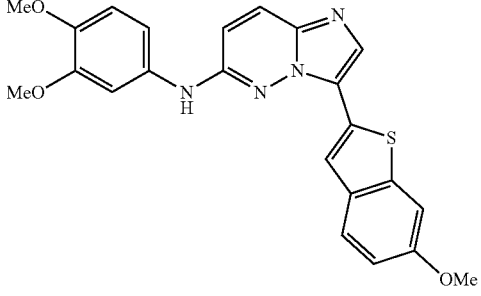 [SMILES: COc1ccc2cc(-c3cnc4ccc(Nc5ccc(OC)c(OC)c5)nn34)sc2c1] |
| 73 | 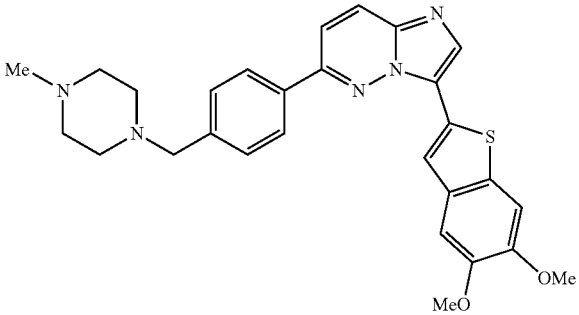 [SMILES: COc1cc2cc(-c3cnc4ccc(-c5ccc(CN6CCN(C)CC6)cc5)nn34)sc2cc1OC] |
| 74 | 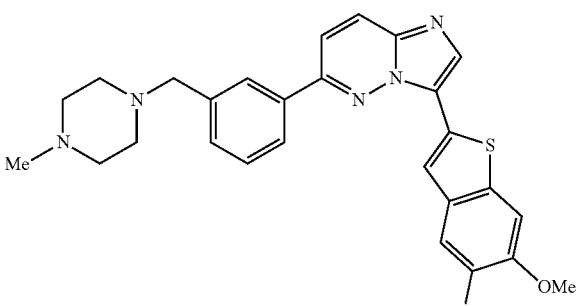 |
| 75 | 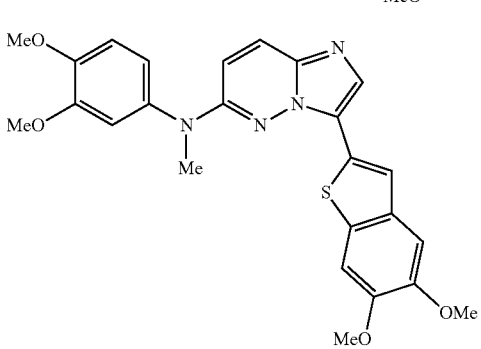 |

-continued
| Compound # | Structure |
|---|---|
| 76 | 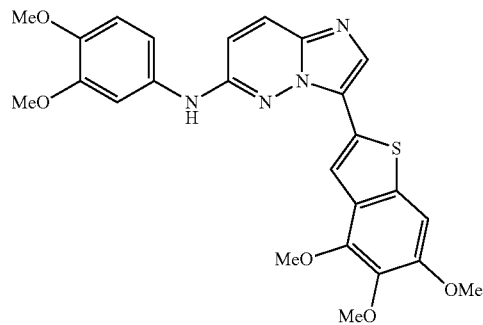 [SMILES: COc1ccc(Nc2ccc3ncc(-c4cc5c(OC)c(OC)c(OC)cc5s4)n3n2)cc1OC] |
| 77 | 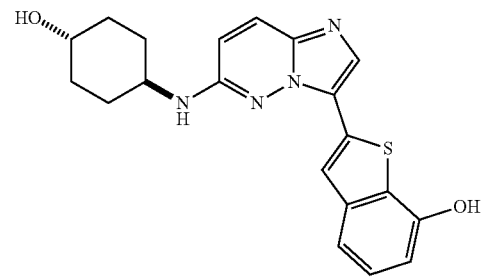 [SMILES: Oc1cccc2cc(-c3cnc4ccc(N[C@H]5CC[C@H](O)CC5)nn34)sc12] |
| 78 | 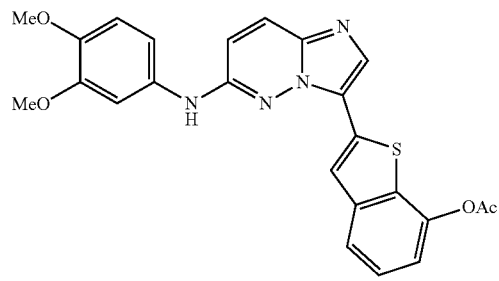 [SMILES: COc1ccc(Nc2ccc3ncc(-c4cc5cccc(OC(C)=O)c5s4)n3n2)cc1OC] |
| 79 | 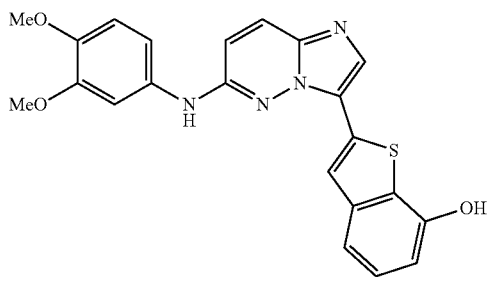 [SMILES: COc1ccc(Nc2ccc3ncc(-c4cc5cccc(O)c5s4)n3n2)cc1OC] |
| 80 | 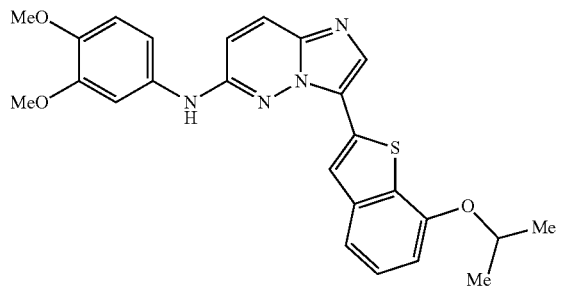 [SMILES: COc1ccc(Nc2ccc3ncc(-c4cc5cccc(OC(C)C)c5s4)n3n2)cc1OC] |

-continued

| Compound # | Structure |
|---|---|
| 81 | 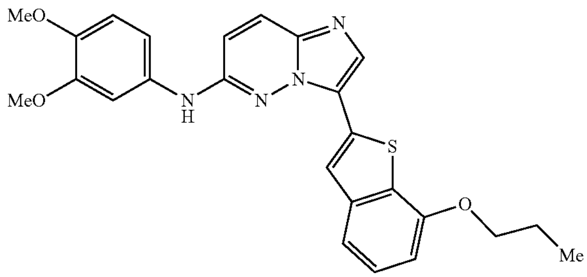 [SMILES: CCCOc1cccc2cc(-c3cnc4ccc(Nc5ccc(OC)c(OC)c5)nn34)sc12] |
| 83 | 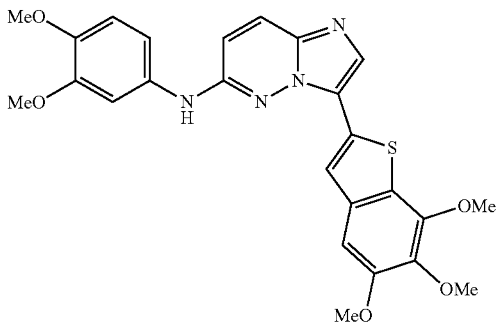 [SMILES: COc1ccc(Nc2ccc3ncc(-c4cc5cc(OC)c(OC)c(OC)c5s4)n3n2)cc1OC] |
| 85 | 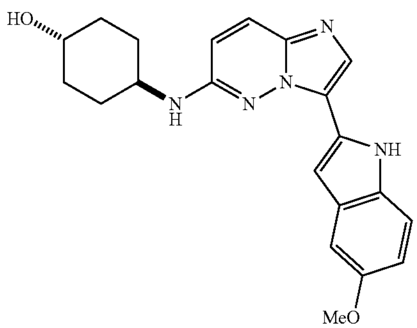 [SMILES: COc1ccc2[nH]c(-c3cnc4ccc(N[C@H]5CC[C@H](O)CC5)nn34)cc2c1] |
| 86 | 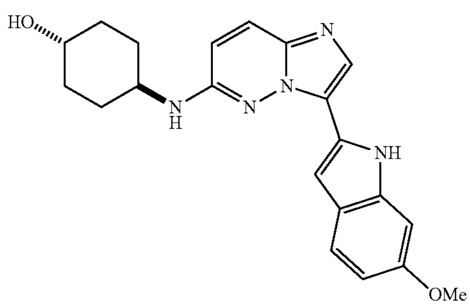 [SMILES: COc1ccc2cc(-c3cnc4ccc(N[C@H]5CC[C@H](O)CC5)nn34)[nH]c2c1] |
| 87 | 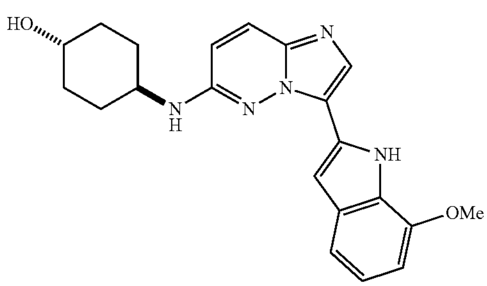 [SMILES: COc1cccc2cc(-c3cnc4ccc(N[C@H]5CC[C@H](O)CC5)nn34)[nH]c12] |

-continued

| Compound # | Structure |
|---|---|
| 92 | (cis-4-hydroxycyclohexyl)amino-imidazo[1,2-b]pyridazin-3-yl linked to 7-methoxybenzo[b]thiophen-4-yl |
| 93 | (3,4-dimethoxyphenyl)amino-imidazo[1,2-b]pyridazin-3-yl linked to 7-methoxybenzo[b]thiophen-4-yl |
| 118 | (4-hydroxybutyl)amino-imidazo[1,2-b]pyridazin-3-yl linked to 6-chloro-3-methylbenzo[b]thiophen-2-yl |
| 166 | (cis-4-hydroxycyclohexyl)amino-imidazo[1,2-b]pyridazin-3-yl linked to 6-fluorobenzo[b]thiophen-2-yl |
| 167 | (3,4-dimethoxyphenyl)amino-imidazo[1,2-b]pyridazin-3-yl linked to 6-methoxybenzo[b]thiophen-2-yl |

-continued
| Compound # | Structure |
|---|---|
| 168 | 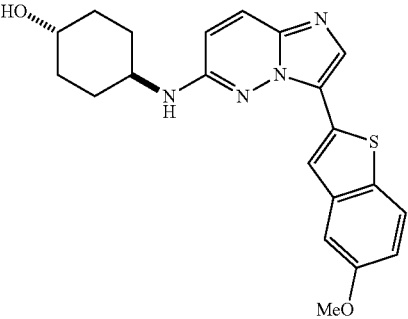 [SMILES: COc1ccc2sc(-c3cnc4ccc(N[C@H]5CC[C@H](O)CC5)nn34)cc2c1] |
| 169 | 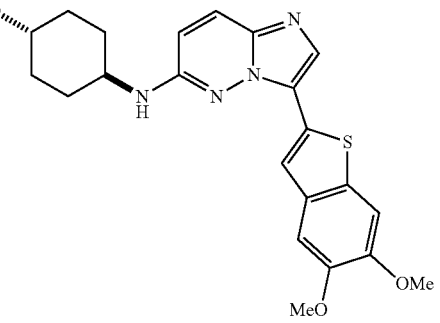 |
| 170 | 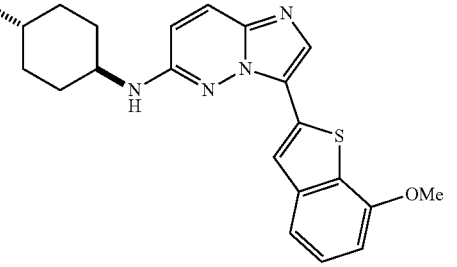 |
| 171 | 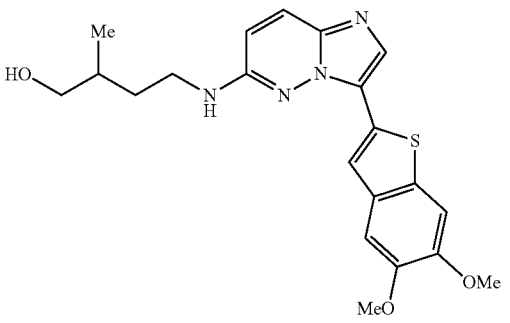 [SMILES: COc1cc2cc(-c3cnc4ccc(NCCC(C)CO)nn34)sc2cc1OC] |
| 172 | 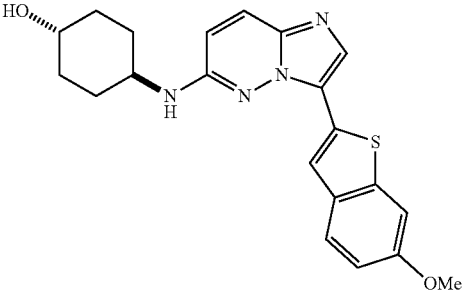 [SMILES: COc1ccc2cc(-c3cnc4ccc(N[C@H]5CC[C@H](O)CC5)nn34)sc2c1] |

-continued
| Compound # | Structure |
|---|---|
| 173 | 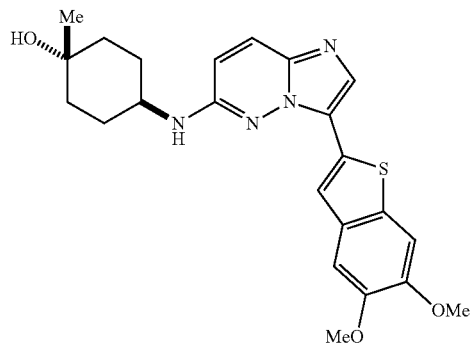 [SMILES: COc1cc2cc(-c3cnc4ccc(N[C@H]5CC[C@](C)(O)CC5)nn34)sc2cc1OC] |
| 174 | 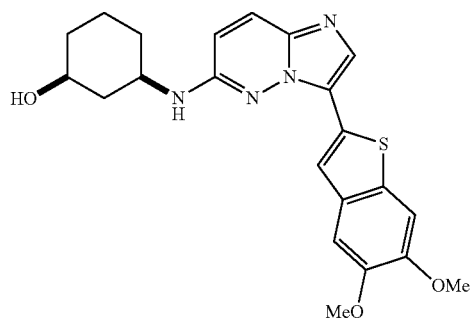 [SMILES: COc1cc2cc(-c3cnc4ccc(N[C@@H]5CCC[C@H](O)C5)nn34)sc2cc1OC] |
| 175 | 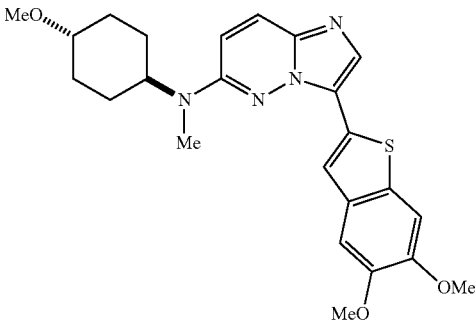 [SMILES: COc1cc2cc(-c3cnc4ccc(N(C)[C@H]5CC[C@H](OC)CC5)nn34)sc2cc1OC] |
| 176 | 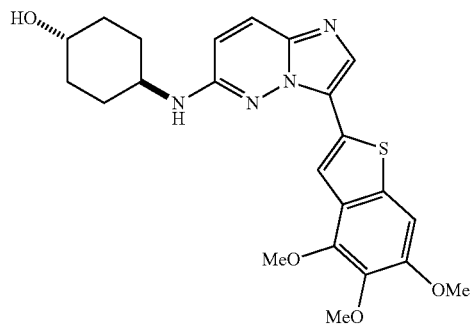 [SMILES: COc1cc2sc(-c3cnc4ccc(N[C@H]5CC[C@H](O)CC5)nn34)cc2c(OC)c1OC] |

-continued
| Compound # | Structure |
|---|---|
| 177 | 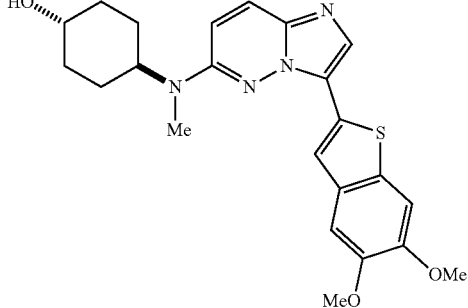 |
| 178 | 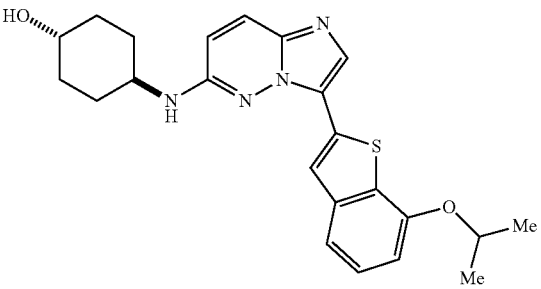 [SMILES: CC(C)Oc1cccc2cc(-c3cnc4ccc(N[C@H]5CC[C@H](O)CC5)nn34)sc12] |
| 179 | 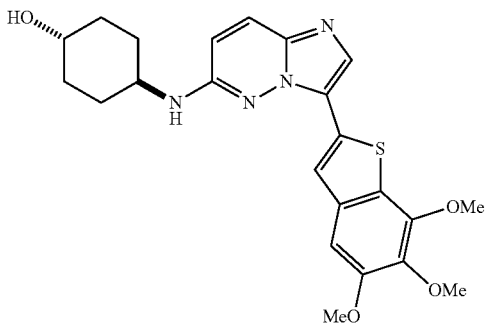 [SMILES: COc1cc2cc(-c3cnc4ccc(N[C@H]5CC[C@H](O)CC5)nn34)sc2c(OC)c1OC] |
| 181 | 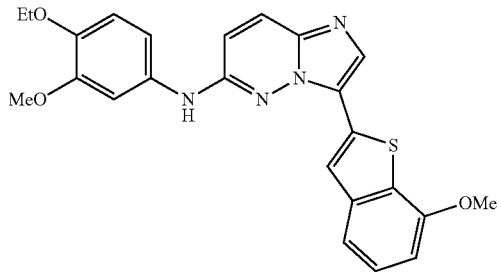 |
| 182 | 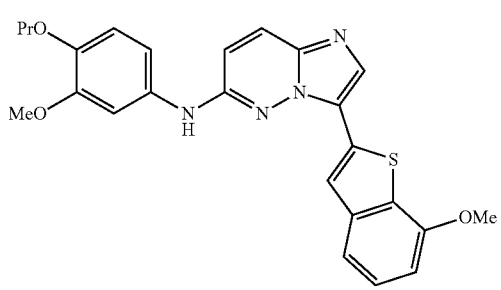 [SMILES: CCOc1ccc(Nc2ccc3ncc(-c4cc5cccc(OC)c5s4)n3n2)cc1OC] |

-continued
| Compound # | Structure |
|---|---|
| 184 | 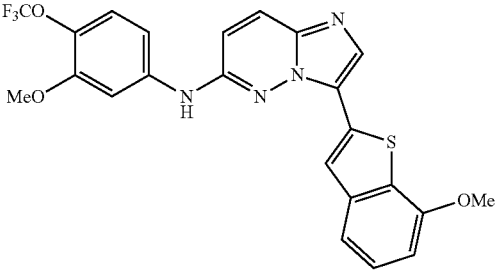 [SMILES: COc1cc(Nc2ccc3ncc(-c4cc5cccc(OC)c5s4)n3n2)ccc1OC(F)(F)F] |
| 185 | 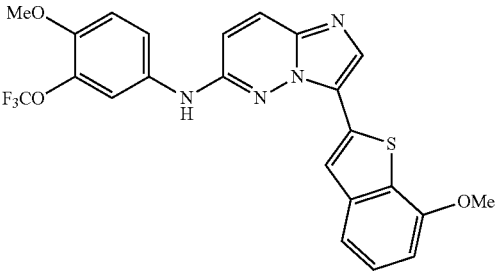 [SMILES: COc1ccc(Nc2ccc3ncc(-c4cc5cccc(OC)c5s4)n3n2)cc1OC(F)(F)F] |
| 186 | 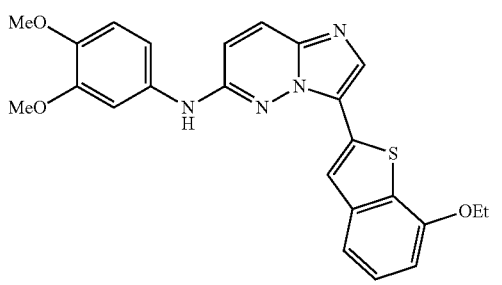 [SMILES: CCOc1cccc2cc(-c3cnc4ccc(Nc5ccc(OC)c(OC)c5)nn34)sc12] |
| 187 | 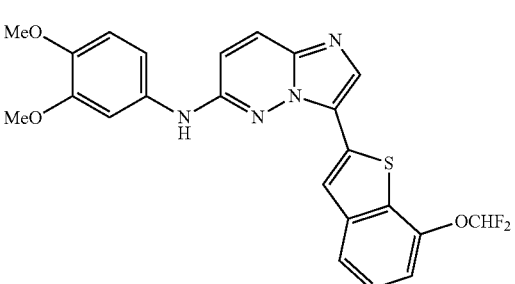 |
| 188 | 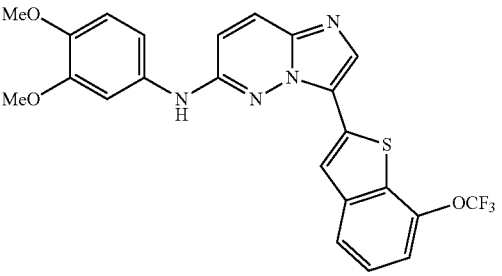 [SMILES: COc1ccc(Nc2ccc3ncc(-c4cc5cccc(OC(F)(F)F)c5s4)n3n2)cc1OC] |

-continued
| Compound # | Structure |
|---|---|
| 189 | 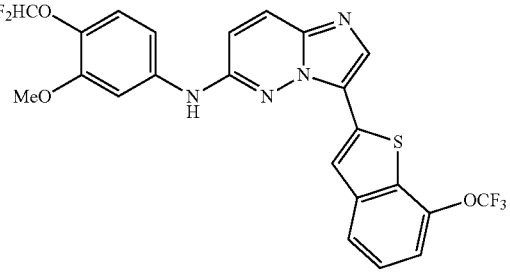 |
| 190 | 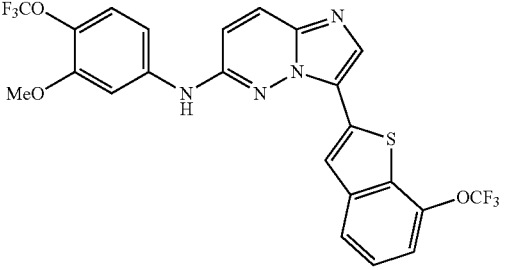 [SMILES: COc1cc(Nc2ccc3ncc(-c4cc5cccc(OC(F)(F)F)c5s4)n3n2)ccc1OC(F)(F)F] |
| 191 | 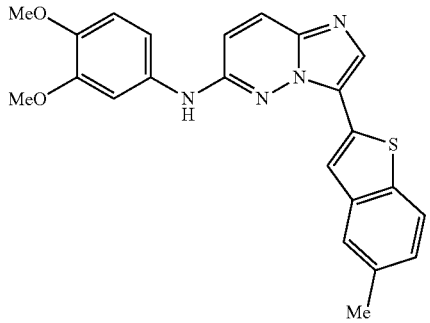 [SMILES: COc1ccc(Nc2ccc3ncc(-c4cc5cc(C)ccc5s4)n3n2)cc1OC] |
| 192 | 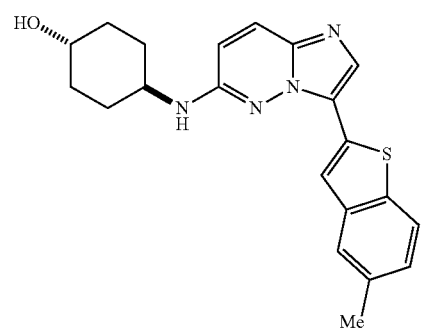 [SMILES: Cc1ccc2sc(-c3cnc4ccc(N[C@H]5CC[C@H](O)CC5)nn34)cc2c1] |
| 193 | 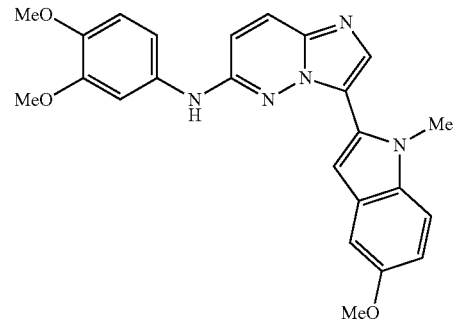 [SMILES: COc1ccc2c(c1)cc(-c1cnc3ccc(Nc4ccc(OC)c(OC)c4)nn13)n2C] |

| Compound # | Structure |
|---|---|
| 194 | (trans-4-hydroxycyclohexyl)amino-imidazo[1,2-b]pyridazine with 1-methyl-6-methoxyindol-2-yl substituent |
| 195 | (3,4-dimethoxyphenyl)amino-imidazo[1,2-b]pyridazine with 7-methyl-1H-indol-2-yl substituent |
| 196 | (trans-4-hydroxycyclohexyl)amino-imidazo[1,2-b]pyridazine with 7-methyl-1H-indol-2-yl substituent |
| 197 | (3,4-dimethoxyphenyl)amino-imidazo[1,2-b]pyridazine with 5,6-dimethoxy-1H-indol-2-yl substituent |
| 198 | (trans-4-methoxycyclohexyl)amino-imidazo[1,2-b]pyridazine with 5-methoxy-1H-indol-2-yl substituent |

| Compound # | Structure |
|---|---|
| 199 | 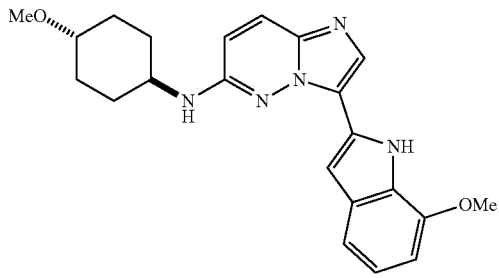 [SMILES: COc1cccc2cc(-c3cnc4ccc(N[C@H]5CC[C@H](OC)CC5)nn34)[nH]c12] |
| 200 | 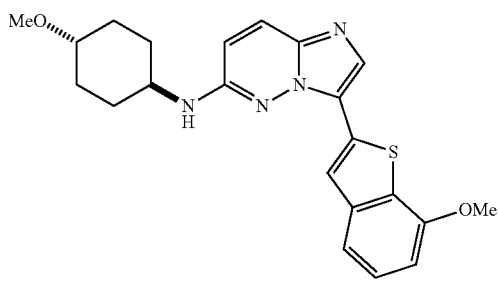 [SMILES: COc1cccc2cc(-c3cnc4ccc(N[C@H]5CC[C@H](OC)CC5)nn34)sc12] |
| 201 | 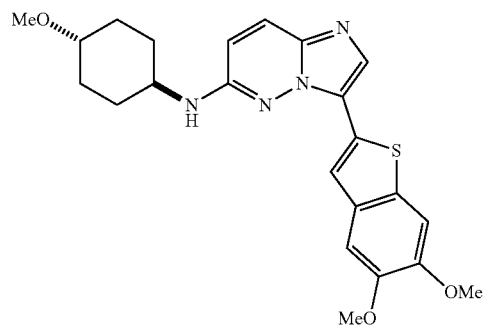 [SMILES: COc1cc2cc(-c3cnc4ccc(N[C@H]5CC[C@H](OC)CC5)nn34)sc2cc1OC] |
| 202 | 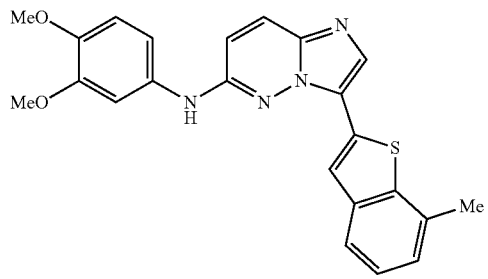 |
| 203 | 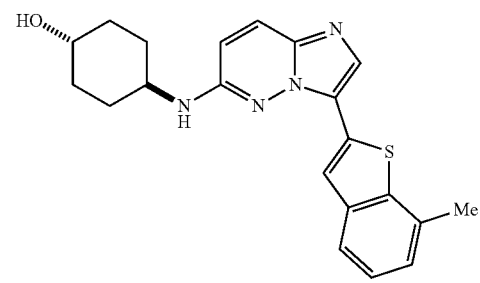 [SMILES: Cc1cccc2cc(-c3cnc4ccc(N[C@H]5CC[C@H](O)CC5)nn34)sc12] |

-continued
| Compound # | Structure |
|---|---|
| 204 | 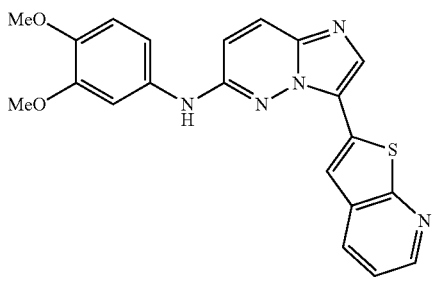 [SMILES: COc1ccc(Nc2ccc3ncc(-c4cc5cccnc5s4)n3n2)cc1OC] |
| 205 | 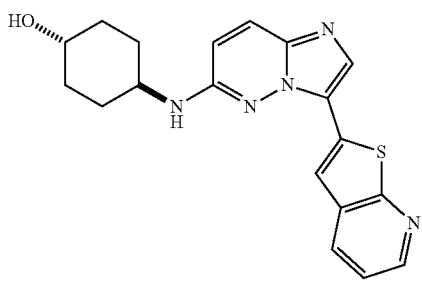 [SMILES: O[C@H]1CC[C@H](Nc2ccc3ncc(-c4cc5cccnc5s4)n3n2)CC1] |
| 206 | 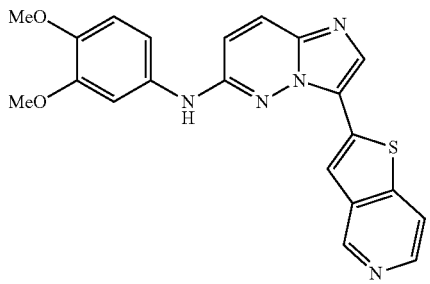 [SMILES: COc1ccc(Nc2ccc3ncc(-c4cc5cnccc5s4)n3n2)cc1OC] |
| 207 | 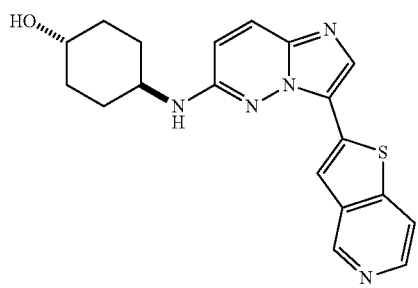 [SMILES: O[C@H]1CC[C@H](Nc2ccc3ncc(-c4cc5cnccc5s4)n3n2)CC1] |
| 208 | 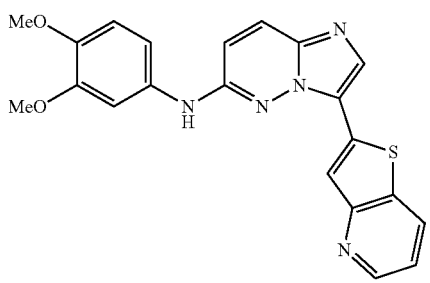 [SMILES: COc1ccc(Nc2ccc3ncc(-c4cc5ncccc5s4)n3n2)cc1OC] |

-continued
| Compound # | Structure |
|---|---|
| 209 | 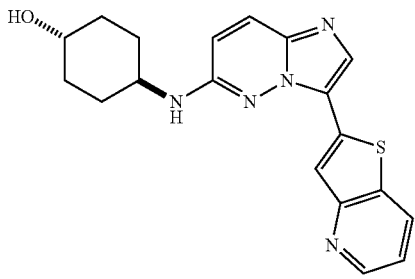 [SMILES: O[C@H]1CC[C@H](Nc2ccc3ncc(-c4cc5ncccc5s4)n3n2)CC1] |
| 210 | 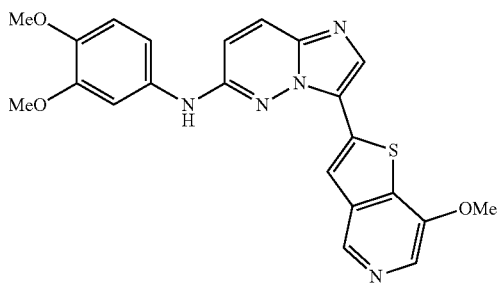 [SMILES: COc1ccc(Nc2ccc3ncc(-c4cc5cncc(OC)c5s4)n3n2)cc1OC] |
| 211 | 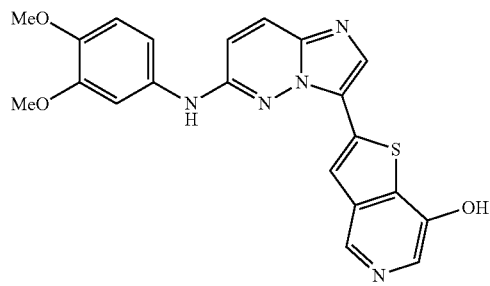 [SMILES: COc1ccc(Nc2ccc3ncc(-c4cc5cncc(O)c5s4)n3n2)cc1OC] |
| 212 | 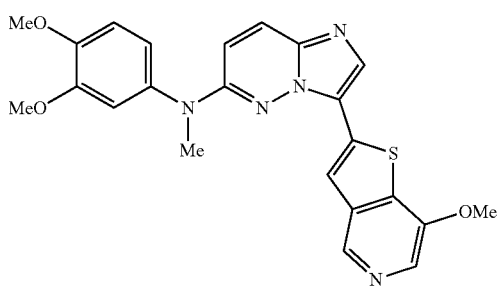 [SMILES: COc1ccc(N(C)c2ccc3ncc(-c4cc5cncc(OC)c5s4)n3n2)cc1OC] |
| 213 | 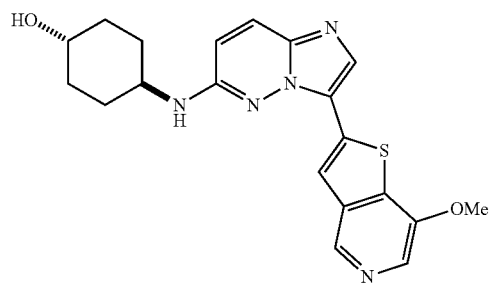 [SMILES: COc1cncc2cc(-c3cnc4ccc(N[C@H]5CC[C@H](O)CC5)nn34)sc12] |

| Compound # | Structure |
|---|---|
| 214 | 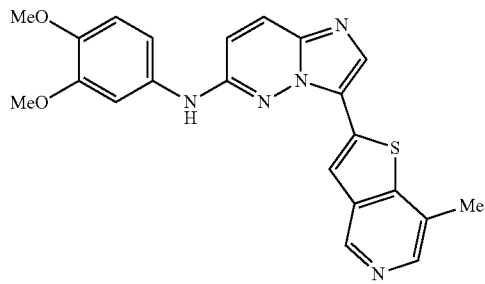 [SMILES: COc1ccc(Nc2ccc3ncc(-c4cc5cncc(C)c5s4)n3n2)cc1OC] |
| 215 | 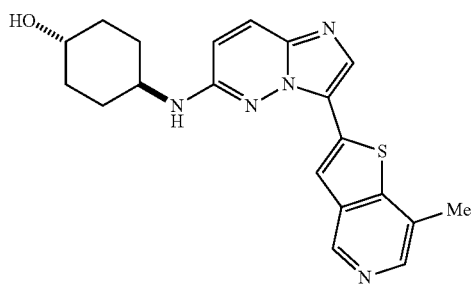 [SMILES: Cc1cncc2cc(-c3cnc4ccc(N[C@H]5CC[C@H](O)CC5)nn34)sc12] |
| 216 | 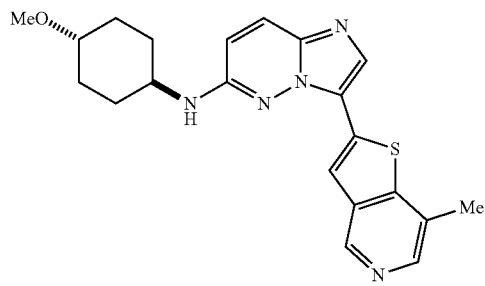 [SMILES: CO[C@H]1CC[C@H](Nc2ccc3ncc(-c4cc5cncc(C)c5s4)n3n2)CC1] |
| 218 | 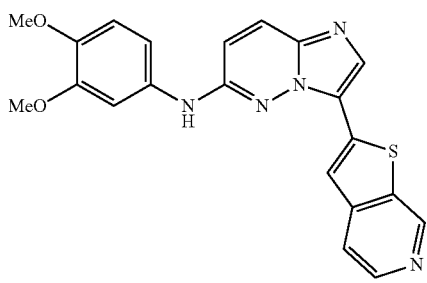 [SMILES: COc1ccc(Nc2ccc3ncc(-c4cc5ccncc5s4)n3n2)cc1OC] |
| 219 | 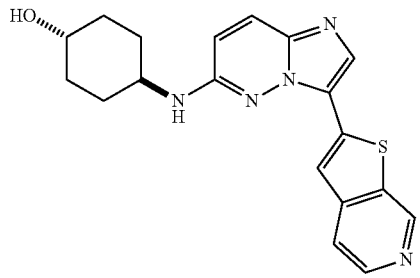 [SMILES: O[C@H]1CC[C@H](Nc2ccc3ncc(-c4cc5ccncc5s4)n3n2)CC1] |

| Compound # | Structure |
|---|---|
| 220 | 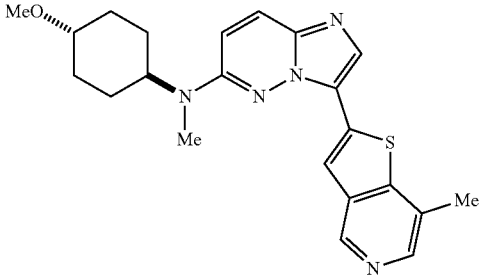 [SMILES: CO[C@H]1CC[C@H](N(C)c2ccc3ncc(-c4cc5cncc(C)c5s4)n3n2)CC1] |
| 221 | 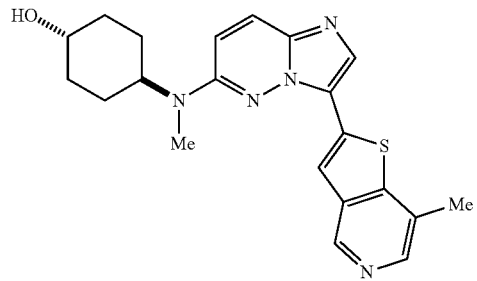 [SMILES: Cc1cncc2cc(-c3cnc4ccc(N(C)[C@H]5CC[C@H](O)CC5)nn34)sc12] |
19. A pharmaceutical composition comprising the compound in any one of claims 1-4 and 5-16 and a suitable excipient.
* * * * *